(12) United States Patent
Mulvihill et al.

(10) Patent No.: US 8,445,510 B2
(45) Date of Patent: May 21, 2013

(54) FUSED BICYCLIC KINASE INHIBITORS

(75) Inventors: Mark J. Mulvihill, Melville, NY (US); Arno G. Steinig, East Northport, NY (US); Andrew Philip Crew, North Babylon, NY (US); Meizhong Jin, Dix Hills, NY (US); Andrew Kleinberg, East Meadow, NY (US); An-Hu Li, Commack, NY (US); Jing Wang, Syosset, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 0 days.

(21) Appl. No.: 13/108,024

(22) Filed: May 16, 2011

(65) Prior Publication Data

US 2011/0281888 A1 Nov. 17, 2011

(51) Int. Cl.
*A61K 31/437* (2006.01)
*C07D 471/04* (2006.01)

(52) U.S. Cl.
USPC .......................................... 514/300; 546/113

(58) Field of Classification Search
None
See application file for complete search history.

(56) References Cited

U.S. PATENT DOCUMENTS

| | | | |
|---|---|---|---|
| 6,235,769 B1 | 5/2001 | Clary | |
| 7,230,098 B2 | 6/2007 | Cui | |
| 7,259,154 B2 | 8/2007 | Cox | |
| 7,452,993 B2 | 11/2008 | Arnold | |
| 7,585,876 B2 | 9/2009 | Bernotas | |
| 2004/0116488 A1 | 6/2004 | Jennings | |
| 2005/0182060 A1 | 8/2005 | Kelly | |
| 2006/0046991 A1 | 3/2006 | Cui | |
| 2006/0128724 A1 | 6/2006 | Cui | |
| 2006/0178374 A1 | 8/2006 | Cui | |
| 2007/0032519 A1 | 2/2007 | Zhang | |
| 2007/0043068 A1 | 2/2007 | Arnold | |
| 2007/0049615 A1 | 3/2007 | Ibrahim | |
| 2007/0060633 A1 | 3/2007 | Mugge | |
| 2007/0066641 A1 | 3/2007 | Ibrahim | |
| 2007/0072874 A1 | 3/2007 | Cui | |
| 2007/0123535 A1 | 5/2007 | Greenhouse | |
| 2007/0287711 A1 | 12/2007 | Arnold | |
| 2008/0167338 A1 | 7/2008 | Spevak | |
| 2008/0221148 A1 | 9/2008 | Ibrahim | |
| 2008/0221197 A1 | 9/2008 | Lam et al. | |
| 2008/0293769 A1 | 11/2008 | Cui | |
| 2009/0005356 A1 | 1/2009 | Blaney | |
| 2009/0005378 A1 | 1/2009 | Arnold | |
| 2009/0076046 A1 | 3/2009 | Zhang | |
| 2009/0143352 A1 | 6/2009 | Arnold | |
| 2010/0063031 A1 | 3/2010 | Liang | |
| 2010/0256365 A1 | 10/2010 | Ibrahim | |
| 2011/0224191 A1* | 9/2011 | Chen et al. | 514/210.21 |
| 2011/0281888 A1 | 11/2011 | Mulvihill | |

FOREIGN PATENT DOCUMENTS

| | | |
|---|---|---|
| WO | 03082868 A1 | 10/2003 |
| WO | 2005004607 A1 | 1/2005 |
| WO | 2005010005 A1 | 2/2005 |
| WO | 2005062795 A2 | 7/2005 |
| WO | 2007002325 A1 | 1/2007 |
| WO | 2007002433 A1 | 1/2007 |
| WO | 2007062998 A1 | 6/2007 |
| WO | 2007064797 A2 | 6/2007 |
| WO | 2007067537 A1 | 6/2007 |
| WO | 2007075567 A1 | 7/2007 |
| WO | 2007132308 A1 | 11/2007 |
| WO | 2007138472 A2 | 12/2007 |
| WO | 2008019968 A1 | 2/2008 |
| WO | 2008031513 A1 | 3/2008 |
| WO | 2008039457 A3 | 4/2008 |
| WO | 2008051805 A2 | 5/2008 |
| WO | 2008051808 A3 | 5/2008 |
| WO | 2008053157 A1 | 5/2008 |
| WO | 2008080015 A2 | 7/2008 |
| WO | 2008124849 A3 | 1/2009 |
| WO | 2008008539 A3 | 2/2009 |
| WO | 2009080534 A1 | 7/2009 |
| WO | 2009094123 A1 | 7/2009 |
| WO | 2009140549 A1 | 11/2009 |
| WO | 2010039248 A1 | 4/2010 |

(Continued)

OTHER PUBLICATIONS

Golub et al. "Molecular Classification of Cancer: Class Discovery and Class Prediction by Gene Expression Monitoring." Science (1999), vol. 286, 521-537.*

(Continued)

*Primary Examiner* — Rebecca Anderson
*Assistant Examiner* — Alicia L Otton
(74) *Attorney, Agent, or Firm* — Frank W. Forman

(57) ABSTRACT

Compounds of Formula I, as shown below and defined herein:

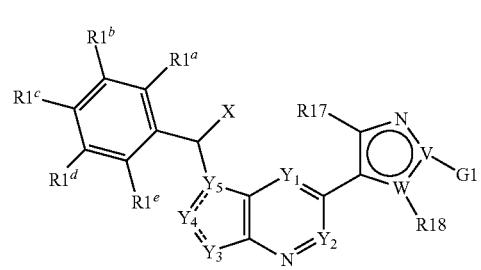

pharmaceutically acceptable salts thereof, synthesis, intermediates, formulations, and methods of disease treatment therewith, including treatment of cancers, such as tumors driven at least in part by at least one of RON, MET or ALK. This Abstract is not limiting of the invention.

15 Claims, No Drawings

FOREIGN PATENT DOCUMENTS

| WO | 2010059771 A1 | 5/2010 |
|---|---|---|
| WO | 2010104945 A1 | 9/2010 |
| WO | 2011143645 A1 | 11/2011 |
| WO | 2011143646 A1 | 11/2011 |

OTHER PUBLICATIONS

Johnson et al. "Relationships between drug activity in NCI preclinical in vitro and in vivo models and early clinical trials." British Journal of Cancer (2001), 84(10), 1424-1431.*

Sausville et al. "Contributions of Human Tumor Xenografts to Anticancer Drug Development." Cancer Res. 2006, 66(7), Apr. 1, 2006.*

"Cancer." MedLine Plus. (2009). Accessed Mar. 17, 2009. <http://www.nlm.nih.gov/medlineplus/cancer.html>.*

Database CA [online] Chemical Abstracts Service, Columbus, Ohio, US; XP002650560; Database Accession No. 143:145775 the whole document.

Brabletz et al., (2005) Nature Rev., 5 pgs. 744-749.

Database CA [online] Chemical Abstracts Service, Columbus, Ohio, US; XP002650560; Database Accession No. 143:145775 the whole document, (2005).

IPRP and Written Opinion of the International Search Authority in PCT/US2009/065058 mailed Jun. 3, 2011.

International Search Report in PCT/US2009/065058, mailed Aug. 2, 2010.

International Search Report and Written Opinion of the International Search Authority in PCT/US2011/036572, mailed Jul. 14, 2011.

International Search Report and Written Opinion of the International Search Authority in PCT/US2011/036573, mailed Jul. 25, 2011.

PCT/US12/37866 filing date May 15, 2012.

Arteaga, (2007) Nature Medicine 13 (6) p. 675.

Brabletz et al., (2005) Nature Rev., 5 pp. 744-749.

Camp et al., (2007)Cancer 109(6) pp. 1030-1039.

Christensen et al., (2005) Cancer Letters, 225(1) pp. 1-26.

Christofori, (2006) Nature 441 pp. 444-450.

Comoglio et al., (2008) Nature Reviews Drug Disc. 7 (6) pp. 504-516.

Eng C., (2008) Nature 455 pp. 883-884.

Engelman, et al. (2007) Science 316 p. 1039-1043.

Gentile et al., (2008) Cancer & Metastasis Reviews, 27 (1) pp. 85-94.

Giam C.S. et al. (1984) "A New Approach to the Preparation of 1, 6- and 1. 7-Naphthyridines". J. Chem. Soc. Chem. Commun., No. 5, pp. 265-266, XP002650561, Compound 4b.

Grotegut et al., (2006) Embo J. 25 (15) pp. 3534-3545.

Gupta et al., (2006) Cell 127 pp. 679-695.

Jarvis, L. (2007) Chemical & Engineering News 85 (34), pp. 15-23.

Lawrence B. et al., (2000) Am J. Pathol., 157 (2) pp. 377-384.

McDermott U. et al., (2008) Cancer Res. 68 pp. 3389-3395.

Maggiora et al., (1997) J. Cell Physiol., 173 pp. 183-186.

Maulik et al., (2002) Cytokine & Growth Factor Reviews, 13 pp. 41-59.

Morris S.W. et al., (1994) Science 263 pp. 1281-1284.

Oft et al., (1996) Genes & Dev. 10 pp. 2462-2477.

Perl et al., (1998) Nature 392 pp. 190-193.

Porter, J. et al. (2009) "Discovery of 4-azaindoles as novel inhibitors of c-Met kinase". Bioorganic & Medicinal Chemistry Letters, Pergamon, Elsevier Science, GB. vol. 19, No. 10, May 15, 2009, pp. 2780-2784, XP026085966, ISSN: 0960-894X, DOI: 10.1016/J.BMCL.2009.03.110 [retrieved on Mar. 27, 2009] compound 52.

Saucier, (2004) PNAS 101 (8) p. 2345-2350.

Smolen et al., (2006) Proc. Natl. Acad. Sci. USA 103 (7) pp. 2316-2321.

Soda M et al., (2007) Nature 448 pp. 561-566.

Sweeney, Z.K. et al. (2008) "Design of Annulated Pyrazoles as Inhibitors of HIV-1 Reverse Transcriptase". J. Med. Chem. vol. 51, pp. 7449-7458, XP002650559, compound 4.

Thiery, (2002) Nature Rev. Cancer 2 (6) 442-454.

Wan, Z-K, et al. (2001) "Dienophilicity of imidazole in inverse electron demand Diels-Alder reactions: cycloadditions with 1, 2,4,5-tetrazines and the structure of zarzissine". Tetrahedron, Elsevier Science Publishers, Amsterdam, NL. vol. 57, No. 26, Jun. 25, 2001, pp. 5497-5507, XP004247085, ISSN: 0040-4020, DIO: 10.1016/S0040-4020(01)00476-8 compound 10c.

Wang et al., (2008) J. Appl. Poly. Sci., 109 (5) pp. 3369-3375.

Wang et al., (2004) Oncogene 23 (9) pp. 1668-1680.

Zeng, et al., (2008) Cancer Letters 265 (2) pp. 258-269.

Zou et al., (2007) Cancer Res., 67 (9) p. 4408-4417.

* cited by examiner

FUSED BICYCLIC KINASE INHIBITORS

This application claims the benefit of U.S. Appl. No. 61/334,734 (filed May 14, 2010), which is incorporated herein in its entirety by this reference.

FIELD AND BACKGROUND

The present invention pertains at least in part to cancer treatment, certain chemical compounds, and methods of treating tumors and cancers with the compounds.

RON (recepteur d'origine nantais) is a receptor tyrosine kinase that is part of the MET proto-oncogene family. It is activated by binding to its natural ligand MSP and signals via the PI3K and MAPK pathways. RON can be deregulated in cancer by mechanisms such as over-expression of the receptor and/or the presence of constitutively active splice variants. Inhibition of RON has been shown to lead to a decrease in proliferation, induction of apoptosis and affects cell metastasis. RON overexpression is observed in a variety of human cancers and exhibits increased expression with progression of the disease.

MET (also known as Met, c-Met, cMet) is a receptor tyrosine kinase that is a heterodimeric protein comprising of a 50 kDa α-subunit and a 145 kDa β-subunit (Maggiora et al., *J. Cell Physiol.*, 173:183-186, 1997). It is activated by binding to its natural ligand HGF (hepatocyte growth factor, also known as scatter factor) and signals via the PI3K and MAPK pathways. MET can be deregulated in cancer by mechanisms such as autocrine/paracrine HGF activation, over-expression of the receptor, and/or the presence of activating mutations. Significant expression of MET has been observed in a variety of human tumors, such as colon, lung, prostate (including bone metastases), gastric, renal, HCC, ovarian, breast, ESCC, and melanoma (Maulik et al., *Cytokine & Growth Factor Reviews*, 13:41-59, 2002). MET is also implicated in atherosclerosis and lung fibrosis. Inhibition of MET can cause a decrease in cell motility, proliferation and metastasis, as reviewed in, e.g., Chemical & Engineering News 2007, 85 (34), 15-23.

Elevated expression of MET has been detected in numerous cancers including lung, breast, colorectal, prostate, pancreatic, head and neck, gastric, hepatocellular, ovarian, renal, glioma, melanoma, and some sarcomas. See Christensen et al., *Cancer Letters*, 225(1):1-26 (2005); Comoglio et al., *Nature Reviews Drug Disc.*, 7(6):504-516 (2008). MET gene amplification and resulting overexpression has been reported in gastric and colorectal cancer. Smolen et al., *Proc. Natl. Acad. Sci. USA*, 103(7):2316-2321 (2006); Zeng et al., *Cancer Letters*, 265(2):258-269 (2008). Taken together, the MET proto-oncogene has a role in human cancer and its overexpression correlates with poor prognosis. Abrogation of MET function with small molecule inhibitors, anti-MET antibodies or anti-HGF antibodies in preclinical xenograft model systems has shown impact when MET signaling serves as the main driver for proliferation and cell survival. Comoglio et al., *Nature Reviews Drug Disc.*, 7(6):504-516 (2008); Comoglio et al., *Cancer & Metastasis Reviews*, 27(1):85-94 (2008).

As human cancers progress to a more invasive, metastatic state, multiple signaling programs regulating cell survival and migration programs are observed depending on cell and tissue contexts. Gupta et al., *Cell*, 127:679-695 (2006). Recent data highlight the transdifferentiation of epithelial cancer cells to a more mesenchymal-like state, a process resembling epithelial-mesenchymal transition (EMT) (Oft et al., *Genes & Dev.*, 10:2462-2477 (1996); Perl et al., *Nature*, 392:190-193 (1998)) to facilitate cell invasion and metastasis. Brabletz et al., *Nature Rev.*, 5:744-749 (2005); Christofori, *Nature*, 41:444-450 (2006). Through EMT-like transitions mesenchymal-like tumor cells are thought to gain migratory capacity at the expense of proliferative potential. A mesenchymal-epithelial transition (MET) has been postulated to regenerate a more proliferative state and allow macrometastases resembling the primary tumor to form at distant sites. Thiery, *Nature Rev. Cancer*, 2(6):442-454 (2002). MET and RON kinases have been shown to play a role in the EMT process. Camp et al., *Cancer*, 109(6):1030-1039 (2007); Grotegut et al., *EMBO J.*, 25(15):3534-3545 (2006); Wang et al., *Oncogene*, 23(9):1668-1680 (2004). It has been documented in vitro that RON and MET can form heterodimers and signal via such RON-MET dimers.

MET and RON are known to interact and influence the activation of one another. Furthermore, co-expression of the two receptors, when compared to each receptor alone, is associated with the poorest clinical prognosis in bladder, CRC, and breast cancer patients. Since co-expression of RON and MET in cancer has been observed, such "cross-talk" may contribute to tumor growth.

ALK (Anaplastic Lymphoma Kinase) is a receptor tyrosine kinase that belongs to the insulin receptor subfamily. Constitutively active fusion proteins, activating mutations, or gene amplifications have been identified in various cancers, for example, kinase domain mutations in Neuroblastoma (Eng C., *Nature*, 2008, 455, 883-884), echinoderm microtubule-associated protein-like 4 (EML4) gene-ALK fusion in non-small cell lung cancer (NSCLC) (Soda M. et al., *Nature*, 2007, 448, 561-566), TPM3 and TPM4-ALK fusions in inflammatory myofibroblastic tumors (IMT) (Lawrence B. et al., *Am. J. Pathol.*, 2000, 157, 377-384), and nucleophosmin (NPM)-ALK fusions in anaplastic large cell lymphomas (ALCL) (Morris S. W. et al., *Science*, 1994, 263, 1281-1284). Cell lines harboring such mutations or fusion proteins have been shown to be sensitive to ALK inhibition (McDermott U. et al., *Cancer Res.*, 2008, 68, 3389-3395).

The following documents are also noted: WO10/104,945; WO10/059,771; WO10/039,248; WO09/140,549; WO09/094,123; WO08/124,849; WO08/53157; WO08/051,808; WO08/051,805; WO08/039,457; WO08/008,539; WO07/138,472; WO07/132,308; WO07/075,567; WO07/067,537; WO07/064,797; WO07/002,433; WO07/002,325; WO05/062795; WO05/010005; WO05/004607; WO03/82868; U.S. Pat. No. 7,585,876; U.S. Pat. No. 7,452,993; U.S. Pat. No. 7,259,154; U.S. Pat. No. 7,230,098; U.S. Pat. No. 6,235,769; US2010/256365; US2010/063031; US2009/143352; US2009/076046; US2009/005378; US2009/005356; US2008/293769; US2008/221197; US2008/221148; US2008/167338; US2007/032519; US2007/287711; US2007/123535; US2007/072874; US2007/066641; US2007/060633; US2007/049615; US2007/043068; US2007/032519; US2006/178374; US2006/128724; US2006/046991; US2005/182060; US2004/116488; U.S. Appl. No. 61/334,690 (filed May 14, 2010); Wang et al., *J. Appl. Poly. Sci.*, 109(5), 3369-3375 (2008); Zou et al., *Cancer Res.*, 67(9), 4408 (2007); Arteaga, *Nature Medicine*, 13, 6, 675 (June 2007); Engelman, *Science*, 316, 1039 (May 2007); Saucier, *PNAS*, 101, 2345 (February 2004).

There is a need for effective therapies for use in proliferative disease, including treatments for primary cancers, prevention of metastatic disease, and targeted therapies, including receptor tyrosine kinase inhibitors, such MET, RON, and ALK inhibitors, dual and multi-target inhibitors, including selective inhibitors (such as selectivity over Aurora kinase B (AKB) and/or KDR), and for potent, orally bioavailable, and efficacious inhibitors, and inhibitors that maintain sensitivity of epithelial cells to epithelial cell directed therapies.

SUMMARY

In some aspects, the present invention concerns compounds of Formula I (and pharmaceutically acceptable salts thereof):

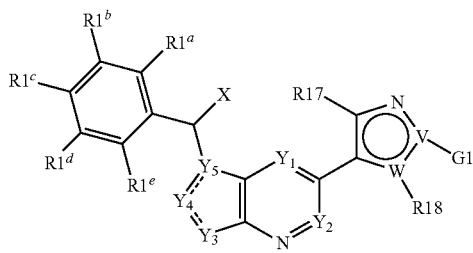

I wherein at least one of R17 and R18 is a substituent, X is an optional substituent, $Y_1$-$Y_5$ are independently carbon or heteroatom, $R1^a$-$R1^e$ are independently optional substituents, and G1 is an optional substituent.

The invention includes the compounds and salts thereof, and their physical forms, preparation of the compounds, useful intermediates, and pharmaceutical compositions and formulations thereof.

In some aspects, compounds of the invention are useful as inhibitors of kinases, including in some embodiments, at least one of the MET, ALK, and RON kinases. In some aspects, compounds of the invention are useful as selective inhibitors. In some embodiments, compounds of the invention are useful as selective inhibitors at least one of the MET, ALK, and RON kinases over other kinase targets, such as KDR and/or AKB.

In some aspects, compounds of the invention can be useful in treating proliferative disease in patients, particularly cancers, including cancers mediated by at least one of the MET, ALK, and RON kinases, alone or in combination with other agents, or for which treatment with a potent inhibitor of at least one of the MET, ALK, and RON kinases is useful.

DETAILED DESCRIPTION

Compounds

In some aspects, the present invention concerns compounds and salts thereof of Formula I, above, wherein (Subgenus 1):

X is selected from H, $C_{1-3}$aliphatic, or —$OC_{1-3}$aliphatic, either of which is optionally substituted with halo or —CN;

W—V is C—N or N—C;

$Y_1$ and $Y_2$ are independently N or CH, provided that not more than one of $Y_1$ and $Y_2$ is N; $Y_3$ is NH or CH; $Y_4$ is N or CH; $Y_5$ is N or C, provided that not more than one of $Y_4$ and $Y_5$ is N;

$R^{1a}$, $R^{1b}$, $R^{1c}$, $R^{1d}$, $R^{1e}$ are each independently selected from H, aliphatic, cyclic, —O-aliphatic, —O-cyclic, sulfide, sulfone, sulfoxide, amino, amido, carboxyl, acyl, ureido, or —S-cyclic, any of the foregoing being optionally substituted, halo, or —CN;

G1 is selected from H, aliphatic, or cyclic, either of which is optionally substituted;

R17 and R18 are independently selected from H, aliphatic, —O-aliphatic, cyclic, amido, carboxyl, or amino, any of the foregoing being optionally substituted, —CN, or halo, provided that at least one of R17 and R18 is not H.

In some aspects of Formula I or Subgenus 1 thereof (Subgenus 2):

$R^{1a}$, $R^{1b}$, $R^{1c}$, $R^{1d}$, $R^{1e}$ are each independently selected from H, halo, —CN, $C_{1-6}$aliphatic, $C_{3-7}$-carbocyclic, —$CF_3$, —$OCHF_2$, —$OCF_3$, —$OC_{0-6}$aliphatic, —$OC_{3-7}$carbocyclic, —O-heterocyclyl, —O-heteroaryl, —S-heteroaryl, —$S(O)_mC_{1-6}$aliphatic, —$SO_2N(C_{0-6}$aliphatic)($C_{0-6}$aliphatic), —$N(C_{0-6}$aliphatic)($C_{0-6}$aliphatic), —$N(C_{0-6}$aliphatic)C(=O)$C_{0-6}$aliphatic, —$N(C_{0-6}$aliphatic)C(=O)$OC_{0-6}$aliphatic, —$N(C_{0-6}$aliphatic)C(=O)N($C_{0-6}$aliphatic)($C_{0-6}$aliphatic), —C(=O)$C_{0-6}$aliphatic, —C(=O)$OC_{0-6}$aliphatic, —C(=O)N($C_{0-6}$aliphatic)($C_{0-6}$aliphatic), —N($C_{0-6}$aliphatic)-heterocyclyl, —N($C_{0-6}$aliphatic)-heteroaryl, aryl, heteroaryl, or heterocyclyl; wherein heterocyclyl is optionally substituted with one or more oxo, $C_{1-6}$aliphatic, C(=O)$OC_{1-6}$aliphatic, C(=O)$C_{0-6}$aliphatic, C(=O)N($C_{0-6}$aliphatic)($C_{0-6}$aliphatic), $SO_2N(C_{0-6}$aliphatic)($C_{0-6}$aliphatic), or $SO_2C_{1-6}$ aliphatic; further wherein any of the foregoing containing aliphatic, carbocyclyl, heterocyclyl, aryl, or heteroaryl is optionally substituted with one or more halo, —CN, $C_{1-6}$aliphatic, —$OC_{0-6}$aliphatic, —$N(C_{0-6}$aliphatic)($C_{0-6}$aliphatic), C(=O)N($C_{0-6}$aliphatic)($C_{0-6}$aliphatic), C(=O)$OC_{0-6}$aliphatic, C(=O)$C_{0-6}$aliphatic, $C_{3-7}$-carbocyclic, heterocyclyl, aryl, or heteroaryl;

G1 is $_{4-8}$heterocycloalkyl optionally substituted by one or more —CN, —$OR^6$, halo, —$R^6$, oxo, —$S(O)_mR^6$, —$SO_2NR^6R^7$, —$C(O)R^b$, —$C(O)NR^6R^7$, —C(O)C(O)$NR^6R^7$, —C(O)$OR^6$, or —C(O)C(O)$OR^6$;

or G1 is $_{3-8}$cycloalkyl optionally substituted by one or more —CN, —$OR^6$, halo, oxo, —$S(O)_mR^6$, —$SO_2NR^6R^7$, —C(O)$R^b$, —C(O)$NR^6R^7$, —C(O)C(O)$NR^6R^7$, —C(O)$OR^6$, —C(O)C(O)$OR^6$, or —$C_{1-6}$aliphatic said aliphatic optionally substituted by halo or —$OC_{0-5}$aliphatic;

or G1 is $C_{1-6}$aliphatic optionally substituted by one or more —CN, —$OR^6$, —$R^6$, oxo, —$NR^6R^7$, —C(O)$R^b$, —C(O)$NR^6R^7$, —C(O)C(O)$NR^6R^7$, —C(O)$OR^6$, —C(O)C(O)$OR^6$, —OC(O)$R^b$, —$NR^6C(O)R^b$, —$NR^6S(O)_2R^7$, —$(CR^8R^9)_nC(O)R^b$, —$(CR^8R^9)_nC(O)OR^6$, —$(CR^8R^9)_nC(O)NR^6R^7$, —$(CR^8R^9)_nS(O)_2NR^6R^7$, —$(CR^8R^9)_nNR^6R^7$, —$(CR^8R^9)_nOR^6$, —$(CR^8R^9)_nS(O)_mR^6$, —$NR^{10}C(O)NR^6R^7$, —$NR^{10}S(O)_2NR^6R^7$, or —$NR^{10}S(O)NR^6R^7$;

wherein each $R^6$, $R^7$, $R^8$, $R^9$, $R^{10}$, and $R^b$ is independently —$C_{0-5}$aliphatic or $C_{3-7}$cycloaliphatic, each independently optionally substituted by one or more halo, —$OCF_3$, or —$OC_{0-3}$aliphatic; or $NR^6R^7$ defines a $_{4-7}$heterocycloaliphatic optionally substituted by one or more $C_{1-6}$aliphatic;

one of R17 and R18 is selected from H, —$OC_{1-6}$aliphatic, —$C_{1-6}$aliphatic, —CN, halo, —$CF_3$, —$OCF_3$, $C_{3-7}$cycloaliphatic, —C(O)$NR^6R^7$, —C(O)$OR^6$, or —N($C_{0-6}$aliphatic)($C_{0-6}$aliphatic); wherein any said aliphatic groups can be substituted with one or more halo, hydroxy, or $C_{1-6}$alkoxy; and the other of R17 and R18 is —CN, halo, or $C_{1-3}$aliphatic;

each m is independently 0-2; and each n is independently 0-7.

In some embodiments of Formula I, G1 is $_{4-10}$heterocyclic or $_{3-10}$cycloaliphatic, either saturated or unsaturated, and each optionally substituted. Nonlimiting substituents may include one or more independent —CN, —$OR^6$, halo, —$S(O)_mR^6$, —$SO_2NR^6R^7$, —C(O)$R^b$, —C(O)$NR^6R^7$, —C(O)C(O)$NR^6R^7$, —C(O)$OR^6$, —C(O)C(O)$OR^6$, or —$C_{1-6}$aliphatic said aliphatic optionally substituted by halo or —$OC_{0-5}$aliphatic; wherein said variables are nonlimiting and can be as in any of the applicable definitions herein. In some embodiments thereof, G1 is aryl or heteroaryl, either of which may be mono- or multi-cyclic, and can be similarly optionally substituted.

For avoidance of doubt, a G1 cyclic group can include any multicyclic moieties, including bridged and spirocyclic systems where applicable. For example, a cycloaliphatic may include bicyclics such as bicyclo[3.1.0]hexyl, or spirocyclics such as spiro[3.3]heptyl. A heterocyclic may include bicyclics such as azabicyclo[3.2.1]octyl, or spirocyclics such as 2-azaspiro[3.3]heptyl, or 2,7-diazaspiro[3.5]nonyl. In case of bicyclics, such can be selected from carbobicyclic and heterobicyclic, any of which can be fused, bridged, or spirocyclic, and any of which is optionally substituted. Nonlimiting substituents may include one or more independent —CN, —OR$^6$, halo, —S(O)$_m$R$^6$, —SO$_2$NR$^6$R$^7$, —C(O)R$^b$, —C(O)NR$^6$R$^7$, —C(O)C(O)NR$^6$R$^7$, —C(O)OR$^6$, —C(O)C(O)OR$^6$, or —C$_{1-6}$aliphatic said aliphatic optionally substituted by halo or —OC$_{0-5}$aliphatic; wherein said variables are nonlimiting and can be as in any of the applicable definitions herein.

In some embodiments of Formula I, G1 is C$_{1-12}$aliphatic, which is optionally interrupted by one or more heteroatoms, and optionally substituted. Nonlimiting substituents may include one or more independent by one or more —CN, —OR$^6$, —R$^6$, oxo, —NR$^6$R$^7$, —C(O)R$^b$, —C(O)NR$^6$R$^7$, —C(O)C(O)NR$^6$R$^7$, —C(O)OR$^6$, —C(O)C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, or —NR$^{10}$S(O)NR$^6$R$^7$;

wherein each R$^6$, R$^7$, R$^8$, R$^9$, R$^{10}$, and R$^b$ can be independently of the nonlimiting substituents —C$_{0-5}$aliphatic or C$_{3-7}$cycloaliphatic, each independently optionally interrupted by one or more heteroatoms and optionally substituted by one or more halo, —OCF$_3$, or —OC$_{0-3}$aliphatic; or NR$^6$R$^7$ defines a $_{4-7}$heterocyclic optionally substituted by one or more C$_{1-6}$aliphatic.

In some embodiments of the above, G1, or R$^6$, R$^7$, R$^8$, R$^9$, R$^{10}$, and R$^b$ can be further optionally substituted.

As indicated above, the G1 position has been found to tolerate a high degree of structural and functional group variability and thus, the optional substituent(s) on G1 are not limited.

In some aspects of Formula I or Subgenus 1 or 2 thereof (Subgenus 3), the compound has the formula:

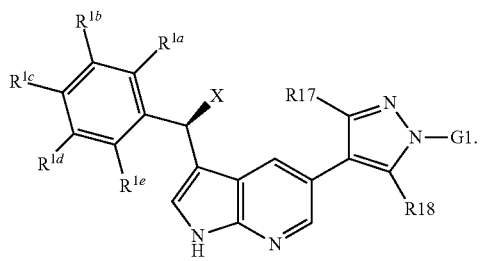

In some alternative embodiments of the above, the compound core is a pyrrolo[2,3-b]pyrazine.

In some aspects of Formula I or Subgenera 1-3 thereof (Subgenus 4):

R$^{1a}$ and R$^{1e}$ are each independently halo, —CN, C$_{1-3}$aliphatic, —OC$_{0-3}$aliphatic, wherein methyl or methoxy can be independently substituted by 1-3 fluorine atoms; and R$^{1b}$, R$^{1c}$, and R$^{1d}$ are each independently H, halo, —CN, C$_{1-3}$aliphatic, —OC$_{0-3}$aliphatic, wherein methyl or methoxy can be independently substituted by 1-3 fluorine atoms; and wherein aliphatic is optionally substituted with one or more —OC$_{0-6}$aliphatic, —N(C$_{0-6}$aliphatic)(C$_{0-6}$aliphatic), —C(=O)N(C$_{0-6}$aliphatic)(C$_{0-6}$aliphatic), —C(=O)OC$_{0-6}$aliphatic, —C(=O)C$_{0-6}$aliphatic, or $_{5-6}$heteroaryl.

In some aspects of Formula I or Subgenera 1-4 thereof (Subgenus 5): R17 and R18 are independently halo, H, C$_{1-3}$aliphatic, or —CN, provide that at least one of R17 and R18 is C$_{1-3}$aliphatic.

In some aspects of Formula I or Subgenera 1-5 thereof (Subgenus 6): X is methyl, ethyl, methoxy, or ethoxy, any of which is optionally substituted with halo or —CN. In some aspects thereof, X is methyl or fluoromethyl.

In some aspects of Formula I or Subgenera 1-5 thereof (Subgenus 7): X is methyl, ethyl, or methoxy.

In some aspects of Formula I or Subgenera 1-7 thereof (Subgenus 8):

G1 is $_{4-6}$heterocycloalkyl optionally substituted by halo, —R$^6$, oxo, —S(O)$_m$R$^6$, —SO$_2$NR$^6$R$^7$, —C(O)R$^b$, —C(O)NR$^6$R$^7$, —C(O)C(O)NR$^6$R$^7$, —C(O)OR$^6$, or —C(O)C(O)OR$^6$;

or G1 is $_{3-7}$cycloalkyl optionally substituted by halo, —CN, —OR$^6$, oxo, —S(O)$_m$R$^6$, —SO$_2$NR$^6$R$^7$, —C(O)R$^b$, —C(O)NR$^6$R$^7$, —C(O)C(O)NR$^6$R$^7$, —C(O)OR$^6$, or —C(O)C(O)OR$^6$, or —C$_{1-6}$aliphatic said aliphatic optionally substituted by halo or —OC$_{0-5}$aliphatic; and wherein each R$^6$, R$^7$, R$^8$, R$^9$, R$^{10}$, and R$^b$ is independently —C$_{0-5}$aliphatic or C$_{3-7}$cycloalkyl, each independently optionally substituted by halo, —OCF$_3$, or —OC$_{0-3}$aliphatic; or NR$^6$R$^7$ defines a $_{4-7}$heterocycloalkyl optionally substituted by —C$_{1-6}$aliphatic.

In some aspects of Formula I or Subgenera 1-8 thereof (Subgenus 9):

R$^{1a}$ and R$^{1e}$ are each independently selected from halo, —CN, C$_{1-3}$aliphatic, or —OC$_{1-3}$aliphatic, wherein aliphatic can be substituted by 1-3 fluorine atoms;

R$^{1b}$ and R$^{1d}$ are each independently selected from H, halo, —CN, C$_{1-3}$aliphatic, or —OC$_{1-3}$aliphatic, wherein aliphatic can be substituted by 1-3 fluorine atoms; and R$^{1c}$ is H.

In some aspects of Formula I or Subgenera 1-9 thereof (Subgenus 10):

G1 is $_{3-7}$cycloalkyl optionally substituted by 1-3 independent halo, —CN, —OR$^6$, oxo, —S(O)$_m$R$^6$, —SO$_2$NR$^6$R$^7$, —C(O)R$^b$, —C(O)NR$^6$R$^7$, —C(O)C(O)NR$^6$R$^7$, —C(O)OR$^6$, —C(O)C(O)OR$^6$, or —C$_{1-3}$aliphatic said aliphatic optionally substituted by halo or —OC$_{0-5}$aliphatic;

wherein each R$^6$, R$^7$, and R$^b$ is independently C$_{0-5}$aliphatic or C$_{3-7}$cycloalkyl; or NR$^6$R$^7$ defines a $_{4-7}$heterocycloalkyl optionally substituted by C$_{1-6}$aliphatic.

In some aspects of Formula I or Subgenera 1-9 thereof (Subgenus 11):

G1 is —C$_{1-6}$aliphatic optionally substituted by 1-3 independent —OR$^6$, —R$^6$, oxo, —NR$^6$R$^7$, —C(O)R$^b$, —C(O)NR$^6$R$^7$, —C(O)C(O)NR$^6$R$^7$, —C(O)OR$^6$, —C(O)C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, —NR$^{10}$S(O)NR$^6$R$^7$, or $_{4-7}$heterocycloalkyl optionally substituted by C$_{1-6}$aliphatic;

wherein each R$^6$, R$^7$, R$^8$, R$^9$, R$^{10}$, and R$^b$ is independently —C$_{0-6}$aliphatic or —C$_{3-7}$cycloalkyl; or —NR$^6$R$^7$ defines a $_{4-7}$heterocycloalkyl optionally substituted by C$_{1-6}$aliphatic.

In some aspects of Formula I or Subgenera 1-9 thereof (Subgenus 12):

G1 is $_{4-6}$heterocycloalkyl optionally substituted by 1-3 independent halo, —R$^6$, oxo, —S(O)$_m$R$^6$, —SO$_2$NR$^6$R$^7$, —C(O)R$^b$, —C(O)NR$^6$R$^7$, —C(O)C(O)NR$^6$R$^7$, —C(O)OR$^6$, or —C(O)—C(O)OR$^6$;

wherein each R$^6$, R$^7$, and R$^b$ is independently C$_{0-6}$aliphatic or C$_{3-7}$cycloalkyl; or —NR$^6$R$^7$ defines a $_{4-7}$heterocycloalkyl optionally substituted by —C$_{1-6}$aliphatic.

In some aspects of Formula I or Subgenera 1-12 thereof (Subgenus 13):

R$^{1a}$ is halo, or is methoxy optionally substituted by 1-3 fluorine atoms; and R$^{1d}$ and R$^{1e}$ are independently halo.

In some aspects of Formula I or Subgenera 1-13 thereof (Subgenus 14): G1 is $_{4-7}$heterocycloalkyl optionally substituted by 1-3 independent halo, —OH, —OCH$_3$, or C$_{1-3}$aliphatic.

In some aspects of Formula I or Subgenus 1, there is provided a compound or salt (Subgenus 15) of the formula:

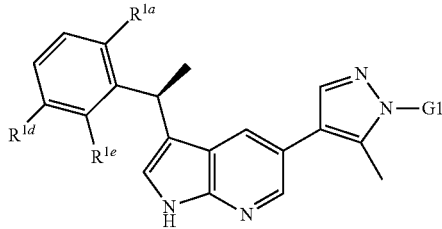

wherein:

G1 is $_{3-7}$cyclic optionally substituted by one or more independent halo, —OH, —OC$_{1-3}$aliphatic, or —C$_{1-3}$aliphatic;

R$^{1a}$ is halo, or is methoxy optionally substituted by 1-3 halo;

R$^{1d}$ and R$^{1e}$ are independently halo.

In some aspects thereof, G1 can be carbocyclic or heterocyclic (either selected from saturated, unsaturated, or aromatic), which are optionally substituted.

In some aspects of Formula I or Subgenera 1-15 thereof (Subgenus 16):

G1 is $_{4-7}$cycloalkyl optionally substituted with one or more independent halo, —OH, —OCH$_3$, or —C$_{1-3}$aliphatic;

R$^{1a}$ is halo, or is methoxy optionally substituted by 1-3 fluorine atoms;

R$^{1d}$ and R$^{1e}$ are independently halo.

In some aspects of Formula I or Subgenera 1-16 thereof, the compound or salt is present as a material that is substantially free of its (S)-1-(phenyl)ethyl enantiomer when Y$_4$ or Y$_5$ of Formula I is N and substantially free of its (R)-1-(phenyl)ethyl enantiomer when Y$_4$ or Y$_5$ is not N.

In some aspects, the invention includes a compound of Formula I or a pharmaceutically acceptable salt thereof, in any of the above recitations, which exhibits inhibition of MET in a cellular assay with an IC$_{50}$ of about 50 nM or less, 100 nM or less, 200 nM or less, or 400 nM or less.

In some aspects, the invention includes a compound of Formula I or a pharmaceutically acceptable salt thereof, in any of the above recitations, which exhibits inhibition of RON in a cellular assay with an IC$_{50}$ of about 50 nM or less, 100 nM or less, 200 nM or less, or 400 nM or less.

In some aspects, the invention includes a compound of Formula I or a pharmaceutically acceptable salt thereof, in any of the above recitations, which exhibits inhibition of ALK in a cellular assay with an IC$_{50}$ of about 50 nM or less, 100 nM or less, 200 nM or less, or 400 nM or less.

In some aspects, the invention includes a compound of Formula I or a pharmaceutically acceptable salt thereof, in any of the above recitations, which exhibits inhibition of both MET and RON within any of the above parameters.

In some aspects, the invention includes a compound of Formula I or a pharmaceutically acceptable salt thereof, in any of the above recitations, which is about 10-fold or more, 20-fold or more, or 40-fold or more selective for MET over KDR and/or over AKB in a cellular assay.

In some aspects, compounds of the invention may be inhibitors of one or more of AXL, Tie-2, Flt3, FGFR3, Abl, Jak2, c-Src, IGF-1R, IR, TRK, PAK1, PAK2, and TAK1 kinases. In some aspects, compounds of the invention may be inhibitors of one or more of Blk, c-Raf, PRK2, Lck, Mek1, PDK-1, GSK3β, EGFR, p70S6K, BMX, SGK, CaMKII, and Tie-2 kinases.

The invention includes a compound of Formula I or a pharmaceutically acceptable salt thereof, which is sufficiently orally bioavailable for effective oral human administration.

The invention includes a compound of Formula I or a pharmaceutically acceptable salt thereof, which has a suitable therapeutic window for effective human administration, oral or otherwise.

Each variable definition above includes any subset thereof and the compounds of Formula I include any combination of such variables or variable subsets.

In some aspects, the compound or salt is selected from any one of the examples herein.

In some aspects, the compound or salt is selected from:
trans-4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)-N-methylcyclohexanecarboxamide;
trans-4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)cyclohexanecarboxamide;
(2R)-3-[4-(3-{(1S)-1-[2-chloro-6-(difluoromethoxy)-3-fluorophenyl]ethyl}-1H-pyrrolo[2,3-b]pyridin-5-yl)-3,5-dimethyl-1H-pyrazol-1-yl]propane-1,2-diol;
(2S)-3-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]propane-1,2-diol;
trans-4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclohexanol;
(1R,2S,4S)-4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclopentane-1,2-diol;
trans-4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclohexanecarboxamide;
trans-4-[4-(3-{(1S)-1-[2-chloro-6-(difluoromethoxy)-3-fluorophenyl]ethyl}-1H-pyrrolo[2,3-b]pyridin-5-yl)-3-ethyl-1H-pyrazol-1-yl]cyclohexanol;
trans-4-[4-(3-{(1S)-1-[2-chloro-6-(difluoromethoxy)-3-fluorophenyl]ethyl}-1H-pyrrolo[2,3-b]pyridin-5-yl)-5-ethyl-1H-pyrazol-1-yl]cyclohexanol;
cis-3-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclobutanol;
trans-4-[4-(3-{(1S)-1-[2-chloro-6-(difluoromethoxy)-3-fluorophenyl]ethyl}-1H-pyrrolo[2,3-b]pyridin-5-yl)-5-(hydroxymethyl)-1H-pyrazol-1-yl]cyclohexanol;

trans-4-[4-(3-{(1S)-1-[2-chloro-6-(difluoromethoxy)-3-fluorophenyl]ethyl}-1H-pyrrolo[2,3-b]pyridin-5-yl)-5-fluoro-1H-pyrazol-1-yl]cyclohexanol;

trans-4-[4-(3-{(1S)-1-[2-chloro-6-(difluoromethoxy)-3-fluorophenyl]ethyl}-1H-pyrrolo[2,3-b]pyridin-5-yl)-5-($^2H_3$)methyl-1H-pyrazol-1-yl]cyclohexanol;

cis-4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclohexanol;

(2R)-3-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]propane-1,2-diol;

4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclohexanone;

trans-4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclohexanamine;

trans-4-{-4-[3-{(1S)-1-[2-chloro-6-(difluoromethoxy)-3-fluorophenyl]ethyl}(2-$^2H$)-1H-pyrrolo[2,3-b]pyridin-5-yl]-5-methyl-1H-pyrazol-1-yl}cyclohexanol;

3-{(1S)-1-[2-chloro-6-(difluoromethoxy)-3-fluorophenyl]ethyl}-5-[5-methyl-1-(piperidin-4-yl)-1H-pyrazol-4-yl]-1H-pyrrolo[2,3-b]pyridine;

1-{4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]piperidin-1-yl}ethanone;

trans-4-(4-{3-[(1S)-1-(2-chloro-3-fluoro-6-methoxyphenyl)ethyl]-1H-pyrrolo[2,3-b]pyridin-5-yl}-3-methoxy-1H-pyrazol-1-yl)cyclohexanol;

trans-4-[4-(3-{(1S)-1-[2-chloro-6-(difluoromethoxy)-3-fluorophenyl]ethyl}-1H-pyrrolo[2,3-b]pyridin-5-yl)-3-methoxy-1H-pyrazol-1-yl]cyclohexanol;

trans-4-(4-{3-[(1S)-1-(2-chloro-6-ethoxy-3-fluorophenyl)ethyl]-1H-pyrrolo[2,3-b]pyridin-5-yl}-5-methyl-1H-pyrazol-1-yl)cyclohexanol;

trans-4-(4-{3-[(1S)-1-[2-chloro-6-(difluoromethoxy)-3-fluorophenyl](2,2,2-$^2H_3$)ethyl]-1H-pyrrolo[2,3-b]pyridin-5-yl}-5-methyl-1H-pyrazol-1-yl)cyclohexanol;

trans-4-(4-{3-[(1S)-1-[2-chloro-6-(difluoromethoxy)-3-fluorophenyl](1-$^2H$)ethyl]-1H-pyrrolo[2,3-b]pyridin-5-yl}-5-methyl-1H-pyrazol-1-yl)cyclohexanol;

trans-4-(4-{3-[(1S)-1-(2,6-dichloro-3-fluorophenyl)-2-fluoroethyl]-1H-pyrrolo[2,3-b]pyridin-5-yl}-5-methyl-1H-pyrazol-1-yl)cyclohexanol;

trans-4-(4-{3-[(1S)-1-(2-chloro-3-fluoro-6-methoxyphenyl)-2-fluoroethyl]-1H-pyrrolo[2,3-b]pyridin-5-yl}-5-methyl-1H-pyrazol-1-yl)cyclohexanol;

trans-4-[4-(3-{(1S)-1-[2-chloro-6-(difluoromethoxy)-3-fluorophenyl]-2-fluoroethyl}-1H-pyrrolo[2,3-b]pyridin-5-yl)-5-methyl-1H-pyrazol-1-yl]cyclohexanol;

1-[5-(3-{(1S)-1-[2-chloro-6-(difluoromethoxy)-3-fluorophenyl]ethyl}-1H-pyrrolo[2,3-b]pyridin-5-yl)-1-methyl-1H-imidazol-2-yl]piperidin-4-ol; or trans-4-[5-(3-{(1S)-1-[2-chloro-6-(difluoromethoxy)-3-fluorophenyl]ethyl}-1H-pyrrolo[2,3-b]pyridin-5-yl)-1-methyl-1H-imidazol-2-yl]cyclohexanol.

In some aspects of the invention, the compound or salt is present as a substantially pure material.

In some aspects, the compound or salt is in a pharmaceutical composition comprising the compound or salt formulated with or without one or more pharmaceutical carriers.

The invention includes the compounds and salts thereof, and their physical forms, preparation of the compounds, useful intermediates, and pharmaceutical compositions and formulations thereof.

The compounds of the invention and term "compound" in the claims include any pharmaceutically acceptable salts or solvates, and any amorphous or crystal forms, or tautomers, whether or not specifically recited in context.

The invention includes the isomers of the compounds. Compounds may have one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

The present invention includes any stereoisomers, even if not specifically shown, individually as well as mixtures, geometric isomers, and pharmaceutically acceptable salts thereof. Where a compound or stereocenter is described or shown without definitive stereochemistry, it is to be taken to embrace all possible individual isomers, configurations, and mixtures thereof. Thus, a material sample containing a mixture of stereoisomers would be embraced by a recitation of either of the stereoisomers or a recitation without definitive stereochemistry. Also contemplated are any cis/trans isomers or tautomers of the compounds described.

Included within the scope of the invention are all stereoisomers, geometric isomers and tautomeric forms of the inventive compounds, including compounds exhibiting more than one type of isomerism, and mixtures of one or more thereof.

When a tautomer of the compound of Formula (I) exists, the compound of formula (I) of the present invention includes any possible tautomers and pharmaceutically acceptable salts thereof, and mixtures thereof, except where specifically stated otherwise.

The compounds of the invention are not limited to those containing all of their atoms in their natural isotopic abundance. The present invention includes compounds wherein one or more hydrogen, carbon or other atoms are replaced by different isotopes thereof. Such compounds can be useful as research and diagnostic tools in metabolism pharmacokinetic studies and in binding assays. A recitation of a compound or an atom within a compound includes isotopologs, i.e., species wherein an atom or compound varies only with respect to isotopic enrichment and/or in the position of isotopic enrichment. For nonlimiting example, in some cases it may be desirable to enrich one or more hydrogen atoms with deuterium (D) or to enrich carbon with $^{13}C$. Other examples of isotopes suitable for inclusion in the compounds of the invention include isotopes of hydrogen, chlorine, fluorine, iodine, nitrogen, oxygen, phosphorus, and sulfur. Certain isotopically-labeled compounds of the invention may be useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Substitution with positron emitting isotopes may be useful in Positron Emission Topography (PET) studies for examining substrate receptor occupancy.

Further, the compounds may be amorphous or may exist or be prepared in various crystal forms or polymorphs, including solvates and hydrates. The invention includes any such forms provided herein, at any purity level. A recitation of a compound per se means the compound regardless of any unspecified stereochemistry, physical form and whether or not associated with solvent or water.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g., $D_2O$, d6-acetone, d 6-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized.

The invention includes prodrugs of compounds of the invention which may, when administered to a patient, be converted into the inventive compounds, for example, by hydrolytic cleavage. Prodrugs in accordance with the invention can, for example, be produced by replacing appropriate functionalities present in the inventive compounds with certain moieties known to those skilled in the art as 'pro-moieties' as known in the art. Particularly favored derivatives and prodrugs of the invention are those that increase the bioavailability of the compounds when such compounds are administered to a patient, enhance delivery of the parent compound to a given biological compartment, increase solubility to allow administration by injection, alter metabolism or alter rate of excretion.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

Compounds that are basic are capable of forming a wide variety of salts with various inorganic and organic acids. The acids that can be used to prepare pharmaceutically acceptable acid addition salts of such basic compounds are those that form acceptable acid addition salts. When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Other salts are aspartate, besylate, bicarbonate/carbonate, bisulphate/sulfate, borate, camsylate, edisylate, gluceptate, glucuronate, hexafluorophosphate, hibenzate, hydrobromide/bromide, hydroiodide/iodide, malonate, methylsulfate, naphthylate, 2-napsylate, nicotinate, orotate, oxalate, palmitate, phosphate/hydrogen, phosphate/dihydrogen, phosphate, saccharate, stearate, tartrate, tosylate, and trifluoroacetate.

When the compound of the present invention is acidic, its corresponding salt can be conveniently prepared from pharmaceutically acceptable bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic bases include salts of primary, secondary, and tertiary amines, as well as cyclic amines and substituted amines such as naturally occurring and synthesized substituted amines. Other pharmaceutically acceptable organic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Other examples include benzathine, diolamine, glycine, meglumine, and olamine.

Preparation

The invention includes the intermediates, examples, and synthetic methods described herein.

The compounds of the Formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art [such as those methods disclosed in standard reference books such as the Compendium of Organic Synthetic Methods, Vol. I-VI (Wiley-Interscience); or the Comprehensive Organic Transformations, by R. C. Larock (Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed hereinbelow and the general skill in the art. Unless otherwise indicated, the substituents in the Schemes are defined as above. Isolation and purification of the products is accomplished by standard procedures, which are known to a chemist of ordinary skill.

When a general or exemplary synthetic procedure is referred to, one skilled in the art can readily determine the appropriate reagents, if not indicated, extrapolating from the general or exemplary procedures. Some of the general procedures are given as examples for preparing specific compounds. One skilled in the art can readily adapt such procedures to the synthesis of other compounds. Representation of an unsubstituted position in structures shown or referred to in the general procedures is for convenience and does not preclude substitution as described elsewhere herein. For specific groups that can be present, either as R groups in the general procedures or as optional substituents not shown, refer to the descriptions in the remainder of this document, including the claims, summary and detailed description.

General Synthesis

Unless otherwise indicated, the substituents in the Schemes are defined as above. Isolation and purification of the products is accomplished by standard procedures, which are known to a chemist of ordinary skill. In the following general descriptions, $R^1$ indicates one or more substituents $R^{1a}$-$R^{1e}$.

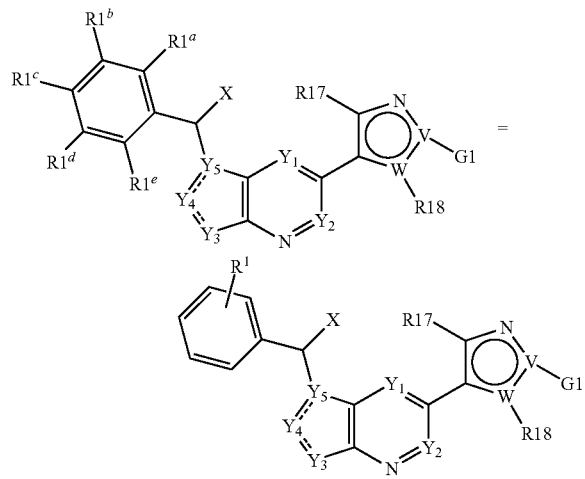

Compounds of Formula Ia (also known as 7-azaindoles or pyrrolo[2,3-b]pyridines) are compounds of Formula I wherein Y3=NH, Y5=C, and Y2, Y4 and Y1=CH. These compounds, or their pharmaceutically acceptable salts, can be prepared according to the reaction Schemes discussed hereinbelow and the general skill in the art.

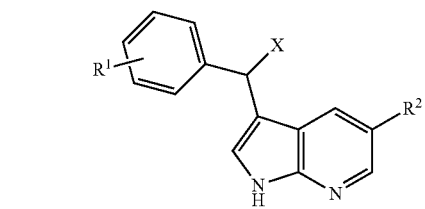

Formula Ia

Scheme 1

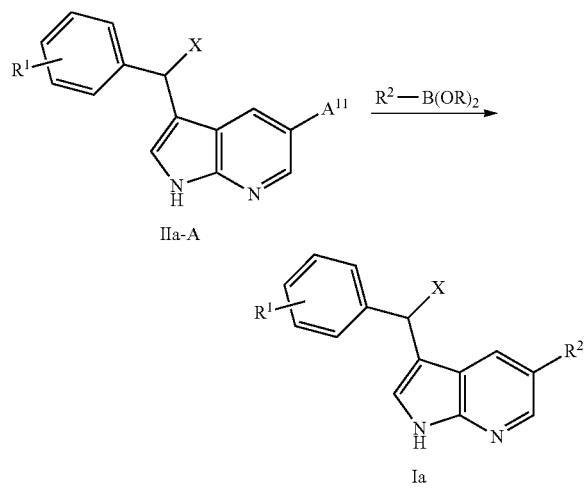

Compounds of Formula Ia can be prepared from IIa-A as in Scheme 1, wherein $R^1$ and $R^2$ are as defined previously, $A^{11}$ is halo such as Cl, Br, or I, or trifluoromethanesulfonate, and $B(OR)_2$ is a suitable boronic acid/ester. In a typical preparation of compounds of Formula Ia, a compound of Formula IIa-A is reacted with a suitable boronic acid/ester ($R^2$—B$(OR)_2$) in a suitable solvent via typical Suzuki coupling procedures. Suitable solvents for use in the above process include, but are not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents can be used; however, preferred solvents are dimethoxyethane/water and dioxane/water. The above process can be carried out at temperatures between about 0° C. and about 120° C. Preferably, the reaction is carried out between 60° C. and about 100° C. The above process is preferably carried out at about atmospheric pressure although higher or lower pressures can be used. Substantially equimolar amounts of reactants are preferably used although higher or lower amounts can be used. One skilled in the art will appreciate that alternative methods may be applicable for preparing compounds of Formula Ia from IIa-A. For example, compound of Formula IIa-A could be reacted with a suitable organotin reagent $R^2$—$SnBu_3$ or the like in a suitable solvent via typical Stille coupling procedures.

Scheme 2

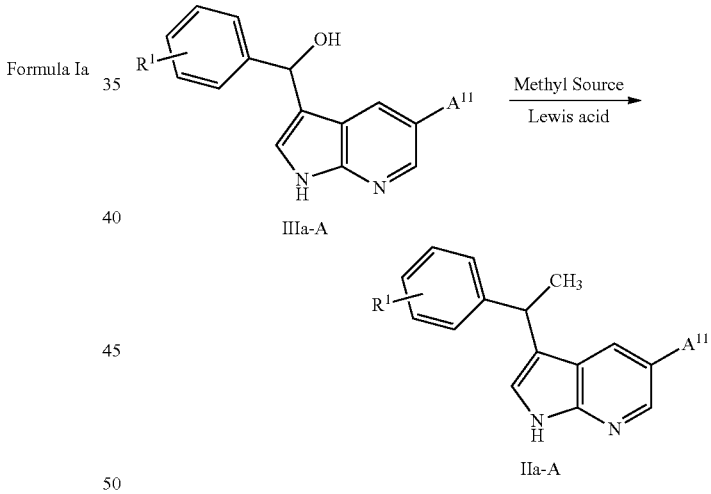

Compounds of Formula IIa-A can be prepared as in Scheme 2, wherein $R^1$ is as defined previously and $A^{11}$ is halo such as Cl, Br, or I, or trifluoromethanesulfonate. In a typical preparation IIIa-A can be reacted with a suitable methyl source in the presence of a Lewis acid in a suitable solvent. Suitable methyl source for use in the above process include, but are not limited to $Me_3Al$, $Me_2Zn$, $Me_2AlCl$, methyl Grignard reagents. A preferred methyl source is $Me_2Zn$. The methyl source may also be generated in situ, such as by reacting a methyl Grignard reagent with zinc chloride and using the resulting reagent without isolation for the above process. Suitable Lewis acids for use in the above process include, but are not limited to $BF_3.OEt_2$, $AlCl_3$, $TiCl_4$, and the like. A preferred Lewis acid is $BF_3.OEt_2$. Suitable solvents for use in the above process include, are not limited to, ethers such as THF, glyme, and the like; DMF; DMSO; MeCN;

toluene; cyclohexane, and chlorinated solvents such as DCM or chloroform (CHCl₃). If desired, mixtures of these solvents can be used; however, a preferred solvent is THF. The above process can be carried out at temperatures between about −78° C. and about 120° C. Preferably, the reaction can be carried out between 40° C. and about 70° C. An excess amount of the methyl source and Lewis acid are preferably used.

Compounds similar to those of Formula IIIa-A wherein the hydroxy group is replaced with an alkoxy group may also be used for the above process using the same Lewis acids and methyl source.

Compounds similar to those of Formula IIa-A wherein the methyl group is replaced by an alkyl group can be prepared by replacing the methyl source with an alkyl source under otherwise similar reaction conditions. For example, an ethyl group may be introduced using reagents such as Et₂Zn, and a propyl group may be introduced using reagents such as PrZnBr.

Compounds of Formula Ia wherein X=CN may be prepared by reacting compounds of Formula IIIa-A with a suitable cyanide source in the presence of a suitable Lewis acid, followed by reacting with a boronic acid/ester R²—B(OR)₂ via Suzuki coupling procedures as described above in Scheme 1. Suitable reagents for the cyanation include, but are not limited to, TMSCN as cyanide source, InBr₃ as Lewis acid, and chlorinated solvents such as DCM. Preferably, the cyanation may be carried out at temperatures between about 0° C. and about 60° C.

Scheme 3

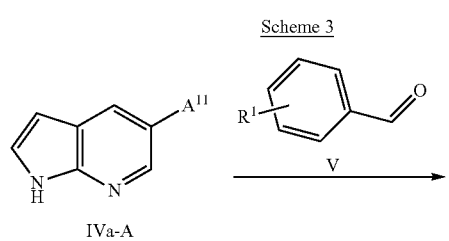

IVa-A

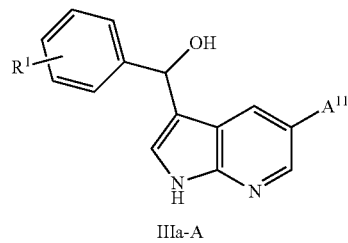

IIIa-A

Compounds of Formula IIIa-A can be prepared as in Scheme 3, wherein R¹ is as defined previously and A¹¹ is halo such as Cl, Br, or I. In a typical preparation, IVa-A is treated with benzaldehyde V in a suitable solvent in the presence of a suitable base at a suitable reaction temperature. Suitable solvents for use in the above process include, but are not limited to, ethers such as THF, glyme, and the like; DMF, DMSO; MeCN; chlorinated solvents such as DCM or chloroform (CHCl₃); and alcohols such as MeOH, EtOH, isopropanol, or trifluoroethanol. If desired, mixtures of these solvents can be used or no solvent can be used. A preferred solvent is MeOH. Suitable bases for use in the above process include, but are not limited to, KOH, NaOH, LiOH, KOtBu, NaOtBu and NaH- MDS and the like. A preferred base is KOH. The above process can be carried out at temperatures between about −78° C. and about 120° C. Preferably, the reaction is carried out between 20° C. and about 60° C. The above process to produce compounds of the present invention is preferably carried out at about atmospheric pressure although higher or lower pressures can be used. Substantially equimolar amounts of reactants are preferably used although higher or lower amounts can be used.

When alcohols are used as solvent, analogs of compounds of Formula IIIa-A wherein the hydroxyl group is replaced with an alkoxy group can also be obtained. For example, with MeOH as solvent one can obtain the methoxy analogs.

Scheme 4

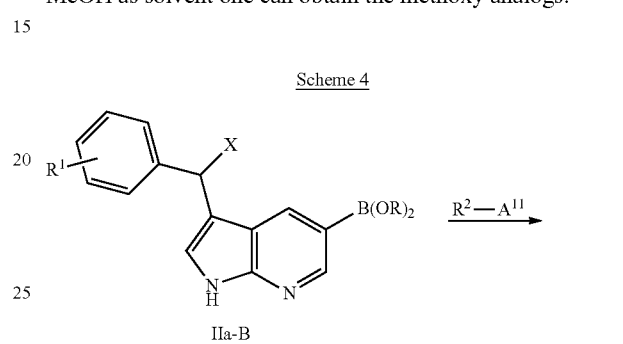

IIa-B

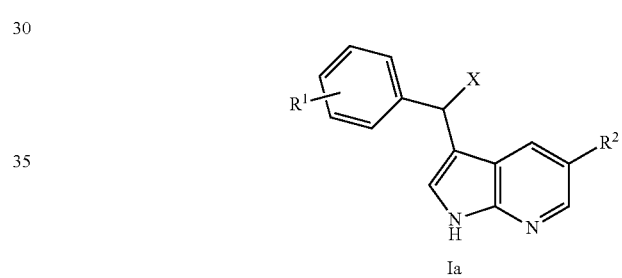

Ia

Compounds of Formula Ia can be prepared as in Scheme 4, wherein R¹ and R² are as defined previously, A¹¹ is halo such as Cl, Br, or I, or trifluoromethanesulfonate, and B(OR)₂ is a suitable boronic acid/ester. Compound IIa-B can be reacted with a suitable coupling partner (R²-A¹¹) in a suitable solvent via typical Suzuki coupling procedures. Suitable solvents for use in the above process include, but are not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform (CHCl₃). If desired, mixtures of these solvents can be used, however, a preferred solvent is dimethoxyethane/water. The above process can be carried out at temperatures between about −78° C. and about 120° C. Preferably, the reaction is carried out between 60° C. and about 100° C. The above process is preferably carried out at about atmospheric pressure although higher or lower pressures can be used. Substantially, equimolar amounts of reactants are preferably used although higher or lower amounts can be used if desired.

One skilled in the art will appreciate that alternative methods may be applicable for preparing compounds of Formula Ia from R²-A¹¹, e.g., via typical Stille coupling procedures.

Scheme 5

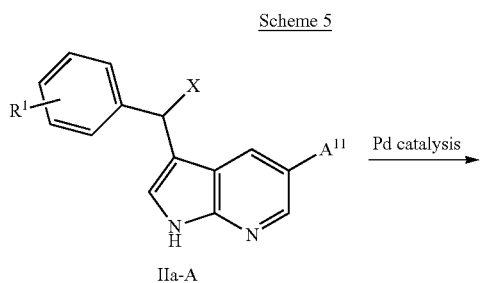

IIa-A rinated solvents such as DCM or chloroform (CHCl$_3$). If desired, mixtures of these solvents can be used; however, preferred solvents are dioxane or DMSO. The above process can be carried out at temperatures between about 0° C. and about 120° C. Preferably, the reaction is carried out between 60° C. and about 100° C. The above process is preferably carried out at about atmospheric pressure although higher or lower pressures can be used. Substantially equimolar amounts of reactants used although higher or lower amounts can be used if desired.

One skilled in the art will appreciate that alternative methods may be applicable for preparing compounds of Formula IIa-B. For example, via halogen-metal exchange (for example, halogen-lithium exchange) and quench with borylation reagents such as tri-isopropyl borate.

Scheme 6

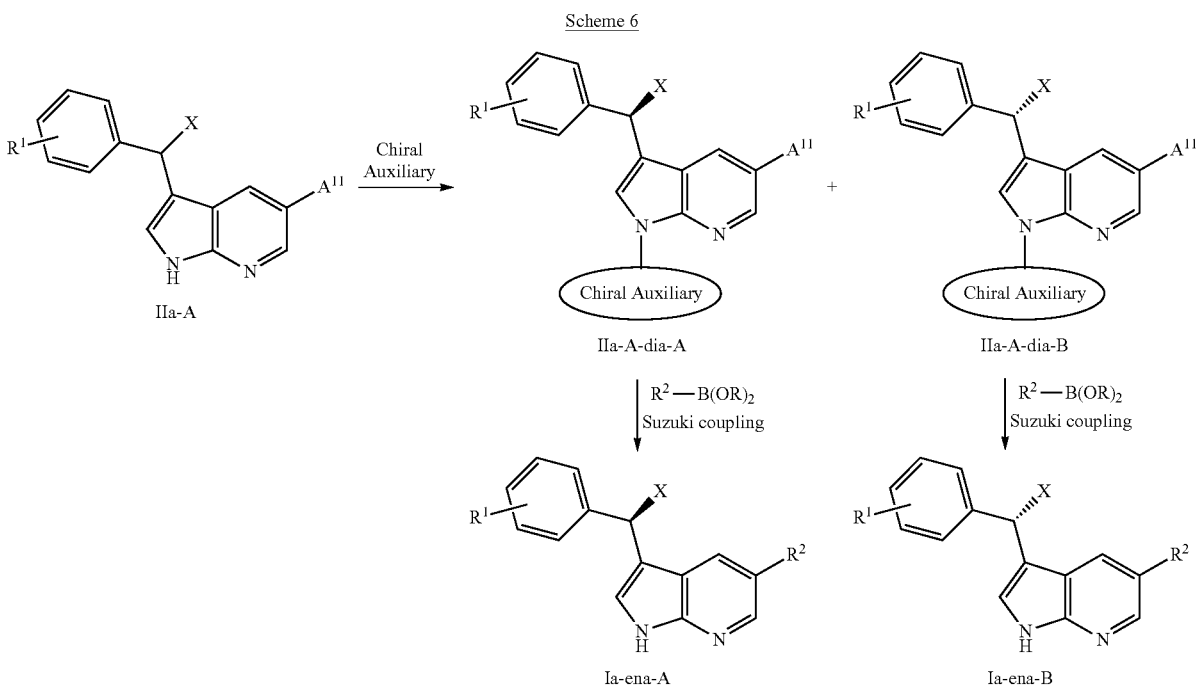

-continued

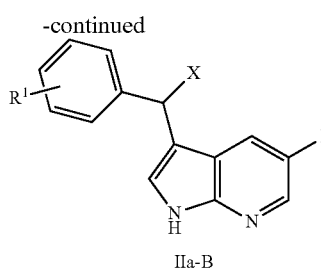

IIa-B

Compounds of Formula IIa-B can be prepared as in Scheme 5, wherein R$^1$ is as defined previously, A$^{11}$ is halo such as Cl, Br, or I, or trifluoromethanesulfonate, and B(OR)$_2$ is a suitable boronic acid/ester. In a typical preparation a compound of Formula IIa-A can be reacted with a suitable coupling partner (Bis(pinacolato)diboron or Pinacolborane)) in a suitable solvent under Palladium catalysis. Suitable solvents for use in the above process include, but are not limited to, ethers such as THF, glyme, dioxane, dimethoxyethane, and the like; DMF; DMSO; MeCN; alcohols such as MeOH, EtOH, isopropanol, trifluoroethanol, and the like; and chlo- Chiral resolution: Compounds of Formula Ia have the carbon chiral center shown in Scheme 6. The enantiomerically pure isomers Ia-ena-A and Ia-ena-B can be prepared by a chiral resolution through a chemical reaction which leads to two diastereomers IIa-A-dia-A and IIa-A-dia-B. After separation of these two diastereomers by flash chromatography or crystallization, each diastereomer can be subjected to a Suzuki coupling as shown in Scheme 6 to produce Ia-ena-A and Ia-ena-B individually.

In a typical preparation of IIa-A-dia-A and IIa-A-dia-B, a compound of Formula IIa-A is reacted with a chiral auxiliary in the presence of a coupling reagent to provide both IIa-A-dia-A and IIa-A-dia-B, which are separated by chromatography. Suitable chiral auxiliaries for use in the above process include, but are not limited to amino acids and their derivatives, (1S)-(+)-camphor-10-sulfonic acid, (1R)-(−)-camphor-10-sulfonic acid and the like. However, a preferred chiral auxiliary is Fmoc-L-Leucine. Suitable solvents for use in the above process included, but are not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform (CHCl$_3$). If desired, mixtures of these solvents can be used; however, a preferred solvent is DMF. The suitable coupling reagents for use in the above process include, but are not limited to DCC, EDC, TBTU, HBTU and the like. A preferred coupling reagent is TBTU. The above process can be carried out at temperatures between about −78° C. and about 120° C. Preferably, the reaction is carried out between 0° C. and about 60° C. The above process is preferably carried out at about atmospheric pressure although higher or lower pressures can be used if desired. Substantially equimolar amounts of reactants are preferably used although higher or lower amounts can be used if desired.

After purification and separation, both IIa-A-dia-A and IIa-A-dia-B are reacted separately with a suitable boronic acid/ester (R$^2$—B(OR)$_2$), to provide both Ia-ena-A and Ia-ena-B, via typical Suzuki coupling procedures as in Scheme 1.

One skilled in the art will appreciate that instead of covalently attaching a chiral auxiliary to compound IIa-A one may form diastereomeric salts that may be separated by crystallization. Neutralization of the separated diastereomeric salts provides the separated enantiomers of IIa-A. Suitable chiral auxiliaries include, but are not limited to amino acids and their derivatives, (1S)-(+)-camphor-10-sulfonic acid, (1R)-(−)-camphor-10-sulfonic acid and the like.

boronic acid/ester (R$^2$—B(OR)$_2$), to provide both Ia-ena-A and Ia-ena-B, via typical Suzuki coupling procedures as in Scheme 1.

As will be apparent to the skilled artisan, the synthetic route/sequence can be modified as desired for the preparation of a given compound. For example, Group R$^2$ can be installed on compound IVa-A under conditions similar to Schemes 1, 5, and 4. The resulting compound can be treated with an appropriate benzaldehyde under conditions similar to Scheme 3, followed by introduction of a methyl group similar to Scheme 2.

A skilled artisan will realize that the reactions shown in Schemes 1, 4-7 can be conducted under similar conditions with compounds in which the methyl group shown is replaced by other alkyl or alkoxy groups within the scope defined for the variable X.

Compounds of Formula Ib {also known as 4-azaindoles or pyrrolo[3,2-b]pyridines} are compounds of Formula I wherein Y5=N, and Y2, Y3, Y4 and Y1=CH. These compounds, or their pharmaceutically acceptable salts, can be prepared according to the reaction Schemes discussed hereinbelow and the general skill in the art.

Scheme 7

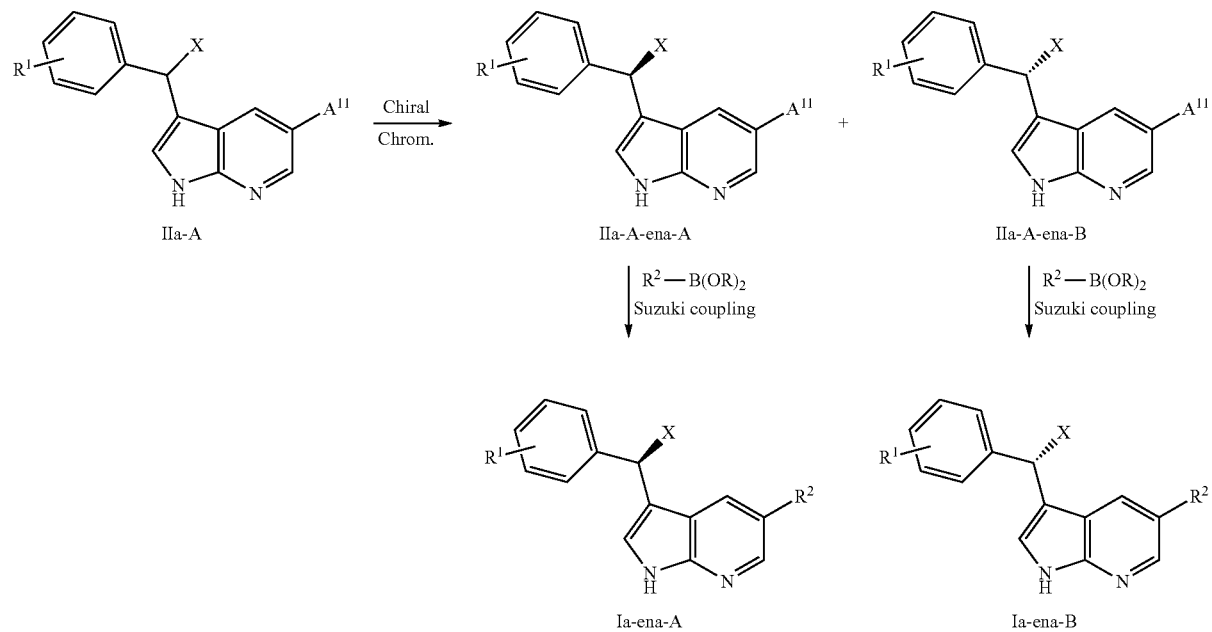

Alternatively, the enantiomerically pure isomers Ia-ena-A and Ia-ena-B can be prepared as in Scheme 7 individually from corresponding enantiomerically pure IIa-A-ena-A and IIa-A-ena-B through Suzuki coupling reactions. Enantiomerically pure IIa-A-ena-A and IIa-A-ena-B can be prepared from separation of racemic mixture IIa-A by a chiral chromatography as in Scheme 7.

The suitable system for separation of IIa-A-ena-A and IIa-A-ena-B by chromatography can be, but is not limited to, chiral HPLC (high performance liquid chromatography) systems, chiral SFC (supercritical fluid chromatography) systems and the like. After separation, both IIa-A-ena-A and IIa-A-ena-B can be reacted individually with a suitable Formula Ib

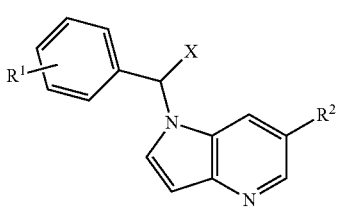

Scheme 8

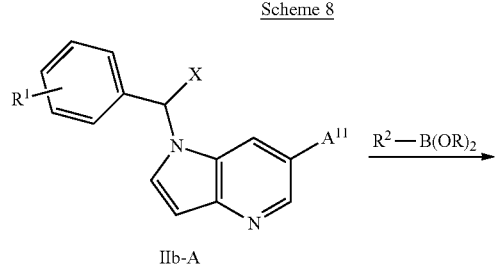

Compounds of Formula Ib can be prepared from IIb-A as in Scheme 8, wherein $R^1$ and $R^2$ are as defined previously, X is $C_{1-3}$alkyl, $A^{11}$ is halo such as Cl, Br, or I, or trifluoromethanesulfonate, and $B(OR)_2$ is a suitable boronic acid/ester. In a typical preparation of compounds of Formula Ib, a compound of Formula IIb-A is reacted with a suitable boronic acid/ester ($R^2$—$B(OR)_2$) in a suitable solvent via typical Suzuki coupling procedures, applying reaction conditions substantially similar to those described for compounds of Formula Ia. One skilled in the art will appreciate that alternative methods may be applicable for preparing compounds of Formula Ib from IIb-A. For example, compound of Formula IIb-A could be reacted with a suitable organotin reagent $R^2$—$SnBu_3$ or the like in a suitable solvent via typical Stille coupling procedures.

Scheme 9

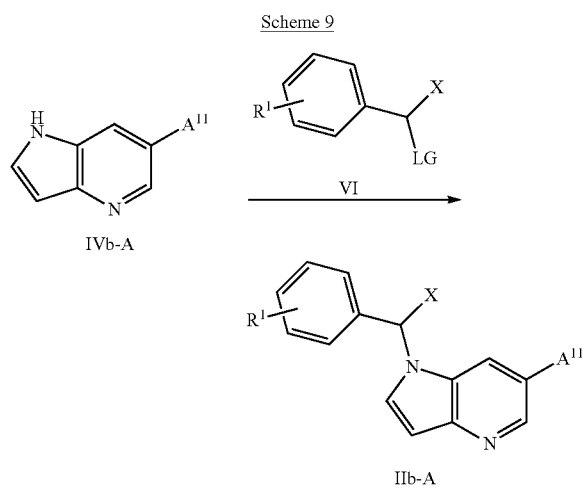

Compounds of Formula IIb-A can be prepared from IVb-A as in Scheme 9, wherein $R^1$ is as defined previously, X is $C_{1-3}$alkyl and $A^{11}$ is halo such as Cl, Br, or I, or trifluoromethanesulfonate, and LG is a suitable leaving group such as halos Cl, Br, or I, or suitable sulfonate esters such as mesylate, tosylate, or triflate. In a typical preparation, IVb-A is treated with VI in a suitable solvent in the presence of a suitable base at a suitable reaction temperature. Suitable solvents for use in the above process include, but are not limited to, ethers such as THF, glyme, and the like; DMF, DMSO; MeCN. If desired, mixtures of these solvents can be used or no solvent can be used. Preferred solvents are THF and DMF.

Suitable bases for use in the above process include, but are not limited to, KOH, NaOH, LiOH, NaH, KOtBu, NaOtBu and NaHMDS and the like. A preferred base is NaH. The above process can be carried out at temperatures between about −78° C. and about 120° C. Preferably, the reaction is carried out between 20° C. and about 60° C. The above process to produce compounds of the present invention is preferably carried out at about atmospheric pressure although higher or lower pressures can be used. Substantially equimolar amounts of reactants are preferably used although higher or lower amounts can be used.

Scheme 10

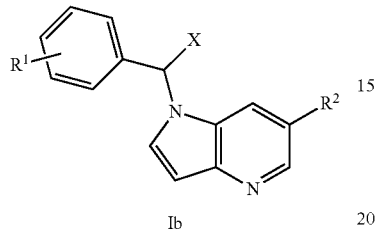

Compounds of Formula Ib can also be prepared as in Scheme 10, wherein $R^1$ and $R^2$ are as defined previously, $A^{11}$ is halo such as Cl, Br, or I, or trifluoromethanesulfonate, and $B(OR)_2$ is a suitable boronic acid/ester. Compound IIb-B can be reacted with a suitable coupling partner ($R^2$-$A^{11}$) in a suitable solvent via typical Suzuki coupling procedures. Suitable solvents for use in the above process include, but are not limited to, ethers such as THF, glyme, dioxane, dimethoxyethane, and the like; DMF; DMSO; MeCN; and alcohols such as MeOH, EtOH, isopropanol, trifluoroethanol, and the like. If desired, mixtures of these solvents can be used; however, a preferred solvent system is dimethoxyethane/water. The above process can be carried out at temperatures between about 0° C. and about 120° C. Preferably, the reaction is carried out between 60° C. and about 100° C. The above process is preferably carried out at about atmospheric pressure although higher or lower pressures can be used. Substantially, equimolar amounts of reactants are preferably used although higher or lower amounts can be used if desired.

One skilled in the art will appreciate that alternative methods may be applicable for preparing compounds of Formula Ib from $R^2$-$A^{11}$, e.g., via typical Stille coupling procedures.

Scheme 11

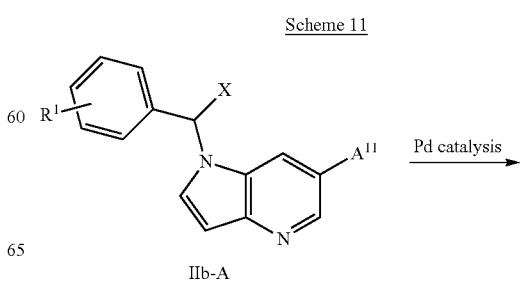

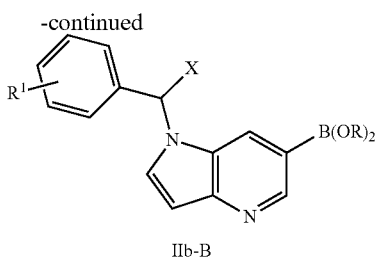

IIb-B

Compounds of Formula IIb-B can be prepared as in Scheme 11, wherein $R^1$ is as defined previously, $A^{11}$ is halo such as Cl, Br, or I, or trifluoromethanesulfonate, and $B(OR)_2$ is a suitable boronic acid/ester. In a typical preparation a compound of Formula IIb-A can be reacted with a suitable coupling partner (Bis(pinacolato)diboron or Pinacolborane)) in a suitable solvent under Palladium catalysis. Suitable solvents for use in the above process include, but are not limited to, ethers such as THF, glyme, dioxane, dimethoxyethane, and the like; DMF; DMSO; MeCN; and alcohols such as MeOH, EtOH, isopropanol, trifluoroethanol. If desired, mixtures of these solvents can be used; however, preferred solvents are DMSO or dioxane. The above process can be carried out at temperatures between about 0° C. and about 120° C. Preferably, the reaction is carried out between 60° C. and about 100° C. The above process is preferably carried out at about atmospheric pressure although higher or lower pressures can be used. Substantially equimolar amounts of reactants used although higher or lower amounts can be used if desired.

One skilled in the art will appreciate that alternative methods may be applicable for preparing compounds of Formula IIb-B. For example, via halogen-metal exchange (for example, halogen-Lithium exchange) and quench with borylation reagents such as tri-isopropyl borate.

As will be apparent to the skilled artisan, the synthetic route/sequence can be modified as desired for the preparation of a given compound. For example, Group $R^2$ can be installed on compound IVb-A under conditions similar to Schemes 8, 10, and 11.

Compounds of Formula Ib have a chiral center at the carbon atom that connects the 4-azaindole core with X and the phenyl ring substituted with $R^1$. Enantiomerically pure IIb-A-ena-A and IIb-A-ena-B can be prepared by separation of racemic mixture IIb-A by chromatography with an enantiomerically pure stationary phase as in Scheme 12. Similarly, enantiomerically pure Ib-A-ena-A and Ib-A-ena-B can be prepared by separation of racemic mixture Ib. Suitable chromatography systems for separation of racemic IIb or Ib include, but are not limited to, chiral HPLC (high performance liquid chromatography) systems, chiral SFC (supercritical fluid chromatography) systems and the like.

One skilled in the art will appreciate that instead of separating the enantiomers by chromatographic means one may form diastereomeric salts that may be separated by crystallization. Neutralization of the separated diastereomeric salts provides the separated enantiomers of IIb or Ib. Suitable chiral auxiliaries include, but are not limited to amino acids and their derivatives, (1S)-(+)-camphor-10-sulfonic acid, (1R)-(−)-camphor-10-sulfonic acid and the like.

Scheme 13

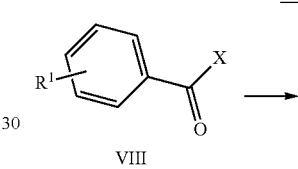

VIII

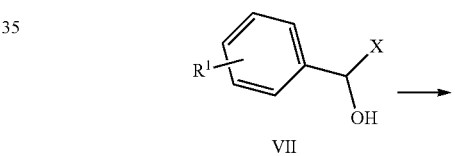

VII

Scheme 12

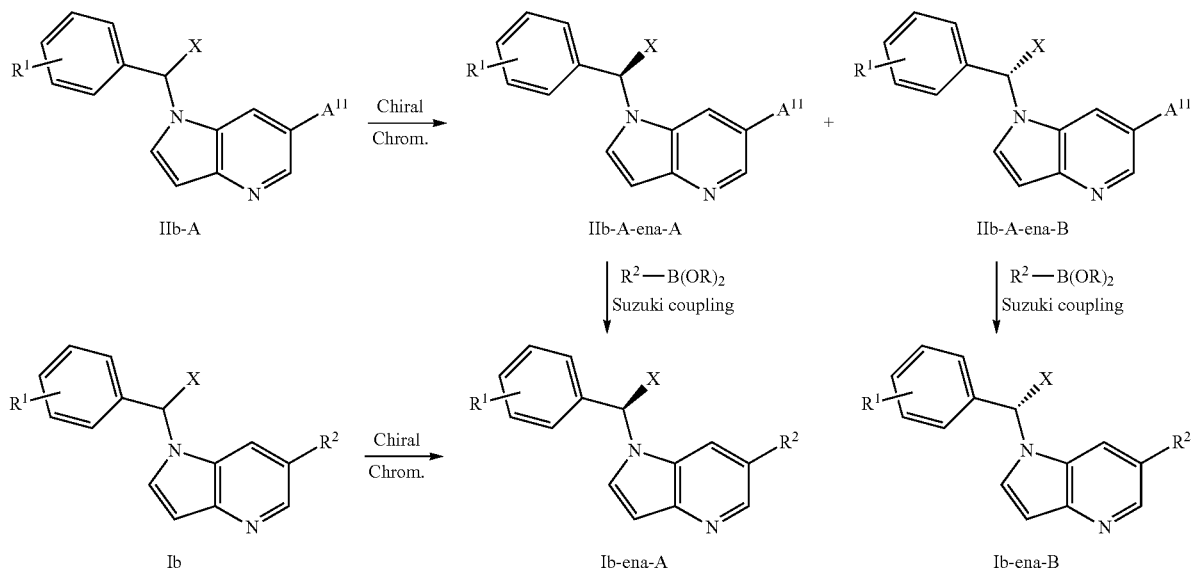

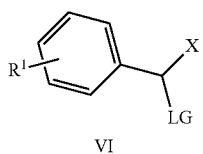

VI

Alternatively, enantiomerically enriched/pure IIb-A-ena-A and IIb-A-ena-B may be obtained by using enantiomerically pure VI for the reaction shown in Scheme 9. Compounds of Formula VI may be obtained as shown in Scheme 13 from ketones VIII by reduction to give the alcohols VII, which are then converted to VI under typical conditions known to the skilled artisan. Racemic compounds VII and VI may be separated into their enantiomers by the chromatographic methods described above. Alternatively, enantiomerically enriched VII may be obtained directly from VIII by using enantiopure reducing agents. Enzymatic resolution of VII may also be used to obtain enantiomerically enriched VII by converting VII to its acetate ester and using a suitable enzyme to hydrolyze one enantiomer in preference over the other.

Compounds of Formula Ic {also known as pyrazolo[3,4-b]pyridines} are compounds of Formula I wherein Y4=N, Y3=NH, Y5=C and Y2, Y1=CH. These compounds, or their pharmaceutically acceptable salts, can be prepared according to the reaction schemes discussed hereinbelow and the general skill in the art.

Compounds of Formula Ic can be prepared from IIc-A as in Scheme 14, wherein $R^1$ and $R^2$ are as defined previously, X is $C_{1-3}$alkyl, $A^{11}$ is halo such as Cl, Br, or I, or trifluoromethanesulfonate, and $B(OR)_2$ is a suitable boronic acid/ester. In a typical preparation of compounds of Formula Ic, a compound of Formula IIc-A is reacted with a suitable boronic acid/ester [$R^2$—$B(OR)_2$] in a suitable solvent via typical Suzuki coupling procedures, applying reaction conditions substantially similar to those described for compounds of Formula Ia. One skilled in the art will appreciate that alternative methods may be applicable for preparing compounds of Formula Ic from IIc-A. For example, compound of Formula IIc-A could be reacted with a suitable organotin reagent $R^2$—$SnBu_3$ or the like in a suitable solvent via typical Stille coupling procedures. Alternatively, a compound of Formula IIc-A may first be converted to a boronic acid/ester of formula IIc-B, followed by reaction with $R^2$-$A^{11}$ via typical Suzuki coupling procedures, applying conditions substantially similar to those described for compounds of Formula Ia in Schemes 4 and 5. One skilled in the art will appreciate that alternative methods may be applicable for preparing compounds of Formula Ic from $R^2$-$A^{11}$, e.g., via typical Stille coupling procedures.

Scheme 15

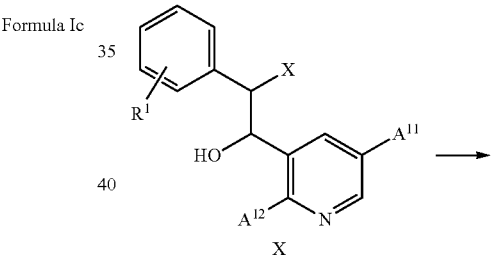

Formula Ic

Scheme 14

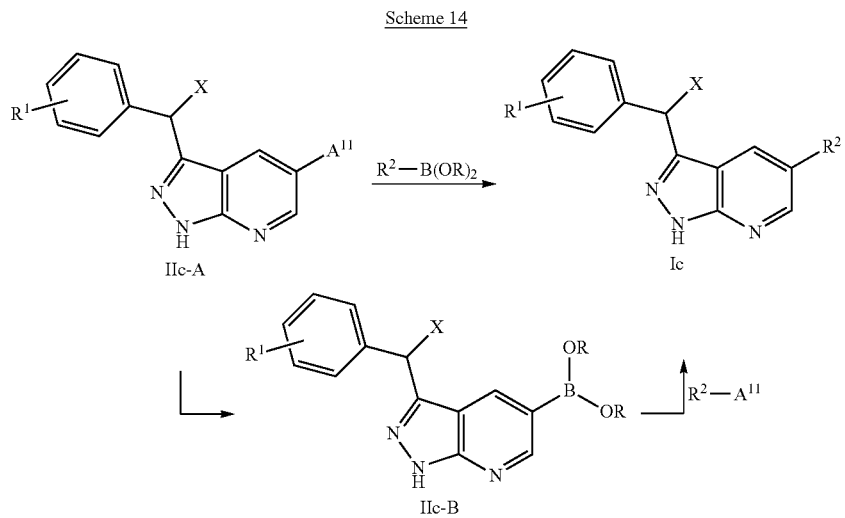

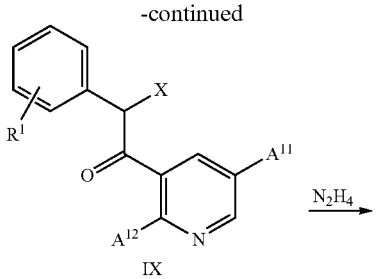

IX

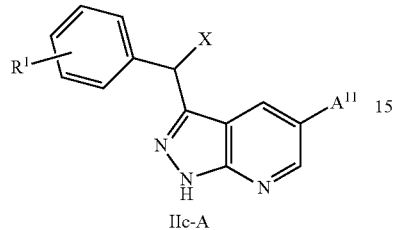

IIc-A

Compounds of Formula IIc-A can be prepared as in Scheme 15, wherein $R^1$ is as defined previously, X is $C_{1-3}$alkyl, $A^{11}$ is halo such as Cl, Br, or I, and $A^{12}$ is F or Cl. The secondary alcohol in compounds of Formula IX can be oxidized by a variety of methods using, e.g., metal-based oxidants such as pyridinium chlorochromate or sulfur-based oxidants such as in the Swern reaction, under conditions known to the skilled artisan. Reaction of compounds of Formula IX with hydrazine gives compounds of Formula IIc-A. This reaction can be conducted with anhydrous hydrazine or hydrazine hydrate. Typical solvents for this reaction include alcoholic solvents, such as ethanol or isopropanol, although other solvents can be used. The reaction can be carried out at temperatures between about 0° C. and about 140° C. Preferably, the reaction is carried out near the reflux temperature of the solvent. Higher temperatures can be used when the reaction is conducted in a sealed vessel.

Scheme 16

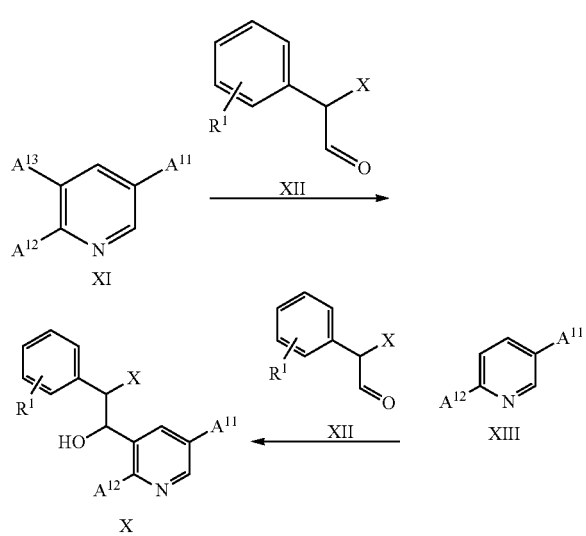

Compounds of Formula X can be prepared from XI or XIII as in Scheme 16 wherein $R^1$ is as defined previously, X is $C_{1-3}$alkyl, $A^{11}$ is halo such as Cl, Br, or I, $A^{12}$ is F or Cl, and $A^{13}$ is Br or I. Selective halogen-metal exchange of $A^{13}$ in XI using organolithium or -magnesium reagents generates an anion that is reacted with the aldehyde XII. A preferred reagent XI is 5-bromo-2-chloro-3-iodopyridine, and the halogen-metal exchange is conducted with iPrMgCl in THF at about −50° C. Another suitable reagent XI is 3-bromo-2,5-dichloropyridine, and the halogen-metal exchange is conducted with nBuLi at about −70° C. Alternatively, the anion may be generated by deprotonation of XIII at C3, which is then reacted with the same aldehyde XII to furnish the compound of Formula X. A preferred reagent XIII is 5-bromo-2-fluoropyridine, and the deprotonation may be conducted with LDA in THF at about −75° C.

Scheme 17

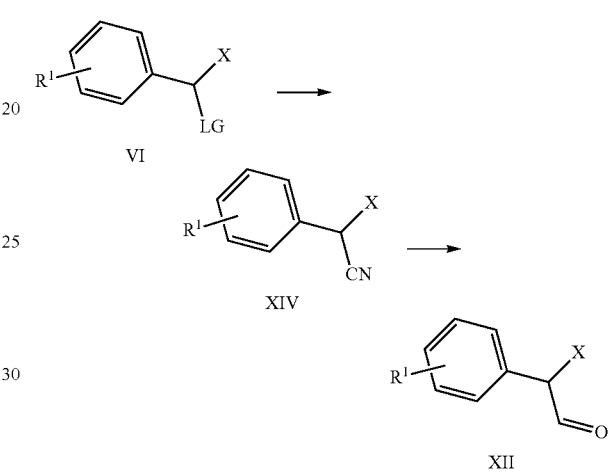

Compounds of Formula XII may be prepared as shown in Scheme 17, wherein $R^1$ is as defined previously, X is $C_{1-3}$alkyl, and LG is a suitable leaving group such as halos Cl, Br, or I, or suitable sulfonate esters such as mesylate, tosylate, or triflate. The leaving group LG in compounds of Formula VI may be displaced with cyanide to obtain compound XIV. Suitable reaction conditions include, but are not limited to, heating VI with NaCN in DMF at about 60-90° C. The nitrile group is then reduced to furnish the aldehyde XII. Suitable reaction conditions include, but are not limited to, reacting XIV with diisobutylaluminum hydride in toluene at about 0-60° C. Depending on the $R^1$ substituents, the skilled artisan will decide whether or not other reaction conditions may be more suitable.

Compounds of Formula Ic have a chiral center at the carbon atom that connects the pyrazolopyridine core with X and the phenyl ring substituted with R1. Enantiomerically pure compounds Ic and IIc can be prepared by separation of the racemic mixtures by chromatography on an enantiomerically pure stationary phase as described for compounds of Formula Ib and IIb in Scheme 12. Alternatively, compounds of Formula Ic or IIc may be reacted with a chiral auxiliary to provide diastereomers that are separated by chromatography, followed by removal of the chiral auxiliary, as described in Scheme 6 for compounds of Formula IIa. Furthermore, one may form diastereomeric salts that may be separated by crystallization. Neutralization of the separated diastereomeric salts provides the separated enantiomers of IIc or Ic.

Compounds of Formula Id {also known as pyrrolo[2,3-b] pyrazines} are compounds of Formula I wherein Y3=NH, Y5=C, Y1=N and Y2, Y4=CH. These compounds, or their pharmaceutically acceptable salts, can be prepared according to the reaction Schemes 1-7 discussed for the compounds of Formula Ia and the general skill in the art.

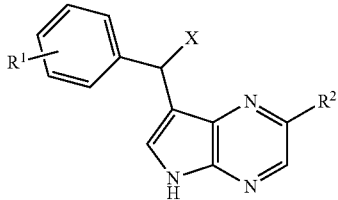

Formula Id

Compounds of Formula Id have a chiral center at the carbon atom that connects the pyrrolopyrazine core with X and the phenyl ring substituted with R1. Enantiomerically pure compounds Id can be prepared by the methods discussed for the compounds of Formula Ia and the general skill in the art.

Compounds of Formula Ie {also known as pyrrolo[2,3-c]pyridazines} are compounds of Formula I wherein Y3=NH, Y5=C, Y2=N, and Y4 & Y1=CH. These compounds, or their pharmaceutically acceptable salts, can be prepared according to the reaction Schemes discussed hereinbelow and the general skill in the art.

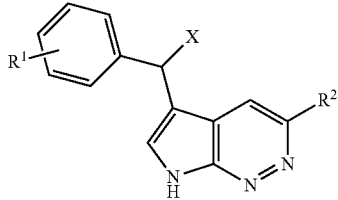

Formula Ie

Scheme 18

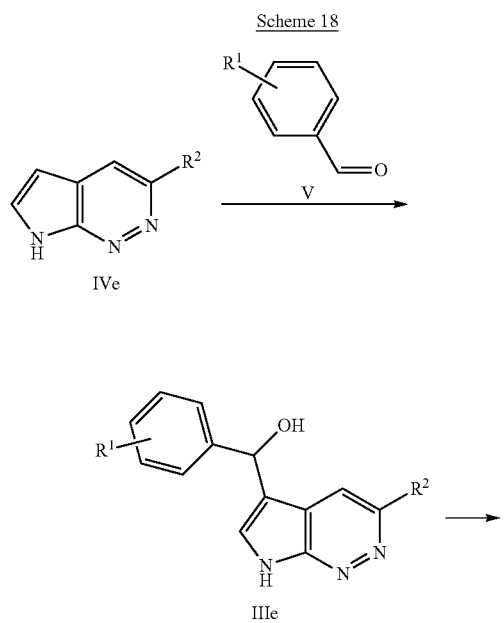

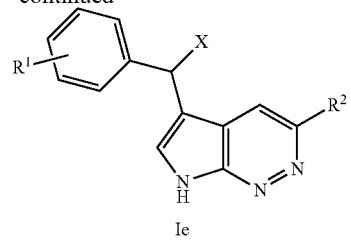

Ie

Compounds of Formula Ie wherein X=$C_{1-3}$alkyl can be prepared from IVe as in Scheme 18, wherein $R^1$ and $R^2$ are as defined previously. In a typical preparation, IVe is treated with benzaldehyde V to give a compound of Formula IIIe which is then reacted with an alkyl transfer reagent in the presence of a Lewis acid to furnish compound Ie. The typical reaction conditions are similar to those described in Schemes 2 and 3 for compounds of Formula Ia, except that the reaction with benzaldehyde V requires higher temperatures, preferably between 100° C. and about 120° C. When alcohols are used as solvent, analogs of compounds of Formula IIIe wherein the hydroxyl group is replaced with an alkoxy group can also be obtained. For example, with MeOH as solvent one can obtain the methoxy analogs.

Scheme 19

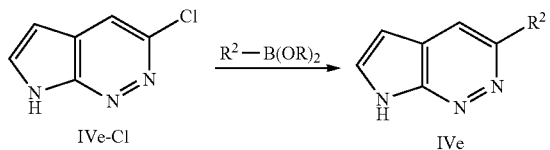

Compounds of Formula IVe can be prepared from IVe-Cl as in Scheme 19, wherein $R^2$ is as defined previously and $B(OR)_2$ is a suitable boronic acid/ester. In a typical preparation of compounds of Formula IVe, the compound of Formula IVe-Cl is reacted with a suitable boronic acid/ester [$R^2$—B(OR)$_2$] in a suitable solvent via typical Suzuki coupling procedures, applying reaction conditions substantially similar to those described for compounds of Formula Ia. One skilled in the art will appreciate that alternative methods may be applicable for preparing compounds of Formula IVe from IVe-Cl. For example, compound of Formula IVe-Cl could be reacted with a suitable organotin reagent $R^2$—SnBu$_3$ or the like in a suitable solvent via typical Stille coupling procedures.

Scheme 20

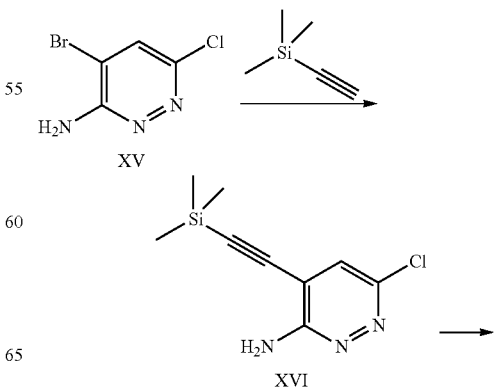

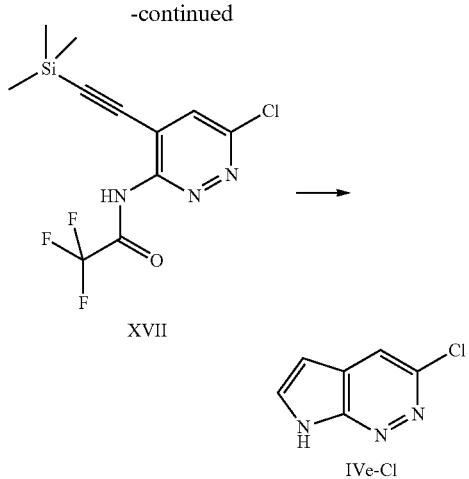

XVII

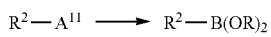

IVe-Cl

The compound of Formula IVe-Cl may be prepared as in Scheme 20, starting from the known 4-Bromo-6-chloro-pyridazin-3-ylamine (compound XV). Sonogashira coupling of XV with TMS-acetylene using a palladium catalyst and CuI followed by acylation with trifluoroacetic anhydride gives compound XVII, which is subsequently cyclized by heating with CuI in N-methylpyrrolidone.

Compounds of Formula Ie have a chiral center at the carbon atom that connects the pyrrolopyridazine core with X and the phenyl ring substituted with R1. Enantiomerically pure compounds Ie can be prepared by the methods discussed for the compounds of Formula Ia and the general skill in the art.

The building blocks $R^2$-$A^{11}$ and $R^2$—$B(OR)_2$ whose use for the preparation of compounds of the present invention is described above may be prepared as follows.

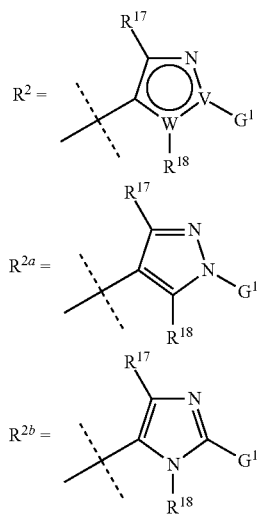

$R^{2a}$=$R^2$ wherein W—V=C—N; $R^{2b}$=$R^2$ wherein W—V=N—C.

Scheme 21

$R^2$—$A^{11}$ ⟶ $R^2$—$B(OR)_2$

The building block $R^2$—$B(OR)_2$ may be prepared as in Scheme 21 from the building block $R^2$-$A^{11}$, wherein $R^2$ is as defined previously, $A^{11}$ is halo such as Cl, Br, or I, or trifluoromethanesulfonate, and $B(OR)_2$ is a suitable boronic acid/ester. The conversion may be accomplished by palladium catalysis under conditions similar to those described above in Schemes 4, 11, and 14. An alternate route for compounds $R^2$-$A^{11}$ wherein $A^{11}$ is Br or I consists of halogen-metal exchange with organolithium or -magnesium reagents followed by reaction with a boron reagent. Suitable reagents for $A^{11}$=I include, but are not limited to, iPrMgCl, iPrMgBr, or iPrMgCl.LiCl as organomagnesium reagents and MeOB(pinacol) or $B(OMe)_3$ as boron reagents. Suitable reagents for $A^{11}$=Br include, but are not limited to, nBuLi as organolithium reagent and MeOB(pinacol) or $B(OMe)_3$ as boron reagents.

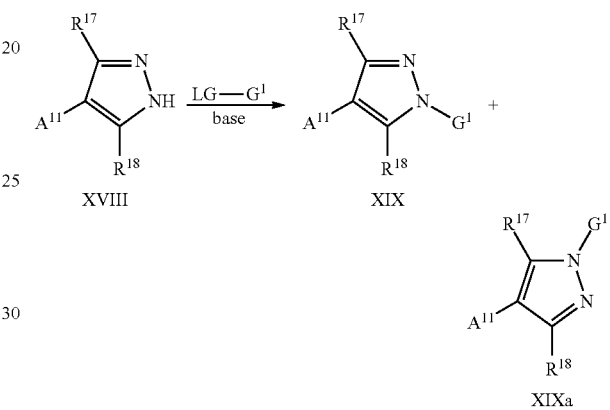

As shown in Scheme 22, building blocks containing $R^{2a}$ may be prepared by alkylating a pyrazole XVIII that is unsubstituted on the nitrogen atoms with an alkylating agent LG-$G^1$, wherein LG is a leaving group such as the halos Cl, Br, and I, or a sulfonate ester such as tosylate, mesylate, or trifluoromethanesulfonate. $A^{11}$ is halo such as Cl, Br, or I. If $R^{17}$≠$R^{18}$, mixtures of regioisomers resulting from alkylation at either of the two nitrogen atoms of the pyrazole may be formed. This reaction can also be conducted with pyrazoles that have a suitable boronic acid/ester $B(OR)_2$ in place of $A^{11}$.

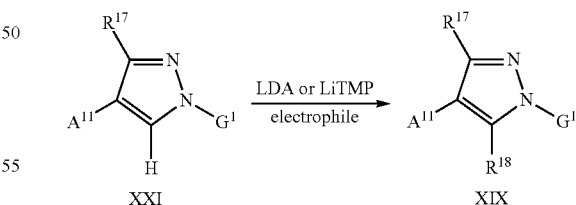

As shown in Scheme 23, building blocks containing $R^{2a}$ of Formula XX that are unsubstituted at C5, i.e., $R^{18}$=H, may be selectively functionalized at C5 by deprotonation with a strong base such as LDA or LiTMP in a solvent such as THF followed by reaction with a suitable electrophile. Examples for electrophiles and the resulting substituents $R^{18}$ include, but are not limited to, methyl iodide ($R^{18}$=methyl), ethyl iodide ($R^{18}$=ethyl), $C_2Cl_6$ ($R^{18}$=Cl), N-fluorobenzenesulfonimide ($R^{18}$=F), DMF ($R^{18}$=CHO), $CO_2$ ($R^{18}$=$CO_2H$). This reaction can also be conducted with pyrazoles that have a suitable boronic acid/ester $B(OR)_2$ in place of $A^{11}$.

Scheme 24

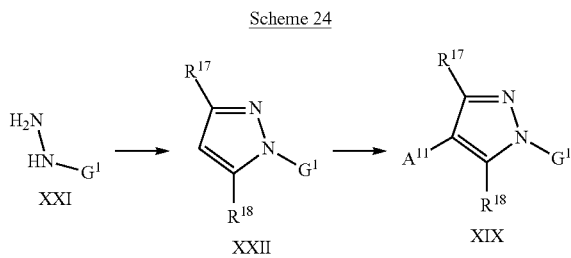

As shown in Scheme 24, the pyrazole ring in building blocks containing $R^{2a}$ of Formula XIX may also be synthesized de novo by condensation of a hydrazine derivative $H_2N$—$NH$-$G^1$ with a 1,3-dicarbonyl-type reagent followed by reaction with a halogenating agent to introduce $A^{11}$. Examples for halogenating agents include, but are not limited to, pyridinium perbromide or NBS (for $A^{11}$=Br), NIS or ICl (for $A^{11}$=I), or NCS (for $A^{11}$=Cl).

*Tetrahedron Letters* 2005, 46, 8369-8372). The imidazole XXVI can be halogenated at C5 to give a compound of Formula XXVII-A with a suitable halogenating agent such as NBS (for $A^{11}$=Br), NIS or ICl (for $A^{11}$=I), or NCS (for $A^{11}$=Cl), in solvents such as THF, EtOAc, DCM, DMF, and the like. It can also be borylated at C5 to give a compound of Formula XXVII-B with pinacolborane or bis(pinacolato)diboron in the presence of a catalyst consisting of an iridium complex and a 2,2'-bipyridine. Preferred catalysts include [Ir(OMe)(COD)]$_2$ and 2,2'-di-tert-butyl-bipyridine.

Building blocks containing $R^{2b}$, wherein $R^{17}$≠H and $R^{18}$ is H, aliphatic, or cycloalkyl, may be prepared following the same route but starting from analogs of the acetal XXIII that are substituted at the acetal carbon atom with $R^{17}$. Alternatively, the imidazole XXVI can be halogenated at C4 and C5 by using >2 equivalents of halogenating agent, and the imidazole XXVII-A can also be halogenated at C4, resulting in compounds wherein $R^{17}$=halogen. Due to the different reactivity of halogens at C5 vs. C4, each position can be modified selectively, allowing the conversion of $R^{17}$=halo to other functionalities as defined above.

Scheme 25

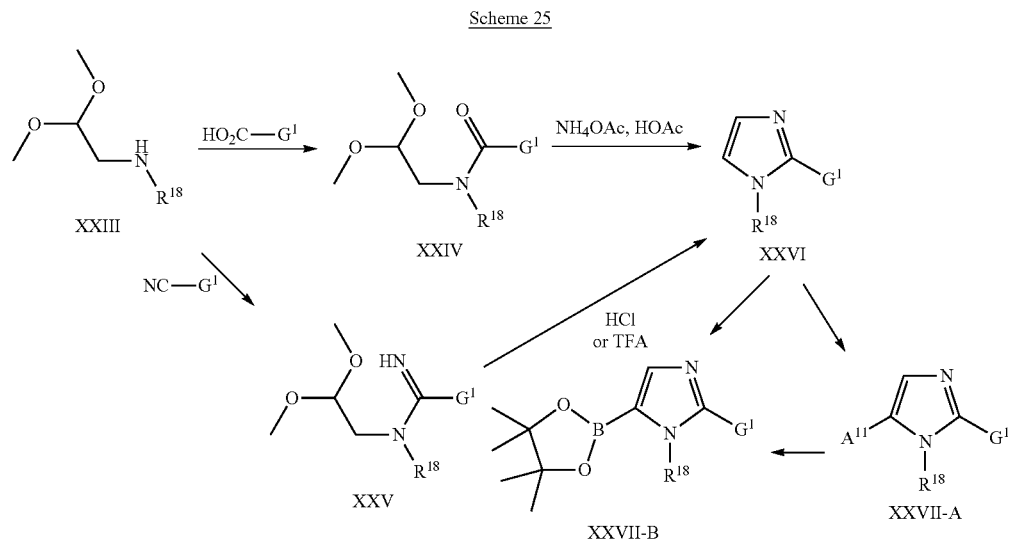

The imidazole ring in building blocks of Formula XXVII-N-B containing $R^{2b}$, wherein $R^{18}$ is H, aliphatic, or cycloalkyl, may be synthesized de novo as shown in Scheme 25. The carboxylic acid $HO_2C$-$G^1$ is reacted with an aminoacetaldehyde acetal XXIII under typical conditions for amide formation (e.g., EDCl+HOBt, mixed anhydrides, TBTU) to give an amide, which upon heating with $NH_4OAc$ in acetic acid cyclizes to form the imidazole ring, yielding a compound of Formula XXVI. $R^{18}$ in the aminoacetaldehyde acetal XXIII can be H, aliphatic, or cycloalkyl; if $R^{18}$=H in XXIII then it is convenient to introduce $R^{18}$≠H by alkylation of XXVI with $R^{18}$-LG wherein LG is a leaving group such as Cl, Br, I, mesylate, tosylate, or triflate. In an alternate route to XXVI, the aminoacetaldehyde acetal XXIII can be reacted with the nitrile in the presence of CuCl without solvent to obtain the amidine of Formula XXV, which is cyclized with HCl or TFA in alcoholic solvents such as methanol or ethanol to give the imidazole of Formula XXVI (as described in Scheme 26

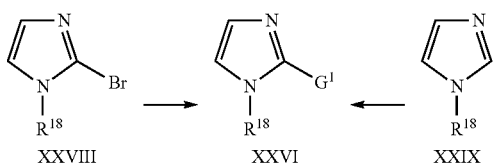

The imidazoles of Formula XXVI may also be prepared from 2-bromoimidazoles XXVIII or imidazoles XXIX as shown in Scheme 26 by a variety of methods depending on the $G^1$ substituent. For example, the Br in XXVIII may be displaced by nucleophiles or reacted in transition metal-catalyzed reactions. Bromine-lithium exchange generates an anion that can be reacted with electrophiles; the same anion can also be obtained by deprotonating XXIX with a strong base such as LDA, LiTMP, or BuLi.

Further methods of functionalizing and building up the pyrazole and imidazole rings can be found in the general literature, e.g., Volume 3 of Comprehensive Heterocyclic Chemistry II (Pergamon).

The functional groups present in $R^{17}$, $R^{18}$, and $G^1$ may be further modified by methods known to someone skilled in the art and the general literature such as the book Comprehensive Organic Transformations by R. C. Larock.

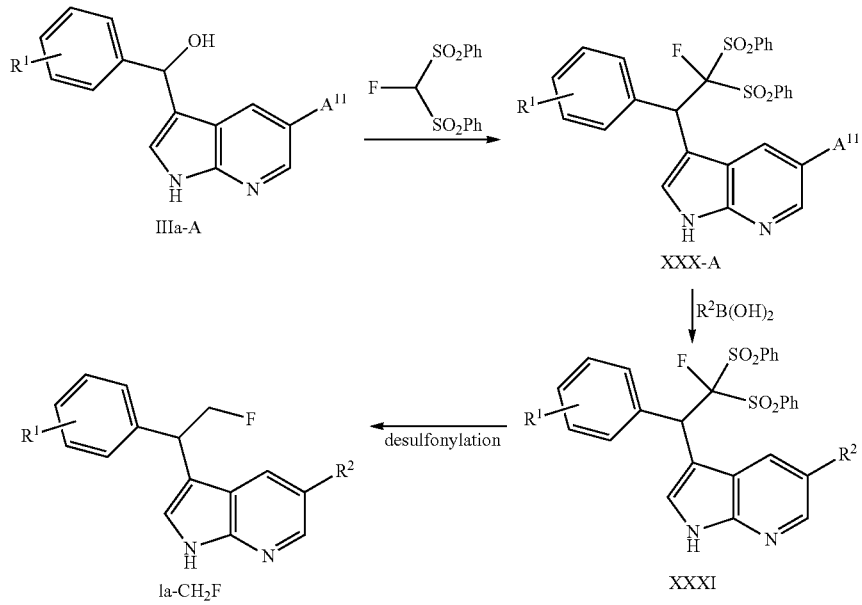

Scheme 27

Compounds of Formula Ia wherein $X=CH_2F$ can be prepared as shown in Scheme 27 wherein $R^1$ and $R^2$ are as defined previously and $A^{11}$ is halo such as Cl, Br, or I, or trifluoromethanesulfonate. In a typical preparation of compounds of Formula XXX-A, a compound of Formula IIIa-A, or an analog of a compound of Formula IIIa-A wherein the hydroxyl group is replaced with an alkoxy group, is reacted first with thionyl chloride in a suitable solvent such as THF or chlorinated solvents like DCM or DCE, followed by evaporation to dryness. The residue is then redissolved in a solvent such as THF, and a solution of lithiated 1-(fluoro(phenylsulfonyl)methylsulfonyl)benzene is added at −78° C., followed by warming up to ambient temperature, to give XXX-A. In a typical preparation of compounds of Formula XXXI, a compound of Formula XXX-A is reacted with a suitable boronic acid/ester ($R^2$—$B(OR)_2$) under conditions similar to those described in Scheme 1. One skilled in the art will appreciate that alternative methods may be applicable for preparing compounds of Formula XXXI from XXX-A. For example, compound of Formula XXX-A could be reacted with a suitable organotin reagent $R^2$—$SnBu_3$ or the like in a suitable solvent via typical Stille coupling procedures. Compounds of Formula XXXI can be desulfonylated to give compounds of Formula Ia-$CH_2F$ (=Formula Ia wherein $X=CH_2F$) with reagents such as, but not limited to, sodium amalgam in buffered alcoholic solution or magnesium in methanol. The preferred reaction conditions for the desulfonylation with sodium amalgam will depend on the sodium content; for example, 20% sodium amalgam may allow the reaction to be conducted at −60 to −78° C. whereas 5% sodium amalgam may require higher temperatures, such as −20° C. to ambient temperature. Depending on the nature of substituents $R^1$ and $R^2$, the conditions may need to be modified to prevent formation of side products, such as, but not limited to, reduction of any halo atoms present in $R^1$ or $R^2$. Suitable solvents for the desulfonylation include, but are not limited to, alcohols such as MeOH, EtOH, or isopropanol. Suitable buffer salts include, but are not limited to, disodium hydrogen phosphate, sodium dihydrogen phosphate, the corresponding potassium salts, or mixtures thereof.

Synthetic equivalents of a nucleophilic $CH_2F$ group other than 1-(Fluoro(phenyl-sulfonyl)methylsulfonyl)benzene are known in the literature and may be used here, e.g., 2-fluoro-1,3-benzodithiole-1,1,3,3-tetroxide (*Angew. Chem. Int. Ed.* 2010, 49, 1642-1647).

Racemic compounds of Formula Ia-$CH_2F$ may be resolved into the enantiomers by any of the methods outlined above in schemes 6 and 7 and other methods known to someone skilled in the art.

As will be apparent to the skilled artisan, the synthetic routes/sequences can be modified as desired for the preparation of a given compound.

Preparations and Intermediates

Unless otherwise noted, all materials/reagents were obtained from commercial suppliers and used without further purification. $^1$H NMR (400 MHz or 300 MHz) and $^{13}$C NMR (100.6 or 75 MHz) spectra were recorded on Bruker or Varian instruments at ambient temperature with tetramethylsilane or the residual solvent peak as the internal standard. The line positions or multiples are given in ppm (δ) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), $m_c$ (centered multiplet), br or broad (broadened), AA'BB'. The signal multiplicities in $^{13}$C NMR spectra were determined using the DEPT135 pulse sequence and are abbreviated as follows: +(CH or CH$_3$), —(CH$_2$), C$_{quart}$ (O). Reactions were monitored by thin layer chromatography (TLC) on silica gel 60 F$_{254}$ (0.2 mm) precoated aluminum foil and visualized using UV light. Flash chromatography was performed with silica gel (400-230 mesh). Preparatory TLC was performed on Whatman LK6F Silica Gel 60 Å size 20×20 cm plates with a thickness of 500 or 1000 µm. Hydromatrix (=diatomaceous earth) was purchased from Varian. Mass-directed HPLC purification of compounds was performed on a Waters system composed of the following: 2767 Sample Manager, 2525 Binary Gradient Module, 600 Controller, 2996 Diode Array Detector, Micromass ZQ2000 for ionization, Phenomenex Luna 5µ C18(2) 100 Å 150×21.2 mm 5µ column with mobile phases of 0.01% Formic Acid Acetonitrile (A) and 0.01% Formic Acid in HPLC water (B), a flow rate of 20 mL/min, and a run time of 13 min. LC-MS data was collected on ZQ2, ZQ3, or UPLC-ACQUITY. ZQ2 is an Agilent 1100 HPLC equipped with a Gilson 215 Liquid Handler, Gilson 819 Injection Module, and Waters Micromass ZQ2000 for ionization. ZQ3 is an Agilent 1100 HPLC equipped with an HP Series 1100 auto injector and Waters Micromass ZQ2000 for ionization. Both systems use the Xterra MS C18, 5µ particle size, 4.6×50 mm with a mobile phase of Acetonitrile (A) and 0.01% Formic Acid in HPLC water (B). The flow rate is 1.3 mL/min, the run time is 5 min, and the gradient profiles are 0.00 min 5% A, 3.00 min 90% A, 3.50 min 90% A, 4.00 min 5% A, 5.00 min 5% A for polar_5 min and 0.00 min 25% A, 3.00 min 99% A, 3.50 min 99% A, 4.00 min 25% A, 5.00 min 25% A for nonpolar_5 min. All Waters Micromass ZQ2000 instruments utilized electrospray ionization in positive (ES+) or negative (ES−) mode. The Waters Micromass ZQ2000 instruments from ZQ2 and ZQ3 can also utilize atmospheric pressure chemical ionization in positive (AP+) or negative (AP−) mode. The Waters UPLC-ACQUITY system consists of an ACQUITY sample manager attached to ACQUITY SQ MS and ACQUITY PDA detectors. It uses an ACQUITY HPLC BEH® C18 2.1×50 mm 1.7 µm column with a mobile phase of 0.1% formic acid in water (A) and 0.1% formic acid in acetonitrile (B). The flow rate is 1.0 mL/min, run time is 2 min, and the gradient profile is 0.00 min 95% A, 1.50 min 1% A, 1.85 min 1% A, 2.0 min 95% A for analytical. UV detection is at 254 nm, and the MS utilizes electrospray ionization in positive mode (ES+). HPLC purification of compounds was performed on a Waters system consisting of a 2767 Sample Manager, 1525EF Binary Pump, and a 2487 Dual λ Absorbance Detector. The system uses Phenomenex Luna C18(2), 5µ particle size, 50×21.2 mm columns with a mobile phase of Acetonitrile/0.25% Formic Acid and HPLC water/0.25% Formic Acid. Alternatively, a Gilson system ("Gilson HPLC") consisting of a 215 Liquid Handler, 819 Injection Module, a 322 Pump, and a 155 UV/VIS dual wavelength detector set to 254 and 210 nm was used. This system uses Phenomenex Luna C18(2), 5µ particle size, 50×21.2 mm or 60×21.2 mm columns with a mobile phase of Acetonitrile and 0.1% Formic Acid in HPLC water. The flow rate is 15 mL/min and the run time is 25 min. The HPLC system for determination of enantiomeric purity consists of an Agilent 1100 HPLC and Chiralcel or Chiralpak 4.6×150 mm columns (Daicel Chemical Ind., Ltd.), eluting with acetonitrile/water mixtures. All melting points were determined with a Mel-Temp II apparatus and are uncorrected. Elemental analyses were obtained by Atlantic Microlab, Inc., Norcross, Ga.

5-Bromo-3-[1-(2,6-dichloro-3-fluorophenyl)ethyl]-1H-pyrrolo[2,3-b]pyridine (5-Bromo-1H-pyrrolo[2,3-b]pyridin-3-yl)-(2,6-dichloro-3-fluorophenyl)methanol (5.05 g, 12.9 mmol) was dissolved in anhydrous THF (100 mL). To this solution was added BF$_3$.OEt$_2$ (10.66 mL, 6.5 eq.) at −78° C. The resulting solution was stirred for 10 min at the same temp before a solution of ZnMe$_2$ (35.60 mL, 5.5 eq., 2 N in toluene) was added. The resulting mixture was allowed to warm up to rt in 1 h. The solution was then stirred at 65° C. for 3.5 h. Reaction was monitored by LC-MS. After achieving >95% conversion, the reaction was allowed to cool down to rt. Then it was further cooled down to −78° C. and quenched by adding sat. aq. NH$_4$Cl solution (10 mL). The mixture was slowly warmed up to rt. Solvents were removed under reduced pressure. To the residue was added aq. NaHCO$_3$ solution and the mixture was then extracted with CHCl$_3$ (100 mL×4). The organic extracts were combined, dried (Na$_2$SO$_4$), and concentrated in vacuo to give a crude residue which was purified by flash chromatography (eluent: 10% ethyl acetate in hexane). $^1$H NMR (400 MHz DMSO-d$_6$): δ=11.85 (br. s., 1H), 8.21 (d, J=2.0 Hz, 1H), 7.49-7.59 (m, 2H), 7.41 (dd, J=8.8, 8.6 Hz, 1H), 7.30 (d, J=2.0 Hz, 1H), 5.11 (q, J=7.3 Hz, 1H), 1.80 (d, J=7.3 Hz, 3H); $^{13}$C NMR (100.6 MHz, DMSO-d$_6$): δ=156.74 (J$_{CF}$=247.4 Hz), 146.91, 142.24, 141.02, 129.37, 127.56, 125.98, 121.73 (J$_{CF}$=19.8 Hz), 120.18, 115.98 (J$_{CF}$=23.4 Hz), 113.62, 109.99, 33.53, 15.94. MS (ES+): m/z=386.93, 388.91, 390.89 [MH$^+$]. HPLC: t$_R$=4.17 min (ZQ3, polar_5 min).

(5-Bromo-1H-pyrrolo[2,3-b]pyridin-3-yl)-(2,6-dichloro-3-fluorophenyl)methanol

To a stirred mixture of 5-bromo-1H-pyrrolo[2,3-b]pyridine (0.100 g, 0.508 mmol) and 2,6-dichloro-3-fluorobenzaldehyde (0.107 g, 0.558 mmol) in MeOH (5 mL) was added potassium hydroxide (0.199 g, 3.553 mmol) at 0° C. under nitrogen atmosphere. The resulting mixture was then stirred at rt. overnight. The mixture was then poured into water (50 mL), acidified with 2N HCl and extracted with ethyl acetate (50 mL×3). The organics were combined, dried (Na$_2$SO$_4$) and concentrated under reduced pressure to give a crude residue which was then purified by chromatography (eluent: 20% ethyl acetate in hexane). MS (ES+): m/z=388.85, 390.84, 392.83 [MH$^+$]. HPLC: t$_R$=3.29 min (ZQ3, polar_5 min).

5-Bromo-3-[1-(2,6-dichlorophenyl)ethyl]-1H-pyrrolo[2,3-b]pyridine

Prepared according to the method described above for synthesis of 5-bromo-3-[1-(2,6-dichloro-3-fluorophenylethyl]-1H-pyrrolo[2,3-b]pyridine, using (5-bromo-1H-pyrrolo[2,3-b]pyridin-3-yl)-(2,6-dichlorophenyl)methanol. MS (ES+): m/z 368.89, 370.86, 372.88 [MH$^+$]; HPLC: t$_R$=3.25 min (ZQ3, polar_5 min).

(5-Bromo-1H-pyrrolo[2,3-b]pyridin-3-yl)-(2,6-dichlorophenyl)methanol

Prepared according to the method described above for synthesis of (5-bromo-1H-pyrrolo[2,3-b]pyridin-3-yl)-(2,6-dichloro-3-fluorophenyl)methanol, using 2,6-dichloro-benzaldehyde. MS (ES+): m/z 370.85, 372.85, 374.83 [MH$^+$]; HPLC: t$_R$=3.25 min (ZQ3, polar_5 min).

3-[1-(2,6-Dichloro-3-fluorophenyl)ethyl]-5-(4,4,5,5-tetramethyl[1,3,2]dioxaborolan-2-yl)-1H-pyrrolo[2,3-b]pyridine To a stirred mixture of 5-bromo-3-[1-(2,6-dichloro-3-fluorophenyl)ethyl]-1H-pyrrolo[2,3-b]pyridine (500.0 mg, 1.288 mmol), potassium acetate (379 mg, 3.86 mmol), bis(pinacolato)diboron (425.3 mg, 1.675 mmol) in 1,4-dioxane (15 mL) was added (1,1'-bis-(diphenylphosphino)ferrocene) palladium dichloride (47.10 mg, 0.0644 mmol) under Nitrogen atmosphere. The mixture was then stirred at 85° C. overnight. LC-MS indicated completion of reaction. Solvents were then removed under reduced pressure to give a residue which was then purified by flash chromatography (eluent: 25% ethyl acetate in DCM). $^1$H NMR (400 MHz, CD$_3$OD): δ=1.20 (s, 12H), 1.86 (d, J=7.3 Hz, 3H), 5.27 (q, J=7.0 Hz, 1H), 7.17 (t, J=8.7 Hz, 1H), 7.33 (d, J=1.3 Hz, 1H), 7.40 (br. s., 1H), 7.75 (d, J=1.5 Hz, 1H), 8.43 (d, J=1.5 Hz, 1H). MS (ES+): m/z=434.02, 435.06, 437.07, 438.11 [MH]$^+$. HPLC: $t_R$=4.22 min (ZQ3, polar__5 min).

3-[(S)-1-(2,6-Dichloro-3-fluorophenyl)ethyl]-5-(4,4,5,5-tetramethyl[1,3,2]dioxaborolan-2-yl)-1H-pyrrolo[2,3-b]pyridine To a stirred mixture of 5-bromo-3-[(S)-1-(2,6-dichloro-3-fluorophenyl)ethyl]-1H-pyrrolo[2,3-b]pyridine (450.0 mg, 1.160 mmol), potassium acetate (341 mg, 3.48 mmol), bis(pinacolato)diboron (412 mg, 1.62 mmol) in 1,4-dioxane (10 mL) was added (1,1'-bis-(diphenylphosphino)ferrocene) palladium dichloride (70 mg, 0.090 mmol) under Nitrogen atmosphere. The mixture was then stirred at 80° C. overnight. Solvents were removed under reduced pressure to give a residue which was then redissolved in DCM and dry-loaded onto silica gel. Column chromatography was used to purify, eluting with 30-40% EtOAc/hexanes. The fractions containing the product were concentrated in vacuo to afford the title compound as yellow gum. $^1$H NMR and LCMS data match with the data for the racemic compound.

((S)-1-{5-Bromo-3-[(S)-1-(2,6-dichloro-3-fluorophenyl)ethyl]pyrrolo[2,3-b]pyridine-1-carbonyl}-3-methylbutyl)carbamic acid 9H-fluoren-9-ylmethyl ester and ((S)-1-{5-Bromo-3-[(R)-1-(2,6-dichloro-3-fluorophenyl)ethyl]pyrrolo[2,3-b]pyridine-1-carbonyl}-3-methylbutyl)carbamic acid 9H-fluoren-9-ylmethyl ester

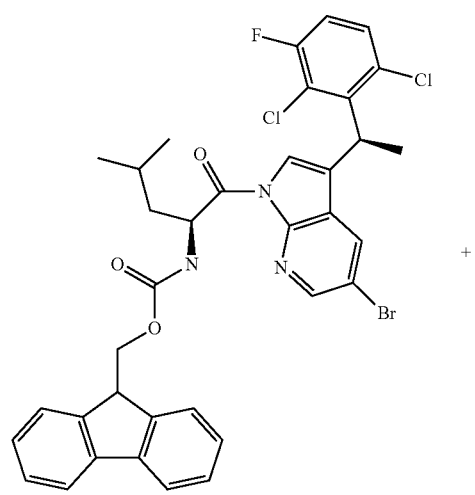

+

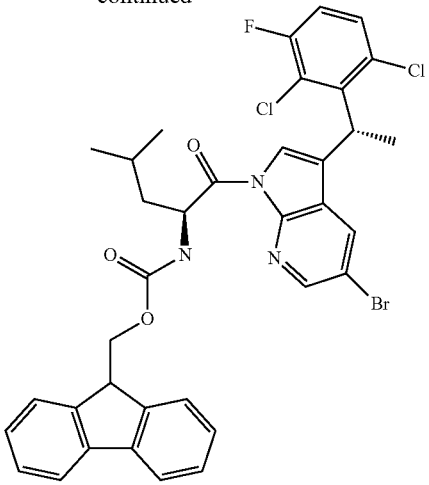

To a stirred mixture of 5-bromo-3-[1-(2,6-dichloro-3-fluorophenyl)ethyl]-1H-pyrrolo[2,3-b]pyridine (100.0 mg, 0.257 mmol), (S)-2-(9H-Fluoren-9-ylmethoxycarbonylamino)-4-methylpentanoic acid (Fmoc-L-Leucine) (136.6 mg, 0.386 mmol) in DMF (4.00 mL) were added DIPEA (0.224 mL, 1.28 mmol) and TBTU (124.1 mg, 0.386 mmol). The resulting mixture was stirred at rt for 16 h. Solvents were then removed under reduced pressure to give a residue which was purified by flash chromatography (eluent: Hexane/ethyl acetate/DCM: 100/3/25, v/v/v) to give both diastereomers as pure compounds.

More polar diastereomer: ((S)-1-{5-Bromo-3-[(S)-1-(2,6-dichloro-3-fluorophenyl)-ethyl]pyrrolo[2,3-b]pyridine-1-carbonyl}-3-methylbutyl)carbamic acid 9H-fluoren-9-ylmethyl ester. MS (ES+): m/z 722.06, 724.07, 726.03 [MH$^+$], HPLC: $t_R$=3.76 min (ZQ3, very very non-polar__5 min). Less polar diastereomer: ((S)-1-{5-Bromo-3-[(R)-1-(2,6-dichloro-3-fluorophenyl)-ethyl]pyrrolo[2,3-b]pyridine-1-carbonyl}-3-methylbutyl)carbamic acid 9H-fluoren-9-ylmethyl ester. MS (ES+): m/z 722.06, 724.07, 726.03 [MH$^+$], HPLC: $t_R$=3.84 min (ZQ3, very very non-polar__5 min).

5-Bromo-3-[(S)-1-(2,6-dichloro-3-fluorophenyl)ethyl]-1H-pyrrolo[2,3-b]pyridine

To a solution of ((S)-1-{5-Bromo-3-[(S)-1-(2,6-dichloro-3-fluorophenyl)ethyl]pyrrolo[2,3-b]pyridine-1-carbonyl}-3-methylbutyl)-carbamic acid 9H-fluoren-9-ylmethyl ester (722 mg, 1.00 mmol) in THF (20 mL) was added NaOH (5N in H$_2$O, 1 mL) at 0° C. with stirring. After stirring for 1 h at that temperature, solvents were removed under reduced pressure to give a residue which was then purified by flash chromatography (eluent: Hexane/ethyl acetate: 75/25, v/v) to give the title compound. $^1$H NMR and LCMS data match with the data for the racemic compound. Optical rotation: [α]$^{25}_D$=−112.8° (c=1.0, MeOH); α] [$^{25}_D$=−152.6° (c=1.0, CH$_2$Cl$_2$). HPLC (Chiralcel OD-RH, solvent 60:40 acetonitrile/water isocratic, flow rate 0.5 mL/min, column temperature 30° C., UV detection at 220 nm): $t_R$=28.0 min. C$_{15}$H$_{10}$BrCl$_2$FN$_2$ (388.07): Calculated: C, 46.43; H, 2.60; Br, 20.59; Cl, 18.27; F, 4.90; N, 7.22. found C, 46.36; H, 2.49; Br, 20.38; Cl, 18.31; F, 4.79; N, 7.09. A crystal structure of Example 85 from application Intl Appl. PCT/US09/65058 prepared using this material, bound to cMet confirmed the absolute configuration as shown.

5-Bromo-3-[(R)-1-(2,6-dichloro-3-fluorophenyl)ethyl]-1H-pyrrolo[2,3-b]pyridine The procedure described above for the (S)enantiomer was followed, starting with ((S)-1-{5-Bromo-3-[(R)-1-(2,6-dichloro-3-fluorophenyl)ethyl]pyrrolo[2,3-b]pyridine-1-carbonyl}-3-methylbutyl)-carbamic acid 9H-fluoren-9-ylmethyl ester. $^1$H NMR and LCMS data match with the data for the racemic compound. Optical rotation: $[\alpha]^{25}_D$=+115.7° (c=1.0, MeOH); $[\alpha]^{25}_D$=+151.7° (c=1.0, $CH_2Cl_2$). HPLC (Chiralcel OD-RH, solvent 60:40 acetonitrile/water isocratic, flow rate 0.5 mL/min, column temperature 30° C., UV detection at 220 nm): $t_R$=32.1 min.

2,6-Dichloro-3-fluorobenzaldehyde

To a solution of (2,6-Dichloro-3-fluorophenyl)methanol (100 g, 0.51 mol) in dichloromethane (450 mL) was added a solution of sodium bromide (54 g, 0.53 mol, in 90 mL water). The rapidly stirred biphasic mixture was cooled to −7° C. and TEMPO (1.54 g, 0.0100 mol) was added. A solution of 0.81M sodium hypochlorite (823 mL, 0.66 mol) saturated with sodium bicarbonate (75 g) was added dropwise over a period of 1 h while maintaining the temperature below −2° C. After the addition the reaction mixture was stirred for 30 min. The two layers separated and the DCM layer was washed with aq. solution of sodium thiosulfate. The DCM layer was dried ($Na_2SO_4$) and concentrated on rotary evaporator without using vacuum (aldehyde is volatile) to give the title compound as a solid, mp. 63-65° C. $^1$H NMR ($CDCl_3$, 300 MHz): δ=7.23 (dd, 1H, J=7.8, 9.0 Hz), 7.35 (dd, 1H, J=4.5, 9.3 Hz), 10.2 (s, 1H).

Alternate Preparation:

To a solution of 2,4-dichloro-1-fluorobenzene (100 g, 0.606 mol) in THF (1.4 L) under nitrogen at −78° C., was added a 2.5 M solution of n-BuLi in hexanes (267 mL, 0.666 mol) dropwise over a period of 30 min, maintaining the temperature between −70 to −78° C. After 1.5 h stirring at −78° C., methyl formate (72.6 mL, 1.21 mol) was added slowly, and the reaction mixture was stirred overnight, warming up to rt. The reaction was quenched with sat. aqueous $NH_4Cl$ (200 mL) and the organic layer was separated. The organic solvents were removed by distillation at atmosphere pressure and the crude material which contained a small amount of THF was crystallized from hexanes to give the title compound.

(2,6-Dichloro-3-fluorophenyl)methanol

To a solution of 2,6-Dichloro-3-fluorobenzoic acid (125 g, 0.59 mol) in THF (200 mL) was added $BH_3$.THF (592 mL, 592 mmol, 1M solution in THF) dropwise at room temperature. The reaction mixture was heated to reflux for 12 h. The borane was quenched with methanol (200 mL) and the resulting solution was concentrated to dryness. The residue was again co-evaporated with methanol to remove most of the trimethylborate. To the residue was added aq. sodium carbonate (50 g in 500 mL). The mixture was cooled and a white fine precipitate was filtered off to give the title compound. $^1$H NMR ($CDCl_3$, 300 MHz): δ=2.10 (t, 1H, J=6.9 Hz), 4.96 (d, 2H, J=6.9 Hz), 7.09 (dd, 1H, J=8.1, 9.0 Hz), 7.29 (dd, 1H, J=4.8, 9.0 Hz).

2,6-Dichloro-3-fluorobenzoic acid

To a cooled (−5° C.) solution of sodium hydroxide (252 g, 6.3 mol) in water (800 mL) was added bromine (86 mL, 1.68 mol) dropwise. The temperature of the reaction mixture was kept below −5° C. during the addition. A solution of 1-(2,6-Dichloro-3-fluorophenyl)ethanone (100 g, 480 mmol) in dioxane (800 ml) was added to the solution of sodium hypobromide in 1 h while maintaining the temperature below 0° C. The reaction mixture was warmed to room temperature and stirred for 2 h. After the TLC showed absence of starting material, the excess sodium hypobromide was destroyed with sodium sulfite (100 g in 100 mL water). The resulting solution was heated to 90° C. for 2 h. The reaction mixture was acidified with conc. HCl with vigorous stirring. The acidic solution was concentrated to remove all the dioxane and then extracted with dichloromethane (2×500 mL). The organic layer was dried ($Na_2SO_4$) and concentrated to give an oily residue, which after trituration with hexanes gave the title compound as a white solid. $^1$H NMR ($CDCl_3$, 300 MHz): δ=7.20 (dd, 1H, J=8.7, 8.4 Hz), 7.33 (dd, 1H, J=9.3, 4.5 Hz).

5-Bromo-3-[(1S)-(2-chloro-3-fluoro-6-methoxyphenyl)ethyl]-1H-pyrrolo[2,3-b]pyridine The racemic mixture of 5-Bromo-3-[1-(2-chloro-3-fluoro-6-methoxyphenyl)ethyl]-1H-pyrrolo[2,3-b]pyridine was separated into the enantiomers by SFC using a chiral stationary phase (column: ChiralPak AD-20 um, 300×30 mm I.D.; solvent 50:50 $scCO_2$/methanol isocratic, flow rate of 120 mL/min; UV detection at 265 nm; racemic material dissolved in THF/MeOH at 80 mg/mL). Optical rotation: $[\alpha]^{25}_D$=−69.0° (c=1.0, DCM). Analytical SFC (ChiralPak AD-3, 150×4.6 mm I.D., solvent 60:40 $scCO_2$/methanol (0.05% diethylamine) isocratic, flow rate 2.4 mL/min, UV detection at 220 nm): $t_R$=4.5 min.

5-Bromo-3-[(1R)-(2-chloro-3-fluoro-6-methoxyphenyl)ethyl]-1H-pyrrolo[2,3-b]pyridine Optical rotation: $[\alpha]^{25}_D$=69.6° (c=1.0, MeOH). Analytical SFC (ChiralPak AD-3, 150×4.6 mm I.D., solvent 60:40 $scCO_2$/methanol (0.05% diethylamine) isocratic, flow rate 2.4 mL/min, UV detection at 220 nm): $t_R$=2.7 min.

5-Bromo-3-[1-(2-chloro-3-fluoro-6-methoxyphenyl)ethyl]-1H-pyrrolo[2,3-b]pyridine To a solution of 5-bromo-3-[(2-chloro-3-fluoro-6-methoxyphenyl)-hydroxymethyl]-1H-pyrrolo[2,3-b]pyridine (30 g, 78 mmol) in THF (500 mL) at −60° C. was added $BF_3.OEt_2$ (78 mL, 615 mol) and the reaction mixture was stirred for 30 min. A cold 0.58 M solution of dimethyl zinc in ether (900 mL, 522 mmol) was added to the reaction flask through canula under nitrogen slowly. After the addition was completed the mixture stirred for 30 minutes at −50° C. to −60° C. and the temperature was brought to RT over a period of 3 h. It was then warmed to 40-45° C. and stirred at this temperature overnight. Some dimethyl zinc vapors which escape through nitrogen trap after from reflux condenser were quenched with ammonium chloride solution. The reaction mixture was cooled again to −50° C. and slowly quenched with saturated ammonium chloride solution (500 mL) added through septum from a syringe. The mixture was warmed to RT, further diluted with water (200 mL) and ethyl acetate (200 mL) and the layers were separated. The aq. phase was extracted with ethyl acetate (2×100 mL) and the combined organic phase was washed with water followed by brine, dried ($Na_2SO_4$) and concentrated to give a yellow residue, which on trituration with hexanes gave solid. The solids were dissolved in methylene chloride:ethyl acetate (90:10, 100 mL) and passed through silica-gel fast filtration type column, using methylene chloride-ethyl acetate (97:3). The eluent on evaporation gave solids (25 g) which were recrystallized from ethyl acetate-diisopropyl ether, to give the title compound (15 g, 50%). $^1$H NMR (CDCl$_3$, 400 MHz): δ=1.76 (d, 3H, J=7.2 Hz), 3.67 (s, 3H), 5.05 (q, 1H, J=7.2 Hz), 6.71 (dd, 1H, J=4.0, 4.4 Hz), 7.00 (t, 1H, J=8.0 Hz), 7.76 (s, 1H), 8.25 (s, 1H), 9.25 (s, 1H). $^{13}$C NMR (CDCl$_3$, 100 MHz): δ=154.84, 152.39 ($J_{CF}$=238.3 Hz), 147.14, 142.41, 132.70, 128.38, 125.68, 120.96, 120.40 ($J_{CF}$=17.9 Hz), 115.57, 114.58 ($J_{CF}$=22.7 Hz), 111.88 ($J_{CF}$=7.4 Hz), 110.32, 56.70, 30.26, 17.42.

The dimethyl zinc/ether solution used above was prepared as follows (alternatively, the commercial 2M solution in toluene can be used):

In a three liter two neck flask thionyl chloride (100 mL) was added to zinc chloride (98 g, 719 mmol) and the mixture was heated under reflux for 2 h. It was cooled to about 50° C. and thionyl chloride was distilled under vacuum over a period of 1 h. The solid residues were further dried under vacuum at 45° C. for about an hour to ensure complete removal of thionyl chloride. The flask was then cooled to RT and equipped with a dropping funnel and a reflux condenser and to it 750 mL of dry ether was added under nitrogen. To the mixture MeMgBr (3M solution in ether, 480 mL, 1.44 mol) was added dropwise under stirring over a period of 1 h to keep gentle reflux of ether. After the addition, the mixture was further stirred for 1 h, cooled in an ice bath and kept in the refrigerator under nitrogen. The solution above the sedimentation was Zn(Me)$_2$ (0.58 molar solution), which was used in the next reaction. Note: the solution of dimethyl zinc is highly flammable when exposed to air and should be handled very carefully.

5-Bromo-3-[(2-chloro-3-fluoro-6-methoxyphenyl)-hydroxymethyl]-1H-pyrrolo[2,3-b]pyridine A solution of 2-chloro-3-fluoro-6-methoxybenzaldehyde (10.55 g, 55.82 mmol), 5-bromo-7-azaindole (10.0 g, 50.76 mmol) and KOH (4.0 g, 71 mmol) in methanol (200 mL) was stirred at ambient temperature for 12 h. The reaction mixture was quenched with water and the crystallizing solid was filtered and dried to give the title compound as a white solid. $^1$H NMR (DMSO-d$_6$, 300 MHz): □ δ=3.71 (s, 3H), 5.69 (d, 1H, J=6.3 Hz), 6.55 (d, 1H, J=4.5 Hz), 7.07 (dd, 1H, J=4.5, 4.2 Hz), 7.19 (s, 1H), 7.32 (t, J=8.0 Hz), 8.30 (s, 1H), 9.60 (s, 1H), 11.38 (s, br, 1H).

2-Chloro-3-fluoro-6-methoxybenzaldehyde

To a solution of 3-chloro-4-fluoroanisole (28.5 g, 178 mmol) in t-butyl methyl ether (200 mL, dried over anhydrous MgSO$_4$) at −78° C. was added 2.5 M n-butyl lithium in hexanes (107 mL, 267.5 mmol). After 3 h, methyl formate (18.76 mL) was added drop-wise while keeping the temperature below −60° C. The reaction mixture was quenched with sat. aq. ammonium chloride (250 mL) after 45 minutes and the organic layer was separated. The aq. layer was extracted with ethyl acetate (2×100 mL) and the combined organic layer was washed with water (200 mL) followed by brine, dried (Na$_2$SO$_4$) and concentrated to give a residue which on trituration with hexanes gave solids. The solids were filtered, taken again in hexanes and heated over steam bath. It was cooled, the light yellow desired product filtered and air dried to give the title compound. $^1$H NMR (400 MHz, CDCl$_3$): δ=10.48 (d, J=0.8 Hz, 1H), 7.31 (dd, J=9.4, 7.8 Hz, 1H), 6.88 (dd, J=7.8, 3.8 Hz, 1H), 3.92 (s, 3H).

5-Bromo-3-[(1S)-(2-chloro-6-ethoxy-3-fluorophenyl)ethyl]-1H-pyrrolo[2,3-b]pyridine The racemic mixture of 5-Bromo-3-[1-(2-chloro-6-ethoxy-3-fluorophenyl)ethyl]-1H-pyrrolo[2,3-b]pyridine was separated into the enantiomers by SFC using a chiral stationary phase. Optical rotation: $[α]^{25}_D$=−76.2° (c=1.0, MeOH). Analytical SFC (ChiralPak AD-3, 150×4.6 mm I.D., solvent 60:40 scCO$_2$/methanol (0.05% diethylamine) isocratic, flow rate 2.4 mL/min, UV detection at 220 nm): $t_R$=3.2 min.

5-Bromo-3-[(1R)-(2-chloro-6-ethoxy-3-fluorophenyl)ethyl]-1H-pyrrolo[2,3-b]pyridine Optical rotation: $[α]^{25}_D$=76.4° (c=1.0, MeOH). Analytical SFC (ChiralPak AD-3, 150×4.6 mm I.D., solvent 60:40 scCO$_2$/methanol (0.05% diethylamine) isocratic, flow rate 2.4 mL/min, UV detection at 220 nm): $t_R$=2.7 min.

5-Bromo-3-[1-(2-chloro-6-ethoxy-3-fluorophenyl)ethyl]-1H-pyrrolo[2,3-b]pyridine

To a cold (−78° C.) solution of 5-Bromo-3-[(2-chloro-6-ethoxy-3-fluorophenyl)-methoxymethyl]-1H-pyrrolo[2,3-b]pyridine (3.0 g, 7.2 mmol) in THF (30 mL) was added BF$_3$.OEt$_2$ (7.1 mL, 56.3 mmol). The reaction mixture was stirred for 1 h, and 2M solution of dimethylzinc in toluene (28 mL, 56 mmol) was added dropwise. The reaction mixture was stirred for 12 h at 50° C. and was quenched with saturate aq. ammonium chloride. The organic layer was separated and aqueous layer was extracted with ethyl acetate (2×30 mL). The combined organic phase was washed with brine, dried (Na$_2$SO$_4$) and concentrated to give a yellowish residue. The residue was adsorbed on silica and purified (100% DCM→5% methanol/DCM) by small pad of silica. The resulting solid was recrystallized with diisopropyl ether to give the title compound. $^1$H NMR (CDCl$_3$, 400 MHz): δ=1.25 (t, 3H, J=7.0 Hz), 1.79 (d, 3H, J=7.0 Hz), 3.74 (bs, 1H), 3.96 (q, 1H, J=7.0 Hz), 5.05 (q, 1H, J=7.0 Hz), 6.66-6.69 (m, 1H), 6.97 (t, 1H, J=9.0 Hz), 7.69 (s, 1H), 8.25 (s, 1H), 9.24 (s, 1H).

5-Bromo-3-[(2-chloro-6-ethoxy-3-fluorophenyl)-methoxymethyl]-1H-pyrrolo[2,3-b]pyridine A solution of 2-Chloro-6-ethoxy-3-fluorobenzaldehyde (2.0 g, 9.8 mmol), 5-bromo-7-azaindole (1.8 g, 8.9 mmol) and KOH (797 mg, 14.2 mmol) in methanol (30 mL) was stirred for 48 h at room temperature. The reaction mixture was concentrated to dryness and diluted with saturated aq. ammonium chloride. The aq. layer was extracted with ethyl acetate (2×30 mL). The combined organic layers were dried (Na$_2$SO$_4$) and concentrated to give a residue that was purified by column chromatography (5/95, methanol/DCM) to give the title compound as foamy solid. $^1$H NMR (CDCl$_3$, 400 MHz): δ=1.35 (t, 3H, J=7.2 Hz), 3.43 (s, 3H), 4.0 (q, 1H, J=7.2 Hz), 4.07 (q, 1H, J=7.2 Hz), 6.39 (s, 1H), 6.81 (dd, 1H, J=4.0, 9.2 Hz), 7.01 (t, 1H, J=8.4 Hz), 8.06 (d, 1H, J=2.0 Hz), 8.29 (d, 1H, J=2.0 Hz), 9.49 (s, 1H).

2-Chloro-6-ethoxy-3-fluorobenzaldehyde

To a cold (−78° C.) solution of 2-Chloro-4-ethoxy-1-fluorobenzene (5.0 g, 28.6 mmol) in THF (100 mL) was added LDA (1.8 M in THF/heptane/ethylbenzene; 40 mL, 72 mmol). After 7 minutes, DMF (7 mL, 85.8 mmol) was added dropwise while keeping the temperature below −60° C. After 40 minutes, the reaction mixture was quenched with sat. aq. ammonium chloride. The organic layer was separated and the aq. layer was washed with ethyl acetate (2×50 mL). The combined organic layer was washed with water (30 mL) followed by brine. The organic layer was dried ($Na_2SO_4$) and concentrated to give a 1:1 mixture of the target compound and a regioisomeric aldehyde. The mixture was purified by column chromatography (5/95, ethyl acetate/hexanes) to give the title compound as a white solid. $^1$H NMR ($CDCl_3$, 400 MHz): δ=1.46 (t, 3H, J=7.2 Hz), 4.11 (q, 2H, J=7.2 Hz), 6.84-6.86 (m, 1H), 7.25-7.28 (m, 1H), 10.48 (s, 1H).

2-Chloro-4-ethoxy-1-fluorobenzene

A mixture of 3-chloro-4-fluorophenol (2.0 g, 13.7 mmol), diethylsulfate (1.58 mL, 17.8 mmol) and $K_2CO_3$ (9.4 g, 68.5 mmol) in acetone (20 mL) was heated under refluxed for 3 h. The reaction mixture was filtered and concentrated. The residue was diluted with ethyl acetate (50 mL), washed with water (30 mL) and brine. The organic layer was dried ($Na_2SO_4$) and concentrated to give the title compound as a liquid. $^1$H NMR ($CDCl_3$, 400 MHz): δ=1.39 (t, 3H, J=7.2 Hz), 3.97 (q, 2H, J=7.2 Hz), 6.71-6.74 (m, 1H), 6.89-6.91 (m, 1H), 7.02 (t, 1H, J=8.8 Hz).

2-Chloro-6-difluoromethoxy-3-fluorobenzaldehyde

To 2-Chloro-4-difluoromethoxy-3-dimethoxymethyl-1-fluorobenzene (45.0 g, 166 mmol) was added acetic acid containing 20% water (80 ml) and heated at 50° C. for 16 h. The reaction mixture was cooled in an ice bath and basified with saturated aqueous sodium carbonate solution. The reaction mixture was extracted with ethyl acetate (200 mL, 100 ml); the combined organic layers were washed with brine, dried over sodium sulfate, filtered and concentrated to give crude product. It was purified by column chromatography on silica gel, eluting with 10% ethyl acetate in hexane. Pure compound isolated 28.0 g (75% yield). $^1$H NMR ($CDCl_3$, 400 MHz): δ=10.41 (s, 1H), 7.37 (dd, J=8.8, 8.0 Hz, 1H), 7.22 (dd, J=9.2, 4.0 Hz, 1H), 6.58 (t, J=73.0 Hz, 1H).

Alternative Preparation:

To a solution of crude 2-chloro-4-difluoromethoxy-3-dimethoxymethyl-1-fluorobenzene (181 g, 670 mmol) in acetone (650 mL) and water (150 mL) was added Amberlyst-15 resin (540 g, pre-washed with water) and the mixture was stirred using mechanical stirrer for 40 h at RT. The Amberlyst-15 resin was removed by filtration using celite bed on sintered funnel, and the filtrate was evaporated on a rotary evaporator at RT (Note: aldehyde evaporates at higher temperatures under reduced pressure). The residue was purified by column chromatography on silica gel using ethyl acetate/hexanes (5% to 10%) to obtain the title compound (60 g, 40%).

2-Chloro-4-difluoromethoxy-3-dimethoxymethyl-1-fluorobenzene

In a single neck flask, 3-chloro-2-dimethoxymethyl-4-fluorophenol (22 g, 100 mmol), sodium chlorodifluoroacetate (30.3 g, 200 mmol) and potassium carbonate (27.5 g, 200 mmol) were taken up in DMF (145 mL) under nitrogen atmosphere and heated at 90° C. for 16 h. The reaction mixture was cooled to room temperature, poured into water and extracted with ethyl acetate (2×200 mL, 100 mL). The combined organic layers were washed with water, dried over sodium sulfate, filtered and concentrated to give crude product, which was purified by column chromatography on silica gel using 10% ethyl acetate in hexane as an eluent to give 17 g (63% yield) of the title compound. $^1$H NMR ($CDCl_3$, 300 MHz): δ=7.11-7.13 (m, 2H), 6.45 (t, J=75 Hz, 1H), 5.70 (s, 1H), 3.46 (s, 6H).

3-Chloro-2-dimethoxymethyl-4-fluorophenol

2-Chloro-3-fluoro-6-hydroxybenzaldehyde (79.0 g, 452 mmol) was taken in a single neck flask equipped with a condenser and a nitrogen inlet. To this, trimethylorthoformate (96.0 g, 99.0 mL, 905 mmol) and a solution of ammonium nitrate (3.6 g, 45 mmol) in methanol (40 mL) were added and heated to reflux for 16 hours. The reaction mixture was cooled to room temperature, poured into saturated aqueous sodium carbonate solution, stirred for few minutes, and extracted with ethyl acetate (300 mL, 200 mL). The combined organic layers were washed with water, dried over sodium sulfate, filtered and concentrated to give crude product. It was purified by column chromatography on silica gel using 10% ethyl acetate in hexane as eluent to give 65 g (64% yield) of the title compound. $^1$HNMR ($CDCl_3$, 300 MHz): δ=8.52 (s, 1H), 7.04 (dd, J=9.0 Hz, 1H), 6.74-6.78 (m, 1H), 5.84 (s, 1H), 3.47 (s, 6H).

2-Chloro-3-fluoro-6-hydroxybenzaldehyde

2-Chloro-3-fluoro-6-methoxybenzaldehyde (46.0 g, 245 mmol) was added in a three neck flask equipped with a nitrogen inlet, a thermometer and an addition funnel. DCM (800 mL) was added and cooled to −70 to −78° C. using an acetone/dry ice bath. Boron tribromide (25.4 mL, 269 mmol) was diluted in 200 mL of dichloromethane and added to the reaction mixture slowly over a period of 1 h. The reaction mixture was allowed to warm to room temperature and stirred for 16 h. Then the reaction mixture was cooled to 0° C. in an ice bath and quenched by adding methanol (150 mL) over a period of 30 minutes and stirred at room temperature for 20 min. The solvents were removed, and the residue was diluted with dichloromethane and washed with aq. sodium bicarbonate solution followed by water. The organic layer was dried over sodium sulfate, filtered and concentrated to give crude product. It was purified by column chromatography on silica gel eluting with 2→3% methanol in dichloromethane, giving 34 g (80% yield) of the title compound. $^1$HNMR (300 MHz, $CDCl_3$): δ=11.68 (s, 1H), 10.39 (s, 1H), 7.26-7.35 (m, 1H), 6.86-6.90 (m, 1H).

EXAMPLES

The following are strictly nonlimiting examples.

Example 1

3-[(1S)-1-(2-Chloro-3-fluoro-6-methoxyphenyl)ethyl]-5-(3-methyl-1H-pyrazol-4-yl)-1H-pyrrolo[2,3-b]pyridine

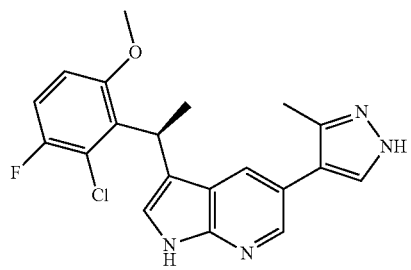 [SMILES: COc1ccc(F)c(Cl)c1[C@@H](C)c1c[nH]c2ncc(-c3c[nH]nc3C)cc12]

A mixture of 5-Bromo-3-[(S)-1-(2-chloro-3-fluoro-6-methoxyphenyl)-ethyl]-1H-pyrrolo[2,3-b]pyridine (12 mg, 0.031 mmol), 3-methyl-4-(4,4,5,5-tetramethyl-[1,3,2]dioxaborolan-2-yl)-1H-pyrazole (13.0 mg, 0.0626 mmol), potassium carbonate (0.0130 g, 0.0938 mmol) and 4:1 Dioxane:water (4:1,1,4-Dioxane:H$_2$O, 0.31 mL, 3.1 mmol) were added to a microwave vessel and the vessel was degassed 3×. The reaction was heated in the microwave at 100° C. for 30 min. Reaction mixture was concentrated in vacuo and purified by HPLC to afford the title compound. $^1$H NMR (400 MHz, CD$_3$OD): δ=1.82 (d, J=7.3 Hz, 3H), 2.23 (s, 3H), 3.66 (br. s., 3H), 5.12 (d, J=6.8 Hz, 1H), 6.91 (dd, J=9.0, 4.2 Hz, 1H), 7.10 (t, J=9.0 Hz, 1H), 7.36 (d, J=1.3 Hz, 1H), 7.48 (s, 1H), 7.62 (br. s., 1H), 8.18 (d, J=1.8 Hz, 1H). MS (ES+): m/z=384.96/386.94 (100/65) [MH$^+$]. HPLC: t$_R$=3.19 min (ZQ3, polar_5 min).

Example 2

3-[(1S)-1-(2-Chloro-3-fluoro-6-methoxyphenyl)ethyl]-5-(1,3-dimethyl-1H-pyrazol-4-yl)-1H-pyrrolo[2,3-b]pyridine

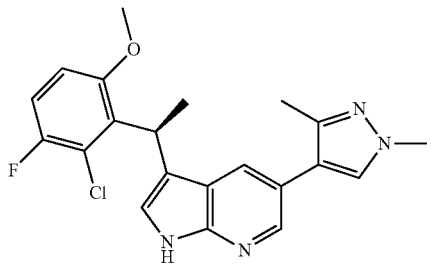 [SMILES: COc1ccc(F)c(Cl)c1[C@@H](C)c1c[nH]c2ncc(-c3cn(C)nc3C)cc12]

Procedure from Example 1 was followed. $^1$H NMR (400 MHz, CD$_3$OD): δ=1.81 (d, J=7.1 Hz, 3H), 2.14 (s, 3H), 3.56-3.71 (m, 3H), 3.85 (s, 3H), 5.11 (q, J=6.8 Hz, 1H), 6.90 (dd, J=9.1, 4.0 Hz, 1H), 7.09 (t, J=8.8 Hz, 1H), 7.35 (d, J=1.3 Hz, 1H), 7.47 (s, 1H), 7.63 (s, 1H), 8.14 (s, 1H). MS (ES+): m/z=399.00/400.97 (100/80) [MH+]. HPLC: t$_R$=3.42 min (ZQ3, polar_5 min).

Example 3

3-[(1S)-1-(2-Chloro-3-fluoro-6-methoxyphenyl)ethyl]-5-(1,5-dimethyl-1H-pyrazol-4-yl)-1H-pyrrolo[2,3-b]pyridine

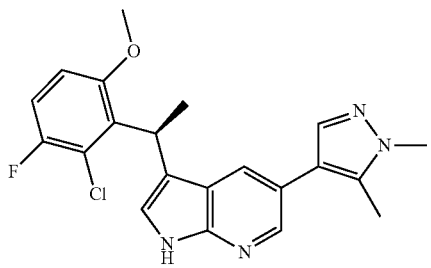 [SMILES: COc1ccc(F)c(Cl)c1[C@@H](C)c1c[nH]c2ncc(-c3cnn(C)c3C)cc12]

Procedure from Example 1 was followed. $^1$H NMR (400 MHz, CD$_3$OD): δ=1.82 (d, J=7.3 Hz, 3H), 2.22 (s, 3H), 3.55-3.73 (m, 3H), 3.84 (s, 3H), 5.12 (q, J=6.7 Hz, 1H), 6.91 (dd, J=9.0, 4.2 Hz, 1H), 7.10 (t, J=8.8 Hz, 1H), 7.36 (s, 1H), 7.38-7.48 (m, 2H), 8.13 (d, J=1.8 Hz, 1H). MS (ES+): m/z=399.00/400.97 (100/80) [MH$^+$]. HPLC: t$_R$=3.44 min (ZQ3, polar_5 min).

Example 4

3-[(1S)-1-(2-Chloro-3-fluoro-6-methoxyphenyl)ethyl]-5-(1,3,5-trimethyl-1H-pyrazol-4-yl)-1H-pyrrolo[2,3-b]pyridine

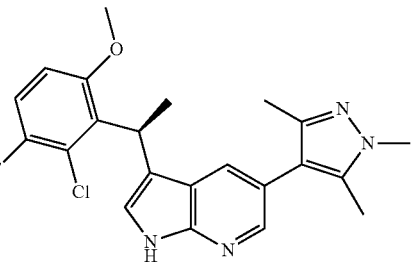

Procedure from example 1 was followed. $^1$H NMR (400 MHz, CD$_3$OD): δ=1.85 (d, J=7.3 Hz, 3H), 2.00-2.13 (m, 3H), 2.18 (s, 3H), 3.71 (s, 3H), 3.81 (s, 3H), 5.18 (d, J=7.1 Hz, 1H), 6.96 (dd, J=9.1, 4.0 Hz, 1H), 7.15 (t, J=8.8 Hz, 1H), 7.66 (d, J=1.5 Hz, 1H), 7.77 (s, 1H), 8.21 (s, 1H). MS (ES+): m/z=412.98/415.98 (100/70) [MH$^+$]. HPLC: t$_R$=3.49 min (ZQ3, polar_5 min).

Example 5

1-(4-{3-[(1S)-1-(2-Chloro-3-fluoro-6-methoxyphenyl)ethyl]-1H-pyrrolo[2,3-b]pyridin-5-yl}-3,5-dimethyl-1H-pyrazol-1-yl)-2-methylpropan-2-ol

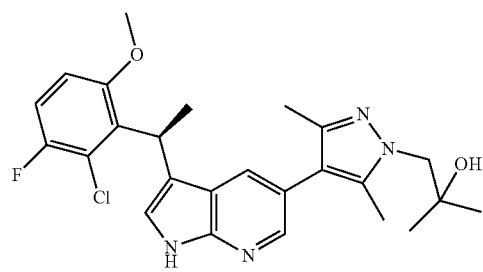 [SMILES: COc1ccc(F)c(Cl)c1[C@@H](C)c1c[nH]c2ncc(-c3c(C)nn(CC(C)(C)O)c3C)cc12]

A mixture of 5-bromo-3-[(S)-1-(2-chloro-3-fluoro-6-methoxyphenyl)-ethyl]-1H-pyrrolo[2,3-b]pyridine (20.0 mg, 0.0521 mmol), 1-[3,5-dimethyl-4-(4,4,5,5-tetramethyl-1,3,2-dioxaborolan-2-yl)-1H-pyrazol-1-yl]-2-methylpropan-2-ol (30.7 mg, 0.104 mmol), Pd(PPh$_3$)$_4$ (3.01 mg, 0.00261 mmol), K$_2$CO$_3$ (21.6 mg, 0.156 mmol) and 4:1 dioxane:water was microwaved at 100° C. for 45 min. The solution was used directly for HPLC purification, and the fractions containing the pure product were concentrated in vacuo to afford the title compound as a white solid. $^1$H NMR (400 MHz, CD$_3$OD): δ=1.23 (s, 3H), 1.24 (s, 3H), 1.80 (d, J=7.3 Hz, 3H), 2.07 (s, 3H), 2.17 (s, 3H), 3.65 (br. s., 3H), 4.01 (s, 2H), 5.06-5.15 (m, 1H), 6.89 (dd, J=9.1, 4.0 Hz, 1H), 7.08 (t, J=8.8 Hz, 1H), 7.32 (s, 1H), 7.36 (d, J=1.3 Hz, 1H), 7.99 (d, J=1.8 Hz, 1H). MS (ES+): m/z=471.03/473.01 (100/50) [MH+]. HPLC: $t_R$=3.47 min (polar__5 min, ZQ3).

1-[3,5-Dimethyl-4-(4,4,5,5-tetramethyl-1,3,2-dioxaborolan-2-yl)-1H-pyrazol-1-yl]-2-methylpropan-2-ol A solution of 3,5-dimethylpyrazole-4-boronic acid, pinacol ester (200.0 mg, 0.9005 mmol) in DMF (4 mL, 50 mmol) was added sodium hydride (21.61 mg, 0.9005 mmol), and stirred for 10 min. Oxirane, 2,2-dimethyl- (0.4 mL, 4 mmol) was added, and the mixture was heated to 80° C. overnight. The material was extracted with EtOAc, washing with water (3×). The organic layer was concentrated in vacuo to afford the title compound as a brown oil. MS (ES+): m/z=295.06 (100) [MH+]. HPLC: $t_R$=3.29 min (polar__5 min, ZQ3).

Example 6 trans-4-(4-{3-[(1S)-1-(2-Chloro-3-fluoro-6-methoxyphenyl)ethyl]-1H-pyrrolo[2,3-b]pyridin-5-yl}-3,5-dimethyl-1H-pyrazol-1-yl)cyclohexanol

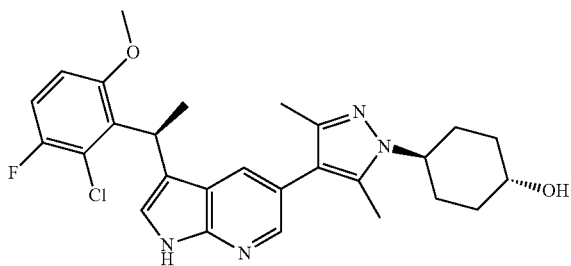 [SMILES: COc1ccc(F)c(Cl)c1[C@@H](C)c1c[nH]c2ncc(-c3c(C)nn([C@H]4CC[C@H](O)CC4)c3C)cc12]

A mixture of 3-[(S)-1-(2-chloro-3-fluoro-6-methoxyphenyl)-ethyl]-5-(4,4,5,5-tetramethyl-[1,3,2]dioxaborolan-2-yl)-1H-pyrrolo[2,3-b]pyridine (30.0 mg, 0.0696 mmol), 1-(trans-4-{[tert-butyl(dimethyl)silyl]oxy}cyclohexyl)-4-iodo-3,5-dimethyl-1H-pyrazole (60.5 mg, 0.139 mmol), Pd(PPh$_3$)$_4$ (4.02 mg, 0.00348 mmol), NaHCO$_3$ (17.6 mg, 0.209 mmol) and 4:1 dioxane:water was heated to 80° C. overnight. 2 M of HCl in H$_2$O (0.5 mL, 1 mmol) was added, and the solution was stirred at rt for 1 h. The material was concentrated in vacuo, redissolved in MeOH (1 mL) and passed through a syringe filter pad for HPLC purification. The fractions containing the pure product were concentrated in vacuo to afford the title compound as a white solid. $^1$H NMR (400 MHz, CD$_3$OD): δ=1.42-1.57 (m, 2H), 1.80 (d, J=7.1 Hz, 3H), 1.87-2.02 (m, 3H), 2.03 (s, 3H), 2.04-2.12 (m, 3H), 2.14 (s, 3H), 3.64 (br. s., 3H), 3.66-3.72 (m, 1H), 4.11 (tt, J=11.5, 3.9 Hz, 1H), 5.04-5.14 (m, 1H), 6.89 (dd, J=9.2, 4.2 Hz, 1H), 7.08 (t, J=8.8 Hz, 1H), 7.28 (s, 1H), 7.35 (d, J=1.3 Hz, 1H), 7.95 (br. s., 1H). MS (ES+): m/z=497.21/499.21 (100/50) [MH+]. HPLC: $t_R$=1.40 min (polar__3 min, UPLC-ACQUITY).

1-(trans-4-{[tert-butyl(dimethyl)silyl]oxy}cyclohexyl)-4-iodo-3,5-dimethyl-1H-pyrazole A mixture of trans-4-(4-iodo-3,5-dimethyl-1H-pyrazol-1-yl)cyclohexanol (206.0 mg, 0.6434 mmol), tert-butyldimethylsilyl chloride (0.194 g, 1.29 mmol), 4-dimethylaminopyridine (20 mg, 0.1 mmol), imidazole (131 mg, 1.93 mmol) and DCM (4 mL, 60 mmol) was stirred at rt for 20 min. The material was transferred to a separatory funnel, extracting with DCM and sat. NaHCO$_3$. The organic layer was dry-loaded onto silica gel for column chromatography, eluting with 3% EtOAc/hexanes. The fractions containing the pure product were concentrated in vacuo to afford the title compound as a clear oil. MS (ES+): m/z=435.14 (100) [MH+]. HPLC: $t_R$=2.26 min (polar__3 min, UPLC-ACQUITY).

trans-4-(4-iodo-3,5-dimethyl-1H-pyrazol-1-yl)cyclohexanol

A mixture of 1-(1,4-dioxaspiro[4.5]dec-8-yl)-4-iodo-3,5-dimethyl-1H-pyrazole (425.0 mg, 1.173 mmol), pyridinium p-toluenesulfonate (589.7 mg, 2.347 mmol), acetone (20 mL, 300 mmol) and H$_2$O (20 mL, 1000 mmol) was heated to 60° C. overnight to form the ketone. The organic solvent was removed in vacuo, and the material was extracted with DCM and water. The organic layer was dried in vacuo, redissolved in EtOH (10 mL, 200 mmol), and sodium borohydride (53.27 mg, 1.408 mmol) was added. The mixture was stirred at rt for 3 h. The material was concentrated in vacuo, extracted with EtOAc, and washed with water (3×). The organic layer was dry-loaded onto silica gel for column chromatography, eluting with 1-2% MeOH/diethyl ether. The cis product eluted first, followed by the trans product. The fractions containing the trans product were concentrated in vacuo to afford the title compound as white solid. $^1$H NMR (400 MHz, DMSO-d$_6$): δ=1.26-1.41 (m, 2H), 1.69-1.83 (m, 4H), 1.85-1.93 (m, 2H), 2.07 (s, 3H), 2.24 (s, 3H), 3.40-3.50 (m, 1H), 4.01-4.12 (m, 1H), 4.62 (d, J=4.3 Hz, 1H). MS (ES+): m/z=321.04 (100) [MH+]. HPLC: $t_R$=1.28 min (polar__3 min, UPLC-ACQUITY).

1-(1,4-Dioxaspiro[4.5]dec-8-yl)-4-iodo-3,5-dimethyl-1H-pyrazole

To a solution of 3,5-dimethyl-4-iodopyrazole (400.0 mg, 1.802 mmol) in DMF (7 mL, 100 mmol) was added sodium hydride (56.20 mg, 2.342 mmol), and the mixture was stirred at rt for 10 min. A solution of 1,4-dioxaspiro[4.5]dec-8-yl 4-methylbenzenesulfonate (619.1 mg, 1.982 mmol), prepared according to U.S. Pat. No. 4,360,531 example 1.B, in DMF was added, and the mixture was heated to 50° C. overnight. The material was extracted with EtOAc, and washed with water (3×). The organic layer was dry-loaded onto silica gel for column chromatography, eluting with 20-30% EtOAc/hexanes. The fractions containing the pure product were concentrated in vacuo to afford the title compound as a clear oil. $^1$H NMR (400 MHz, DMSO-d$_6$): δ=1.61-1.80 (m, 6H), 1.94-2.06 (m, 2H), 2.08 (s, 3H), 2.25 (s, 3H), 3.82-3.93 (m, 4H), 4.23 (tt, J=11.5, 3.7 Hz, 1H). MS (ES+): m/z=364.07 (100) [MH+]. HPLC: $t_R$=1.51 min (polar__3 min, UPLC-ACQUITY).

Example 7

1-(4-{3-[(1S)-1-(2-Chloro-3-fluoro-6-methoxyphenyl)ethyl]-1H-pyrrolo[2,3-b]pyridin-5-yl}-3-methyl-1H-pyrazol-1-yl)-2-methylpropan-2-ol

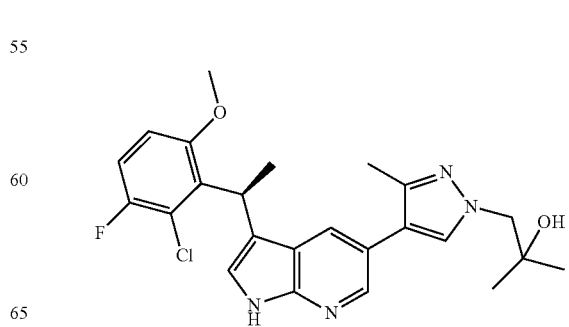

Prepared using the procedure described for Example 5, using 2-Methyl-1-[3-methyl-4-(4,4,5,5-tetramethyl-1,3,2-dioxaborolan-2-yl)-1H-pyrazol-1-yl]propan-2-ol in place of 1-[3,5-dimethyl-4-(4,4,5,5-tetramethyl-1,3,2-dioxaborolan-2-yl)-1H-pyrazol-1-yl]-2-methylpropan-2-ol. $^1$H NMR (400 MHz, CD$_3$OD): δ=1.19 (s, 6H), 1.80 (d, J=7.3 Hz, 3H), 2.16 (s, 3H), 3.64 (br. s., 3H), 4.03 (s, 2H), 5.10 (q, J=7.4 Hz, 1H), 6.89 (dd, J=9.2, 4.2 Hz, 1H), 7.08 (t, J=8.8 Hz, 1H), 7.34 (d, J=1.3 Hz, 1H), 7.48 (s, 1H), 7.67 (s, 1H), 8.16 (br. s., 1H). MS (ES+): m/z=457.17/458.18 (100/50) [MH$^+$]. HPLC: $t_R$=1.48 min (polar_3 min, UPLC-ACQUITY).

2-Methyl-1-[3-methyl-4-(4,4,5,5-tetramethyl-1,3,2-dioxaborolan-2-yl)-1H-pyrazol-1-yl]propan-2-ol A solution of 1-(4-iodo-3-methyl-1H-pyrazol-1-yl)-2-methylpropan-2-ol (250.0 mg, 0.8925 mmol) in THF (10 mL, 200 mmol) was added 2 M of isopropylmagnesium chloride in THF (1.339 mL, 2.678 mmol) at rt, and the reaction was allowed to stir for 1 h. 2-Methoxy-4,4,5,5-tetramethyl-1,3,2-dioxaborolane (0.5850 mL, 3.570 mmol) was then added, and the mixture was stirred at rt for 2 h. Sat. NH$_4$Cl was added to quench, and the organic solvent was removed in vacuo. The material was extracted with DCM and water, and the organic layer was concentrated in vacuo to afford the title compound as a white solid. The material was used in the next step without further purification.

1-(4-Iodo-3-methyl-1H-pyrazol-1-yl)-2-methylpropan-2-ol and 1-(4-Iodo-5-methyl-1H-pyrazol-1-yl)-2-methylpropan-2-ol A mixture of 4-iodo-5-methyl-1H-pyrazole (500.0 mg, 2.404 mmol), oxirane, 2,2-dimethyl- (2 mL, 20 mmol), K$_2$CO$_3$ (398.7 mg, 2.885 mmol), 1,4,7,10,13,16-hexaoxacyclooctadecane (63.54 mg, 0.2404 mmol) and DMF (10 mL, 100 mmol) was heated to 70° C. overnight. The solution was extracted with EtOAc, and washed with water (3×). The organic layer was dry-loaded onto silica gel for column chromatography, eluting with 5% MeOH/Et$_2$O. The fractions containing the pure product were concentrated in vacuo to afford the title compounds as white solids. 3-methyl isomer: $^1$H NMR (400 MHz, DMSO-d$_6$): δ=1.03 (s, 6H), 2.10 (s, 3H), 3.92 (s, 2H), 4.66 (s, 1H), 7.68 (s, 1H). 5-methyl isomer: $^1$H NMR (400 MHz, DMSO-d$_6$): δ=1.08 (s, 6H), 2.29 (s, 3H), 4.01 (s, 2H), 4.63 (s, 1H), 7.44 (s, 1H).

Example 8

1-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)-2-methylpropan-2-ol

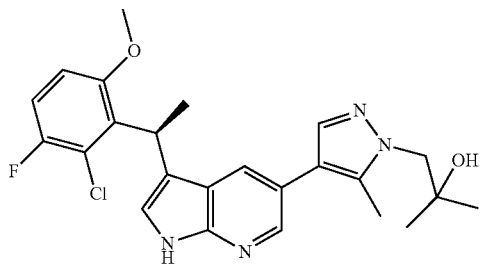 [SMILES: COc1ccc(F)c(Cl)c1[C@@H](C)c1c[nH]c2ncc(-c3cnn(CC(C)(C)O)c3C)cc12]

Prepared using the procedure described for Example 5, using 2-Methyl-1-[5-methyl-4-(4,4,5,5-tetramethyl-1,3,2-dioxaborolan-2-yl)-1H-pyrazol-1-yl]propan-2-ol in place of 1-[3,5-dimethyl-4-(4,4,5,5-tetramethyl-1,3,2-dioxaborolan-2-yl)-1H-pyrazol-1-yl]-2-methylpropan-2-ol. $^1$H NMR (400 MHz, CD$_3$OD): δ=1.24 (d, J=1.8 Hz, 6H), 1.80 (d, J=7.1 Hz, 3H), 2.26 (s, 3H), 3.65 (br. s., 3H), 4.09 (s, 2H), 5.05-5.15 (m, 1H), 6.89 (dd, J=9.0, 4.2 Hz, 1H), 7.08 (t, J=8.8 Hz, 1H), 7.34 (d, J=1.3 Hz, 1H), 7.40-7.46 (m, 1H), 7.51 (s, 1H), 8.13 (d, J=2.0 Hz, 1H). MS (ES+): m/z=457.18/458.17 (100/50) [MH$^+$]. HPLC: $t_R$=1.47 min (polar_3 min, UPLC-ACQUITY).

2-Methyl-1-[5-methyl-4-(4,4,5,5-tetramethyl-1,3,2-dioxaborolan-2-yl)-1H-pyrazol-1-yl]propan-2-ol A solution of 1-(4-iodo-5-methyl-1H-pyrazol-1-yl)-2-methylpropan-2-ol (150.0 mg, 0.5355 mmol) in THF (8 mL, 100 mmol) was added 2 M isopropylmagnesium chloride in THF (0.80 mL, 1.6 mmol) at 0° C., and the reaction was allowed to warm to rt over 30 min. 2-Methoxy-4,4,5,5-tetramethyl-1,3,2-dioxaborolane (0.35 mL, 2.1 mmol) was then added, and the mixture was stirred at rt overnight. Sat. NH$_4$Cl was added to quench, and the organic solvent was removed in vacuo. The material was extracted with DCM and water, and the organic layer was concentrated in vacuo to afford the title compound as a white solid. The material was used in the next step without further purification.

Example 9

(2S)-3-(4-{3-[(1S)-1-(2-Chloro-3-fluoro-6-methoxyphenyl)ethyl]-1H-pyrrolo[2,3-b]pyridin-5-yl}-3-methyl-1H-pyrazol-1-yl)propane-1,2-diol

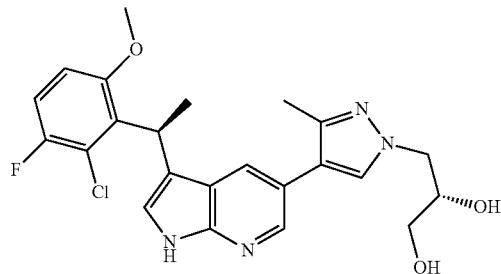 [SMILES: COc1ccc(F)c(Cl)c1[C@@H](C)c1c[nH]c2ncc(-c3cn(C[C@H](O)CO)nc3C)cc12]

Prepared using the procedure described for Example 5. $^1$H NMR (400 MHz, CD$_3$OD): δ=1.80 (d, J=7.1 Hz, 3H), 2.15 (s, 3H), 3.48-3.57 (m, 2H), 3.65 (br. s., 3H), 3.93-4.02 (m, 1H), 4.03-4.11 (m, 1H), 4.25 (dd, J=13.9, 4.0 Hz, 1H), 5.05-5.16 (m, 1H), 6.90 (dd, J=9.2, 3.9 Hz, 1H), 7.09 (t, J=8.8 Hz, 1H), 7.34 (s, 1H), 7.48 (s, 1H), 7.69 (s, 1H), 8.16 (br. s., 1H). MS (ES+): m/z=459.16/461.16 (100/50) [MH$^+$]. HPLC: $t_R$=1.29 min (polar_3 min, UPLC-ACQUITY).

(2S)-3-[3-Methyl-4-(4,4,5,5-tetramethyl-1,3,2-dioxaborolan-2-yl)-1H-pyrazol-1-yl]propane-1,2-diol To a solution of (S)-3-(4-iodo-3-methylpyrazol-1-yl)-propane-1,2-diol (20.0 mg, 0.0709 mmol) and (S)-3-(4-Iodo-5-methylpyrazol-1-yl)-propane-1,2-diol (20.0 mg, 0.0709 mmol) in THF (1 mL, 10 mmol) was added 2 M isopropylmagnesium chloride in THF (0.18 mL, 0.36 mmol) at 0° C., and the reaction was allowed to warm to rt over 30 min. 2-Methoxy-4,4,5,5-tetramethyl-1,3,2-dioxaborolane (0.070 mL, 0.43 mmol) was then added, and the mixture was stirred at rt for 30 min. Sat. NH$_4$Cl was added to quench, and the organic solvent was removed in vacuo. The material was extracted with DCM and water, and the organic layer was concentrated in vacuo to afford the title compound as a clear oil. It was used in the Suzuki coupling without further purification.

Example 10

(2S)-3-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)propane-1,2-diol

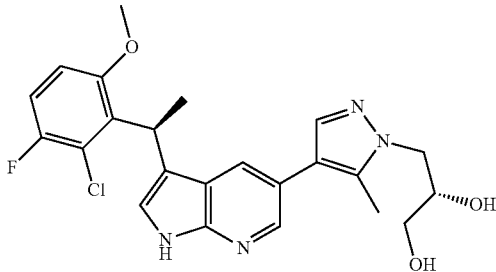 [SMILES: COc1ccc(F)c(Cl)c1[C@@H](C)c1c[nH]c2ncc(-c3cnn(C[C@H](O)CO)c3C)cc12]

Prepared using the procedure described for Example 5. ¹H NMR (400 MHz, CD₃OD): δ=1.80 (d, J=7.1 Hz, 3H), 2.26 (s, 3H), 3.48-3.59 (m, 2H), 3.65 (br. s., 3H), 4.03 (dd, J=7.6, 4.8 Hz, 1H), 4.14 (dd, J=14.1, 7.6 Hz, 1H), 4.20-4.28 (m, 1H), 5.11 (q, J=6.5 Hz, 1H), 6.89 (dd, J=8.8, 4.0 Hz, 1H), 7.08 (t, J=9.0 Hz, 1H), 7.35 (s, 1H), 7.43 (br. s., 1H), 7.51 (s, 1H), 8.13 (br. s., 1H). MS (ES+): m/z=459.16/461.16 (100/50) [MH⁺]. HPLC: t_R=1.28 min (polar_3 min, UPLC-ACQUITY).

(2S)-3-[5-Methyl-4-(4,4,5,5-tetramethyl-1,3,2-dioxaborolan-2-yl)-1H-pyrazol-1-yl]propane-1,2-diol To a solution of (S)-3-(4-Iodo-5-methylpyrazol-1-yl)-propane-1,2-diol (20.0 mg, 0.0709 mmol) in THF (1 mL, 10 mmol) was added 2 M isopropylmagnesium chloride in THF (0.18 mL, 0.36 mmol) at 0° C., and the reaction was allowed to warm to rt over 30 min. 2-Methoxy-4,4,5,5-tetramethyl-1,3,2-dioxaborolane (0.070 mL, 0.43 mmol) was then added, and the mixture was stirred at rt for 30 min. Sat. NH₄Cl was added to quench, and the organic solvent was removed in vacuo. The material was extracted with DCM and water, and the organic layer was concentrated in vacuo to afford the title compound as a clear oil. It was used in the Suzuki coupling without further purification.

Example 11

1-(4-{3-[(1S)-1-(2-Chloro-3-fluoro-6-methoxyphenyl)ethyl]-1H-pyrrolo[2,3-b]pyridin-5-yl}-5-ethyl-1H-pyrazol-1-yl)-2-methylpropan-2-ol

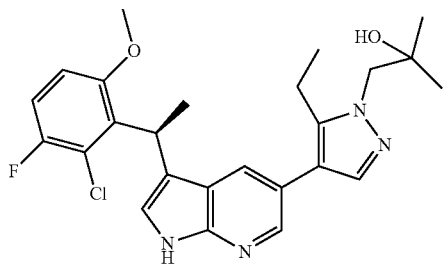 [SMILES: CCc1c(-c2cnc3[nH]cc([C@H](C)c4c(OC)ccc(F)c4Cl)c3c2)cnn1CC(C)(C)O]

Prepared using the procedure described for Example 5, using 1-[5-ethyl-4-(4,4,5,5-tetramethyl-1,3,2-dioxaborolan-2-yl)-1H-pyrazol-1-yl]-2-methylpropan-2-ol in place of 1-[3,5-dimethyl-4-(4,4,5,5-tetramethyl-1,3,2-dioxaborolan-2-yl)-1H-pyrazol-1-yl]-2-methylpropan-2-ol. ¹H NMR (400 MHz, CD₃OD): δ=1.01 (t, J=7.5 Hz, 3H), 1.22 (s, 6H), 1.79 (d, J=7.1 Hz, 3H), 2.73 (q, J=7.6 Hz, 2H), 3.61 (br. s., 3H), 4.08 (s, 2H), 5.04-5.14 (m, 1H), 6.88 (dd, J=9.0, 4.2 Hz, 1H), 7.04-7.11 (m, 1H), 7.35 (s, 1H), 7.44 (s, 1H), 7.49 (s, 1H), 8.12 (s, 1H). MS (ES+): m/z=471.19/473.19 (100/50) [MH⁺]. HPLC: t_R=1.55 min (polar_3 min, UPLC-ACQUITY).

1-[3-Ethyl-4-(4,4,5,5-tetramethyl-1,3,2-dioxaborolan-2-yl)-1H-pyrazol-1-yl]-2-methylpropan-2-ol and 1-[5-Ethyl-4-(4,4,5,5-tetramethyl-1,3,2-dioxaborolan-2-yl)-1H-pyrazol-1-yl]-2-methylpropan-2-ol

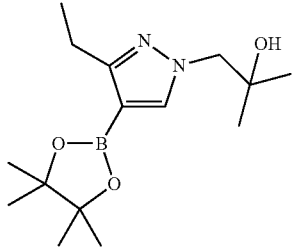

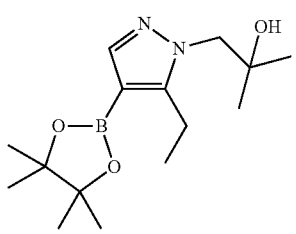

A mixture of 5-ethyl-4-iodo-1H-pyrazole (100.0 mg, 0.4504 mmol), oxirane, 2,2-dimethyl-(0.2 mL, 2 mmol), K₂CO₃ (124.5 mg, 0.9008 mmol), 1,4,7,10,13,16-hexaoxacyclooctadecane (11.90 mg, 0.04504 mmol) and DMF (3 mL, 40 mmol) was heated to 80° C. overnight. The material was extracted with EtOAc, washing with water (3×). The organic layer was concentrated in vacuo, redissolved in hexanes and loaded silica gel for column chromatography. The material was eluted with 10-30% EtOAc/hexanes. The fractions containing each pure regioisomer were concentrated in vacuo. Each one was dissolved in THF (3 mL, 40 mmol), and 2 M isopropylmagnesium chloride in THF (0.90 mL, 1.8 mmol) was added and stirred at rt for 20 min. The solution was quenched with 2-methoxy-4,4,5,5-tetramethyl-1,3,2-dioxaborolane (0.37 mL, 2.3 mmol), and stirred for 20 min. Sat. NH₄Cl was added to each mixture, and the organic solvent was removed in vacuo. The material was extracted with DCM and water, and the organic layers were concentrated in vacuo to afford the title compounds as clear oils. 3-Ethyl isomer: ¹H NMR (400 MHz, CD₃OD): δ=1.18-1.20 (m, 3H), 1.31 (s, 12H), 2.75 (q, J=7.5 Hz, 2H), 4.02 (s, 2H), 7.73 (s, 1H). 5-Ethyl isomer: ¹H NMR (400 MHz, CD₃OD): δ=1.14-1.17 (m, 3H), 1.32 (s, 12H), 2.95 (q, J=7.6 Hz, 2H), 4.05 (s, 2H), 7.60 (s, 1H).

Example 12

1-(4-{3-[(1S)-1-(2-Chloro-3-fluoro-6-methoxyphenyl)ethyl]-1H-pyrrolo[2,3-b]pyridin-5-yl}-3-ethyl-1H-pyrazol-1-yl)-2-methylpropan-2-ol

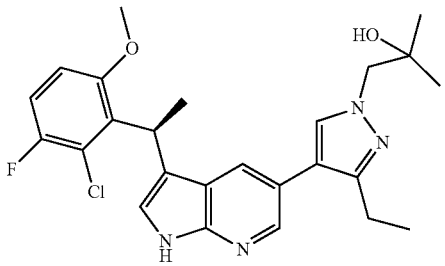 [SMILES: CCc1nn(CC(C)(C)O)cc1-c1cnc2[nH]cc([C@H](C)c3c(OC)ccc(F)c3Cl)c2c1]

Prepared using the procedure described for Example 5, using 1-[3-ethyl-4-(4,4,5,5-tetramethyl-1,3,2-dioxaborolan-2-yl)-1H-pyrazol-1-yl]-2-methylpropan-2-ol in place of 1-[3,5-dimethyl-4-(4,4,5,5-tetramethyl-1,3,2-dioxaborolan-2-yl)-1H-pyrazol-1-yl]-2-methylpropan-2-ol. $^1$H NMR (400 MHz, CD$_3$OD): δ=1.06 (t, J=7.6 Hz, 3H), 1.19 (s, 6H), 1.79 (d, J=7.1 Hz, 3H), 2.54 (qd, J=7.5, 2.9 Hz, 2H), 3.62 (br. s., 3H), 4.05 (s, 2H), 5.09 (q, J=7.3 Hz, 1H), 6.89 (dd, J=9.1, 4.3 Hz, 1H), 7.09 (t, J=8.8 Hz, 1H), 7.34 (d, J=1.3 Hz, 1H), 7.45 (s, 1H), 7.64 (s, 1H), 8.13 (br. s., 1H). MS (ES+): m/z=471.19/473.20 (100/50) [MH$^+$]. HPLC: t$_R$=1.51 min (polar_3 min, UPLC-ACQUITY).

Example 13

(2R)-3-(4-{3-[(1S)-1-(2-Chloro-3-fluoro-6-methoxyphenyl)ethyl]-1H-pyrrolo[2,3-b]pyridin-5-yl}-3,5-dimethyl-1H-pyrazol-1-yl)propane-1,2-diol

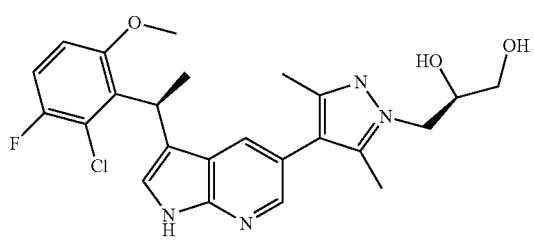

A mixture of 5-bromo-3-[(S)-1-(2-chloro-3-fluoro-6-methoxyphenyl)-ethyl]-1H-pyrrolo[2,3-b]pyridine (100.0 mg, 0.2606 mmol), 1-{[(4R)-2,2-dimethyl-1,3-dioxolan-4-yl]methyl}-3,5-dimethyl-4-(4,4,5,5-tetramethyl-1,3,2-dioxaborolan-2-yl)-1H-pyrazole (175 mg, 0.521 mmol), Pd(PPh$_3$)$_4$ (15.1 mg, 0.0130 mmol), K$_2$CO$_3$ (108 mg, 0.782 mmol) and 4:1 dioxane:H$_2$O (10 mL, 100 mmol) was heated to 95° C. for 5 h. After cooling to rt, 2 M of HCl in H$_2$O (1.3 mL, 2.6 mmol) was added, and the mixture was heated to 40° C. for 2 h. The organic solvent was removed in vacuo, and the material was extracted with DCM and sat. NaHCO$_3$. The organic layer was purified via column chromatography, eluting with 3-5% MeOH/DCM. The fractions containing the pure product were concentrated in vacuo, redissolved in MeOH, and 2.0 M of HCl in Et$_2$O (1 mL, 2 mmol) was added at rt. The solution was stirred for 30 min, and concentrated in vacuo to afford the title compound as an HCl salt. $^1$H NMR (400 MHz, CD$_3$OD): δ=1.79 (d, J=7.1 Hz, 3H), 2.00-2.07 (m, 3H), 2.17 (s, 3H), 3.51-3.59 (m, 2H), 3.63 (br. s., 3H), 3.98-4.09 (m, 2H), 4.12-4.19 (m, 1H), 5.09 (q, J=6.8 Hz, 1H), 6.88 (dd, J=9.1, 4.3 Hz, 1H), 7.07 (t, J=8.8 Hz, 1H), 7.30 (s, 1H), 7.35 (d, J=1.3 Hz, 1H), 7.97 (d, J=1.8 Hz, 1H). MS (ES+): m/z=473.07/475.06 (100/50) [MH$^+$]. HPLC: t$_R$=3.13 min (polar_5 min, ZQ3).

1-{[(4R)-2,2-Dimethyl-1,3-dioxolan-4-yl]methyl}-3,5-dimethyl-4-(4,4,5,5-tetramethyl-1,3,2-dioxaborolan-2-yl)-1H-pyrazole To a solution of 1-{[(4R)-2,2-dimethyl-1,3-dioxolan-4-yl]methyl}-4-iodo-3,5-dimethyl-1H-pyrazole (180.0 mg, 0.5354 mmol) in THF (5 mL, 60 mmol) was added 2 M isopropylmagnesium chloride in THF (0.5354 mL, 1.071 mmol) at rt, and the mixture was stirred for 10 min. 2-Methoxy-4,4,5,5-tetramethyl-1,3,2-dioxaborolane (0.2632 mL, 1.606 mmol) was added, and the mixture stirred at rt for 20 min. The reaction was quenched with sat. NH$_4$Cl, and the organic solvent was removed in vacuo. The material was extracted with DCM and water, and the organic layer was concentrated in vacuo to afford the title compound as a clear oil. The material was used in the next step without further purification.

1-{[(4R)-2,2-Dimethyl-1,3-dioxolan-4-yl]methyl}-4-iodo-3,5-dimethyl-1H-pyrazole

A mixture of 3,5-dimethyl-4-iodopyrazole (200.0 mg, 0.9008 mmol), ((4S)-2,2-dimethyl-1,3-dioxolan-4-yl)methyl 4-methylbenzenesulfonate (515.9 mg, 1.802 mmol), K$_2$CO$_3$ (136.9 mg, 0.9909 mmol), 1,4,7,10,13,16-hexaoxacyclooctadecane (23.81 mg, 0.09008 mmol) and DMF (4 mL, 50 mmol) was heated to 70° C. overnight. The material was extracted in EtOAc, and washed with water (3x). The organic layer was dry-loaded onto silica gel for column chromatography, eluting with 20-30% EtOAc/hexanes. The fractions containing the pure product were concentrated in vacuo to afford the title compound as a white solid.

Example 14

Trans-4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)-N,N-dimethylcyclohexanecarboxamide

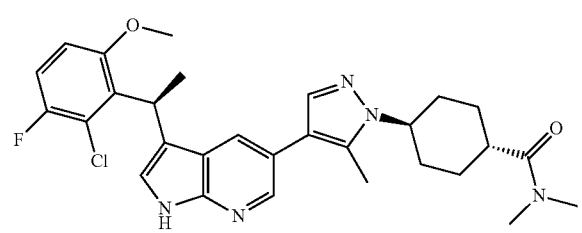 [SMILES: COc1ccc(F)c(Cl)c1[C@@H](C)c1c[nH]c2ncc(-c3cnn([C@H]4CC[C@H](C(=O)N(C)C)CC4)c3C)cc12]

A mixture of trans-4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)cyclohexanecarboxylic acid (9.00 mg, 0.0176 mmol), dimethylamine hydrochloride (14.4 mg, 0.176 mmol), TBTU (8.48 mg, 0.0264 mmol), DIPEA (0.0153 mL, 0.0881 mmol) and DCM (3 mL, 50 mmol) was stirred at rt for 1 min. The solution was concentrated in vacuo, redissolved in MeOH (1 mL) and purified via HPLC. The fractions containing the pure product were concentrated in vacuo to afford the title compound as a white solid. $^1$H NMR (400 MHz, CD$_3$OD): δ=1.65-1.77 (m, 2H), 1.80 (d, J=7.3 Hz, 3H), 1.89-1.97 (m, 2H), 1.98-2.08 (m, 4H), 2.23 (s, 3H), 2.81 (m, J=11.8, 11.8, 3.4, 3.3 Hz, 1H), 2.95 (s, 3H), 3.16 (s, 3H), 3.65 (br. s., 3H), 4.16-4.30 (m, 1H), 5.06-5.15 (m, 1H), 6.89 (dd, J=9.0, 4.4 Hz, 1H), 7.08 (t, J=8.8 Hz, 1H), 7.34 (d, J=1.3 Hz, 1H), 7.40 (s, 1H), 7.48 (s, 1H), 8.11 (s, 1H). MS (ES+): m/z=538.24/540.24 (100/50) [MH$^+$]. HPLC: t$_R$=1.45 min (polar_3 min, UPLC-ACQUITY).

Example 15 trans-4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)cyclohexanecarboxylic acid

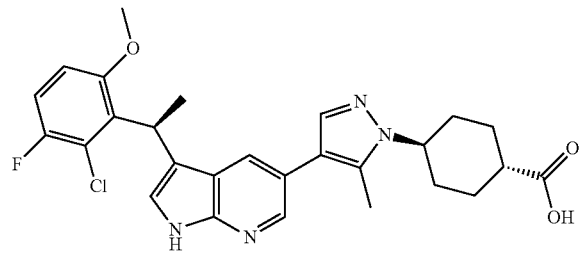

A solution of ethyl trans-4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)cyclohexanecarboxylate (20.0 mg, 0.0371 mmol) in MeOH (3 mL, 70 mmol) was added lithium hydroxide (4.44 mg, 0.186 mmol) and H$_2$O (1 mL, 60 mmol). The mixture was stirred at rt for 2 h. The organic solvent was removed in vacuo, and the material was extracted with DCM and water (pH=2). The organic layer was concentrated in vacuo to afford the title compound as a white solid. MS (ES+): m/z=511.19/513.19 (100/50) [MH$^+$]. HPLC: t$_R$=1.44 min (polar_3 min, UPLC-ACQUITY).

Example 16

Ethyl trans-4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)cyclohexanecarboxylate

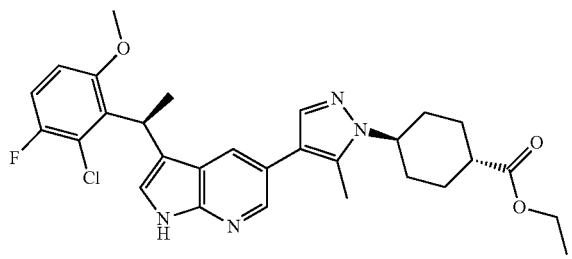

A mixture of 5-bromo-3-[(S)-1-(2-chloro-3-fluoro-6-methoxyphenyl)-ethyl]-1H-pyrrolo[2,3-b]pyridine (57.8 mg, 0.150 mmol), ethyl trans-4-[5-methyl-4-(4,4,5,5-tetramethyl-1,3,2-dioxaborolan-2-yl)-1H-pyrazol-1-yl]cyclohexanecarboxylate (60.0 mg, 0.166 mmol), Pd(PPh$_3$)$_4$ (8.70 mg, 0.00753 mmol), potassium fluoride (26.2 mg, 0.452 mmol) and 4:1 dioxane:H$_2$O (3 mL, 30 mmol) was heated to 90° C. for 2 h. The organic solvent was removed in vacuo, and the material was extracted with DCM and water. The organic layer was purified via column chromatography, eluting with 1-3% MeOH/DCM. The fractions containing the pure product were concentrated in vacuo to afford the title compound as a white solid. MS (ES+): m/z=539.16/541.16 (100/50) [MH$^+$]. HPLC: t$_R$=3.98 min (polar_5 min, ZQ3).

Ethyl trans-4-[5-methyl-4-(4,4,5,5-tetramethyl-1,3,2-dioxaborolan-2-yl)-1H-pyrazol-1-yl]cyclohexanecarboxylate To a solution of ethyl trans-4-(4-iodo-5-methyl-1H-pyrazol-1-yl)cyclohexanecarboxylate (100.0 mg, 0.2761 mmol) in THF (5 mL, 60 mmol) was added 2 M isopropylmagnesium chloride in THF (0.5522 mL, 1.104 mmol) at rt, and the mixture was stirred for 30 min. 2-Methoxy-4,4,5,5-tetramethyl-1,3,2-dioxaborolane (0.2262 mL, 1.380 mmol) was added, and the mixture stirred at rt for 2 h. The reaction was quenched with sat. NH$_4$Cl, and the organic solvent was removed in vacuo. The material was extracted with DCM and water, and the organic layer was concentrated in vacuo to afford the title compound as a clear oil. The material was used in the next step without further purification.

Ethyl trans-4-(4-iodo-3-methyl-1H-pyrazol-1-yl)cyclohexanecarboxylate and ethyl trans-4-(4-iodo-5-methyl-1H-pyrazol-1-yl)cyclohexanecarboxylate

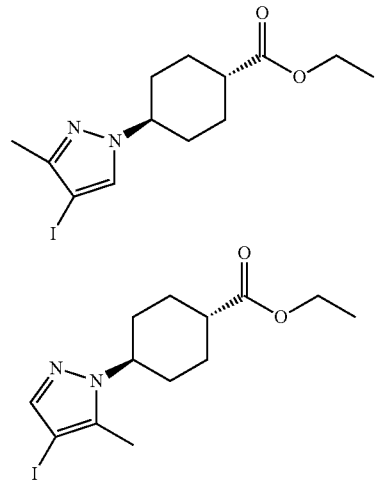

A mixture of 3-methyl-4-iodopyrazole (500.0 mg, 2.404 mmol), cis-4-(toluene-4-sulfonyloxy)-cyclohexanecarboxylic acid ethyl ester (1.569 g, 4.808 mmol), K$_2$CO$_3$ (664.4 mg, 4.808 mmol), 1,4,7,10,13,16-hexaoxacyclooctadecane (127.1 mg, 0.4808 mmol) and DMF (10 mL, 100 mmol) was heated to 80° C. overnight. The material was extracted with EtOAc, and washed with water (3×). The organic layer was dry-loaded onto silica gel for column chromatography, eluting with 10-20% EtOAc in hexanes. The fractions containing the pure products were concentrated in vacuo to afford the title compounds as clear oils. 3-methyl isomer: MS (ES+): m/z=363.06 (100) [MH$^+$]. HPLC: t$_R$=1.61 min (polar_3 min, UPLC-ACQUITY). 5-methyl isomer: MS (ES+): m/z=363.06 (100) [MH$^+$]. HPLC: t$_R$=1.63 min (polar_3 min, UPLC-ACQUITY).

Alternative Conditions:

To a solution of 3-methyl-4-iodopyrazole (1.529 g, 7.353 mmol) in DMF (20 mL, 200 mmol) was added sodium hydride (176.4 mg, 7.353 mmol), and stirred until bubbling stopped. cis-4-(Toluene-4-sulfonyloxy)-cyclohexanecarboxylic acid ethyl ester (1.200 g, 3.676 mmol) was added, and the mixture was heated to 80° C. overnight. The material was extracted with EtOAc, and washed with water (3×). The organic layer was dry-loaded onto silica gel for column chromatography, eluting with 10-20% EtOAc in hexanes. The fractions containing the pure products were concentrated in vacuo to afford the title compounds as clear oils.

cis-4-(Toluene-4-sulfonyloxy)-cyclohexanecarboxylic acid ethyl ester

To a solution of ethyl cis-4-hydroxycyclohexanecarboxylate (4.30 g, 25.0 mmol), p-toluenesulfonyl chloride (7.14 g, 37.4 mmol) and DCM (100 mL, 2000 mmol) was added triethylamine (6.96 mL, 49.9 mmol) at rt. The mixture was stirred at 25° C. overnight. The solution was transferred to a separatory funnel, washed with 2 M HCl to remove base, then washed with sat. NaHCO$_3$. The organic layer was dry-loaded onto silica gel for column chromatography, eluting with 10-20% EtOAc/hexanes. The fractions containing the pure product were concentrated in vacuo to afford the title compound as a clear oil. $^1$H NMR (400 MHz, DMSO-d$_6$): δ=1.16 (t, J=7.2 Hz, 3H), 1.52-1.67 (m, 8H), 2.31-2.40 (m, 1H), 2.42 (s, 3H), 4.05 (q, J=7.1 Hz, 2H), 4.66 (br. s., 1H), 7.47 (m, J=7.8 Hz, 2H), 7.80 (m, J=8.3 Hz, 2H).

Ethyl cis-4-hydroxycyclohexanecarboxylate

To a solution of cis-4-hydroxycyclohexanecarboxylic acid (4.00 g, 27.7 mmol) in EtOH (20 mL, 300 mmol) was added sulfuric acid (0.1 mL, 2 mmol), and the solution was heated to 70° C. for 2 h. After cooling to rt, Na$_2$CO$_3$ solution was added slowly to bring to pH=8. The organic solvent was removed in vacuo, and the material was extracted with EtOAc and washed with water. The organic layer was concentrated in vacuo to afford the title compound as a clear oil. $^1$H NMR (400 MHz, DMSO-d$_6$): δ=1.17 (t, J=7.1 Hz, 3H), 1.42-1.56 (m, 6H), 1.73-1.86 (m, 2H), 2.26-2.39 (m, 1H), 3.60-3.71 (m, 1H), 4.04 (q, J=7.1 Hz, 2H), 4.38 (d, J=3.5 Hz, 1H).

Example 17 trans-4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)-N-methyl cyclohexanecarboxamide

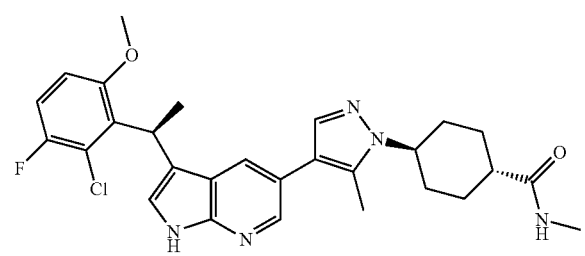 [SMILES: CNC(=O)[C@H]1CC[C@H](n2ncc(-c3cnc4[nH]cc([C@H](C)c5c(OC)ccc(F)c5Cl)c4c3)c2C)CC1]

Prepared using the procedure described for Example 14, using methylamine hydrochloride in place of dimethylamine hydrochloride. $^1$H NMR (400 MHz, CD$_3$OD): δ=1.67-1.78 (m, 2H), 1.80 (d, J=7.1 Hz, 3H), 1.94-2.05 (m, 6H), 2.23 (s, 3H), 2.25-2.34 (m, 1H), 2.74 (d, J=4.5 Hz, 3H), 3.65 (br. s., 3H), 4.16-4.27 (m, 1H), 5.10 (q, J=6.9 Hz, 1H), 6.89 (dd, J=9.1, 3.8 Hz, 1H), 7.09 (t, J=8.8 Hz, 1H), 7.35 (d, J=1.0 Hz, 1H), 7.40 (s, 1H), 7.48 (s, 1H), 7.92 (d, J=4.5 Hz, 1H). MS (ES+): m/z=524.20/526.21 (100/50) [MH$^+$]. HPLC: t$_R$=1.39 min (polar_3 min, UPLC-ACQUITY).

Example 18 trans-4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)cyclohexanecarboxamide

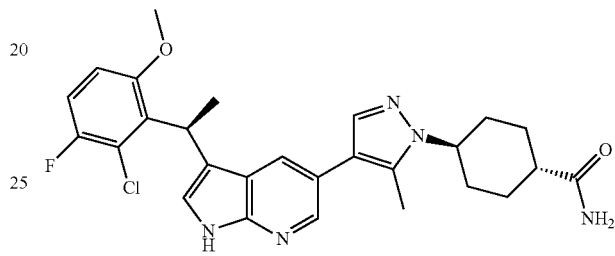

Prepared using the procedure described for Example 14, using ammonium chloride in place of dimethylamine hydrochloride. $^1$H NMR (400 MHz, CD$_3$OD): δ=1.62-1.76 (m, 2H), 1.80 (d, J=7.1 Hz, 3H), 1.89-2.08 (m, 6H), 2.22 (s, 3H), 2.30-2.40 (m, 1H), 3.64 (br. s., 3H), 4.15-4.26 (m, 1H), 5.10 (q, J=7.0 Hz, 1H), 6.84-6.93 (m, 1H), 7.08 (t, J=8.8 Hz, 1H), 7.34 (d, J=1.3 Hz, 1H), 7.40 (s, 1H), 7.47 (s, 1H), 8.11 (br. s., 1H). MS (ES+): m/z=510.19/512.20 (100/50) [MH$^+$]. HPLC: t$_R$=1.35 min (polar_3 min, UPLC-ACQUITY).

Example 19 trans-4-(4-{3-[(1S)-1-(2-Chloro-3-fluoro-6-methoxyphenyl)ethyl]-1H-pyrrolo[2,3-b]pyridin-5-yl}-3-methyl-1H-pyrazol-1-yl)cyclohexanecarboxamide

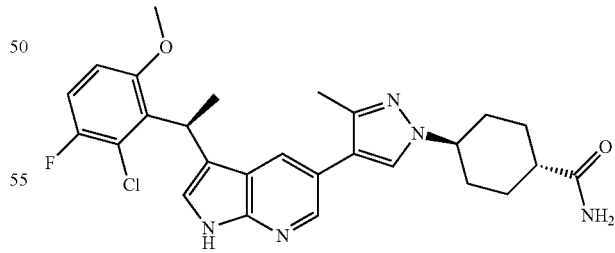

Prepared using the procedure described for Example 14, using ammonium chloride in place of dimethylamine hydrochloride. $^1$H NMR (400 MHz, CD$_3$OD): δ=1.60-1.75 (m, 2H), 1.80 (d, J=7.3 Hz, 3H), 1.82-1.94 (m, 2H), 2.00-2.07 (m, 2H), 2.14 (s, 3H), 2.15-2.26 (m, 2H), 2.29-2.39 (m, 1H), 3.64 (br. s., 3H), 4.11 (dddd, J=11.8, 8.0, 3.9, 3.8 Hz, 1H), 5.10 (q, J=7.1 Hz, 1H), 6.83-6.94 (m, 1H), 7.09 (t, J=8.8 Hz, 1H), 7.34 (s, 1H), 7.46 (s, 1H), 7.72 (s, 1H), 8.15 (br. s., 1H). MS (ES+):

m/z=510.20/512.21 (100/50) [MH⁺]. HPLC: t_R=1.36 min (polar_3 min, UPLC-ACQUITY).

Example 20 trans-4-(4-{3-[(1S)-1-(2-Chloro-3-fluoro-6-methoxyphenyl)ethyl]-1H-pyrrolo[2,3-b]pyridin-5-yl}-3-methyl-1H-pyrazol-1-yl)cyclohexanecarboxylic acid

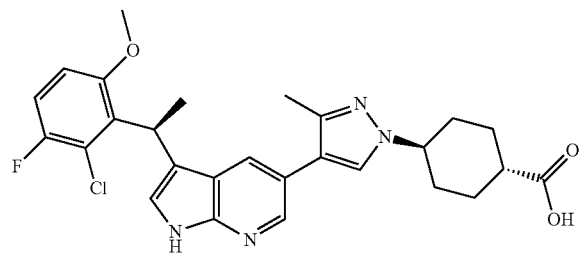 [SMILES: COc1ccc(F)c(Cl)c1[C@@H](C)c1c[nH]c2ncc(-c3cn([C@H]4CC[C@H](C(N)=O)CC4)nc3C)cc12]

To a solution of ethyl trans-4-(4-{3-[(1S)-1-(2-chloro-3-fluoro-6-methoxyphenyl)ethyl]-1H-pyrrolo[2,3-b]pyridin-5-yl}-3-methyl-1H-pyrazol-1-yl)cyclohexanecarboxylate (20.0 mg, 0.0371 mmol) in MeOH (3 mL, 70 mmol) was added lithium hydroxide (4.44 mg, 0.186 mmol) and H₂O (1 mL, 60 mmol). The mixture was stirred at rt for 2 h. The organic solvent was removed in vacuo, and the material was extracted with DCM and water (pH=2). The organic layer was concentrated in vacuo to afford the title compound as a white solid. MS (ES+): m/z=511.20/513.20 (100/50) [MH⁺]. HPLC: t_R=1.45 min (polar_3 min, UPLC-ACQUITY).

Example 21

Ethyl trans-4-(4-{3-[(1S)-1-(2-chloro-3-fluoro-6-methoxyphenyl)ethyl]-1H-pyrrolo[2,3-b]pyridin-5-yl}-3-methyl-1H-pyrazol-1-yl)cyclohexanecarboxylate

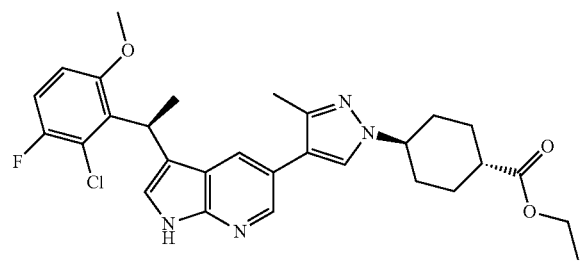 [SMILES: CCOC(=O)[C@H]1CC[C@H](n2cc(-c3cnc4[nH]cc([C@H](C)c5c(OC)ccc(F)c5Cl)c4c3)c(C)n2)CC1]

A mixture of 5-bromo-3-[(S)-1-(2-chloro-3-fluoro-6-methoxyphenyl)-ethyl]-1H-pyrrolo[2,3-b]pyridine (57.8 mg, 0.150 mmol), ethyl trans-4-[3-methyl-4-(4,4,5,5-tetramethyl-1,3,2-dioxaborolan-2-yl)-1H-pyrazol-1-yl]cyclohexanecarboxylate (60.0 mg, 0.166 mmol), Pd(PPh₃)₄ (8.70 mg, 0.00753 mmol), potassium fluoride (26.2 mg, 0.452 mmol) and 4:1 dioxane:H₂O (3 mL, 30 mmol) was heated to 90° C. for 2 h. The organic solvent was removed in vacuo, and the material was extracted with DCM and water. The organic layer was purified via column chromatography, eluting with 1-3% MeOH/DCM. The fractions containing the pure product were concentrated in vacuo to afford the title compound as a white solid. MS (ES+): m/z=539.18/541.20 (100/50) [MH⁺]. HPLC: t_R=1.70 min (polar_3 min, UPLC-ACQUITY).

Ethyl trans-4-[3-methyl-4-(4,4,5,5-tetramethyl-1,3,2-dioxaborolan-2-yl)-1H-pyrazol-1-yl]cyclohexanecarboxylate To a solution of ethyl trans-4-(4-iodo-3-methyl-1H-pyrazol-1-yl)cyclohexanecarboxylate (120.0 mg, 0.3313 mmol) in THF (6 mL, 80 mmol) was added 2 M isopropylmagnesium chloride in THF (0.66 mL, 1.3 mmol) at rt, and the mixture was stirred for 30 min. 2-Methoxy-4,4,5,5-tetramethyl-1,3,2-dioxaborolane (0.27 mL, 1.7 mmol) was added, and the mixture stirred at rt for 2 h. The reaction was quenched with sat. NH₄Cl, and the organic solvent was removed in vacuo. The material was extracted with DCM and water, and the organic layer was concentrated in vacuo to afford the title compound as a clear oil.

Example 22 trans-4-(4-{3-[(1S)-1-(2-Chloro-3-fluoro-6-methoxyphenyl)ethyl]-1H-pyrrolo[2,3-b]pyridin-5-yl}-3-methyl-1H-pyrazol-1-yl)-N-methylcyclohexanecarboxamide

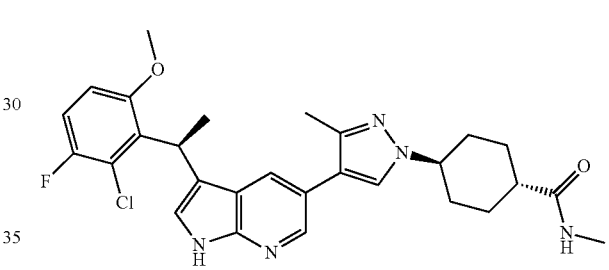

Prepared using the procedure described for Example 14, using methylamine hydrochloride in place of dimethylamine hydrochloride. ¹H NMR (400 MHz, CD₃OD): δ=1.63-1.75 (m, 2H), 1.80 (d, J=7.1 Hz, 3H), 1.86 (dd, J=12.5, 3.2 Hz, 2H), 1.97 (br. s., 2H), 2.13 (s, 3H), 2.17 (d, J=13.1 Hz, 2H), 2.22-2.32 (m, 1H), 2.73 (s, 3H), 3.64 (br. s., 3H), 4.06-4.16 (m, 1H), 5.10 (q, J=6.9 Hz, 1H), 6.85-6.94 (m, 1H), 7.09 (t, J=8.8 Hz, 1H), 7.34 (d, J=1.3 Hz, 1H), 7.46 (s, 1H), 7.71 (s, 1H), 8.16 (br. s., 1H). MS (ES+): m/z=524.22/526.22 (100/50) [MH⁺]. HPLC: t_R=1.39 min (polar_3 min, UPLC-ACQUITY).

Example 23 trans-4-(4-{3-[(1S)-1-(2-chloro-3-fluoro-6-methoxyphenyl)ethyl]-1H-pyrrolo[2,3-b]pyridin-5-yl}-3-methyl-1H-pyrazol-1-yl)-N,N-dimethylcyclohexanecarboxamide

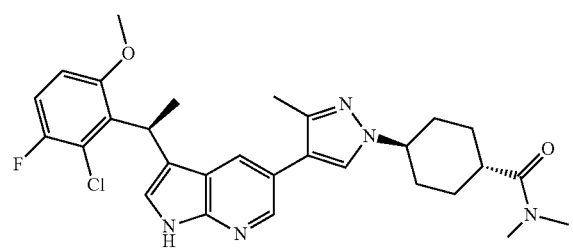 [SMILES: COc1ccc(F)c(Cl)c1[C@@H](C)c1c[nH]c2ncc(-c3cn([C@H]4CC[C@H](C(=O)N(C)C)CC4)nc3C)cc12]

Prepared using the procedure described for Example 14. $^1$H NMR (400 MHz, CD$_3$OD): δ=1.62-1.74 (m, 2H), 1.79 (d, J=7.1 Hz, 3H), 1.83-1.97 (m, 4H), 2.13 (s, 3H), 2.14-2.21 (m, 2H), 2.72-2.83 (m, 1H), 2.94 (s, 3H), 3.14 (s, 3H), 3.63 (br. s., 3H), 4.12 (m, J=11.6, 11.6, 3.8, 3.7 Hz, 1H), 5.02-5.14 (m, 1H), 6.88 (dd, J=9.1, 4.3 Hz, 1H), 7.07 (t, J=8.8 Hz, 1H), 7.32 (d, J=1.3 Hz, 1H), 7.45 (s, 1H), 7.71 (s, 1H), 8.13 (br. s., 1H). MS (ES+): m/z=538.24/540.24 (100/50) [MH$^+$]. HPLC: t$_R$=1.46 min (polar_3 min, UPLC-ACQUITY).

Example 24 trans-4-(4-{3-[(1S)-1-(2-Chloro-3-fluoro-6-methoxyphenyl)ethyl]-1H-pyrrolo[2,3-b]pyridin-5-yl}-3,5-dimethyl-1H-pyrazol-1-yl)-N-methylcyclohexanecarboxamide

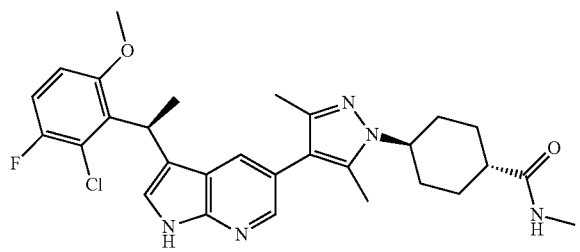 [SMILES: CNC(=O)[C@H]1CC[C@H](n2nc(C)c(-c3cnc4[nH]cc([C@H](C)c5c(OC)ccc(F)c5Cl)c4c3)c2C)CC1]

Prepared using the procedure described for Example 14, using methylamine hydrochloride. $^1$H NMR (400 MHz, CD$_3$OD): δ=1.72 (dd, J=11.4, 5.6 Hz, 2H), 1.79 (d, J=7.1 Hz, 3H), 1.92-2.02 (m, 6H), 2.04 (s, 3H), 2.14 (s, 3H), 2.28 (tt, J=12.1, 3.0 Hz, 1H), 2.73 (d, J=4.5 Hz, 3H), 3.63 (br. s., 3H), 4.10-4.18 (m, 1H), 5.09 (q, J=7.1 Hz, 1H), 6.88 (dd, J=9.1, 4.3 Hz, 1H), 7.07 (t, J=8.8 Hz, 1H), 7.28 (s, 1H), 7.35 (d, J=1.3 Hz, 1H), 7.95 (s, 1H). MS (ES+): m/z=538.24/540.25 (100/50) [MH$^+$]. HPLC: t$_R$=1.39 min (polar_3 min, UPLC-ACQUITY).

Example 25 trans-4-(4-{3-[(1S)-1-(2-Chloro-3-fluoro-6-methoxyphenyl)ethyl]-1H-pyrrolo[2,3-b]pyridin-5-yl}-3,5-dimethyl-1H-pyrazol-1-yl)cyclohexanecarboxylic acid

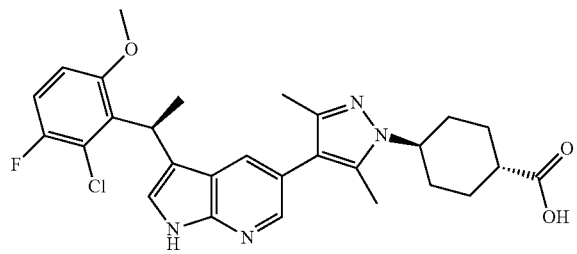 [SMILES: COc1ccc(F)c(Cl)c1[C@@H](C)c1c[nH]c2ncc(-c3c(C)nn([C@H]4CC[C@H](C(=O)O)CC4)c3C)cc12]

A solution of ethyl trans-4-(4-{3-[(1S)-1-(2-chloro-3-fluoro-6-methoxyphenyl)ethyl]-1H-pyrrolo[2,3-b]pyridin-5-yl}-3,5-dimethyl-1H-pyrazol-1-yl)cyclohexanecarboxylate (9.00 mg, 0.0163 mmol) in MeOH (1 mL, 30 mmol) was added lithium hydroxide (1.95 mg, 0.0814 mmol) and H$_2$O (0.4 mL, 20 mmol). The mixture was stirred at rt for 2 h. The organic solvent was removed in vacuo, and the material was extracted with DCM and water at pH 2. The organic layer was concentrated in vacuo to afford the title compound as a white solid. MS (ES+): m/z=525.21/527.21 (100/50) [MH$^+$]. HPLC: t$_R$=1.45 min (polar_3 min, UPLC-ACQUITY).

Example 26

Ethyl trans-4-(4-{3-[(1S)-1-(2-chloro-3-fluoro-6-methoxyphenyl)ethyl]-1H-pyrrolo[2,3-b]pyridin-5-yl}-3,5-dimethyl-1H-pyrazol-1-yl)cyclohexanecarboxylate

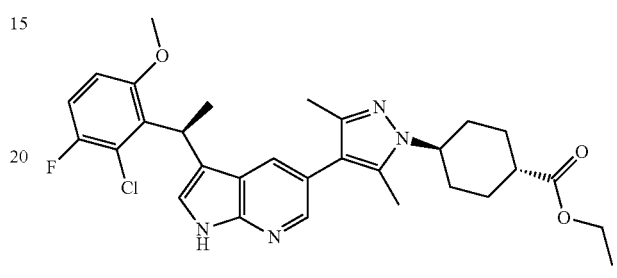

A mixture of 5-bromo-3-[(S)-1-(2-chloro-3-fluoro-6-methoxyphenyl)-ethyl]-1H-pyrrolo[2,3-b]pyridine (57.8 mg, 0.150 mmol), ethyl trans-4-[3,5-dimethyl-4-(4,4,5,5-tetramethyl-1,3,2-dioxaborolan-2-yl)-1H-pyrazol-1-yl]cyclohexanecarboxylate (62.3 mg, 0.166 mmol), Pd(PPh$_3$)$_4$ (8.70 mg, 0.00753 mmol), potassium fluoride (26.2 mg, 0.452 mmol) and 4:1 dioxane:H$_2$O (3 mL, 30 mmol) was heated to 90° C. for 2 h. The organic solvent was removed in vacuo, and the material was extracted with DCM and water. The organic layer was purified via column chromatography, eluting with 1-3% MeOH/DCM. The fractions containing the pure product were concentrated in vacuo to afford the title compound as a white solid. MS (ES+): m/z=553.24/555.24 (100/50) [MH$^+$]. HPLC: t$_R$=1.71 min (polar_3 min, UPLC-ACQUITY).

Ethyl trans-4-[3,5-dimethyl-4-(4,4,5,5-tetramethyl-1,3,2-dioxaborolan-2-yl)-1H-pyrazol-1-yl]cyclohexanecarboxylate To a solution of ethyl trans-4-(4-iodo-3,5-dimethyl-1H-pyrazol-1-yl)cyclohexane-carboxylate (100.0 mg, 0.2658 mmol) in THF (5 mL, 60 mmol) was added 2 M isopropylmagnesium chloride in THF (0.5316 mL, 1.063 mmol) at rt, and the mixture was stirred for 30 min. 2-Methoxy-4,4,5,5-tetramethyl-1,3,2-dioxaborolane (0.2178 mL, 1.329 mmol) was added, and the mixture stirred at rt overnight. The reaction was quenched with sat. NH$_4$Cl, and the organic solvent was removed in vacuo. The material was extracted with DCM and water, and the organic layer was concentrated in vacuo to afford the title compound as a clear oil.

Ethyl trans-4-(4-iodo-3,5-dimethyl-1H-pyrazol-1-yl)cyclohexanecarboxylate

A mixture of 3,5-dimethyl-4-iodopyrazole (300.0 mg, 1.351 mmol), cis-4-(toluene-4-sulfonyloxy)-cyclohexanecarboxylic acid ethyl ester (573.4 mg, 1.756 mmol), K$_2$CO$_3$ (373.5 mg, 2.702 mmol), 1,4,7,10,13,16-hexaoxacyclooctadecane (71.43 mg, 0.2702 mmol) and DMF (6 mL, 70 mmol) was heated to 80° C. overnight. The material was extracted with EtOAc, and washed with water (3×). The organic layer was dry-loaded onto silica gel for column chromatography, eluting with 10-20% EtOAc in hexanes. The fractions containing the pure product were concentrated in vacuo to afford the title compound as a clear oil. MS (ES+): m/z=377.03 (100) [MH+]. HPLC: $t_R$=3.74 min (polar_5 min, ZQ3).

Example 27 trans-4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)cyclohexanol

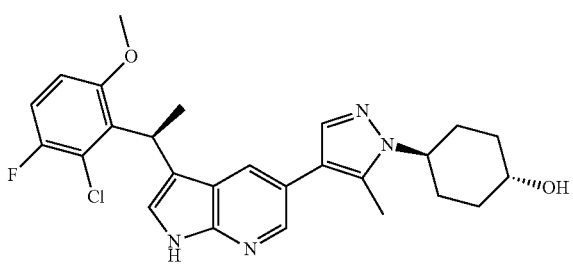 [SMILES: COc1ccc(F)c(Cl)c1[C@@H](C)c1c[nH]c2ncc(-c3cnn([C@H]4CC[C@H](O)CC4)c3C)cc12]

Prepared using the procedure described for Example 5. $^1$H NMR (400 MHz, CD$_3$OD): δ=1.42-1.59 (m, 2H), 1.80 (d, J=7.3 Hz, 3H), 1.89-2.14 (m, 6H), 2.22 (s, 3H), 3.52-3.76 (m, 4H), 4.06-4.25 (m, 1H), 5.03-5.15 (m, 1H), 6.89 (dd, J=8.7, 3.9 Hz, 1H), 7.08 (t, J=8.8 Hz, 1H), 7.34 (s, 1H), 7.39 (br. s., 1H), 7.46 (s, 1H), 8.09 (br. s., 1H). MS (ES+): m/z=483.17/485.19 (100/50) [MH+]. HPLC: $t_R$=1.43 min (polar_3 min, UPLC-ACQUITY).

trans-4-[5-Methyl-4-(4,4,5,5-tetramethyl-1,3,2-dioxaborolan-2-yl)-1H-pyrazol-1-yl]cyclohexanol To a solution of trans-4-(4-iodo-5-methyl-1H-pyrazol-1-yl)cyclohexanol (150.0 mg, 0.4900 mmol) in THF (9 mL, 100 mmol) was added 2 M isopropylmagnesium chloride in THF (0.73 mL, 1.5 mmol) at rt, and the mixture was stirred for 30 min. 2-Methoxy-4,4,5,5-tetramethyl-1,3,2-dioxaborolane (0.32 mL, 2.0 mmol) was added, and the mixture stirred at rt for 2 h. The reaction was quenched with sat. NH$_4$Cl, and the organic solvent was removed in vacuo. The material was extracted with DCM and water, and the organic layer was concentrated in vacuo to afford the title compound as a clear oil.

trans-4-(4-Iodo-5-methyl-1H-pyrazol-1-yl)cyclohexanol

A mixture of 1-(1,4-dioxaspiro[4.5]dec-8-yl)-4-iodo-5-methyl-1H-pyrazole (300.0 mg, 0.8616 mmol), pyridinium p-toluenesulfonate (433.0 mg, 1.723 mmol), acetone (10 mL, 200 mmol) and H$_2$O (10 mL, 800 mmol) was heated to 60° C. overnight to form the ketone. The organic solvent was removed in vacuo, and the material was extracted with DCM and water. The organic layer was dried in vacuo, redissolved in EtOH (7 mL, 100 mmol), and sodium borohydride (39.12 mg, 1.034 mmol) was added. The mixture was stirred at rt for 3 h. The material was concentrated in vacuo, extracted with EtOAc, and washed with water (3×). The organic layer was dry-loaded onto silica gel for column chromatography, eluting with 1-2% MeOH/diethyl ether. The cis product eluted first, followed by the trans product. The fractions containing the pure product were concentrated in vacuo to afford the title compound as a white solid. MS (ES+): m/z=307.02 (100) [MH+]. HPLC: $t_R$=1.26 min (polar_3 min, UPLC-ACQUITY).

1-(1,4-Dioxaspiro[4.5]dec-8-yl)-4-iodo-3-methyl-1H-pyrazole and 1-(1,4-Dioxaspiro[4.5]dec-8-yl)-4-iodo-5-methyl-1H-pyrazole

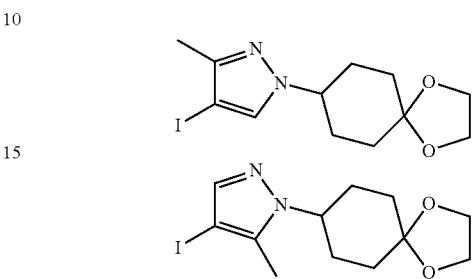

A mixture of 4-Iodo-5-methyl-1H-pyrazole (1.00 g, 4.81 mmol), 1,4-dioxaspiro[4.5]dec-8-yl 4-methylbenzenesulfonate (3.004 g, 9.615 mmol), K$_2$CO$_3$ (1.329 g, 9.615 mmol), 1,4,7,10,13,16-hexaoxacyclooctadecane (254.1 mg, 0.9615 mmol) and DMF (15 mL, 190 mmol) was heated to 80° C. for 72 hours. The material was extracted with EtOAc, and washed with water (3×). The organic layer was purified via column chromatography, eluting with 10-20% EtOAc/hexanes. The fractions containing the separate regioisomers were concentrated in vacuo to afford the title compounds as white solids. 3-methyl isomer: $^1$H NMR (400 MHz, DMSO-d$_6$): δ=1.03 (s, 6H), 2.10 (s, 3H), 3.92 (s, 2H), 4.66 (s, 1H), 7.68 (s, 1H). MS (ES+): m/z=281.01 (100) [MH+]. HPLC: $t_R$=1.22 min (polar_3 min, UPLC-ACQUITY). 5-methyl isomer: $^1$H NMR (400 MHz, DMSO-d$_6$): δ=1.08 (s, 6H), 2.29 (s, 3H), 4.01 (s, 2H), 4.63 (s, 1H), 7.44 (s, 1H). MS (ES+): m/z=281.01 (100) [MH+]. HPLC: $t_R$=1.19 min (polar_3 min, UPLC-ACQUITY).

Example 28 trans-4-(4-{3-[(1S)-1-(2-Chloro-3-fluoro-6-methoxyphenyl)ethyl]-1H-pyrrolo[2,3-b]pyridin-5-yl}-3-methyl-1H-pyrazol-1-yl)cyclohexanol

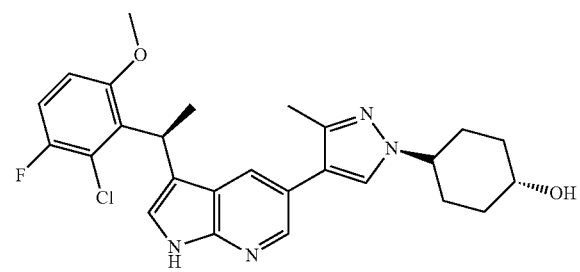

Prepared using the procedure described for Example 5. $^1$H NMR (400 MHz, CD$_3$OD): δ=1.42-1.55 (m, 2H), 1.81 (d, J=7.1 Hz, 3H), 1.85-1.97 (m, 2H), 2.06-2.19 (m, 7H), 3.58-3.74 (m, 4H), 4.05-4.17 (m, 1H), 5.05-5.17 (m, 1H), 6.92 (br. s., 1H), 7.10 (t, J=8.8 Hz, 1H), 7.35 (s, 1H), 7.47 (br. s., 1H), 7.72 (s, 1H), 8.16 (br. s., 1H). MS (ES+): m/z=483.19/485.20 (100/50) [MH+]. HPLC: $t_R$=1.44 min (polar_3 min, UPLC-ACQUITY).

trans-4-[3-Methyl-4-(4,4,5,5-tetramethyl-1,3,2-dioxaborolan-2-yl)-1H-pyrazol-1-yl]cyclohexanol To a solution of trans-4-(4-iodo-3-methyl-1H-pyrazol-1-yl)cyclohexanol (150.0 mg, 0.4900 mmol) in THF (9 mL, 100 mmol) was added 2 M isopropylmagnesium chloride in THF (0.7349 mL, 1.470 mmol) at rt, and the mixture was stirred for 30 min. 2-Methoxy-4,4,5,5-tetramethyl-1,3,2-dioxaborolane (0.3212 mL, 1.960 mmol) was added, and the mixture stirred at rt for 2 h. The reaction was quenched with sat. NH$_4$Cl, and the organic solvent was removed in vacuo. The material was extracted with DCM and water, and the organic layer was concentrated in vacuo to afford the title compound as a clear oil.

trans-4-(4-Iodo-3-methyl-1H-pyrazol-1-yl)cyclohexanol

A mixture of 1-(1,4-dioxaspiro[4.5]dec-8-yl)-4-iodo-3-methyl-1H-pyrazole (300.0 mg, 0.8616 mmol), pyridinium p-toluenesulfonate (433.0 mg, 1.723 mmol), acetone (10 mL, 200 mmol) and H$_2$O (10 mL, 800 mmol) was heated to 60° C. overnight to form the ketone. The organic solvent was removed in vacuo, and the material was extracted with DCM and water. The organic layer was dried in vacuo, redissolved in EtOH (7 mL, 100 mmol), and sodium borohydride (39.12 mg, 1.034 mmol) was added. The mixture was stirred at rt for 3 h. The material was concentrated in vacuo, extracted with EtOAc, and washed with water (3×). The organic layer was dry-loaded onto silica gel for column chromatography, eluting with 1-2% MeOH/diethyl ether. The cis product eluted first, followed by the trans product. The fractions containing the pure product were concentrated in vacuo to afford the title compound as a white solid. MS (ES+): m/z=307.02 (100) [MH$^+$]. HPLC: t$_R$=1.25 min (polar_3 min, UPLC-ACQUITY).

Example 29

3-[(1S)-1-(2-Chloro-3-fluoro-6-methoxyphenyl)ethyl]-5-[1-methyl-3-(trifluoromethyl)-1H-pyrazol-4-yl]-1H-pyrrolo[2,3-b]pyridine

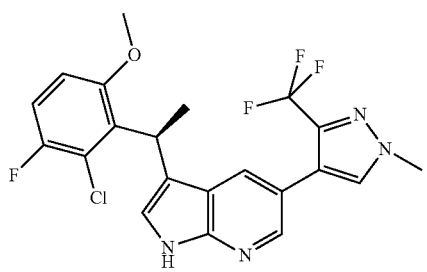 [SMILES: COc1ccc(F)c(Cl)c1[C@@H](C)c1c[nH]c2ncc(-c3cn(C)nc3C(F)(F)F)cc12]

A mixture of 3-[(S)-1-(2-chloro-3-fluoro-6-methoxyphenyl)-ethyl]-5-(4,4,5,5-tetramethyl-[1,3,2]dioxaborolan-2-yl)-1H-pyrrolo[2,3-b]pyridine (9.00 mg, 0.0209 mmol), 4-bromo-1-methyl-3-(trifluoromethyl)-1H-pyrazole (9.57 mg, 0.0418 mmol), Pd(PPh$_3$)$_4$ (1.21 mg, 0.00104 mmol), K$_2$CO$_3$ (0.00866 g, 0.0627 mmol) and 4:1 dioxane:H$_2$O (0.8 mL, 8 mmol) was heated in a microwave reactor at 95° C. for 20 min. The solution was used directly for HPLC purification, and the fractions containing the pure product were concentrated in vacuo to afford the title compound as a white solid. $^1$H NMR (400 MHz, CD$_3$OD): δ=1.78 (d, J=7.1 Hz, 3H), 3.62 (br. s., 3H), 3.96 (s, 3H), 5.08 (q, J=6.9 Hz, 1H), 6.86 (dd, J=9.1, 4.3 Hz, 1H), 7.01-7.09 (m, 1H), 7.35 (d, J=1.3 Hz, 1H), 7.52 (s, 1H), 7.78 (s, 1H), 8.10 (d, J=2.0 Hz, 1H). MS (ES+): m/z=453.11/455.11 (100/50) [MH$^+$]. HPLC: t$_R$=1.36 min (polar_3 min, UPLC-ACQUITY).

3-[(S)-1-(2-Chloro-3-fluoro-6-methoxyphenyl)-ethyl]-5-(4,4,5,5-tetramethyl-[1,3,2]dioxaborolan-2-yl)-1H-pyrrolo[2,3-b]pyridine A suspension of 5-bromo-3-[(S)-1-(2-chloro-3-fluoro-6-methoxyphenyl)-ethyl]-1H-pyrrolo[2,3-b]pyridine (303.8 mg, 0.7919 mmol), bis(pinacolato)diboron (294.2 mg, 1.158 mmol), (1,1'bis-(diphenylphosphino)-ferrocene) palladium dichloride (70.7 mg, 0.0966 mmol), and potassium acetate (239.0 mg, 2.435 mmol) in dioxane (7 mL) was heated at 80° C. over the course of 20.5 h. The reaction flask was removed from the heat and additional reagents [bis(pinacolato)diboron (290.3 mg, 1.143 mmol), (1,1'bis-(diphenylphosphino)-ferrocene) palladium dichloride (59.7 mg, 0.0816 mmol), and potassium acetate (245.6 mg, 2.502 mmol)] in dioxane (3 mL) were added. The reaction was then heated again at 80° C. for an additional 8 h. The reaction was again removed from the heat and additional reagents [bis(pinacolato)diboron (319.9 mg, 1.260 mmol), (1,1'bis-(diphenylphosphino)-ferrocene) palladium dichloride (79.8 mg, 0.109 mmol), and potassium acetate (267.2 mg, 2.722 mmol)] in dioxane (3 mL) were added and the reaction mixture was heated to 80° C. for an additional 4 h. The reaction was cooled to ambient temperature and concentrated in vacuo. The crude material was dissolved in a mixture of CH$_2$Cl$_2$ and MeOH, adsorbed onto a pre-packed silica gel loading cartridge (RediSep Rf, 25 gram), and purified using the Teledyne ISCO system [RediSepRf (24 gram silica column)], using a 30-50% EtOAc:Heptane gradient. All fractions containing product were pooled together and concentrated in vacuo. The material was purified a second time via the Teledyne/ISCO system [RediSepRf 5 g preloaded silica cartridge/12 g silica column], eluting with a 10-80% EtOAc:Heptane solvent system. The fractions containing product were combined and concentrated in vacuo. The product residue was dissolved in minimal EtOAc and precipitated with heptane; the solid was filtered off and dried, giving the title compound as off-white solid. The filtrate was concentrated in vacuo and recrystallized a second time, giving a second crop of the title compound. $^1$H NMR (DMSO-d$_6$) δ=11.53 (s, 1H), 8.36 (d, J=1.5 Hz, 1H), 7.92 (s, 1H), 7.33 (d, J=1.3 Hz, 1H), 7.25 (t, J=9.0 Hz, 1H), 7.02 (dd, J=9.2, 4.4 Hz, 1H), 5.04 (q, J=7.1 Hz, 1H), 3.75 (br s, 3H), 1.74 (d, J=7.3 Hz, 3H), 1.28 (d, J=2.0 Hz, 12H). MS (ES$^+$): m/z 429.96/430.91/432.96 (49/100/73) [MH$^+$]. HPLC: t$_R$=4.02 min (ZQ3, polar_5 min).

Example 30

1-[4-{3-[(1S)-1-(2-Chloro-3-fluoro-6-methoxyphenyl)ethyl]-1H-pyrrolo[2,3-b]pyridin-5-yl}-3-(trifluoromethyl)-1H-pyrazol-1-yl]-2-methylpropan-2-ol

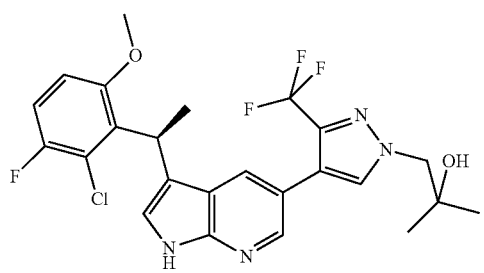 [SMILES: COc1ccc(F)c(Cl)c1[C@@H](C)c1c[nH]c2ncc(-c3cn(CC(C)(C)O)nc3C(F)(F)F)cc12]

Prepared using the procedure described for Example 29. $^1$H NMR (400 MHz, CD$_3$OD): δ=1.22 (s, 6H), 1.79 (d, J=7.1 Hz, 3H), 3.64 (br. s., 3H), 4.17 (s, 2H), 5.05-5.15 (m, 1H), 6.88 (dd, J=9.1, 4.3 Hz, 1H), 7.06 (t, J=8.8 Hz, 1H), 7.36 (s, 1H), 7.55 (s, 1H), 7.80 (s, 1H), 8.14 (s, 1H). MS (ES+): m/z=511.13/513.14 (100/50) [MH$^+$]. HPLC: t$_R$=1.63 min (polar_3 min, UPLC-ACQUITY).

1-[4-Bromo-3-(trifluoromethyl)-1H-pyrazol-1-yl]-2-methylpropan-2-ol

To a mixture of 4-bromo-3-trifluoromethyl-1H-pyrazole (200.0 mg, 0.9304 mmol), K$_2$CO$_3$ (200.0 mg, 1.447 mmol) and DMF (3 mL, 40 mmol) was added 2,2-dimethyloxirane (0.5 mL, 6 mmol), and the mixture was heated to 90° C. for 2 h in a sealed tube. The material was transferred to a separation funnel, extracting with EtOAc and washing with water (3×). The organic layer was loaded onto silica gel for column chromatography, eluting with 10-30% EtOAc/heptane. The fractions containing the 3-trifluoromethyl product were concentrated in vacuo to afford the title compound as a brown oil. $^1$H NMR (400 MHz, CD$_3$OD): δ=1.17 (s, 6H), 4.13 (s, 2H), 7.87 (s, 1H). MS (ES+): m/z=287.00/289.00 (100/100) [MH$^+$]. HPLC: t$_R$=1.35 min (polar_3 min, UPLC-ACQUITY).

Example 31

(1R,2S,4S)-4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)cyclopentane-1,2-diol

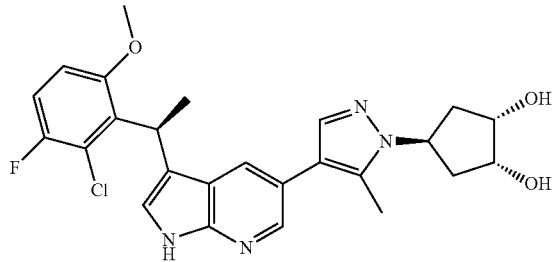 [SMILES: COc1ccc(F)c(Cl)c1[C@@H](C)c1c[nH]c2ncc(-c3cnn([C@@H]4C[C@@H](O)[C@@H](O)C4)c3C)cc12]

Prepared using the procedure described for Example 29. $^1$H NMR (400 MHz, CD$_3$OD): δ=1.80 (d, J=7.1 Hz, 3H), 2.14-2.26 (m, 7H), 3.64 (br. s., 3H), 4.35 (t, J=4.3 Hz, 2H), 5.07 (dt, J=14.8, 7.4 Hz, 2H), 6.85-6.93 (m, 1H), 7.08 (t, J=8.8 Hz, 1H), 7.34 (d, J=1.3 Hz, 1H), 7.39 (s, 1H), 7.48 (s, 1H), 8.10 (s, 1H). MS (ES+): m/z=485.08/487.09 (100/50) [MH$^+$]. HPLC: t$_R$=3.08 min (polar_5 min, ZQ3).

(1R,2S,4s)-4-(4-Iodo-5-methyl-1H-pyrazol-1-yl)cyclopentane-1,2-diol

To a solution of 1-(Cyclopent-3-en-1-yl)-4-iodo-5-methyl-1H-pyrazole (3.00 g, 10.9 mmol) in a mixture of acetone/water (67.5 mL, 8:1) was added N-methylmorphone-N-oxide (2.10 g, 18.6 mmol) at room temperature. After 2 minutes, OsO$_4$ (138 mg, 0.547 mmol) was added and the resulting mixture was then stirred at room temperature for 18 h. The reaction mixture was quenched by addition of aqueous Na$_2$S$_2$O$_3$ (0.2 M, 30 mL) and extracted with methylene chloride. The organic layer was washed with aqueous Na$_2$S$_2$O$_3$, dried over Na$_2$SO$_4$, filtered and concentrated. The crude residue was purified by column chromatography using ethyl acetate to yield the title compound as viscous oil. $^1$H NMR (300 MHz, CDCl$_3$): δ=7.30 (s, 1H), 4.82 (m, 1H), 4.34 (br s, 2H), 3.72 (br s, 2H), 2.24 (s, 3H), 2.19 (m, 4H) and 2.17 (s, 3H). $^{13}$C NMR (75 MHz, CDCl$_3$): δ=151.30, 133.82, 72.90, 59.38, 59.08, 38.76, 14.36 and 13.84.

1-(Cyclopent-3-en-1-yl)-4-iodo-5-methyl-1H-pyrazole and 1-(Cyclopent-3-en-1-yl)-4-iodo-3-methyl-1H-pyrazole

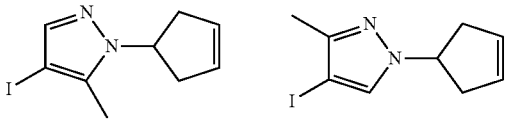

To an ice-cold solution of 3-methyl-4-iodo-1H-pyrazole (6.00 g, 28.8 mmol) in DMF (20 mL) was added NaH (60%, 1.3 g, 34.5 mmol) in portions and stirred at room temperature for 1 h. To this was added methanesulfonic acid cyclopent-3-enyl ester (5.13 g, 31.7 mmol) and heated at 60° C. overnight. The reaction mixture was poured into water and extracted with ethyl acetate (60 mL). The ethyl acetate layer was washed with brine, dried over Na$_2$SO$_4$, filtered and concentrated. The crude residue was purified by column chromatography using 5% ethyl acetate in hexane to give the separated title compounds as oils. 3-Methyl isomer: $^1$H NMR (300 MHz, CDCl$_3$): δ=7.45 (s, 1H), 5.77 (s, 2H), 4.99 (m, 1H), 2.82 (m, 4H), 2.32 (s, 3H). 5-Methyl isomer: $^1$H NMR (300 MHz, CDCl$_3$): δ=7.36 (s, 1H), 5.77 (m, 2H), 4.94 (m, 1H), 2.88 (m, 2H), 2.68-2.61 (m, 2H) and 2.22 (s, 3H).

Methanesulfonic acid cyclopent-3-enyl ester

To a solution of 3-cyclopentene-1-ol (9.00 g, 107 mmol) in dry methylene chloride (150 mL) was added TEA (23.0 mL, 160 mmol) followed by DMAP (100 mg). To this solution was added methanesulfonyl chloride (14.72 g, 128 mmol) at 10-20° C. slowly over 15 minutes and stirred overnight at room temperature. To the reaction mixture was added aqueous saturated NaHCO$_3$ (50 mL) and stirred for 15 minutes at room temperature. The organic layer was separated, washed with water, followed by brine and dried over NaSO$_4$. It was filtered and concentrated to give the title compound as an oil that was used without purification in the next reaction. $^1$H NMR (300 MHz, CDCl$_3$): δ=5.72 (s, 2H), 5.38 (m$_c$, 1H), 3.00 (s, 3H), 2.81-2.61 (m, 4H).

Example 32

(1R,2S,4S)-4-(4-{3-[(1S)-1-(2-Chloro-3-fluoro-6-methoxyphenyl)ethyl]-1H-pyrrolo[2,3-b]pyridin-5-yl}-3-methyl-1H-pyrazol-1-yl)cyclopentane-1,2-diol

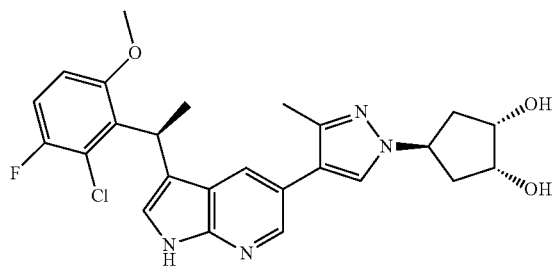

Prepared using the procedure described for Example 29. $^1$H NMR (400 MHz, CD$_3$OD): δ=1.80 (d, J=7.1 Hz, 3H), 2.14 (s, 3H), 2.17-2.31 (m, 4H), 3.64 (br. s., 3H), 4.25-4.36 (m, 2H), 4.92-5.03 (m, 1H), 5.10 (q, J=7.2 Hz, 1H), 6.89 (d, J=9.1 Hz, 1H), 7.03-7.12 (m, 1H), 7.33 (s, 1H), 7.45 (br. s., 1H), 7.70 (s, 1H), 8.07-8.17 (m, 1H). MS (ES+): m/z=485.08/ 487.08 (100/50) [MH$^+$]. HPLC: t$_R$=3.11 min (polar_5 min, ZQ3).

(1R,2S,4s)-4-(4-Iodo-3-methyl-1H-pyrazol-1-yl) cyclopentane-1,2-diol

To a solution of 1-(Cyclopent-3-en-1-yl)-4-iodo-3-methyl-1H-pyrazole (1.50 g, 5.47 mmol) in a mixture of acetone/water (36 mL, 8:1) was added N-methylmorphone-N-oxide (1.09 g, 9.30 mmol) at room temperature. After 2 minutes, OsO$_4$ (69 mg, 0.273 mmol) was added and the resulting mixture was then stirred at room temperature for 18 h. The reaction mixture was quenched by addition of aqueous Na$_2$S$_2$O$_3$ (0.2 M, 30 mL) and extracted with methylene chloride. The organic layer was washed with aqueous Na$_2$S$_2$O$_3$, dried over Na$_2$SO$_4$, filtered and concentrated. The crude residue was purified by column chromatography using ethyl acetate to yield the title compound as a colorless solid. $^1$H NMR (300 MHz, CDCl$_3$): δ=7.39 (s, 1H), 4.91 (m, 1H), 4.39 (br s, 2H), 3.04 (s, 2H), 2.23 (s, 3H) and 2.17 (m, 4H). $^{13}$C NMR (75 MHz, CDCl$_3$): δ=143.30, 143.23, 139.88, 73.22, 59.49, 56.44, 38.31 and 11.55.

Example 33

(1R,2S,4S)-4-(4-{3-[(1S)-1-(2-Chloro-3-fluoro-6-methoxyphenyl)ethyl]-1H-pyrrolo[2,3-b]pyridin-5-yl}-3,5-dimethyl-1H-pyrazol-1-yl)cyclopentane-1,2-diol

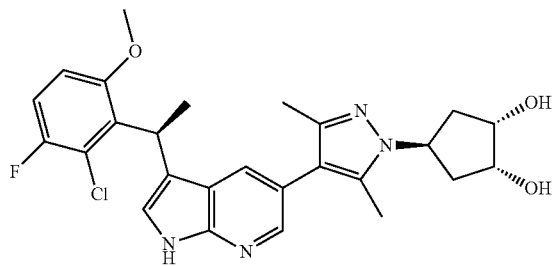 [SMILES: COc1ccc(F)c(Cl)c1[C@@H](C)c1c[nH]c2ncc(-c3cn([C@@H]4C[C@@H](O)[C@@H](O)C4)nc3C)cc12]

Prepared using the procedure described for Example 29. $^1$H NMR (400 MHz, CD$_3$OD): δ=1.80 (d, J=7.3 Hz, 3H), 2.05 (s, 3H), 2.12 (s, 3H), 2.16-2.23 (m, 4H), 3.64 (br. s., 3H), 4.36 (t, J=4.4 Hz, 2H), 5.01 (quint, J=7.8 Hz, 1H), 5.09 (q, J=7.0 Hz, 1H), 6.89 (dd, J=9.2, 4.2 Hz, 1H), 7.08 (t, J=8.8 Hz, 1H), 7.28 (s, 1H), 7.35 (d, J=1.3 Hz, 1H), 7.96 (d, J=2.0 Hz, 1H). MS (ES+): m/z=499.14/501.13 (100/50) [MH$^+$]. HPLC: t$_R$=3.12 min (polar_5 min, ZQ3).

(1R,2S,4s)-4-(4-Iodo-3,5-dimethyl-1H-pyrazol-1-yl) cyclopentane-1,2-diol

To a solution of 1-(cyclopent-3-en-1-yl)-4-iodo-3,5-dimethyl-1H-pyrazole (3.90 g, 13.5 mmol) in a mixture of acetone/water (90 mL, 8:1) was added N-methylmorphone-N-oxide (3.0 g, 26 mmol) at room temperature. After 2 minutes, OsO$_4$ (120 mg, 0.472 mmol) was added and the resulting mixture was then stirred at room temperature for 18 h. The reaction mixture was quenched by addition of aqueous Na$_2$S$_2$O$_3$ (0.2 M, 30 mL) and extracted with methylene chloride. The organic layer was washed with aqueous Na$_2$S$_2$O$_3$, dried over Na$_2$SO$_4$, filtered and concentrated. The crude residue was purified by column chromatography using ethyl acetate to yield the title compound as a colorless solid. $^1$H NMR (300 MHz, CDCl$_3$): δ=4.90 (m, 1H), 4.43 (br s, 2H), 2.24 (s, 3H), 2.20 (m, 4H), 2.17 (s, 3H). $^{13}$C NMR (75 MHz, CDCl$_3$): δ=149.57, 140.36, 73.19, 62.87, 56.07, 38.33, 14.36, 12.23.

1-(Cyclopent-3-en-1-yl)-4-iodo-3,5-dimethyl-1H-pyrazole

To an ice-cold solution of 3,5-dimethyl-4-iodo-1H-pyrazole (5.00 g, 22.5 mmol) in DMF (15 mL) was added NaH (60%, 1.08 g, 27 mmol) in portions and stirred at room temperature for 1 h. To this was added methanesulfonic acid cyclopent-3-enyl ester (4.00 g, 24.7 mmol) and heated at 60° C. overnight. The reaction mixture was poured into water and extracted with ethyl acetate (60 mL). The ethyl acetate layer was washed with brine, dried over Na$_2$SO$_4$, filtered and concentrated. The crude residue was purified by column chromatography using 5-10% ethyl acetate in hexane to give the title compound as an oil. $^1$H NMR (300 MHz, CDCl$_3$): δ=5.75 (s, 2H), 4.97 (m, 1H), 2.79 (d, 4H, J=7.2 Hz), 2.28 (s, 3H), 2.22 (s, 3H).

Example 34

(2R)-3-[4-{3-[(1S)-1-(2-Chloro-3-fluoro-6-methoxyphenyl)ethyl]-1H-pyrrolo[2,3-b]pyridin-5-yl}-3-(trifluoromethyl)-1H-pyrazol-1-yl]propane-1,2-diol

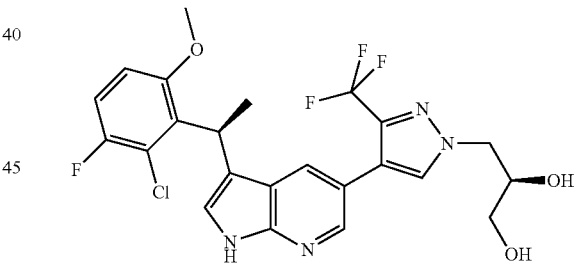

A mixture of 3-[(S)-1-(2-chloro-3-fluoro-6-methoxyphenyl)-ethyl]-5-(4,4,5,5-tetramethyl-[1,3,2]dioxaborolan-2-yl)-1H-pyrrolo[2,3-b]pyridine (10.0 mg, 0.0232 mmol), 4-bromo-1-{[(4R)-2,2-dimethyl-1,3-dioxolan-4-yl]methyl}-3-(trifluoromethyl)-1H-pyrazole (15.3 mg, 0.0464 mmol), Pd(PPh$_3$)$_4$ (1.34 mg, 0.00116 mmol), K$_2$CO$_3$ (9.63 mg, 0.0696 mmol) and 4:1 dioxane:H$_2$O (0.5 mL, 5 mmol) was heated in a microwave reactor at 95° C. for 20 min. 12 M of HCl in H$_2$O (0.1 mL, 1 mmol) was added, and the solution was heated to 45° C. for 1 h. The solution was used directly for HPLC purification, and the fractions containing the pure product were concentrated in vacuo to afford the title compound as a white solid. $^1$H NMR (400 MHz, CD$_3$OD): δ=1.79 (d, J=7.1 Hz, 3H), 3.56 (d, J=5.3 Hz, 2H), 3.63 (br. s., 3H), 4.04 (dd, J=8.1, 3.8 Hz, 1H), 4.19 (dd, J=13.9, 8.1 Hz, 1H), 4.38 (dd, J=13.9, 3.8 Hz, 1H), 5.10 (q, J=7.0 Hz, 1H), 6.87 (dd, J=9.0, 4.2 Hz, 1H), 7.06 (t, J=8.8 Hz, 1H), 7.35 (d, J=1.3

Hz, 1H), 7.54 (s, 1H), 7.82 (s, 1H), 8.13 (br. s., 1H). MS (ES+): m/z=513.06/515.06 (100/50) [MH+]. HPLC: $t_R$=3.26 min (polar_5 min, ZQ3).

4-Bromo-1-{[(4R)-2,2-dimethyl-1,3-dioxolan-4-yl]methyl}-5-(trifluoromethyl)-1H-pyrazole and 4-bromo-1-{[(4R)-2,2-dimethyl-1,3-dioxolan-4-yl]methyl}-3-(trifluoromethyl)-1H-pyrazole

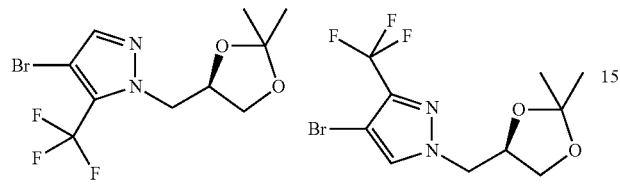

A mixture of 4-bromo-3-trifluoromethyl-1H-pyrazole (400.0 mg, 1.861 mmol), toluene-4-sulfonic acid (S)-2,2-dimethyl-[1,3]dioxolan-4-ylmethyl ester (799.2 mg, 2.791 mmol), $K_2CO_3$ (400.0 mg, 2.894 mmol) and DMF (6 mL, 80 mmol) was heated to 90° C. for 2 h. The material was extracted with EtOAc, washing with water (3×). The organic layer was dry-loaded onto silica gel, and purified via column chromatography, eluting with 10-30% EtOAc/heptane. The fractions containing each pure product were concentrated in vacuo to afford the title compounds as clear oils. 3-Trifluoromethyl isomer: $^1$H NMR (400 MHz, $CD_3OD$): δ=1.31 (s, 3H), 1.34 (s, 3H), 3.78 (dd, J=8.6, 5.8 Hz, 1H), 4.10 (dd, J=8.8, 6.6 Hz, 1H), 4.22-4.31 (m, 1H), 4.36 (dd, J=14.1, 4.0 Hz, 1H), 4.41-4.49 (m, 1H), 7.92 (s, 1H). MS (ES+): m/z=329.01/331.01 (100/100) [MH+]. HPLC: $t_R$=1.59 min (polar_3 min, UPLC-ACQUITY). 5-Trifluoromethyl isomer: MS (ES+): m/z=329.01/331.01 (100/100) [MH+]. HPLC: $t_R$=1.62 min (polar_3 min, UPLC-ACQUITY).

Example 35

(2R)-3-[4-{3-[(1S)-1-(2-Chloro-3-fluoro-6-methoxyphenyl)ethyl]-1H-pyrrolo[2,3-b]pyridin-5-yl}-5-(trifluoromethyl)-1H-pyrazol-1-yl]propane-1,2-diol

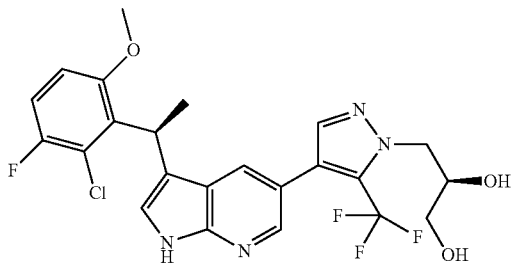 [SMILES: COc1ccc(F)c(Cl)c1[C@@H](C)c1c[nH]c2ncc(-c3cnn(C[C@@H](O)CO)c3C(F)(F)F)cc12]

Prepared using the procedure described for Example 34. $^1$H NMR (400 MHz, $CD_3OD$): δ=1.79 (d, J=7.1 Hz, 3H), 3.50-3.72 (m, 5H), 4.15 (dd, J=8.0, 4.7 Hz, 1H), 4.31 (dd, J=14.0, 8.2 Hz, 1H), 4.45 (dd, J=14.1, 4.3 Hz, 1H), 5.09 (q, J=6.9 Hz, 1H), 6.87 (dd, J=9.1, 4.3 Hz, 1H), 7.06 (t, J=8.8 Hz, 1H), 7.37 (d, J=1.3 Hz, 1H), 7.46 (s, 1H), 7.57 (s, 1H), 8.09 (br. s., 1H). MS (ES+): m/z=513.06/515.05 (100/50) [MH+]. HPLC: $t_R$=3.24 min (polar_5 min, ZQ3).

Example 36

(2S)-3-[4-{3-[(1S)-1-(2-Chloro-3-fluoro-6-methoxyphenyl)ethyl]-1H-pyrrolo[2,3-b]pyridin-5-yl}-5-(trifluoromethyl)-1H-pyrazol-1-yl]propane-1,2-diol

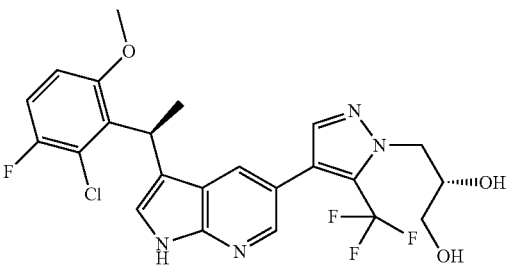 [SMILES: COc1ccc(F)c(Cl)c1[C@@H](C)c1c[nH]c2ncc(-c3cnn(C[C@H](O)CO)c3C(F)(F)F)cc12]

Prepared using the procedure described for Example 34. $^1$H NMR (400 MHz, $CD_3OD$): δ=1.79 (d, J=7.3 Hz, 3H), 3.50-3.61 (m, 2H), 3.63 (br. s., 3H), 4.08-4.19 (m, 1H), 4.30 (dd, J=14.1, 8.1 Hz, 1H), 4.45 (dd, J=14.1, 4.3 Hz, 1H), 5.09 (q, J=7.2 Hz, 1H), 6.88 (dd, J=9.0, 4.4 Hz, 1H), 7.07 (t, J=8.8 Hz, 1H), 7.38 (s, 1H), 7.46 (s, 1H), 7.57 (s, 1H), 8.09 (d, J=1.5 Hz, 1H). MS (ES+): m/z=513.06/515.05 (100/50) [MH+]. HPLC: $t_R$=3.24 min (polar_5 min, ZQ3).

4-Bromo-1-{[(4S)-2,2-dimethyl-1,3-dioxolan-4-yl]methyl}-5-(trifluoromethyl)-1H-pyrazole and 4-Bromo-1-{[(4S)-2,2-dimethyl-1,3-dioxolan-4-yl]methyl}-3-(trifluoromethyl)-1H-pyrazole

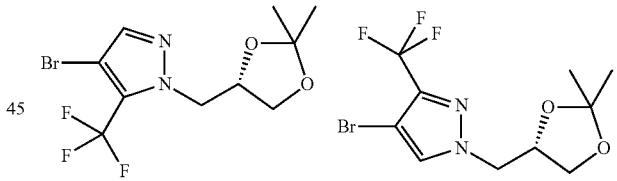

A mixture of 4-bromo-3-trifluoromethyl-1H-pyrazole (400.0 mg, 1.861 mmol), toluene-4-sulfonic acid (R)-2,2-dimethyl-[1,3]dioxolan-4-ylmethyl ester (799.2 mg, 2.791 mmol), $K_2CO_3$ (400.0 mg, 2.894 mmol) and DMF (6 mL, 80 mmol) was heated to 90° C. for 2 h. The material was extracted with EtOAc, washing with water (3×). The organic layer was dry-loaded onto silica gel, and purified via column chromatography, eluting with 10-30% EtOAc/heptane. The fractions containing each pure product were concentrated in vacuo to afford the title compounds as clear oils. 3-Trifluoromethyl isomer: $^1$H NMR (400 MHz, $CD_3OD$): δ=1.34 (s, 3H), 1.31 (s, 3H), 3.78 (dd, J=8.8, 5.8 Hz, 1H), 4.10 (dd, J=8.7, 6.4 Hz, 1H), 4.22-4.30 (m, 1H), 4.36 (dd, J=14.1, 4.0 Hz, 1H), 4.45 (dd, J=5.8, 4.3 Hz, 1H), 7.93 (s, 1H). MS (ES+): m/z=329.01/331.01 (100/100) [MH+]. HPLC: $t_R$=1.59 min (polar_3 min, UPLC-ACQUITY). 5-Trifluoromethyl isomer: MS (ES+): m/z=329.01/331.01 (100/100) [MH+]. HPLC: $t_R$=1.62 min (polar_3 min, UPLC-ACQUITY).

Example 37

(2S)-3-[4-{3-[(1S)-1-(2-Chloro-3-fluoro-6-methoxyphenyl)ethyl]-1H-pyrrolo[2,3-b]pyridin-5-yl}-3-(trifluoromethyl)-1H-pyrazol-1-yl]propane-1,2-diol

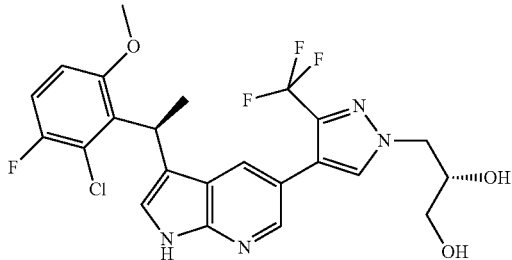 [SMILES: COc1ccc(F)c(Cl)c1[C@@H](C)c1c[nH]c2ncc(-c3cn(C[C@H](O)CO)nc3C(F)(F)F)cc12]

Prepared using the procedure described for Example 34. $^1$H NMR (400 MHz, CD$_3$OD): δ=1.78 (d, J=7.1 Hz, 3H), 3.56 (d, J=5.3 Hz, 2H), 3.64 (br. s., 3H), 3.98-4.08 (m, 1H), 4.19 (dd, J=13.9, 8.1 Hz, 1H), 4.38 (dd, J=14.0, 3.7 Hz, 1H), 5.10 (q, J=6.7 Hz, 1H), 6.87 (dd, J=9.1, 4.3 Hz, 1H), 7.06 (t, J=8.8 Hz, 1H), 7.36 (d, J=1.3 Hz, 1H), 7.54 (s, 1H), 7.83 (s, 1H), 8.10-8.14 (m, 1H). MS (ES+): m/z=513.06/515.05 (100/50) [MH$^+$]. HPLC: t$_R$=3.24 min (polar_5 min, ZQ3).

Example 38

4-{3-[(1S)-1-(2-Chloro-3-fluoro-6-methoxyphenyl)ethyl]-1H-pyrrolo[2,3-b]pyridin-5-yl}-1-methyl-1H-pyrazol-5-amine

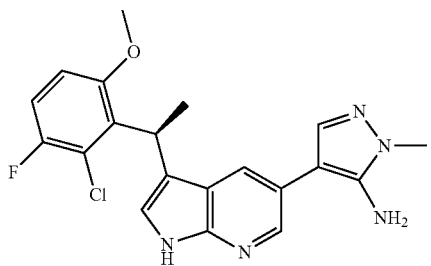 [SMILES: COc1ccc(F)c(Cl)c1[C@@H](C)c1c[nH]c2ncc(-c3cnn(C)c3N)cc12]

Prepared using the procedure described for Example 29. $^1$H NMR (400 MHz, CD$_3$OD): δ=1.80 (d, J=7.1 Hz, 3H), 3.67 (s, 3H), 3.69 (br. s., 3H), 5.09-5.18 (m, 1H), 6.90 (dd, J=9.0, 3.9 Hz, 1H), 7.08 (t, J=8.8 Hz, 1H), 7.26 (s, 1H), 7.32 (s, 1H), 7.50 (br. s., 1H), 8.18 (br. s., 1H). MS (ES+): m/z=400.13/402.13 (100/50) [MH$^+$]. HPLC: t$_R$=1.33 min (polar_3 min, UPLC-ACQUITY).

Example 39

4-{3-[(1S)-1-(2-Chloro-3-fluoro-6-methoxyphenyl)ethyl]-1H-pyrrolo[2,3-b]pyridin-5-yl}-1-methyl-1H-pyrazole-3-carboxamide

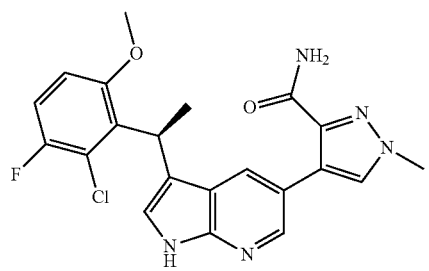 [SMILES: COc1ccc(F)c(Cl)c1[C@@H](C)c1c[nH]c2ncc(-c3cn(C)nc3C(N)=O)cc12]

A mixture of 4-bromo-1-methyl-1H-pyrazole-3-carboxylic acid (20.0 mg, 0.0976 mmol), NH$_4$Cl (52.2 mg, 0.976 mmol), TBTU (62.6 mg, 0.195 mmol), DIPEA (0.0340 mL, 0.195 mmol) and DMF (2 mL, 20 mmol) was stirred at rt for 10 min. The material was extracted with EtOAc, and washed with sat. NaHCO$_3$ (3×) to remove carboxylic acid starting material. The organic layer was concentrated in vacuo. 3-[(S)-1-(2-Chloro-3-fluoro-6-methoxyphenyl)-ethyl]-5-(4,4,5,5-tetramethyl-[1,3,2]dioxaborolan-2-yl)-1H-pyrrolo[2,3-b]pyridine (15.0 mg, 0.0348 mmol), (1,1'bis-(diphenylphosphino)-ferrocene) palladium dichloride (3.57 mg, 0.00488 mmol), K$_2$CO$_3$ (20.2 mg, 0.146 mmol) and 4:1 dioxane:H$_2$O (1 mL, 10 mmol) were added, and the mixture was heated to 95° C. for 30 min. The solution was used directly for HPLC purification, and the fractions containing the pure product were concentrated in vacuo to afford the title compound as a white solid. $^1$H NMR (400 MHz, CD$_3$OD): δ=1.80 (d, J=7.1 Hz, 3H), 3.70 (br. s., 3H), 3.96 (s, 3H), 5.14 (q, J=7.2 Hz, 1H), 6.88 (dd, J=9.2, 4.2 Hz, 1H), 7.05 (t, J=8.8 Hz, 1H), 7.30 (d, J=1.0 Hz, 1H), 7.66 (s, 1H), 7.72 (s, 1H), 8.22 (br. s., 1H). MS (ES+): m/z=428.11/430.12 (100/50) [MH$^+$]. HPLC: t$_R$=1.33 min (polar_3 min, UPLC-ACQUITY).

Example 40 trans-4-[4-{3-[(1S)-1-(2-Chloro-3-fluoro-6-methoxyphenyl)ethyl]-1H-pyrrolo[2,3-b]pyridin-5-yl}-5-(trifluoromethyl)-1H-pyrazol-1-yl]cyclohexanol

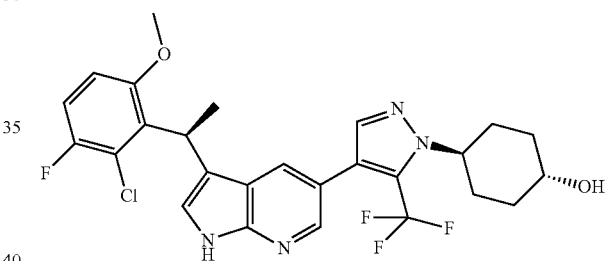

Prepared using the procedure described for Example 29. $^1$H NMR (400 MHz, CD$_3$OD): δ=1.40-1.55 (m, 2H), 1.79 (d, J=7.1 Hz, 3H), 2.00-2.05 (m, 2H), 2.07-2.21 (m, 4H), 3.64 (br. s., 3H), 3.66-3.73 (m, 1H), 4.31 (dddd, J=15.0, 7.5, 3.8, 3.5 Hz, 1H), 5.04-5.14 (m, 1H), 6.88 (dd, J=9.1, 4.3 Hz, 1H), 7.08 (t, J=8.8 Hz, 1H), 7.37 (d, J=1.3 Hz, 1H), 7.42 (br. s., 1H), 7.54 (s, 1H), 8.06 (br. s., 1H). MS (ES+): m/z=537.14/539.16 (100/50) [MH$^+$]. HPLC: t$_R$=1.59 min (polar_3 min, UPLC-ACQUITY).

trans-4-[4-Bromo-5-(trifluoromethyl)-1H-pyrazol-1-yl]cyclohexanol

A mixture of 4-bromo-1-(1,4-dioxaspiro[4.5]dec-8-yl)-5-(trifluoromethyl)-1H-pyrazole (500 mg, 1.41 mmol), pyridinium p-toluenesulfonate (800 mg, 3 mmol), acetone (20 mL, 300 mmol) and H$_2$O (20 mL, 1000 mmol) was heated to 60° C. overnight to form the ketone. The organic solvent was removed in vacuo, and the material was extracted with DCM and water. The organic layer was dried in vacuo, redissolved in EtOH (10 mL, 200 mmol), and sodium borohydride (79.89 mg, 2.112 mmol) was added. The mixture was stirred at rt for 3 h. The material was concentrated in vacuo, extracted with EtOAc, and washed with water (3×). The organic layer was dry-loaded onto silica gel for column chromatography, eluting with Et$_2$O. The cis-product eluted first, followed by the trans-product. The fractions containing the pure trans-product were concentrated in vacuo to afford the title compound as white solid. MS (ES+): m/z=313.02/315.02 (100/100) [MH+]. HPLC: $t_R$=1.46 min (polar_3 min, UPLC-ACQUITY).

4-Bromo-1-(1,4-dioxaspiro[4.5]dec-8-yl)-3-(trifluoromethyl)-1H-pyrazole and 4-Bromo-1-(1,4-dioxaspiro[4.5]dec-8-yl)-5-(trifluoromethyl)-1H-pyrazole

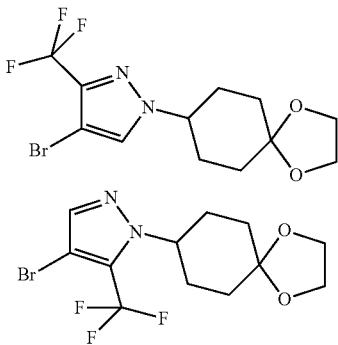

A mixture of 4-bromo-3-trifluoromethyl-1H-pyrazole (1.50 g, 6.98 mmol), 1,4-dioxaspiro[4.5]dec-8-yl 4-methylbenzenesulfonate (2.834 g, 9.071 mmol), K$_2$CO$_3$ (1.929 g, 13.96 mmol), and DMF (22 mL, 280 mmol) was heated to 90° C. for 2 hours. The material was extracted with EtOAc, and washed with water (3×). The organic layer was purified via column chromatography, eluting with 10-20% EtOAc/hexanes. The fractions containing the separate regioisomers were concentrated in vacuo to afford the title compounds as white solids. 3-Trifluoromethyl isomer: $^1$H NMR (400 MHz, CD$_3$OD): δ=1.73 (td, J=12.9, 5.3 Hz, 2H), 1.82-1.92 (m, 2H), 2.02-2.18 (m, 4H), 3.91-4.03 (m, 4H), 4.31 (dt, J=10.4, 5.2 Hz, 1H), 7.96 (s, 1H). MS (ES+): m/z=355.02/357.02 (100/100) [MH+]. HPLC: $t_R$=1.63 min (polar_3 min, UPLC-ACQUITY). 5-Trifluoromethyl isomer: MS (ES+): m/z=355.02/357.02 (100/100) [MH+]. HPLC: $t_R$=1.58 min (polar_3 min, UPLC-ACQUITY).

Example 41

4-{3-[(1S)-1-(2-Chloro-3-fluoro-6-methoxyphenyl)ethyl]-1H-pyrrolo[2,3-b]pyridin-5-yl}-1,3-dimethyl-1H-pyrazole-5-carboxamide

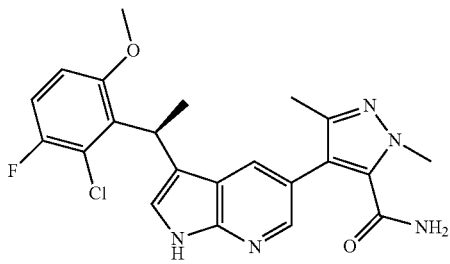 [SMILES: COc1ccc(F)c(Cl)c1[C@@H](C)c1c[nH]c2ncc(-c3c(C)nn(C)c3C(N)=O)cc12]

A mixture of 4-bromo-1,3-dimethyl-1H-pyrazole-5-carboxylic acid (20.0 mg, 0.0913 mmol), NH$_4$Cl (48.8 mg, 0.913 mmol), TBTU (58.6 mg, 0.183 mmol), DIPEA (0.159 mL, 0.913 mmol) and DMF (2 mL, 20 mmol) was stirred at rt for 10 min. The material was extracted with EtOAc, and washed with sat. NaHCO$_3$ (3×) to remove carboxylic acid starting material. The organic layer was concentrated in vacuo. 3-[(S)-1-(2-Chloro-3-fluoro-6-methoxyphenyl)-ethyl]-5-(4,4,5,5-tetramethyl-[1,3,2]dioxaborolan-2-yl)-1H-pyrrolo[2,3-b]pyridine (15.0 mg, 0.0348 mmol), (1,1'bis-(diphenylphosphino)-ferrocene) palladium dichloride (3.34 mg, 0.00456 mmol), K$_2$CO$_3$ (18.9 mg, 0.137 mmol) and 4:1 dioxane:H$_2$O (1 mL, 10 mmol) were added, and the mixture was heated to 95° C. for 30 min. The solution was used directly for HPLC purification, and the fractions containing the pure product were concentrated in vacuo to afford the title compound as a white solid. $^1$H NMR (400 MHz, CD$_3$OD): δ=1.80 (d, J=7.3 Hz, 3H), 2.04 (s, 3H), 3.66 (br. s., 3H), 3.95 (s, 3H), 5.11 (q, J=6.8 Hz, 1H), 6.90 (dd, J=9.0, 4.2 Hz, 1H), 7.08 (t, J=8.8 Hz, 1H), 7.37 (d, J=1.3 Hz, 1H), 7.45 (s, 1H), 8.07 (br. s., 1H). MS (ES+): m/z=442.14/444.14 (100/50) [MH+]. HPLC: $t_R$=1.37 min (polar_3 min, UPLC-ACQUITY).

Example 42

(4-{3-[(1S)-1-(2-Chloro-3-fluoro-6-methoxyphenyl)ethyl]-1H-pyrrolo[2,3-b]pyridin-5-yl}-1-methyl-1H-pyrazol-3-yl)methanol

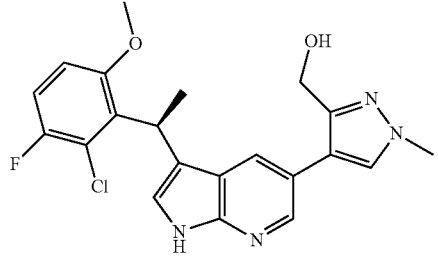 [SMILES: COc1ccc(F)c(Cl)c1[C@@H](C)c1c[nH]c2ncc(-c3cn(C)nc3CO)cc12]

To a solution of 4-bromo-1-methyl-1H-pyrazole-3-carboxylic acid (20.0 mg, 0.0976 mmol) in THF (3 mL, 40 mmol) was added 1.0 M of BH$_3$.THF in THF (0.49 mL, 0.49 mmol), and the resulting solution was heated to 60° C. overnight. The material was extracted with EtOAc and washed with sat. NaHCO$_3$ (3×) to remove carboxylic acid starting material. The organic layer was concentrated in vacuo. 3-[(S)-1-(2-Chloro-3-fluoro-6-methoxyphenyl)-ethyl]-5-(4,4,5,5-tetramethyl-[1,3,2]dioxaborolan-2-yl)-1H-pyrrolo[2,3-b]pyridine (15.0 mg, 0.0348 mmol), (1,1'bis-(diphenylphosphino)-ferrocene) palladium dichloride (3.57 mg, 0.00488 mmol), K$_2$CO$_3$ (20.2 mg, 0.146 mmol) and 4:1 dioxane:H$_2$O (1 mL, 10 mmol) were added, and the mixture was heated to 95° C. for 30 min. The solution was used directly for HPLC purification, and the fractions containing the pure product were concentrated in vacuo to afford the title compound as a white solid. $^1$H NMR (400 MHz, CD$_3$OD): δ=1.80 (d, J=7.1 Hz, 3H), 3.68 (br. s., 3H), 3.90 (s, 3H), 4.45-4.55 (m, 2H), 5.10-5.16 (m, 1H), 6.89 (dd, J=9.1, 4.3 Hz, 1H), 7.07 (t, J=8.8 Hz, 1H), 7.31 (d, J=1.3 Hz, 1H), 7.65 (s, 1H), 7.68 (s, 1H), 8.27 (br. s., 1H). MS (ES+): m/z=415.12/417.13 (100/50) [MH+]. HPLC: $t_R$=1.35 min (polar_3 min, UPLC-ACQUITY).

Example 43

4-{3-[(1S)-1-(2-Chloro-3-fluoro-6-methoxyphenyl)ethyl]-1H-pyrrolo[2,3-b]pyridin-5-yl}-1-methyl-1H-pyrazole-5-carboxamide

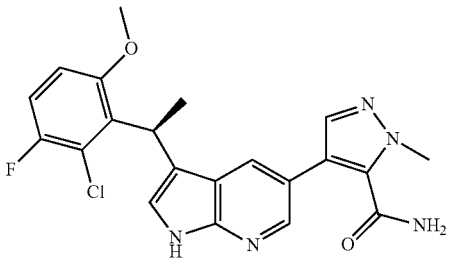 [SMILES: COc1ccc(F)c(Cl)c1[C@@H](C)c1c[nH]c2ncc(-c3cnn(C)c3C(N)=O)cc12]

A mixture of 4-bromo-2-methyl-2H-pyrazole-3-carboxylic acid (20.0 mg, 0.0976 mmol), NH$_4$Cl (52.2 mg, 0.976 mmol), TBTU (62.6 mg, 0.195 mmol), DIPEA (0.170 mL, 0.976 mmol) and DMF (2 mL, 20 mmol) was stirred at rt for 10 min. The material was extracted with EtOAc, and washed with sat. NaHCO$_3$ (3×) to remove carboxylic acid starting material. The organic layer was concentrated in vacuo. 3-[(S)-1-(2-Chloro-3-fluoro-6-methoxyphenyl)-ethyl]-5-(4,4,5,5-tetramethyl-[1,3,2]dioxaborolan-2-yl)-1H-pyrrolo[2,3-b]pyridine (15.0 mg, 0.0348 mmol), (1,1'bis-(diphenylphosphino)-ferrocene) palladium dichloride (3.57 mg, 0.00488 mmol), K$_2$CO$_3$ (20.2 mg, 0.146 mmol) and 4:1 dioxane:H$_2$O (1 mL, 10 mmol) were added, and the mixture was heated to 95° C. for 30 min. The solution was used directly for HPLC purification, and the fractions containing the pure product were concentrated in vacuo to afford the title compound as a white solid. $^1$H NMR (400 MHz, CD$_3$OD): δ=1.79 (d, J=7.3 Hz, 3H), 3.70 (br. s., 3H), 3.99 (s, 3H), 5.09-5.16 (m, 1H), 6.90 (dd, J=9.2, 4.2 Hz, 1H), 7.08 (t, J=8.8 Hz, 1H), 7.34 (s, 1H), 7.50 (s, 1H), 7.59 (br. s., 1H), 8.20 (br. s., 1H). MS (ES+): m/z=428.11/430.12 (100/50) [MH$^+$]. HPLC: t$_R$=1.34 min (polar_3 min, UPLC-ACQUITY).

Example 44

(4-{3-[(1S)-1-(2-Chloro-3-fluoro-6-methoxyphenyl)ethyl]-1H-pyrrolo[2,3-b]pyridin-5-yl}-1-methyl-1H-pyrazol-5-yl)methanol

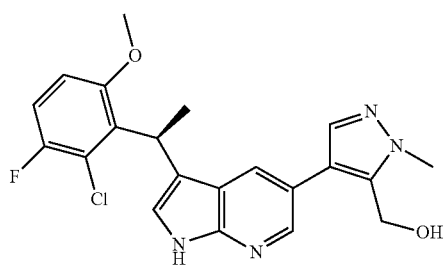 [SMILES: COc1ccc(F)c(Cl)c1[C@@H](C)c1c[nH]c2ncc(-c3cnn(C)c3CO)cc12]

To a solution of 4-bromo-2-methyl-2H-pyrazole-3-carboxylic acid (20.0 mg, 0.0976 mmol) in THF (3 mL, 40 mmol) was added 1.0 M of BH$_3$.THF in THF (0.49 mL, 0.49 mmol), and the resulting solution was heated to 60° C. overnight. The material was extracted with EtOAc, and washed with sat. NaHCO$_3$ (3×) to remove carboxylic acid starting material. The organic layer was concentrated in vacuo. 3-[(S)-1-(2-Chloro-3-fluoro-6-methoxyphenyl)-ethyl]-5-(4,4,5,5-tetramethyl-[1,3,2]dioxaborolan-2-yl)-1H-pyrrolo[2,3-b]pyridine (15.0 mg, 0.0348 mmol), (1,1'bis-(diphenylphosphino)-ferrocene) palladium dichloride (3.57 mg, 0.00488 mmol), K$_2$CO$_3$ (20.2 mg, 0.146 mmol) and 4:1 dioxane:H$_2$O (1 mL, 10 mmol) were added, and the mixture was heated to 95° C. for 30 min. The solution was used directly for HPLC purification, and the fractions containing the pure product were concentrated in vacuo to afford the title compound as a white solid. $^1$H NMR (400 MHz, CD$_3$OD): δ=1.80 (d, J=7.1 Hz, 3H), 3.67 (br. s., 3H), 3.96 (s, 3H), 4.55 (s, 2H), 5.08-5.17 (m, 1H), 6.90 (dd, J=9.1, 4.3 Hz, 1H), 7.08 (t, J=8.8 Hz, 1H), 7.34 (d, J=1.3 Hz, 1H), 7.46 (s, 1H), 7.53 (s, 1H), 8.15-8.22 (m, 1H). MS (ES+): m/z=415.13/417.13 (100/50) [MH$^+$]. HPLC: t$_R$=1.37 min (polar_3 min, UPLC-ACQUITY).

Example 45

(4-{3-[(1S)-1-(2-Chloro-3-fluoro-6-methoxyphenyl)ethyl]-1H-pyrrolo[2,3-b]pyridin-5-yl}-1,3-dimethyl-1H-pyrazol-5-yl)methanol

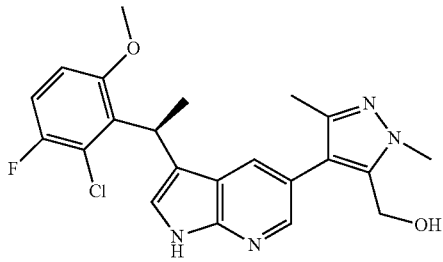 [SMILES: COc1ccc(F)c(Cl)c1[C@@H](C)c1c[nH]c2ncc(-c3c(C)nn(C)c3CO)cc12]

To a solution of 4-bromo-1,3-dimethyl-1H-pyrazole-5-carboxylic acid (20.0 mg, 0.0913 mmol) in THF (3 mL, 30 mmol) was added 1.0 M of BH$_3$.THF in THF (0.456 mL, 0.456 mmol), and the mixture was heated to 60° C. overnight. The material was extracted with EtOAc, and washed with sat. NaHCO$_3$ (3×). The organic layer was concentrated in vacuo. 3-[(S)-1-(2-Chloro-3-fluoro-6-methoxyphenyl)-ethyl]-5-(4,4,5,5-tetramethyl-[1,3,2]dioxaborolan-2-yl)-1H-pyrrolo[2,3-b]pyridine (15.0 mg, 0.0348 mmol), (1,1'bis-(diphenylphosphino)-ferrocene) palladium dichloride (3.34 mg, 0.00456 mmol), K$_2$CO$_3$ (18.9 mg, 0.137 mmol) and 4:1 dioxane:H$_2$O (1 mL, 10 mmol) were added, and the mixture was heated to 95° C. for 30 min. The solution was used directly for HPLC purification, and the fractions containing the pure product were concentrated in vacuo to afford the title compound as a white solid. $^1$H NMR (400 MHz, CD$_3$OD): δ=1.80 (d, J=7.1 Hz, 3H), 2.04 (s, 3H), 3.64 (br. s., 3H), 3.89 (s, 3H), 4.46 (s, 2H), 5.05-5.15 (m, 1H), 6.88 (dd, J=9.1, 4.3 Hz, 1H), 7.07 (t, J=8.8 Hz, 1H), 7.36 (s, 1H), 7.38 (br. s., 1H), 8.07 (d, J=2.0 Hz, 1H). MS (ES+): m/z=429.14/431.15 (100/50) [MH$^+$]. HPLC: t$_R$=1.38 min (polar_3 min, UPLC-ACQUITY).

Example 46

4-{3-[(1S)-1-(2-Chloro-3-fluoro-6-methoxyphenyl)ethyl]-1H-pyrrolo[2,3-b]pyridin-5-yl}-1-methyl-1H-pyrazole-3-carbonitrile

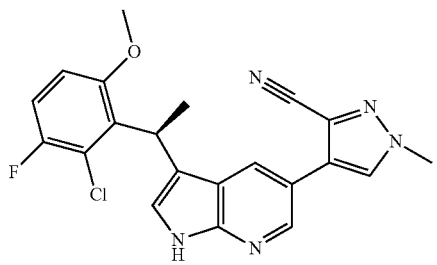 [SMILES: COc1ccc(F)c(Cl)c1[C@@H](C)c1c[nH]c2ncc(-c3cn(C)nc3C#N)cc12]

To a solution of 4-bromo-1-methyl-1H-pyrazole-3-carboxamide (10.0 mg, 0.0490 mmol) in DMF (2 mL, 20 mmol) was added thionyl chloride (0.1 mL, 1 mmol) at 0° C., and the mixture was allowed to warm to rt. The material was extracted with EtOAc, and washed with sat. NaHCO₃ (3×). The organic layer was concentrated in vacuo. 3-[(S)-1-(2-Chloro-3-fluoro-6-methoxyphenyl)-ethyl]-5-(4,4,5,5-tetramethyl-[1,3,2]dioxaborolan-2-yl)-1H-pyrrolo[2,3-b]pyridine (10.0 mg, 0.0232 mmol), (1,1'bis-(diphenylphosphino)-ferrocene) palladium dichloride (1.79 mg, 0.00245 mmol), K₂CO₃ (10.0 mg, 0.0724 mmol) and 4:1 dioxane:H₂O (1 mL, 10 mmol) were added, and the mixture was heated in a microwave reactor at 100° C. for 30 min. The solution was used directly for HPLC purification, and the fractions containing the pure product were concentrated in vacuo to afford the title compound as a white solid. $^1$H NMR (400 MHz, CD₃OD): δ=1.80 (d, J=7.3 Hz, 3H), 3.72 (br. s., 3H), 4.00 (s, 3H), 5.15 (q, J=6.7 Hz, 1H), 6.90 (dd, J=9.1, 4.3 Hz, 1H), 7.05 (t, J=8.8 Hz, 1H), 7.37 (d, J=1.3 Hz, 1H), 7.82 (s, 1H), 7.98 (s, 1H), 8.31 (d, J=2.0 Hz, 1H). MS (ES+): m/z=410.05/412.06 (100/50) [MH⁺]. HPLC: $t_R$=4.08 min (polar_5 min, ZQ3).

Example 47 trans-4-(4-{3-[(1S)-1-(2-Chloro-3-fluoro-6-methoxyphenyl)ethyl]-1H-pyrrolo[2,3-b]pyridin-5-yl}-3-ethyl-1H-pyrazol-1-yl)cyclohexanol

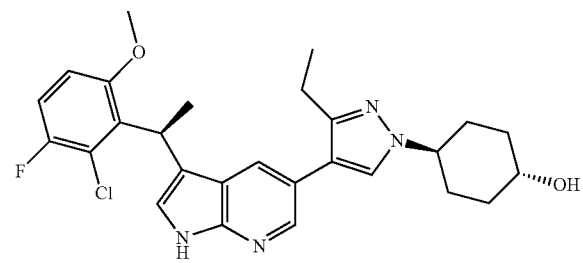 [SMILES: CCc1nn([C@H]2CC[C@H](O)CC2)cc1-c1cnc2[nH]cc([C@H](C)c3c(OC)ccc(F)c3Cl)c2c1]

Prepared using the procedure described for Example 5. $^1$H NMR (400 MHz, CD₃OD): δ=1.02 (t, J=7.6 Hz, 3H), 1.40-1.54 (m, 2H), 1.79 (d, J=7.1 Hz, 3H), 1.83-1.94 (m, 2H), 2.05-2.16 (m, 4H), 2.51 (qd, J=7.5, 2.7 Hz, 2H), 3.62 (br. s., 3H), 3.65-3.71 (m, 1H), 4.11 (tt, J=11.8, 3.6 Hz, 1H), 5.09 (q, J=7.2 Hz, 1H), 6.89 (dd, J=8.7, 3.9 Hz, 1H), 7.09 (t, J=8.8 Hz, 1H), 7.34 (d, J=1.3 Hz, 1H), 7.67 (s, 1H), 8.05-8.14 (m, 1H). MS (ES+): m/z=497.31/499.31 (100/50) [MH⁺]. HPLC: $t_R$=1.28 min (polar_2 min, UPLC-ACQUITY).

trans-4-[3-Ethyl-4-(4,4,5,5-tetramethyl-1,3,2-dioxaborolan-2-yl)-1H-pyrazol-1-yl]cyclohexanol To a solution of trans-4-(3-ethyl-4-iodo-1H-pyrazol-1-yl)cyclohexanol (150.0 mg, 0.4685 mmol) in THF (10 mL, 100 mmol) at rt was added 2 M isopropylmagnesium chloride in THF (0.70 mL, 1.4 mmol), and the mixture was stirred for 1 h. The reaction was quenched with 2-methoxy-4,4,5,5-tetramethyl-1,3,2-dioxaborolane (0.31 mL, 1.9 mmol), and allowed to stir at rt for 1 h. Sat. NH₄Cl was added, and the organic solvent was removed in vacuo. The material was extracted with DCM and water. The organic layer was concentrated in vacuo to afford the title compound as a white solid. The material was used in the next step without further purification.

trans-4-(3-Ethyl-4-iodo-1H-pyrazol-1-yl)cyclohexanol

A mixture of 1-(1,4-dioxaspiro[4.5]dec-8-yl)-3-ethyl-4-iodo-1H-pyrazole (300.0 mg, 0.8282 mmol), pyridinium p-toluenesulfonate (416.3 mg, 1.656 mmol), acetone (10 mL, 200 mmol) and H₂O (10 mL, 800 mmol) was heated to 70° C. overnight to form the ketone. The organic solvent was removed in vacuo, and the material was extracted with EtOAc, washed with sat. NaHCO₃, then washed with 0.5 M HCl. The organic layer was dried in vacuo, redissolved in EtOH (7 mL, 100 mmol), and sodium borohydride (47.00 mg, 1.242 mmol) was added. The mixture was stirred at rt for 1 h. The material was concentrated in vacuo, extracted with DCM and water. The organic layer was dry-loaded onto silica gel for column chromatography, eluting with 15-40% EtOAc/heptane. The cis-product eluted first, followed by the trans-product. The fractions containing the pure trans-product were concentrated in vacuo to afford the title compound as a white solid. $^1$H NMR (400 MHz, CD₃OD): δ=1.14-1.21 (m, 3H), 1.37-1.50 (m, 2H), 1.75-1.89 (m, 2H), 1.98-2.11 (m, 4H), 2.57 (q, J=7.6 Hz, 2H), 3.63 (m, J=10.8, 10.8, 3.7, 3.4 Hz, 1H), 4.08 (tt, J=12.0, 3.6 Hz, 1H), 7.65 (s, 1H).

1-(1,4-Dioxaspiro[4.5]dec-8-yl)-3-ethyl-4-iodo-1H-pyrazole and 1-(1,4-Dioxaspiro[4.5]dec-8-yl)-5-ethyl-4-iodo-1H-pyrazole

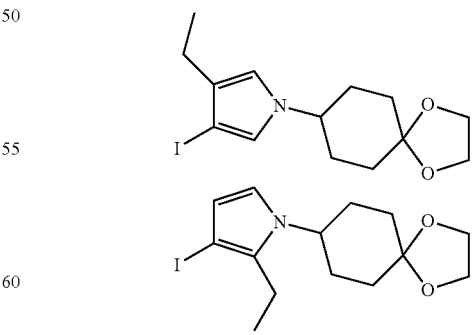

A mixture of 5-ethyl-4-iodo-1H-pyrazole (500.0 mg, 2.252 mmol), 1,4-dioxaspiro[4.5]dec-8-yl 4-methylbenzenesulfonate (914.5 mg, 2.928 mmol), sodium hydride (64.85 mg, 2.702 mmol) and DMF (7.0 mL, 91 mmol) was heated to 85° C. overnight. The mixture was diluted with EtOAc and washed with water (3×). The organic layer was purified via column chromatography, eluting with 10-20% EtOAc/hexanes. Both regioisomers eluted together. The fractions were concentrated in vacuo, redissolved in MeOH and purified via SFC. The fractions containing each pure regioisomer were concentrated in vacuo to afford the title compounds as white solids. 3-Ethyl isomer: $^1$H NMR (400 MHz, CD$_3$OD): δ=1.18 (t, J=7.6 Hz, 3H), 1.64-1.78 (m, 2H), 1.85 (m, J=14.4, 3.3, 3.2, 3.2 Hz, 2H), 1.98-2.12 (m, 4H), 2.58 (q, J=7.6 Hz, 2H), 3.89-4.01 (m, 4H), 4.11-4.22 (m, 1H), 7.65 (s, 1H). 5-Ethyl isomer: 1.14 (t, J=7.6 Hz, 3H), 1.68-1.91 (m, 6H), 2.16-2.33 (m, 2H), 2.77 (q, J=7.6 Hz, 2H), 3.89-4.02 (m, 4H), 4.21-4.34 (m, 1H), 7.41 (s, 1H).

Example 48 trans-4-(4-{3-[(1S)-1-(2-Chloro-3-fluoro-6-methoxyphenyl)ethyl]-1H-pyrrolo[2,3-b]pyridin-5-yl}-5-ethyl-1H-pyrazol-1-yl)cyclohexanol

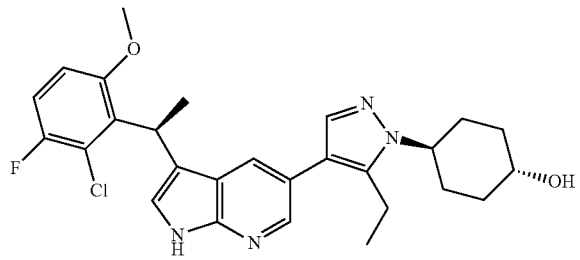 [SMILES: CCc1c(-c2cnc3[nH]cc([C@H](C)c4c(OC)ccc(F)c4Cl)c3c2)cnn1[C@H]1CC[C@H](O)CC1]

Prepared using the procedure described for Example 5. $^1$H NMR (400 MHz, CD$_3$OD): δ=1.11 (t, J=7.5 Hz, 3H), 1.45-1.58 (m, 2H), 1.79 (d, J=7.1 Hz, 3H), 1.93 (td, J=6.6, 3.4 Hz, 2H), 2.01-2.14 (m, 4H), 2.55-2.72 (m, 2H), 3.61 (br. s., 3H), 3.66-3.73 (m, 1H), 4.09-4.21 (m, 1H), 5.09 (q, J=7.2 Hz, 1H), 6.89 (dd, J=9.1, 4.3 Hz, 1H), 7.09 (t, J=8.8 Hz, 1H), 7.35 (d, J=1.3 Hz, 1H), 7.39 (d, J=1.5 Hz, 1H), 7.46 (s, 1H), 8.09 (d, J=2.0 Hz, 1H). MS (ES+): m/z=497.18/499.18 (100/50) [MH$^+$]. HPLC: t$_R$=1.43 min (polar_3 min, UPLC-ACQUITY).

Example 49 trans-4-(5-Chloro-4-{3-[(1S)-1-(2-chloro-3-fluoro-6-methoxyphenyl)ethyl]-1H-pyrrolo[2,3-b]pyridin-5-yl}-1H-pyrazol-1-yl)cyclohexanol

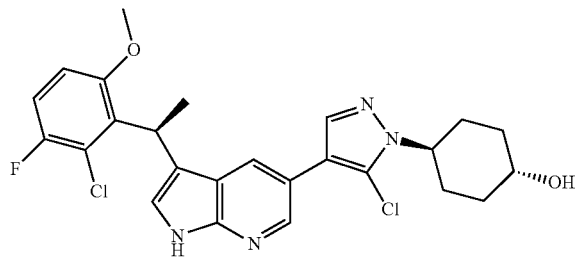 [SMILES: COc1ccc(F)c(Cl)c1[C@@H](C)c1c[nH]c2ncc(-c3cnn([C@H]4CC[C@H](O)CC4)c3Cl)cc12]

Prepared using the procedure described for Example 69. $^1$H NMR (400 MHz, CD$_3$OD): δ=1.43-1.58 (m, 2H), 1.81 (d, J=7.1 Hz, 3H), 1.93-2.07 (m, 4H), 2.12 (dd, J=12.8, 3.4 Hz, 2H), 3.56-3.78 (m, 4H), 4.34-4.46 (m, 1H), 5.07-5.18 (m, 1H), 6.90 (dd, J=9.0, 3.9 Hz, 1H), 7.10 (t, J=8.8 Hz, 1H), 7.37 (d, J=1.3 Hz, 1H), 7.72 (s, 2H), 8.27 (s, 1H). MS (ES+): m/z=503.14/505.14 (100/50) [MH$^+$]. HPLC: t$_R$=1.48 min (polar_3 min, UPLC-ACQUITY).

1-(trans-4-{[tert-Butyl(dimethyl)silyl]oxy}cyclohexyl)-5-chloro-4-(4,4,5,5-tetramethyl-1,3,2-dioxaborolan-2-yl)-1H-pyrazole To a solution of 1-(trans-4-{[tert-butyl(dimethyl)silyl]oxy}cyclohexyl)-5-chloro-4-iodo-1H-pyrazole (30.0 mg, 0.0680 mmol) in THF (1 mL, 20 mmol) at rt was added 2 M isopropylmagnesium chloride in THF (0.10 mL, 0.20 mmol), and the mixture was stirred for 20 min. The reaction was quenched with 2-methoxy-4,4,5,5-tetramethyl-1,3,2-dioxaborolane (0.045 mL, 0.27 mmol), and allowed to stir at rt for 1 h. Sat. NH$_4$Cl was added, and the organic solvent was removed in vacuo. The material was extracted with DCM and water. The organic layer was concentrated in vacuo to afford the title compound as a white solid. The material was used in the next step without further purification. $^1$H NMR (400 MHz, CD$_3$OD): δ=0.12 (s, 6H), 0.93 (s, 9H), 1.33 (s, 8H), 1.46-1.60 (m, 2H), 1.86-2.09 (m, 6H), 3.70-3.82 (m, 1H), 4.38 (ddd, J=10.5, 5.2, 5.1 Hz, 1H), 7.69 (s, 1H).

1-(trans-4-{[tert-Butyl(dimethyl)silyl]oxy}cyclohexyl)-5-chloro-4-iodo-1H-pyrazole A solution of 1-[4-(tert-butyldimethylsilyloxy)cyclohexyl]-4-iodo-1H-pyrazole (50.0 mg, 0.123 mmol) in THF (3 mL, 40 mmol) was cooled to −78° C. and added 1.5 M of LDA in cyclohexane (0.107 mL, 0.160 mmol). After stirring for 5 min, a solution of hexachloroethane (35.0 mg, 0.148 mmol) in THF was added, and the mixture was stirred at −78° C. for 30 min. Sat. NH$_4$Cl was added to quench, and the organic solvent was removed in vacuo. The material was extracted with DCM and water, and the organic layer was dry-loaded onto silica gel for column chromatography, eluting with 1-3% EtOAc/heptane. The fractions containing the pure product were concentrated in vacuo to afford the title compound as a clear oil. $^1$H NMR (400 MHz, CD$_3$OD): δ=0.11 (s, 6H), 0.93 (s, 9H), 1.46-1.60 (m, 2H), 1.88-2.08 (m, 6H), 3.69-3.80 (m, 1H), 4.32-4.43 (m, 1H), 7.58 (s, 1H).

1-(trans-4-{[tert-Butyl(dimethyl)silyl]oxy}cyclohexyl)-4-iodo-1H-pyrazole

A mixture of trans-4-(4-iodo-1H-pyrazol-1-yl)cyclohexanol (1.00 g, 3.42 mmol), tert-butyldimethylsilyl chloride (1.03 g, 6.85 mmol), 4-dimethylaminopyridine (80 mg, 0.7 mmol), imidazole (699 mg, 10.3 mmol) and DCM (20 mL, 300 mmol) was stirred rt for 20 min. The material was transferred to a separatory funnel, extracting with DCM and sat. NaHCO$_3$. The organic layer was dry-loaded onto silica gel for column chromatography, eluting with 3% EtOAc/hexanes. The fractions containing the pure product were concentrated in vacuo to afford the title compound as a clear oil. Typical yields are 95%. $^1$H NMR (400 MHz, DMSO-d$_6$): δ=0.05 (s, 6H), 0.86 (s, 9H), 1.33-1.47 (m, 2H), 1.70-1.91 (m, 4H), 1.96 (d, J=11.9 Hz, 2H), 3.58-3.75 (m, 1H), 4.11-4.21 (m, 1H), 7.49 (s, 1H), 7.92 (s, 1H). MS (ES+): m/z=407.05 (100) [MH$^+$]. HPLC: t$_R$=3.22 min (v.v. non-polar_5 min, ZQ3).

Trans- and cis-4-(4-Iodopyrazol-1-yl)cyclohexanol

Sodium borohydride (0.29 g, 7.6 mmol) was added into the EtOH (20 mL) solution of 4-(4-iodopyrazol-1-yl)cyclohexanone (4.50 g, 15.5 mmol) at RT under an atmosphere of nitrogen. The mixture was stirred at RT for 2 h. Work-up: Solvent was evaporated and added water to the residue and extracted with EtOAc (3×60 mL). The combined organic extracts were dried over Na$_2$SO$_4$, filtered, and concentrated in vacuo to give an off-white solid. This material was purified by column chromatography on silica gel by eluting with 40% EtOAc/hexanes. The first (less polar) spot obtained was identified as cis isomer and the second (more polar) spot obtained was identified as trans isomer. Alternatively, the trans isomer may be isolated from the mixture of cis/trans isomers obtained in the reduction described above by crystallization from EtOAc/hexanes.

Cis-isomer: off-white solid, mp. 98-99° C. $^1$H NMR (300 MHz, CDCl$_3$): δ=1.63-1.74 (m, 4H), 1.87-1.96 (m, 4H), 2.09-2.19 (m, 2H), 4.07-4.20 (m, 2H), 7.50 (s, 2H). $^{13}$C NMR (100.6 MHz, CDCl$_3$, DEPT135): δ=143.57 (+), 131.11 (+), 64.88 (+), 60.69 (+), 55.47 (C$_{quart}$), 31.59 (−), 27.09 (−).

Trans-isomer: white solid, mp. 82-86° C. $^1$H NMR (400 MHz, CDCl$_3$): δ=1.42-1.51 (m, 2H), 1.79 (brs, 1H), 1.77-1.99 (m, 2H), 2.09-2.22 (m, 4H), 3.74 (br.tt, J=10.8, 4.0 Hz, 1H), 4.13 (tt, J=11.6, 3.8 Hz, 1H), 7.44 (d, J=0.4 Hz, 1H), 7.50 (d, J=0.4 Hz, 1H). $^{13}$C NMR (100.6 MHz, CDCl$_3$, DEPT135): δ=143.79 (+), 131.40 (+), 69.37 (+), 60.57 (+), 55.43 (C$_{quart}$), 33.93 (−), 30.94 (−). MS (ES+): m/z=293.11 [MH]$^+$. HPLC: t$_R$=2.58 min (polar_5 min, ZQ3).

4-(4-Iodopyrazol-1-yl)cyclohexanone

The mixture of 1-(1,4-dioxaspiro[4.5]dec-8-yl)-4-iodo-1H-pyrazole (20.0 g, 59.8 mmol), pyridinium p-toluenesulfonate (30.1 g, 120 mmol) in acetone (300 mL) and H$_2$O (300 mL) was heated at 65° C. for 16 h. The reaction mixture was partitioned between EtOAc (200 mL) and H$_2$O (100 mL), and the layers were separated. The aqueous layer was re-extracted with EtOAc (3×100 mL), and the combined organic fractions were washed with brine (1×), dried over Na$_2$SO$_4$, filtered and concentrated in vacuo resulting in 17.1 g (98% yield) of the title compound as a white solid. The material was used in the next step without further purification. $^1$H NMR (400 MHz, CDCl$_3$): δ=7.54 (s, 1H), 7.52 (s, 1H), 4.62 (tt, J=4.0, 10.1 Hz, 1H), 2.64-2.38 (m, 6H), 2.36-2.24 (m, 2H). MS (ES+): m/z=291.00 [MH]$^+$. HPLC: t$_R$=3.37 min (polar_5 min, ZQ3).

1-(1,4-Dioxaspiro[4.5]dec-8-yl)-4-iodo-1H-pyrazole

A solution of 4-iodopyrazole (23.8 g, 123 mmol), 1,4-dioxaspiro[4.5]dec-8-yl 4-methylbenzenesulfonate (prepared according to U.S. Pat. No. 4,360,531) (42.2 g, 135 mmol), and Cs$_2$CO$_3$ (60.0 g, 184 mmol) in anhydrous degassed DMF (600 mL) was heated to 100° C. for 4 h. The reaction mixture was charged with an additional 1,4-dioxaspiro[4.5]dec-8-yl 4-methylbenzenesulfonate (5.20 g, 16.6 mmol) and Cs$_2$CO$_3$ (16.0 g, 49.1 mmol) and heated at 100° C. for an additional 16 h. The reaction mixture was cooled to ambient temperature, partitioned between EtOAc (400 mL) and sat. aq. NaHCO$_3$ solution (200 mL), and the layers were separated. The aqueous layer was re-extracted with EtOAc (3×150 mL), and the combined organic fractions were washed with H$_2$O (3×150 mL), brine (1×100 mL), dried over Na$_2$SO$_4$, filtered and concentrated in vacuo resulting in 45 g of an off-white solid. This solid was crystallized from i-PrOH (250 mL) and the white crystals were filtered through a fritted funnel resulting in the title compound as white crystals (31 g, 76% yield). A second crop of crystals from the mother liquor was slightly less pure. $^1$H NMR (400 MHz, CDCl$_3$): δ=7.49 (s, 1H), 7.48 (s, 1H), 4.22 (tt, J=4.2, 11.2 Hz, 1H), 3.99-3.95 (m, 4H), 2.18-1.99 (m, 4H), 1.91-1.83 (m, 2H), 1.77-1.65 (m, 2H). MS (ES+): m/z=334.93 [MH]$^+$. HPLC: t$_R$=3.74 min (polar_5 min, ZQ3).

Example 50

1-(4-{3-[(1S)-1-(2-Chloro-3-fluoro-6-methoxyphenyl)ethyl]-1H-pyrrolo[2,3-b]pyridin-5-yl}-1-methyl-1H-pyrazol-3-yl)methanamine

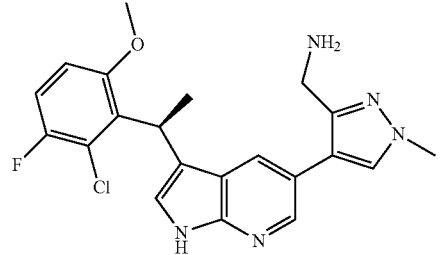 [SMILES: COc1ccc(F)c(Cl)c1[C@@H](C)c1c[nH]c2ncc(-c3cn(C)nc3CN)cc12]

A mixture of (4-bromo-1-methyl-1H-pyrazol-3-yl)methanol (100.0 mg, 0.5235 mmol), diphenylphosphonic azide (0.141 mL, 0.654 mmol), 1,8-diazabicyclo[5.4.0]undec-7-ene (0.106 mL, 0.707 mmol) and DCM (5 mL, 80 mmol) was stirred at rt overnight. The solution was dried in vacuo, and 3-[(S)-1-(2-chloro-3-fluoro-6-methoxyphenyl)-ethyl]-5-(4,4,5,5-tetramethyl-[1,3,2]dioxaborolan-2-yl)-1H-pyrrolo[2,3-b]pyridine (15.0 mg, 0.0348 mmol), Pd(PPh$_3$)$_4$ (2 mg, 0.002 mmol), (1,1'bis-(diphenylphosphino)-ferrocene) palladium dichloride (2 mg, 0.003 mmol), K$_2$CO$_3$ (15.0 mg, 0.108 mmol) and 4:1 dioxane:H$_2$O (3 mL, 30 mmol) were added to the flask. The mixture was heated to 95° C. for 1 h. The reaction was cooled to 60° C., and PPh$_3$ (30.0 mg, 0.114 mmol) was added. The solution was heated at 65° C. until all azide was reduced to the primary amine. The organic solvent was removed in vacuo, and the material was extracted with DCM and water at pH=2. The organic layer was removed, and the aq. layer was brought to pH=9 with sat. K$_2$CO$_3$. The material was extracted with DCM, and the organic layer concentrated in vacuo, redissolved in MeOH (1 mL) and purified via HPLC. The fractions containing the pure product were concentrated in vacuo to afford the title compound as a white solid. $^1$H NMR (400 MHz, CD$_3$OD): δ=1.83 (d, J=7.3 Hz, 3H), 3.69 (s, 3H), 3.96 (s, 3H), 4.09 (q, J=14.5 Hz, 2H), 5.09-5.17 (m, 1H), 6.92 (dd, J=9.1, 4.3 Hz, 1H), 7.12 (t, J=8.8 Hz, 1H), 7.40 (d, J=1.0 Hz, 1H), 7.47 (s, 1H), 7.74 (s, 1H), 8.13 (d, J=2.0 Hz, 1H). MS (ES+): m/z=414.02/416.01 (100/50) [MH]$^+$. HPLC: t$_R$=2.77 min (polar_5 min, ZQ3).

Example 51

(4-{3-[(1S)-1-(2-Chloro-3-fluoro-6-methoxyphenyl)ethyl]-1H-pyrrolo[2,3-b]pyridin-5-yl}-1,5-dimethyl-1H-pyrazol-3-yl)methanol

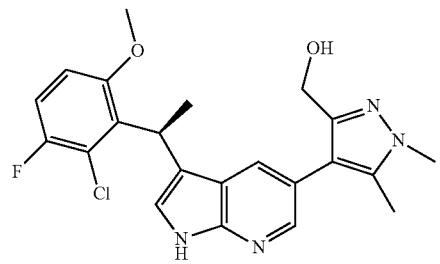 [SMILES: COc1ccc(F)c(Cl)c1[C@@H](C)c1c[nH]c2ncc(-c3c(CO)nn(C)c3C)cc12]

Prepared using the procedure described for Example 34. $^1$H NMR (400 MHz, CD$_3$OD): δ=1.81 (d, J=7.3 Hz, 3H), 2.13 (s, 3H), 3.66 (s, 3H), 3.82 (s, 3H), 4.44 (s, 2H), 5.13 (q, J=6.9 Hz, 1H), 6.90 (dd, J=9.1, 4.3 Hz, 1H), 7.09 (t, J=8.8 Hz, 1H), 7.36 (d, J=1.3 Hz, 1H), 7.40-7.46 (m, 1H), 8.17 (d, J=2.0 Hz, 1H). MS (ES+): m/z=429.13/431.13 (100/50) [MH$^+$]. HPLC: t$_R$=1.34 min (polar_3 min, UPLC-ACQUITY).

4-Bromo-3-({[tert-butyl(dimethyl)silyl]oxy}methyl)-1,5-dimethyl-1H-pyrazole

A solution of 4-bromo-3-({[tert-butyl(dimethyl)silyl]oxy}methyl)-1-methyl-1H-pyrazole (130.0 mg, 0.4258 mmol) in THF (2 mL, 20 mmol) was cooled to −78° C., and 1.5 M of LDA in cyclohexane (0.85 mL, 1.3 mmol) was added. After stirring for 1 h, methyliodide (0.1 mL, 2 mmol) was added slowly, and the mixture was stirred at −78° C. for 1 h. Sat. NH$_4$Cl was added to quench, and the organic solvent was removed in vacuo. The material was extracted with DCM and water, and the organic layer was concentrated in vacuo to afford the title compound as yellow solid. $^1$H NMR (400 MHz, CD$_3$OD): δ=0.07 (s, 6H), 0.86 (s, 9H), 2.21 (s, 3H), 3.73 (s, 3H), 4.50 (s, 2H).

4-Bromo-3-({[tert-butyl(dimethyl)silyl]oxy}methyl)-1-methyl-1H-pyrazole

A mixture of (4-bromo-1-methyl-1H-pyrazol-3-yl)methanol (100.0 mg, 0.5235 mmol), tert-butyldimethylsilyl chloride (236.7 mg, 1.570 mmol), 4-dimethylaminopyridine (12.79 mg, 0.1047 mmol), 1H-Imidazole (106.9 mg, 1.570 mmol) and DCM (40 mL, 700 mmol) was stirred at rt for 1 h. The material was transferred to a separatory funnel and partitioned between DCM and water. The organic layer was dry-loaded onto silica gel for column chromatography, eluting with 2% EtOAc/hexanes. The fractions containing the pure product were concentrated in vacuo to afford the title compound as a clear oil. MS (ES+): m/z=305.06/307.06 (100/100) [MH$^+$]. HPLC: t$_R$=1.82 min (polar_3 min, UPLC-ACQUITY).

Example 52 cis-4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)cyclohexanol

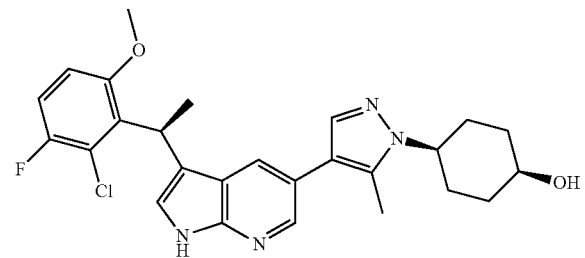 [SMILES: COc1ccc(F)c(Cl)c1[C@@H](C)c1c[nH]c2ncc(-c3cnn([C@H]4CC[C@@H](O)CC4)c3C)cc12]

A mixture of 5-bromo-3-[(S)-1-(2-chloro-3-fluoro-6-methoxyphenyl)-ethyl]-1H-pyrrolo[2,3-b]pyridine (200.0 mg, 0.5213 mmol), 1-(cis-4-{[tert-butyl(dimethyl)silyl]oxy}cyclohexyl)-5-methyl-4-(4,4,5,5-tetramethyl-1,3,2-dioxaborolan-2-yl)-1H-pyrazole (328.8 mg, 0.7820 mmol), Pd(PPh$_3$)$_4$ (30.12 mg, 0.02606 mmol), K$_2$CO$_3$ (216.1 mg, 1.564 mmol) and 4:1 dioxane:H$_2$O (10 mL, 100 mmol) was heated to 95° C. for 2 h. The solution was cooled to rt, and 12 M of HCl in H$_2$O (0.4344 mL, 5.213 mmol) was added. The material was concentrated in vacuo, and extracted with DCM and sat. NaHCO$_3$. The organic layer was dry-loaded onto silica gel and purified via column chromatography, eluting with 2-4% (7N NH$_3$ in MeOH)/DCM. The fractions containing the pure product were concentrated in vacuo to afford the title compound as a light yellow solid. $^1$H NMR (400 MHz, CD$_3$OD): δ=1.69-1.80 (m, 4H), 1.82 (d, J=7.3 Hz, 3H), 1.94-2.05 (m, 2H), 2.25 (s, 3H), 2.32-2.46 (m, 2H), 3.67 (br. s., 3H), 4.02-4.08 (m, 1H), 4.17-4.27 (m, 1H), 5.08-5.17 (m, 1H), 6.91 (dd, J=9.1, 4.3 Hz, 1H), 7.10 (t, J=8.8 Hz, 1H), 7.36 (d, J=1.3 Hz, 1H), 7.38-7.45 (m, 1H), 7.47 (s, 1H), 8.12 (d, J=2.0 Hz, 1H). MS (ES+): m/z=483.16/485.18 (100/50) [MH$^+$]. HPLC: t$_R$=1.46 min (polar_3 min, UPLC-ACQUITY).

1-(cis-4-{[tert-Butyl(dimethyl)silyl]oxy}cyclohexyl)-5-methyl-4-(4,4,5,5-tetramethyl-1,3,2-dioxaborolan-2-yl)-1H-pyrazole To a solution of 1-(cis-4-{[tert-butyl(dimethyl)silyl]oxy}cyclohexyl)-4-iodo-5-methyl-1H-pyrazole (870.0 mg, 2.069 mmol) in THF (20 mL, 200 mmol) at rt was added 1.3 M of isopropylmagnesium chloride in THF (6.367 mL, 8.278 mmol), and the mixture was stirred for 1 h. The reaction was quenched with 2-methoxy-4,4,5,5-tetramethyl-1,3,2-dioxaborolane (1.696 mL, 10.35 mmol), and allowed to stir at rt for 1 h. Sat. NH$_4$Cl was added, and the organic solvent was removed in vacuo. The material was extracted with DCM and water. The organic layer was concentrated in vacuo to afford the title compound as a yellow solid. $^1$H NMR (400 MHz, CD$_3$OD): δ=0.12 (s, 6H), 0.97 (s, 9H), 1.33 (s, 9H), 1.60-1.75 (m, 4H), 1.83-1.92 (m, 2H), 2.32-2.40 (m, 2H), 2.47 (s, 3H), 4.07-4.21 (m, 2H), 7.58 (s, 1H).

Example 53 trans-4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)-N,N-dimethylcyclohexanamine

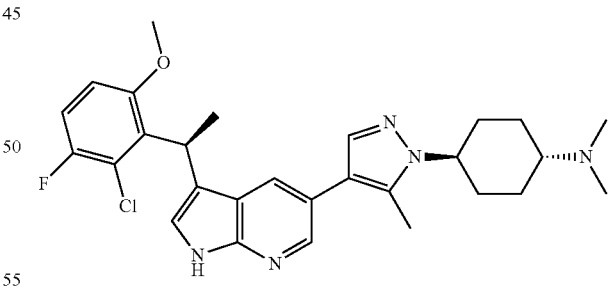

A mixture of 4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)cyclohexanone (12.0 mg, 0.0250 mmol), dimethylamine hydrochloride (20.34 mg, 0.2495 mmol), sodium triacetoxyborohydride (10.58 mg, 0.04990 mmol) and triethylamine (0.06 mL, 0.4 mmol) in 1,2-dichloroethane (3 mL, 40 mmol) was heated to 60° C. in a sealed tube for 1 h. The solution was extracted with DCM and sat. NaHCO$_3$, and the organic layer was loaded onto silica gel for column chromatography, eluting with 3-7% (7N NH$_3$ in MeOH)/DCM. The fractions containing the cis and trans products separately were concentrated in vacuo to afford the title compound as white solid. $^1$H NMR (400 MHz, CD$_3$OD): δ=1.42-1.65 (m, 2H), 1.82 (d, J=7.1 Hz, 3H), 1.95-2.19 (m, 6H), 2.24 (s, 3H), 2.36-2.42 (m, 6H), 2.44-2.53 (m, 1H), 3.66 (br. s., 3H), 4.13-4.26 (m, 1H), 5.12 (q, J=7.1 Hz, 1H), 6.91 (dd, J=9.0, 4.2 Hz, 1H), 7.10 (t, J=9.0 Hz, 1H), 7.36 (d, J=1.3 Hz, 1H), 7.42 (s, 1H), 7.49 (s, 1H), 8.12 (d, J=2.0 Hz, 1H). MS (ES+): m/z=510.25/512.25 (100/50) [MH$^+$]. HPLC: $t_R$=1.18 min (polar_3 min, UPLC-ACQUITY).

Example 54 cis-4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)-N,N-dimethylcyclohexanamine

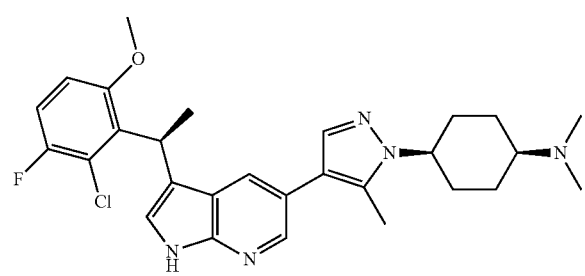 [SMILES: COc1ccc(F)c(Cl)c1[C@@H](C)c1c[nH]c2ncc(-c3cnn([C@H]4CC[C@@H](N(C)C)CC4)c3C)cc12]

Obtained from above reaction as white solid. $^1$H NMR (400 MHz, CD$_3$OD): δ=1.77-1.94 (m, 7H), 2.18-2.34 (m, 7H), 2.58 (s, 6H), 2.75 (dq, J=7.1, 3.6 Hz, 1H), 3.66 (br. s., 3H), 4.38-4.49 (m, 1H), 5.11 (q, J=6.7 Hz, 1H), 6.91 (dd, J=9.1, 4.0 Hz, 1H), 7.10 (t, J=8.8 Hz, 1H), 7.36 (d, J=1.3 Hz, 1H), 7.42 (s, 1H), 7.46 (s, 1H), 8.12 (d, J=2.0 Hz, 1H). MS (ES+): m/z=510.25/512.25 (100/50) [MH$^+$]. HPLC: $t_R$=1.20 min (polar_3 min, UPLC-ACQUITY).

Example 55

4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)cyclohexanone

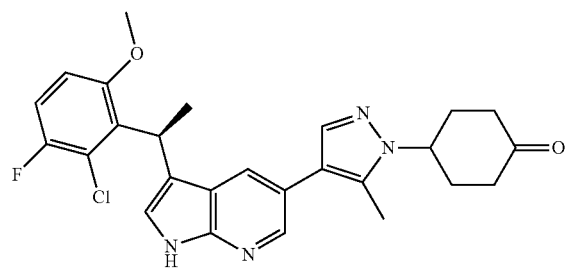 [SMILES: COc1ccc(F)c(Cl)c1[C@@H](C)c1c[nH]c2ncc(-c3cnn(C4CCC(=O)CC4)c3C)cc12]

A solution of cis-4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)cyclohexanol (140.0 mg, 0.2899 mmol), Dess-Martin periodinane (184.4 mg, 0.4348 mmol) and DCM (10 mL, 200 mmol) was stirred at rt for 1 h. The material was extracted with DCM and sat. NaHCO$_3$, and the organic layer was loaded onto silica gel for column chromatography, eluting with 2-4% MeOH/DCM. The fractions containing the pure product were concentrated in vacuo to afford the title compound as a tan solid. MS (ES+): m/z=481.18/483.18 (100/50) [MH$^+$]. HPLC: $t_R$=1.49 min (polar_3 min, UPLC-ACQUITY).

Example 56

3-[(1S)-1-(2-Chloro-3-fluoro-6-methoxyphenyl)ethyl]-5-{5-methyl-1-[cis-4-(piperazin-1-yl)cyclohexyl]-1H-pyrazol-4-yl}-1H-pyrrolo[2,3-b]pyridine

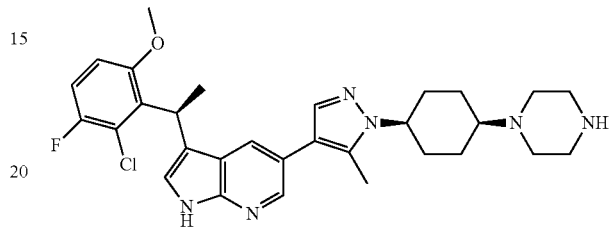

A mixture of 4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)cyclohexanone (12.0 mg, 0.0250 mmol), tert-butyl 1-piperazinecarboxylate (46.47 mg, 0.2495 mmol), sodium triacetoxyborohydride (10.58 mg, 0.04990 mmol) and 1,2-dichloroethane (3 mL, 40 mmol) was heated to 60° C. in a sealed tube for 1 h. The solution was extracted with DCM and sat. NaHCO$_3$, and the organic layer was concentrated in vacuo. The material was dissolved in 1,4-dioxane (35 mL, 450 mmol), 4 M of HCl in 1,4-dioxane (1 mL, 4 mmol) was added, and the solution was allowed to stir at rt for 4 h. The material was concentrated in vacuo, loaded onto silica gel for column chromatography, and eluted with 5-10% (7N NH$_3$ in MeOH)/DCM. The fractions containing the cis product were concentrated in vacuo to afford the title compound as a white solid. $^1$H NMR (400 MHz, CD$_3$OD): δ=1.59-1.77 (m, 4H), 1.82 (d, J=7.3 Hz, 3H), 2.16-2.36 (m, 8H), 2.57 (br. s., 4H), 2.95 (t, J=4.9 Hz, 4H), 3.66 (br. s., 3H), 4.28-4.38 (m, 1H), 5.12 (q, J=7.1 Hz, 1H), 6.90 (dd, J=9.1, 4.3 Hz, 1H), 7.10 (t, J=8.8 Hz, 1H), 7.36 (d, J=1.3 Hz, 1H), 7.42 (s, 1H), 7.46 (s, 1H), 8.12 (d, J=2.0 Hz, 1H). MS (ES+): m/z=551.27/553.27 (100/50) [MH$^+$]. HPLC: $t_R$=1.15 min (polar_3 min, UPLC-ACQUITY).

Example 57

1-{4-[cis-4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)cyclohexyl]piperazin-1-yl}ethanone

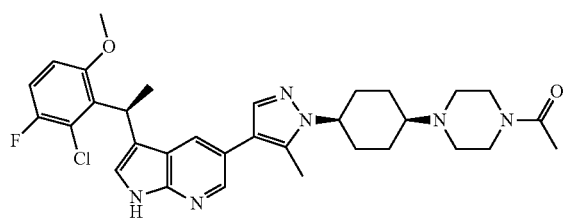 [SMILES: COc1ccc(F)c(Cl)c1[C@@H](C)c1c[nH]c2ncc(-c3cnn([C@H]4CC[C@@H](N5CCN(C(C)=O)CC5)CC4)c3C)cc12]

A mixture of 4-(4-{3-[(1S)-1-(2-chloro-3-fluoro-6-methoxyphenyl)ethyl]-1H-pyrrolo[2,3-b]pyridin-5-yl}-5-methyl-1H-pyrazol-1-yl)cyclohexanone (12.0 mg, 0.0250 mmol), 1-acetylpiperazine (31.98 mg, 0.2495 mmol), sodium triacetoxyborohydride (10.58 mg, 0.04990 mmol) and 1,2-dichloroethane (3 mL, 40 mmol) was heated to 60° C. in a sealed tube for 6 h. The solution was extracted with DCM and sat. NaHCO$_3$, and the organic layer was loaded onto silica gel for column chromatography, eluting with 3-7% (7N NH$_3$ in MeOH)/DCM. The fractions containing the product were concentrated in vacuo to afford the title compound as a white solid. $^1$H NMR (400 MHz, CD$_3$OD): δ=1.63-1.73 (m, 3H), 1.81 (d, J=7.1 Hz, 3H), 2.00 (s, 3H), 2.10-2.14 (m, 4H), 2.25-2.43 (m, 4H), 2.58-2.66 (m, 4H), 3.59-3.70 (m, 8H), 4.34 (tdd, J=9.3, 9.3, 4.7, 4.3 Hz, 1H), 5.12 (q, J=6.8 Hz, 1H), 6.90 (dd, J=9.1, 4.3 Hz, 1H), 7.09 (t, J=8.8 Hz, 1H), 7.36 (d, J=1.0 Hz, 1H), 7.42 (s, 1H), 7.47 (s, 1H), 8.12 (s, 1H). MS (ES+): m/z=593.27/595.27 (100/50) [MH$^+$]. HPLC: t$_R$=1.19 min (polar_3 min, UPLC-ACQUITY).

Example 58 trans-4-(4-{3-[(1S)-1-(2-Chloro-3-fluoro-6-methoxyphenyl)ethyl]-1H-pyrrolo[2,3-b]pyridin-5-yl}-5-methyl-1H-pyrazol-1-yl)cyclohexanamine

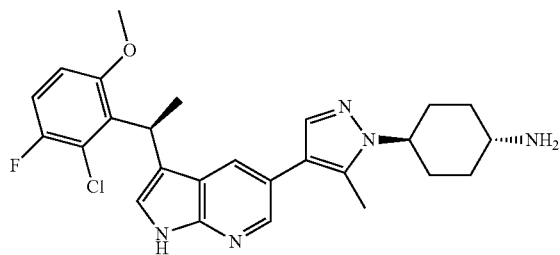 [SMILES: COc1ccc(F)c(Cl)c1[C@@H](C)c1c[nH]c2ncc(-c3cnn([C@H]4CC[C@H](N)CC4)c3C)cc12]

Prepared using the procedure described for Example 29. $^1$H NMR (400 MHz, CD$_3$OD): δ=1.61-1.74 (m, 2H), 1.81 (d, J=7.3 Hz, 3H), 2.04-2.15 (m, 4H), 2.16-2.24 (m, 2H), 2.26 (s, 3H), 3.24 (tt, J=11.9, 4.0 Hz, 1H), 3.65 (br. s., 3H), 4.20-4.32 (m, 1H), 5.11 (q, J=6.5 Hz, 1H), 6.90 (dd, J=9.1, 4.3 Hz, 1H), 7.09 (t, J=8.8 Hz, 1H), 7.37 (d, J=1.3 Hz, 1H), 7.43 (s, 1H), 7.51 (s, 1H), 8.12 (br. s., 1H). MS (ES+): m/z=482.20/484.20 (100/50) [MH$^+$]. HPLC: t$_R$=1.09 min (polar_3 min, UPLC-ACQUITY).

trans-4-(4-Iodo-5-methyl-1H-pyrazol-1-yl)cyclohexanamine

To a solution of cis-4-(4-iodo-5-methyl-1H-pyrazol-1-yl)cyclohexanol (400.0 mg, 1.306 mmol), triethylamine (0.5463 mL, 3.920 mmol) and DCM (10 mL, 200 mmol) was added methanesulfonyl chloride (0.2022 mL, 2.613 mmol), and the reaction was stirred at rt for 2 h. The material was extracted with DCM and water, which was titrated to pH=5. The organic layer was concentrated in vacuo, redissolved in DMF (5 mL, 60 mmol), and sodium azide (169.9 mg, 2.613 mmol) was added. The mixture was heated to 90° C. for 3 h. The material was extracted with EtOAc, and washed with water (2×). The organic layer was concentrated in vacuo, redissolved in 1,4-dioxane (5 mL, 60 mmol), and PPh$_3$ (514.0 mg, 1.960 mmol) was added. The mixture was heated to 70° C. for 3 h. The solvent was removed in vacuo, and the material was extracted with DCM and water, which was titrated to pH=2. The organic layer was discarded, more DCM was added, and the aqueous layer was titrated to pH=9. The organic layer was concentrated in vacuo to afford the title compound as a light yellow solid. MS (ES+): m/z=306.04 (100) [MH$^+$]. HPLC: t$_R$=0.89 min (polar_3 min, UPLC-ACQUITY).

Example 59

3-[(1S)-1-(2-Chloro-3-fluoro-6-methoxyphenyl)ethyl]-5-(5-chloro-1-methyl-1H-pyrazol-4-yl)-1H-pyrrolo[2,3-b]pyridine

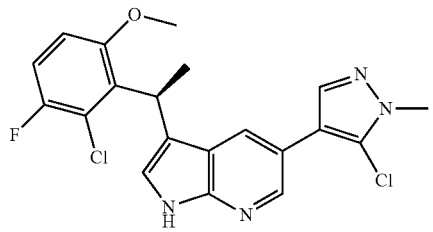 [SMILES: COc1ccc(F)c(Cl)c1[C@@H](C)c1c[nH]c2ncc(-c3cnn(C)c3Cl)cc12]

A solution of 4-bromo-5-chloro-1-methyl-1H-pyrazole (10.2 mg, 0.0522 mmol), 3-[(S)-1-(2-chloro-3-fluoro-6-methoxy-phenyl)-ethyl]-5-(4,4,5,5-tetramethyl-[1,3,2]dioxaborolan-2-yl)-1H-pyrrolo[2,3-b]pyridine (15 mg, 0.035 mmol), potassium carbonate (14.4 mg, 0.104 mmol), and 1,1'-bis(diphenylphosphino)ferrocenepalladium(II) dichloride, dichloromethane (1.42 mg, 0.00174 mmol) in previously degassed 4:1 dioxane:water (1.0 mL) was evacuated and charged with N$_2$ (2×) and heated under microwave conditions [Biotage, 100° C., 30 min, high absorption]. The reaction was then charged with an additional 4-bromo-5-chloro-1-methyl-1H-pyrazole (10.2 mg, 0.0522 mmol) and charged with Pd(PPh$_3$)$_4$ (2.01 mg, 0.00174 mmol) and evacuated and charged with N$_2$ (2×) and heated under microwave conditions [Biotage, 100° C., 30 min, high absorption]. A small water layer was removed from MW vial and the crude sample was purified by HPLC resulting the title compound as an off-white solid. $^1$H NMR (400 MHz, CD$_3$OD): δ=1.80 (d, J=7.1 Hz, 3H), 3.64 (br. s., 3H), 3.88 (s, 3H), 5.11 (d, J=6.8 Hz, 1H), 6.89 (dd, J=4.0, 8.6 Hz, 1H), 7.08 (dd, J=8.8, 8.8 Hz, 1H), 7.35 (s, 1H), 7.65-7.73 (m, 2H), 8.22-8.29 (m, 1H). MS (ES+): m/z 419.05, 421.03 (76/24) [MH$^+$]. HPLC: t$_R$=3.70 min (polar_5 min, ZQ3).

4-Bromo-5-chloro-1-methyl-1H-pyrazole

A solution of 4-bromo-1-methyl-1H-pyrazol-5-amine (2.04 g, 11.6 mmol) in 12.0 M of HCl in H$_2$O (20.4 mL) was cooled to 0° C. and charged with a solution of sodium nitrite (0.880 g, 12.7 mmol) in H$_2$O (18.0 mL) over a 10 min period. The reaction was stirred for an additional 10 min at 0° C. then added in portions to a solution of cuprous monochloride (1.15 g, 11.6 mmol) in 12.00 M of HCl in H$_2$O (10.2 mL) and stirred at rt for an additional 3 h. The reaction mixture was partitioned between CHCl$_3$ and H$_2$O and separated. The aqueous was re-extracted with CHCl$_3$ (3×) and the combined organic fractions were washed with sat. NaHCO$_3$, dried over Na$_2$SO$_4$, filtered and concentrated in vacuo. The resulting crude yellow solid was purified by chromatography on silica gel [ISCO Combiflash, 24 g cartridge, eluting with 100% heptane-30.7% EtOAc in heptane] resulting in the title compound as a white solid. $^1$H NMR (400 MHz, CDCl$_3$): δ=7.48 (s, 1H), 3.88 (s, 3H). MS (ES+): m/z 194.92, 196.95, 198.94 (100/68/17) [MH$^+$]. HPLC: t$_R$=3.07 min (polar_5 min, ZQ3).

Example 60

3-[(1S)-1-(2-chloro-3-fluoro-6-methoxyphenyl)ethyl]-5-(3-chloro-1-methyl-1H-pyrazol-4-yl)-1H-pyrrolo[2,3-b]pyridine

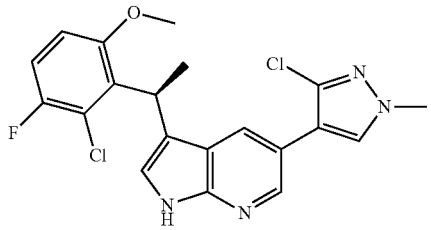 [SMILES: COc1ccc(F)c(Cl)c1[C@@H](C)c1c[nH]c2ncc(-c3cn(C)nc3Cl)cc12]

A solution of 4-bromo-3-chloro-1-methyl-1H-pyrazole (0.0136 g, 0.0697 mmol), 3-[(S)-1-(2-chloro-3-fluoro-6-methoxy-phenyl)-ethyl]-5-(4,4,5,5-tetramethyl-[1,3,2]dioxaborolan-2-yl)-1H-pyrrolo[2,3-b]pyridine (0.020 g, 0.046 mmol), potassium carbonate (0.0193 g, 0.139 mmol) and Pd(PPh$_3$)$_4$ (5.37 mg, 0.00464 mmol) in previously degassed 4:1 dioxane:water (1.0 mL) was evacuated and charged with N$_2$ (2×) and heated under microwave conditions [Biotage, 100° C., 30 min, high absorption]. This was purified by Gilson HPLC. The combined fractions were concentrated in vacuo resulting in the title compound as off-white solid. $^1$H NMR (400 MHz, CD$_3$OD): δ=1.80 (d, J=7.3 Hz, 3H), 3.60-3.71 (m, 2H), 3.87 (s, 3H), 5.11 (q, J=7.1 Hz, 1H), 6.89 (dd, J=4.2, 9.0 Hz, 1H), 7.06 (d, J=8.8 Hz, 1H), 7.34 (d, J=1.3 Hz, 2H), 7.72-7.77 (m, 2H), 7.80 (s, 2H), 8.20 (d, J=1.8 Hz, 2H). MS (ES+): m/z 419.05, 421.03 (76, 24) [MH$^+$]. HPLC: t$_R$=1.84 min (polar_3 min, TOF)

4-Bromo-3-chloro-1-methyl-1H-pyrazole

A solution of 4-bromo-1-methyl-1H-pyrazol-3-amine (1.48 g, 8.40 mmol) in 12.0 M of HCl in H$_2$O (14.8 mL) was cooled to 0° C. and charged with a solution of sodium nitrite (0.637 g, 9.24 mmol) in H$_2$O (13.0 mL) over a 10 min period. The reaction was stirred for an additional 10 min at 0° C. then was added portionwise to a solution of cuprous monochloride (0.831 g, 8.40 mmol) in 12.00 M of HCl in H$_2$O (7.39 mL) and stirred at rt for an additional 3 h. The reaction mixture was partitioned between CHCl$_3$ and H$_2$O and separated. The aqueous was re-extracted with CHCl$_3$ (3×) and the combined organic fractions were washed with sat. NaHCO$_3$, dried over Na$_2$SO$_4$, filtered and concentrated in vacuo. The crude reaction was purified by chromatography on silica gel [ISCO Combiflash, 24 g cartridge, 100% heptane→50% EtOAc in heptane] resulting in 586 mg, 36% yield of the title compound as a white solid. $^1$H NMR (400 MHz, CDCl$_3$): δ=3.85 (s, 3H), 7.36 (s, 1H). MS (ES+): m/z 194.98, 196.96, 198.94 (100/68/17) [MH$^+$]. HPLC: t$_R$=2.98 min (polar_5 min, ZQ3).

Example 61

3-[(1S)-1-(2-Chloro-3-fluoro-6-methoxyphenyl)ethyl]-5-(3-methoxy-1-methyl-1H-pyrazol-4-yl)-1H-pyrrolo[2,3-b]pyridine

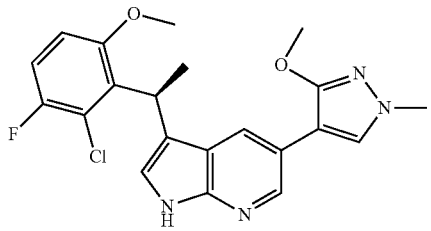 [SMILES: COc1ccc(F)c(Cl)c1[C@@H](C)c1c[nH]c2ncc(-c3cn(C)nc3OC)cc12]

A solution of 4-bromo-3-methoxy-1-methyl-1H-pyrazole (0.0399 g, 0.209 mmol), 3-[(S)-1-(2-chloro-3-fluoro-6-methoxy-phenyl)-ethyl]-5-(4,4,5,5-tetramethyl-[1,3,2]dioxaborolan-2-yl)-1H-pyrrolo[2,3-b]pyridine (0.0300 g, 0.0697 mmol), potassium carbonate (0.0289 g, 0.209 mmol) and 1,1'-bis(diphenylphosphino)ferrocenepalladium(II) dichloride.dichloromethane (2.84 mg, 0.00348 mmol) in previously degassed 4:1 dioxane:water (1.50 mL) was evacuated and charged with N$_2$ (2×) and heated under microwave conditions [Biotage, 100° C., 30 min, high absorption]. The reaction mixture was charged with an additional amount of 4-bromo-3-methoxy-1-methyl-1H-pyrazole (0.0399 g, 0.209) followed by Pd(PPh$_3$)$_4$ (4.02 mg, 0.00348 mmol) and evacuated and charged with N$_2$ gas (3×) and heated under microwave conditions [Biotage, 100° C., 45 min, high absorption]. The dioxane layer was removed and diluted with CHCl$_3$ and charged with silica gel. The sample was then dry loaded and purified by chromatography on silica gel [ISCO Combiflash, 12 g cartridge, 100% DCM→5% MeOH in DCM]. This resulted in the title compound as an off-white solid. $^1$H NMR (400 MHz, CD$_3$OD): δ=1.78 (d, J=7.1 Hz, 3H), 3.75 (s, 3H), 3.93 (s, 3H), 5.07 (q, J=6.8 Hz, 1H), 6.83-6.91 (m, 1H), 7.09 (dd, J=8.8, 8.8 Hz, 1H), 7.27 (d, J=1.0 Hz, 1H), 7.65 (s, 1H), 7.83 (br. s., 1H), 8.27 (d, J=2.0 Hz, 1H). MS (ES+): m/z 415.06, 417.07 (76/24) [MH$^+$]. HPLC: t$_R$=3.97 min (polar_5 min, ZQ3).

4-Bromo-3-methoxy-1-methyl-1H-pyrazole

A solution of 3-methoxy-1-methyl-1H-pyrazole (0.500 g, 4.46 mmol) in MeOH (50.0 mL) was cooled to 0° C. and charged with pyridinium tribromide (1.43 g, 4.46 mmol) in portions. The solution was stirred for 1 h at 0° C. then for an additional 16 h at rt. The reaction mixture was charged with sat. NaHCO$_3$ (2.5 mL) and diluted with H$_2$O and extracted with CHCl$_3$ (3×). The combined organic fractions were dried over Na$_2$SO$_4$, filtered and concentrated in vacuo resulting in the title compound as a red oil. This material was used in the next step without further purification. $^1$H NMR (400 MHz, CD$_3$OD): δ=3.66 (s, 3H), 4.07 (s, 3H), 7.30 (s, 1H). MS (ES+): m/z 190.98, 192.99 (49.5/50.5) [MH$^+$]. HPLC: t$_R$=2.29 min (polar_5 min, ZQ3).

3-Methoxy-1-methyl-1H-pyrazole

A solution of 1-methyl-1,2-dihydro-3H-pyrazol-3-one (0.200 g, 2.04 mmol) and potassium carbonate (0.564 g, 4.08 mmol) in anhydrous DMF (3.0 mL) was charged with methyl 4-methylbenzenesulfonate (0.308 mL, 2.04 mmol) and stirred at rt for 16 h. The reaction mixture was poured into 2.0 M of HCl in H$_2$O (16 mL) and extracted with petroleum ether (3×). The aqueous was charged with solid Na$_2$CO$_3$ until alkaline and extracted with diethyl ether (3×). The combined etherate fractions were washed with H$_2$O (1×), brine (1×), dried over Na$_2$SO$_4$, filtered and concentrated in vacuo resulting 115 mg, 50.3% yield of the title compound as a clear yellow oil. The sample was taken on to the next step without further purification. $^1$H NMR (400 MHz, CD$_3$OD): δ=3.70 (s, 3H), 3.81 (s, 3H), 5.64 (d, J=2.5 Hz, 1H), 7.33 (d, J=2.3 Hz, 1H). MS (ES+): m/z 113.01 [MH$^+$]. HPLC: t$_R$=2.37 min (polar_5 min, ZQ3).

1-Methyl-1,2-dihydro-3H-pyrazol-3-one

A solution of methyl 2-chloroprop-2-enoate (3.00 g, 24.9 mmol) in anhydrous THF (17.7 mL) was dropwise charged with N-methylhydrazine (2.65 mL, 49.8 mmol) over a 5 min period at rt. The reaction was stirred at rt for an additional 16 h. The reaction mixture was partitioned between EtOAc and H$_2$O and separated. The aqueous was re-extracted with EtOAc (3×) and the combined organic fractions were dried over Na$_2$SO$_4$, filtered, and concentrated in vacuo resulting in 2.05 g, 84% yield of the title compound as an off-white solid. The material was taken on to the next step without further purification. $^1$H NMR (400 MHz, CD$_3$OD): δ=3.65 (s, 3H), 5.49 (d, J=2.5 Hz, 1H), 7.24 (d, J=2.3 Hz, 1H). MS (ES+): m/z 99.32 [MH$^+$]. HPLC: t$_R$=1.19 min (polar__5 min, ZQ3).

Example 62

3-[(1S)-1-(2-chloro-3-fluoro-6-methoxyphenyl)ethyl]-5-(5-methoxy-1-methyl-1H-pyrazol-4-yl)-1H-pyrrolo[2,3-b]pyridine

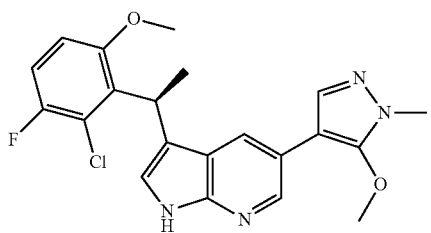 [SMILES: COc1ccc(F)c(Cl)c1[C@@H](C)c1c[nH]c2ncc(-c3cnn(C)c3OC)cc12]

A solution of 4-bromo-5-methoxy-1-methyl-1H-pyrazole (0.0133 g, 0.0697 mmol), 3-[(1S)-1-(2-chloro-3-fluoro-6-methoxyphenyl)ethyl]-5-(4,4,5,5-tetramethyl-1,3,2-dioxaborolan-2-yl)-1H-pyrrolo[2,3-b]pyridine (0.020 g, 0.046 mmol), potassium carbonate (0.0193 g, 0.139 mmol) 1,1'-bis(diphenylphosphino)ferrocenepalladium(II) dichloride, dichloromethane (3.79 mg, 0.00464 mmol) in previously degassed 4:1 dioxane:water (1.0 mL) was evacuated and charged with N$_2$ (2×) and heated under microwave conditions [Biotage, 100° C., 30 min, high absorption]. This was further purified by Gilson HPLC. The combined fractions were concentrated in vacuo resulting in the title compound an off-white solid. $^1$H NMR (400 MHz, CD$_3$OD): δ=1.80 (d, J=7.3 Hz, 3H), 3.63 (s, 3H), 3.67 (br. s., 2H), 3.72 (s, 3H), 5.07-5.16 (m, 1H), 6.91 (dd, J=4.2, 9.0 Hz, 1H), 7.10 (dd, J=8.8, 8.8 Hz, 1H), 7.34 (d, J=1.3 Hz, 1H), 7.52 (s, 2H), 7.67 (s, 1H). MS (ES+): m/z 415.09, 417.07 [MH$^+$]. HPLC: t$_R$=3.95 min (polar__5 min, ZQ3)

4-Bromo-5-methoxy-1-methyl-1H-pyrazole

A solution of 5-methoxy-1-methyl-1H-pyrazole (0.500 g, 4.46 mmol) in MeOH (50.0 mL) was cooled to 0° C. and charged with pyridinium tribromide (1.43 g, 4.46 mmol) in portions. The solution was stirred for 1 h at 0° C. then for an additional 16 h at rt. The reaction mixture was charged with sat. NaHCO$_3$ (2.5 mL) and diluted with H$_2$O and extracted with CHCl$_3$ (3×). The combined organic fractions were dried over Na$_2$SO$_4$, filtered and concentrated in vacuo resulting in 647 mg, 76% yield of the title compound as a red oil. This material was used in the next step without further purification. $^1$H NMR (400 MHz, CD$_3$OD): δ=3.66 (s, 3H), 4.07 (s, 3H), 7.30 (s, 1H). MS (ES+): m/z 190.98, 192.99 (49.5/50.5) [MH$^+$]. HPLC: t$_R$=3.33 min (polar__5 min, ZQ3).

5-Methoxy-1-methyl-1H-pyrazole

A solution of 1-methyl-1H-pyrazol-5-ol (0.250 g, 2.55 mmol) and potassium carbonate (0.704 g, 5.10 mmol) in anhydrous DMF (3.0 mL) was charged with methyl 4-methylbenzenesulfonate (0.384 mL, 2.55 mmol) and stirred at rt for 16 h. The reaction mixture was poured into 2.0 M of HCl in H$_2$O (20.0 mL) and extracted with petroleum ether (3×). The aqueous was charged with NaHCO$_3$ until alkaline and extracted with diethyl ether (3×). The combined etherate fractions were washed with H$_2$O (1×), brine (1×), dried over Na$_2$SO$_4$, filtered and concentrated in vacuo resulting in the title compound as a clear, amber oil. This sample was taken on to the next step without further purification. $^1$H NMR (400 MHz, CD$_3$OD): δ=3.58 (s, 3H), 3.91 (s, 3H), 5.63 (d, J=2.3 Hz, 1H), 7.26 (d, J=2.3 Hz, 1H). MS (ES+): m/z 113.0 (100) [MH$^+$]. HPLC: t$_R$=2.46 min (nonpolar__5 min, ZQ3).

Example 63

5-(5-Chloro-1,3-dimethyl-1H-pyrazol-4-yl)-3-[(1S)-1-(2-chloro-3-fluoro-6-methoxyphenyl)ethyl]-1H-pyrrolo[2,3-b]pyridine

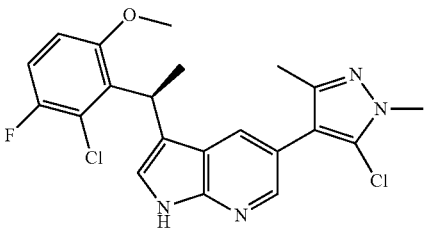 [SMILES: COc1ccc(F)c(Cl)c1[C@@H](C)c1c[nH]c2ncc(-c3c(C)nn(C)c3Cl)cc12]

A solution of 4-bromo-5-chloro-1,3-dimethyl-1H-pyrazole (0.0219 g, 0.104 mmol), 3-[(S)-1-(2-chloro-3-fluoro-6-methoxyphenyl)-ethyl]-5-(4,4,5,5-tetramethyl-[1,3,2]dioxaborolan-2-yl)-1H-pyrrolo[2,3-b]pyridine (0.030 g, 0.070 mmol), potassium carbonate (0.0289 g, 0.209 mmol) and Pd(PPh$_3$)$_4$ (8.04 mg, 0.00697 mmol) in previously degassed 4:1 dioxane:water (1.50 mL) was evacuated and charged with N$_2$ (2×) and heated under microwave conditions [Biotage, 100° C., 30 min, high absorption]. This was further purified by Gilson HPLC resulting in the title compound as white solid. $^1$H NMR (400 MHz, CD$_3$OD): δ=1.82 (d, J=7.3 Hz, 3H), 2.13 (s, 3H), 3.66 (br. s., 3H), 3.84 (s, 3H), 5.12 (q, J=7.2 Hz, 1H), 6.91 (dd, J=4.2, 9.0 Hz, 1H), 7.09 (dd, J=8.8, 8.8 Hz, 1H), 7.39 (d, J=1.3 Hz, 1H), 7.45 (s, 2H). MS (ES+): m/z 433.03, 435.01 (76/24) [MH$^+$]. HPLC: t$_R$=4.25 min (polar__5 min, ZQ3).

4-Bromo-5-chloro-1,3-dimethyl-1H-pyrazole

A solution of 5-chloro-1,3-dimethyl-1H-pyrazole (0.500 g, 3.83 mmol) in carbon tetrachloride (2.0 mL) was charged with NBS (0.750 g, 4.21 mmol) and stirred at rt for 16 h. The reaction mixture was charged with silica gel and purified by chromatography on silica gel [ISCO Combiflash, 12 g cartridge, eluting with 100% heptane 10% EtOAc in heptane]. This resulted in 419 mg, 52% yield of the title compound as a white solid. $^1$H NMR (400 MHz, CDCl$_3$): δ=2.23 (s, 3H), 3.81 (s, 3H). MS (ES+): m/z 208.96, 210.93 (76/24) [MH$^+$]. HPLC: t$_R$=2.62 min (polar__5 min, ZQ3).

Example 64

3-[(1S)-1-(2-Chloro-3-fluoro-6-methoxyphenyl)ethyl]-5-(1-methyl-1H-imidazol-5-yl)-1H-pyrrolo[2,3-b]pyridine

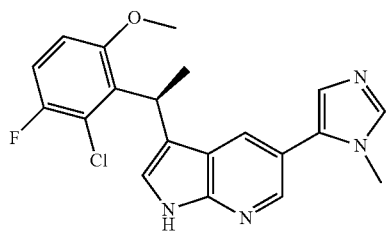 [SMILES: COc1ccc(F)c(Cl)c1[C@@H](C)c1c[nH]c2ncc(-c3cncn3C)cc12]

A solution of 5-iodo-1-methyl-1H-imidazole (0.0217 g, 0.104 mmol), 3-[(S)-1-(2-chloro-3-fluoro-6-methoxy-phenyl)-ethyl]-5-(4,4,5,5-tetramethyl-[1,3,2]dioxaborolan-2-yl)-1H-pyrrolo[2,3-b]pyridine (0.030 g, 0.070 mmol), potassium carbonate (0.0289 g, 0.209 mmol) and 1,1'-bis(diphenylphosphino)ferrocenepalladium(II) dichloride, dichloromethane (2.84 mg, 0.00348 mmol) in previously degassed 4:1 dioxane:water (1.50 mL) was evacuated and charged with $N_2$ (2×) and heated under microwave conditions [Biotage, 100° C., 30 min, high absorption]. The reaction mixture was partitioned between EtOAc and $H_2O$ and separated. The aqueous was back extracted with EtOAc (3×) and the combined organic fractions were dried over $Na_2SO_4$, filtered and concentrated in vacuo resulting in a crude brown oil. The crude was purified by chromatography on silica gel [ISCO Combiflash, 12 g cartridge, eluting with 100% DCM→8% MeOH in DCM]. This resulted in the title compound as an off-white solid. $^1$H NMR (400 MHz, $CD_3OD$): δ=1.82 (d, J=7.3 Hz, 3H), 3.51 (s, 3H), 3.66 (br. s., 3H), 5.12 (q, J=7.1 Hz, 1H), 6.90 (dd, J=4.2, 9.0 Hz, 1H), 6.95 (s, 1H), 7.08 (dd, J=8.8, 8.8 Hz, 1H), 7.41 (d, J=1.0 Hz, 1H), 7.51 (s, 1H), 7.69 (s, 1H), 8.17 (d, J=2.0 Hz, 1H). MS (ES+): m/z 385.11, 387.07 (76/24) [MH$^+$]. HPLC: $t_R$=2.87 min (polar_5 min, ZQ3).

Example 65

3-[(1S)-1-(2-chloro-3-fluoro-6-methoxyphenyl)ethyl]-5-(1,2-dimethyl-1H-imidazol-5-yl)-1H-pyrrolo[2,3-b]pyridine

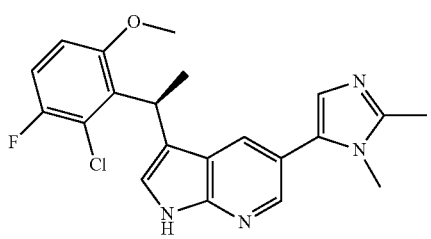 [SMILES: COc1ccc(F)c(Cl)c1[C@@H](C)c1c[nH]c2ncc(-c3cnc(C)n3C)cc12]

A solution of 5-bromo-1,2-dimethyl-1H-imidazole (0.0183 g, 0.104 mmol), 3-[(S)-1-(2-chloro-3-fluoro-6-methoxy-phenyl)-ethyl]-5-(4,4,5,5-tetramethyl-[1,3,2]dioxaborolan-2-yl)-1H-pyrrolo[2,3-b]pyridine (0.030 g, 0.070 mmol), potassium carbonate (0.0289 g, 0.209 mmol) and 1,1'-bis(diphenylphosphino)ferrocenepalladium(II) dichloride, dichloromethane (2.84 mg, 0.00348 mmol) in previously degassed 4:1 dioxane:water (1.50 mL) was evacuated and charged with $N_2$ (2×) and heated under microwave conditions [Biotage, 100° C., 30 min, high absorption]. The reaction mixture was purified by Gilson HPLC resulting in the title compound as a white solid. $^1$H NMR (400 MHz, $CD_3OD$): δ=1.80 (d, J=7.1 Hz, 3H), 2.58 (s, 3H), 3.47 (s, 3H), 3.67 (s, 3H), 5.12 (q, J=7.1 Hz, 1H), 6.90 (dd, J=4.3, 9.1 Hz, 1H), 7.08 (dd, J=9.0, 9.0 Hz, 1H), 7.22 (s, 1H), 7.46 (d, J=1.0 Hz, 1H), 7.56 (s, 1H), 8.18 (d, J=1.8 Hz, 1H). MS (ES+): m/z 399.12, 401.11 (76/24) [MH$^+$]. HPLC: $t_R$=2.77 min (polar_5 min, ZQ3).

Example 66

(2R)-3-(4-{3-[(1S)-1-(2,6-Dichloro-3-fluorophenyl)ethyl]-1H-pyrrolo[2,3-b]pyridin-5-yl}-3,5-dimethyl-1H-pyrazol-1-yl)propane-1,2-diol

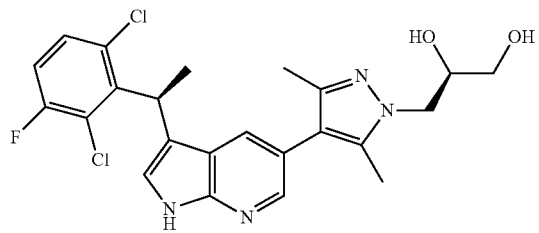 [SMILES: Cc1nn(C[C@@H](O)CO)c(C)c1-c1cnc2[nH]cc([C@H](C)c3c(Cl)ccc(F)c3Cl)c2c1]

Prepared using the procedure described for Example 69. $^1$H NMR (400 MHz, $CD_3OD$): δ=1.87 (d, J=7.3 Hz, 3H), 2.01 (s, 3H), 2.15 (s, 3H), 3.49-3.60 (m, 2H), 3.96-4.08 (m, 2H), 4.09-4.19 (m, 1H), 5.27 (q, J=7.2 Hz, 1H), 7.09 (d, J=1.8 Hz, 1H), 7.17 (t, J=8.6 Hz, 1H), 7.41 (d, J=1.5 Hz, 2H), 8.01 (s, 1H). MS (ES+): m/z=477.13/479.14 (100/68) [MH$^+$]. HPLC: $t_R$=1.36 min (polar_3 min, UPLC-ACQUITY).

Example 67 trans-4-(4-{3-[(1S)-1-(2,6-Dichloro-3-fluorophenyl)ethyl]-1H-pyrrolo[2,3-b]pyridin-5-yl}-5-methyl-1H-pyrazol-1-yl)cyclohexanol

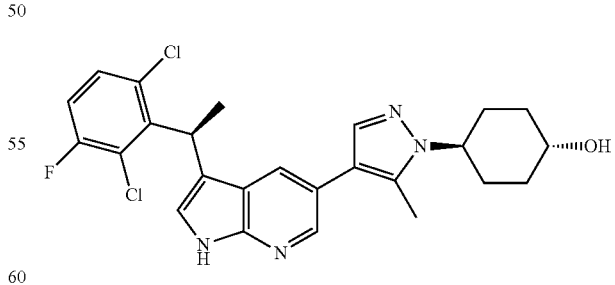

Prepared using the procedure described for Example 5. $^1$H NMR (400 MHz, $CD_3OD$): δ=1.44-1.57 (m, 2H), 1.88 (d, J=7.1 Hz, 3H), 1.92-2.13 (m, 6H), 2.18 (s, 3H), 3.67 (tt, J=10.9, 4.2 Hz, 1H), 4.18 (tt, J=11.0, 4.4 Hz, 1H), 5.28 (q, J=6.7 Hz, 1H), 7.15-7.22 (m, 2H), 7.32 (br. s., 1H), 7.41 (d, J=1.3 Hz, 1H), 7.44 (s, 1H), 8.17 (br. s., 1H). MS (ES+):

m/z=487.15/489.15 (100/68) [MH$^+$]. HPLC: t$_R$=1.48 min (polar_3 min, UPLC-ACQUITY).

Example 68

(2S)-3-(3-Chloro-2-{(1S)-1-[5-(1,5-dimethyl-1H-pyrazol-4-yl)-1H-pyrrolo[2,3-b]pyridin-3-yl]ethyl}-4-fluorophenoxy)propane-1,2-diol

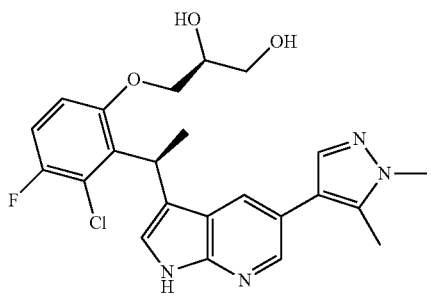 [SMILES: Cc1c(-c2cnc3[nH]cc([C@H](C)c4c(OC[C@@H](O)CO)ccc(F)c4Cl)c3c2)cnn1C]

A suspension of tert-butyl 5-bromo-3-[(1S)-1-(2-chloro-6-{[(4R)-2,2-dimethyl-1,3-dioxolan-4-yl]methoxy}-3-fluorophenyl)ethyl]-1H-pyrrolo[2,3-b]pyridine-1-carboxylate (29.2 mg, 0.0500 mmol), 1,5-dimethyl-1H-pyrazole-4-boronic acid, pinacol ester (20.7 mg, 0.0885 mmol), Pd(PPh$_3$)$_4$ (2.8 mg, 0.0024 mmol), and potassium carbonate (33.2 mg, 0.240 mmol) in a 4:1 mixture of 1,4-dioxane (2 mL) to H$_2$O (0.5 mL) was subjected to microwave heating [Biotage, 95° C.] for 20 min. The reaction was again subjected to microwave heating for an additional 20 minutes, which resulted in protected intermediate, tert-butyl 3-[(1S)-1-(2-chloro-6-{[(4R)-2,2-dimethyl-1,3-dioxolan-4-yl]methoxy}-3-fluorophenyl)ethyl]-5-(1,5-dimethyl-1H-pyrazol-4-yl)-1H-pyrrolo[2,3-b]pyridine-1-carboxylate. The microwave vial was opened, 4.0 M of HCl in 1,4-dioxane (1 mL, 4 mmol) was added to the stirring suspension, and the reaction was stirred at rt for 1 h, which lead to the BOC-protected intermediate, tert-butyl 3-[(1S)-1-(2-chloro-6-{[(2S)-2,3-dihydroxypropyl]oxy}-3-fluorophenyl)ethyl]-5-(1,5-dimethyl-1H-pyrazol-4-yl)-1H-pyrrolo[2,3-b]pyridine-1-carboxylate. 37% HCl (1 mL, 10 mmol) was added and stirred for 1 h at rt. Additional 37% HCl (1 mL, 10 mmol) was added and the reaction was stirred at rt for 15 h. The reaction mixture was concentrated in vacuo. The sample was dissolved in a mixture of CH$_2$Cl$_2$ and MeOH, passed through a syringe filter to remove excess K$_2$CO$_3$, and concentrated in vacuo. The crude was adsorbed onto a pre-filled silica loading cartridge [RediSepRf, 5 gram] and purified using the Teledyne/ISCO purification system [RediSepRf 4 gram silica], eluting with a solvent gradient of 0-20% 7N NH$_3$(MeOH):EtOAc. Fractions containing product were combined and concentrated in vacuo. The sample was dissolved in MeOH, syringe filtered, and purified a second time using MDP, under acidic conditions (TFA). Fractions containing product were combined and concentrated in vacuo. The sample was dissolved in minimal MeOH, syringe filtered, and purified a third time using HPLC, under acidic conditions (formic acid). Fractions containing product were combined and concentrated in vacuo, yielding the title material as a clear and colorless film. $^1$H NMR (400 MHz, CD$_3$OD): δ=8.10 (br s, 1H), 7.44 (s, 1H), 7.39 (d, J=1.3 Hz, 1H), 7.36 (d, J=1.8 Hz, 1H), 7.08 (dd, J=8.8 Hz, 1H), 6.90 (dd, J=8.7, 4.2 Hz, 1H), 5.12 (br d, J=6.6 Hz, 1H), 3.83-3.90 (m, 1H), 3.81 (s, 3H), 3.76-3.80 (m, 1H), 3.70 (br s, 1H), 3.42-3.51 (m, 1H), 3.34-3.42 (m, 1H), 2.18 (s, 3H), 1.83 (d, J=7.1 Hz, 3H). MS (ES$^+$): m/z 459.08/461.03 (100/74) [MH$^+$]. HPLC: t$_R$=2.93 min (ZQ3, polar_5 min).

tert-Butyl 5-bromo-3-[(1S)-1-(2-chloro-6-{[(4R)-2,2-dimethyl-1,3-dioxolan-4-yl]methoxy}-3-fluorophenyl)ethyl]-1H-pyrrolo[2,3-b]pyridine-1-carboxylate To a suspension of tert-butyl 5-bromo-3-[(1S)-1-(2-chloro-3-fluoro-6-hydroxyphenyl)ethyl]-1H-pyrrolo[2,3-b]pyridine-1-carboxylate (84.5 mg, 0.180 mmol) and potassium carbonate (104.5 mg, 0.7561 mmol) in DMF (3 mL), ((4S)-2,2-dimethyl-1,3-dioxolan-4-yl)methyl 4-methylbenzenesulfonate (103.6 mg, 0.3618 mmol) in DMF (2 mL) was added and the reaction mixture was heated to 60° C. for a total of 23 h. EtOAc was added to dilute the reaction mixture and a standard aqueous workup was performed. The combined organic layers were washed with brine, dried over anhydrous Na$_2$SO$_4$, filtered, and concentrated in vacuo. The crude was adsorbed onto a pre-filled silica gel loading cartridge [RediSepRf 5 gram] and purified using the Teledyne/ISCO system [RediSepRf 12 g Gold Silica], eluting with a 5-20% EtOAc: heptane solvent system. Fractions containing product were combined and concentrated in vacuo. The material obtained was dissolved in MeOH, passed through a syringe filter, and purified a second time by MDP, under acidic conditions (formic acid). Fractions containing product were pooled together and concentrated in vacuo, affording the title material as a clear and colorless film. $^1$H NMR (400 MHz, CDCl$_3$): δ=8.43 (d, J=2.3 Hz, 1H), 7.53 (s, 1H), 7.53 (s, 1H), 7.02 (dd, J=9.1, 8.3 Hz, 1H), 6.70 (dd, J=9.1, 4.0 Hz, 1H), 4.92 (q, J=7.0 Hz, 1H), 4.31 (quint, J=5.7 Hz, 1H), 3.97 (dd, J=8.3, 6.6 Hz, 1H), 3.91 (dd, J=9.0, 5.9 Hz, 1H), 3.65 (br s, 1H), 3.46 (br s, 1H), 1.76 (d, J=7.1 Hz, 3H), 1.69 (s, 9H), 1.36 (d, J=5.3 Hz, 6H). MS (ES$^+$): m/z 605.30/606.98/608.99 (23/61/9) [MH$^+$+Na]. HPLC: t$_R$ 4.15 min (ZQ3, nonpolar_5 min).

Example 69

(2R)-3-[4-(3-{(1S)-1-[2-Chloro-6-(difluoromethoxy)-3-fluorophenyl]ethyl}-1H-pyrrolo[2,3-b]pyridin-5-yl)-3,5-dimethyl-1H-pyrazol-1-yl]propane-1,2-diol

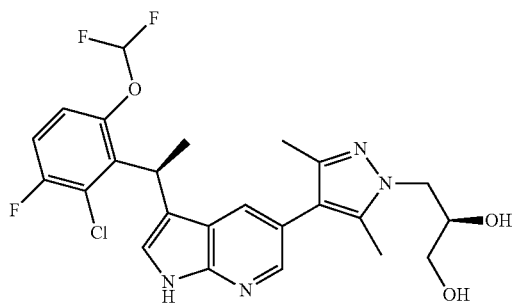 [SMILES: Cc1nn(C[C@@H](O)CO)c(C)c1-c1cnc2[nH]cc([C@H](C)c3c(OC(F)F)ccc(F)c3Cl)c2c1]

A mixture of tert-butyl 5-bromo-3-{(1S)-1-[2-chloro-6-(difluoromethoxy)-3-fluorophenyl]-ethyl}-1H-pyrrolo[2,3-b]pyridine-1-carboxylate (10.0 mg, 0.0192 mmol), 1-{[(4R)-2,2-dimethyl-1,3-dioxolan-4-yl]methyl}-3,5-dimethyl-4-(4,4,5,5-tetramethyl-1,3,2-dioxaborolan-2-yl)-1H-pyrazole (12.9 mg, 0.0385 mmol), Pd(PPh$_3$)$_4$ (1.1 mg, 0.00096 mmol), K$_2$CO$_3$ (7.98 mg, 0.00577 mmol) and 4:1 dioxane:H$_2$O (0.7 mL, 8 mmol) was heated in a microwave reactor at 100° C. for 45 min. 12 M of HCl in H$_2$O (0.04 mL, 0.5 mmol) was added, and the solution was heated to 40° C. for 20 min. The solution was used directly for HPLC purification, and the fractions containing the pure product were concentrated in vacuo to afford the title compound as a white solid. $^1$H NMR (400 MHz, CD$_3$OD): δ=1.84 (d, J=7.3 Hz, 3H), 2.04 (s, 3H), 2.17 (s, 3H), 3.50-3.61 (m, 2H), 3.96-4.10 (m, 2H), 4.13-4.19 (m, 1H), 5.07-5.15 (m, 1H), 6.43 (br. s., 1H), 7.12 (dd, J=9.2, 4.4 Hz, 1H), 7.19 (t, J=8.7 Hz, 1H), 7.28 (d, J=1.8 Hz, 1H), 7.41 (d, J=1.3 Hz, 1H), 7.96-8.04 (m, 1H). MS (ES+): m/z=509.15/511.15 (100/50) [MH$^+$]. HPLC: t$_R$=1.33 min (polar_3 min, UPLC-ACQUITY).

tert-Butyl 5-bromo-3-{(1S)-1-[2-chloro-6-(difluoromethoxy)-3-fluorophenyl]ethyl}-1H-pyrrolo[2,3-b]pyridine-1-carboxylate A mixture of tert-butyl 5-bromo-3-[(1S)-1-(2-chloro-3-fluoro-6-hydroxyphenyl)ethyl]-1H-pyrrolo[2,3-b]pyridine-1-carboxylate (1.00 g, 2.13 mmol), chlorodifluoroacetic acid ethyl ester (2.700 mL, 21.29 mmol), K$_2$CO$_3$ (882.7 mg, 6.387 mmol) and DMF (40 mL, 500 mmol) was heated to 70° C. for 6 h in a sealed tube. The material was extracted with EtOAc, and washed with water (3×). The organic layer was purified via column chromatography, eluting with 3-10% EtOAc/hexanes. The fractions containing the pure product were concentrated in vacuo to afford the title compound as a light yellow solid. $^1$H NMR (400 MHz, CD$_3$OD): δ=1.67-1.69 (m, 9H), 1.80 (d, J=7.1 Hz, 3H), 4.94-5.03 (m, 1H), 6.63 (s, 1H), 7.15 (dd, J=9.1, 4.5 Hz, 1H), 7.22-7.28 (m, 1H), 7.55 (d, J=2.0 Hz, 1H), 7.70 (d, J=1.5 Hz, 1H), 8.34 (d, J=2.0 Hz, 1H). MS (ES+): m/z=519.03/521.03 (75/100) [MH$^+$]. HPLC: t$_R$=1.93 min (polar_3 min, UPLC-ACQUITY).

tert-Butyl 5-bromo-3-[(1S)-1-(2-chloro-3-fluoro-6-hydroxyphenyl)ethyl]-1H-pyrrolo[2,3-b]pyridine-1-carboxylate A solution of tert-butyl 5-bromo-3-[(1S)-1-{6-[(tert-butoxycarbonyl)oxy]-2-chloro-3-fluorophenyl}ethyl]-1H-pyrrolo[2,3-b]pyridine-1-carboxylate (1.982 g, 3.478 mmol) in CH$_2$Cl$_2$ (40 mL) was charged with piperidine (12 mL, 120 mmol) and was stirred at rt for 16 h. The reaction mixture was diluted with CH$_2$Cl$_2$ and washed with 0.5 N HCl (4×50 mL). The combined organic layers were washed with brine, dried over anhydrous Na$_2$SO$_4$, filtered, and concentrated in vacuo. The crude was adsorbed onto a pre-filled silica gel loading cartridge [RediSepRf, 5 g] and purified using the Teledyne/ISCO system [RediSepRf 24 gram silica], eluting with a 10-50% EtOAc:Heptane solvent gradient. Fractions containing the desired product were pooled together and concentrated in vacuo, yielding the title material as a white solid. $^1$H NMR (400 MHz, CDCl$_3$): δ=8.39 (d, J=2.3 Hz, 1H), 7.65 (d, J=1.5 Hz, 1H), 7.54 (d, J=2.0 Hz, 1H), 6.97 (dd, J=8.8, 8.3 Hz, 1H), 6.67 (dd, J=8.8, 4.5 Hz, 1H), 4.93 (qd, J=7.1, 1.3 Hz, 1H), 1.78 (d, J=7.1 Hz, 3H), 1.68 (s, 9H). MS (ES$^+$): m/z 412.78/414.75/416.76 (75/100/27) [MH$^+$–C$_4$H$_8$]. HPLC: t$_R$=4.13 min (ZQ3, polar_5 min).

tert-Butyl 5-bromo-3-[(1S)-1-{6-[(tert-butoxycarbonyl)oxy]-2-chloro-3-fluorophenyl}ethyl]-1H-pyrrolo[2,3-b]pyridine-1-carboxylate To a cold solution (−40° C.) of 2-[(1S)-1-(5-bromo-1H-pyrrolo[2,3-b]pyridin-3-yl)ethyl]-3-chloro-4-fluorophenol (708.2 mg, 1.916 mmol) in THF (15 mL), NaH (60% dispersion in mineral oil) (311.9 mg, 7.798 mmol) was added in parts. The reaction mixture was allowed to warm to −10° C., over the course of 1 h, after which it was cooled back down to −40° C. A solution of di-tert-butyldicarbonate (1.786 g, 8.183 mmol) in THF (3 mL) was added and the reaction was slowly warmed to rt over the course of 17 h. The reaction mixture was cooled back down to 0° C., after which saturated aqueous NH$_4$Cl was added. After warming to rt, EtOAc and water were added and a standard aqueous workup was performed. The combined organic layers were washed with brine, dried over anhydrous Na$_2$SO$_4$, filtered, and concentrated in vacuo, giving the title material as a thick yellow oil. $^1$H NMR (400 MHz, CDCl$_3$): δ=8.45 (d, J=2.3 Hz, 1H), 7.58 (d, J=1.5 Hz, 1H), 7.52 (d, J=2.0 Hz, 1H), 7.11 (dd, J=9.0, 8.0 Hz, 1H), 6.99 (dd, J=9.1, 4.8 Hz, 1H), 4.80 (qd, J=7.1, 1.0 Hz, 1H), 1.76 (d, J=7.3 Hz, 1H), 1.69 (s, 3H), 1.38 (s, 3H). MS (ES$^+$): m/z 513.02/515.02/517.02 (72/100/31) [MH$^+$–C$_4$H$_8$]. HPLC: t$_R$=2.10 min (UPLC-ACQUITY, polar_3 min).

2-[(1S)-1-(5-Bromo-1H-pyrrolo[2,3-b]pyridin-3-yl)ethyl]-3-chloro-4-fluorophenol

To a solution of 5-bromo-3-[(S)-1-(2-chloro-3-fluoro-6-methoxyphenyl)-ethyl]-1H-pyrrolo[2,3-b]pyridine (1.015 g, 2.646 mmol) in CH$_2$Cl$_2$ (25 mL), cooled to −78° C., 1.0 M of boron tribromide in CH$_2$Cl$_2$ (8 mL, 8 mmol) was added in parts, over the course of 10 min. The solution was allowed to warm to ambient temperature for 18 h (acetone/dry ice bath removed at 1.5 h). The reaction mixture was cooled to 0° C., after which methanol was added to quench the reaction. After stirring at rt for 30 min, the reaction solution was concentrated in vacuo. The sample was resuspended in CH$_2$Cl$_2$ and a standard aqueous workup with saturated aqueous NaHCO$_3$ solution was performed. The organic layers were washed with brine, dried over anhydrous Na$_2$SO$_4$, filtered, and concentrated in vacuo. The crude was dissolved in minimal CH$_2$Cl$_2$/MeOH, adsorbed onto a pre-packed silica solid load cartridge (RediSepRf 25 g size), and purified by the ISCO/Teledyne purification system [RediSepRf silica column, 12 g size], using a 0-50% EtOAc:CH$_2$Cl$_2$ solvent gradient. Fractions containing product were combined and concentrated in vacuo, giving the title material as a yellow solid. $^1$H NMR (400 MHz, CDCl$_3$): δ=9.50 (br s, 1H), 8.34 (s, 1H), 7.62 (s, 1H), 7.43 (s, 1H), 6.99 (dd, J=8.6, 8.6 Hz, 1H), 6.62 (dd, J=9.1, 4.5 Hz, 1H), 5.03 (dtd, J=7.3, 7.2, 1.3 Hz, 1H), 1.77 (d, J=7.1 Hz, 3H). MS (ES$^+$): m/z 370.97/372.98 (100/43) [MH$^+$]. HPLC: t$_R$=1.56 min (TOF, polar_3 min).

Example 70

(2S)-3-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]propane-1,2-diol

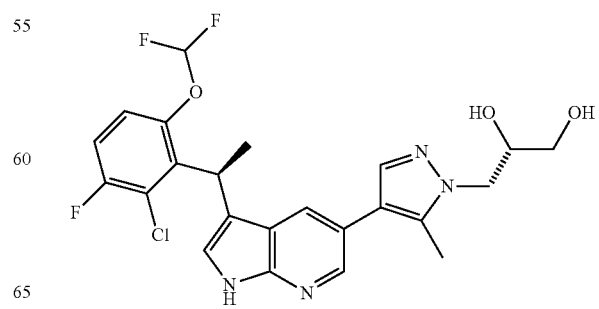

A mixture of tert-butyl 5-bromo-3-{(1S)-1-[2-chloro-6-(difluoromethoxy)-3-fluorophenyl]ethyl}-1H-pyrrolo[2,3-b]pyridine-1-carboxylate (45.0 mg, 0.0866 mmol), 1-{[(4S)-2,2-dimethyl-1,3-dioxolan-4-yl]methyl}-5-methyl-4-(4,4,5,5-tetramethyl-1,3,2-dioxaborolan-2-yl)-1H-pyrazole (41.85 mg, 0.1299 mmol), Pd(PPh$_3$)$_4$ (5.002 mg, 0.004329 mmol), K$_2$CO$_3$ (35.90 mg, 0.2597 mmol) and 4:1 dioxane:H$_2$O (2 mL, 20 mmol) was heated to 95° C. for 2 h. The solution was cooled to rt, and 12 M of HCl in H$_2$O (0.072 mL, 0.87 mmol) was added. The material was concentrated in vacuo, and extracted with DCM and sat. NaHCO$_3$. The organic layer was dry-loaded onto silica gel and purified via column chromatography, eluting with 2-4% (7N NH$_3$ in MeOH)/DCM. The fractions containing the pure product were concentrated in vacuo, redissolved in MeOH, and 2.0 M of HCl in Et$_2$O (0.4329 mL, 0.8658 mmol) was added at rt. The solution was concentrated in vacuo to afford the title compound as an HCl salt. $^1$H NMR (400 MHz, CD$_3$OD): δ=1.85 (d, J=7.3 Hz, 3H), 2.27 (s, 3H), 3.50-3.63 (m, 2H), 4.00-4.09 (m, 1H), 4.15 (dd, J=14.1, 7.6 Hz, 1H), 4.25 (dd, J=14.3, 4.4 Hz, 1H), 5.12 (q, J=7.1 Hz, 1H), 6.44 (br. s., 1H), 7.14 (dd, J=8.7, 4.4 Hz, 1H), 7.20 (t, J=8.7 Hz, 1H), 7.35-7.45 (m, 2H), 7.52 (s, 1H), 8.16 (d, J=2.0 Hz, 1H). MS (ES+): m/z=494.99/496.98 (100/50) [MH$^+$]. HPLC: t$_R$=1.29 min (polar_3 min, UPLC-ACQUITY).

1-{[(4S)-2,2-Dimethyl-1,3-dioxolan-4-yl]methyl}-5-methyl-4-(4,4,5,5-tetramethyl-1,3,2-dioxaborolan-2-yl)-1H-pyrazole To a solution of 1-((S)-2,2-dimethyl-[1,3]dioxolan-4-ylmethyl)-4-iodo-5-methyl-1H-pyrazole (55.0 mg, 0.171 mmol) in THF (1 mL, 20 mmol) at rt was added 1.3 M of isopropylmagnesium chloride in THF (0.53 mL, 0.68 mmol), and the mixture was stirred for 1 h. The reaction was quenched with 2-methoxy-4,4,5,5-tetramethyl-1,3,2-dioxaborolane (0.14 mL, 0.85 mmol) and allowed to stir at rt for 1 h. Sat. NH$_4$Cl was added, and the organic solvent was removed in vacuo. The material was extracted with DCM and water. The organic layer was purified via column chromatography, eluting with 5-10% EtOAc/hexanes. The fractions containing the pure product were concentrated in vacuo to afford the title compound as a white solid. MS (ES+): m/z=322.21/323.20/324.20 (50/100/50) [MH$^+$]. HPLC: t$_R$=1.49 min (polar_3 min, UPLC-ACQUITY).

1-((S)-2,2-Dimethyl-[1,3]dioxolan-4-ylmethyl)-4-iodo-5-methyl-1H-pyrazole

A solution of 1-{[(4S)-2,2-Dimethyl-1,3-dioxolan-4-yl]methyl}-4-iodo-1H-pyrazole (700 mg, 2.27 mmol) in THF (6 mL, 70 mmol) was cooled to −78° C., and 1.5 M of LDA in cyclohexane (4.5 mL, 6.8 mmol) was added. After stirring for 1 h, methyliodide (1.41 mL, 22.7 mmol) was added slowly, and the mixture was stirred at −78° C. for 1 h. Sat. NH$_4$Cl was added to quench, and the organic solvent was removed in vacuo. The material was extracted with DCM and water, and the organic layer purified via column chromatography, eluting with 5-10% EtOAc/hexanes. The fractions containing the pure product were concentrated in vacuo to afford the title compound as a white solid. MS (ES+): m/z=323.06 (100) [MH$^+$]. HPLC: t$_R$=1.20 min (polar_3 min, UPLC-ACQUITY).

1-{[(4S)-2,2-Dimethyl-1,3-dioxolan-4-yl]methyl}-4-iodo-1H-pyrazole

A mixture of 4-iodopyrazole (1.00 g, 5.16 mmol), (R)-(−)-(2,2-Dimethyl-1,3-dioxolan-4-yl)methyl p-toluenesulfonate (1.624 g, 5.671 mmol), Cs$_2$CO$_3$ (2.52 g, 7.73 mmol) and DMF (8 mL, 100 mmol) was heated to 100° C. for 2 h. The solution was extracted with EtOAc, and washed with water (2×). The organic layer was concentrated in vacuo and purified via column chromatography, eluting with 2-10% EtOAc/hexanes. The fractions containing the pure product were concentrated in vacuo to afford the title compound as a white solid. MS (ES+): m/z=309.00 (100) [MH$^+$]. HPLC: t$_R$=1.32 min (polar_3 min, UPLC-ACQUITY).

Example 71

(2S)-3-[4-(3-{(1S)-1-[2-Chloro-6-(difluoromethoxy)-3-fluorophenyl]ethyl}-1H-pyrrolo[2,3-b]pyridin-5-yl)-3-methyl-1H-pyrazol-1-yl]propane-1,2-diol

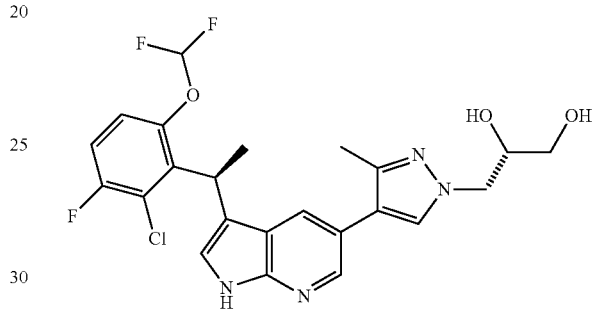

Prepared using the procedure described for Example 69. $^1$H NMR (400 MHz, CD$_3$OD): δ=1.85 (d, J=7.3 Hz, 3H), 2.15 (s, 3H), 3.46-3.57 (m, 2H), 3.94-4.01 (m, 1H), 4.02-4.10 (m, 1H), 4.25 (dd, J=13.9, 4.0 Hz, 1H), 5.12 (q, J=7.0 Hz, 1H), 6.45 (br. s., 1H), 7.14 (dd, J=8.8, 4.3 Hz, 1H), 7.20 (t, J=8.6 Hz, 1H), 7.42 (d, J=1.3 Hz, 1H), 7.46-7.54 (m, 1H), 7.71 (s, 1H), 8.21 (br. s., 1H). MS (ES+): m/z=495.14/497.14 (100/50) [MH$^+$]. HPLC: t$_R$=1.31 min (polar_3 min, UPLC-ACQUITY).

Example 72

1-[4-(3-{(1S)-1-[2-Chloro-6-(difluoromethoxy)-3-fluorophenyl]ethyl}-1H-pyrrolo[2,3-b]pyridin-5-yl)-5-ethyl-1H-pyrazol-1-yl]-2-methylpropan-2-ol

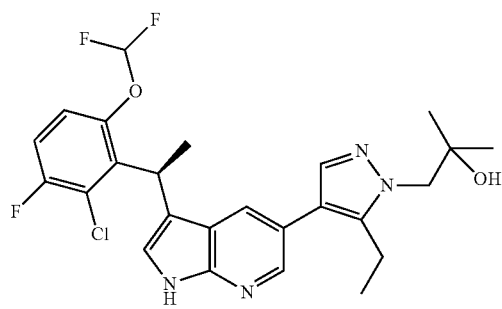 [SMILES: CCc1c(-c2cnc3[nH]cc([C@H](C)c4c(OC(F)F)ccc(F)c4Cl)c3c2)cnn1CC(C)(C)O]

Prepared using the procedure described for Example 69. $^1$H NMR (400 MHz, CD$_3$OD): δ=1.01 (t, J=7.6 Hz, 3H), 1.22 (s, 6H), 1.84 (d, J=7.1 Hz, 3H), 2.68-2.78 (m, 2H), 4.09 (s, 2H), 5.11 (q, J=7.0 Hz, 1H), 6.39 (br. s., 1H), 7.12 (dd, J=9.1, 4.5 Hz, 1H), 7.20 (t, J=8.7 Hz, 1H), 7.37-7.44 (m, 2H), 7.50 (s, 1H), 8.11-8.21 (m, 1H). MS (ES+): m/z=507.18/509.18 (100/50) [MH+]. HPLC: $t_R$=1.59 min (polar_3 min, UPLC-ACQUITY).

Example 73

1-[4-(3-{(1S)-1-[2-Chloro-6-(difluoromethoxy)-3-fluorophenyl]ethyl}-1H-pyrrolo[2,3-b]pyridin-5-yl)-3-ethyl-1H-pyrazol-1-yl]-2-methylpropan-2-ol

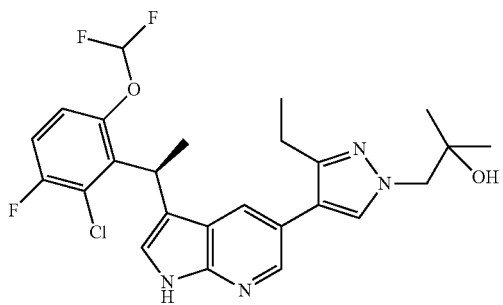 [SMILES: CCc1nn(CC(C)(C)O)cc1-c1cnc2[nH]cc([C@H](C)c3c(OC(F)F)ccc(F)c3Cl)c2c1]

Prepared using the procedure described for Example 69. $^1$H NMR (400 MHz, CD$_3$OD): δ=1.06 (t, J=7.6 Hz, 3H), 1.19 (s, 6H), 1.84 (d, J=7.1 Hz, 3H), 2.54 (qd, J=7.5, 2.8 Hz, 2H), 4.05 (s, 2H), 5.11 (q, J=6.9 Hz, 1H), 6.39 (br. s., 1H), 7.13 (dd, J=8.7, 4.7 Hz, 1H), 7.21 (t, J=8.7 Hz, 1H), 7.39 (s, 1H), 7.43 (d, J=1.8 Hz, 1H), 7.65 (s, 1H), 8.10-8.21 (m, 1H). MS (ES+): m/z=507.18/509.18 (100/50) [MH+]. HPLC: $t_R$=1.56 min (polar_3 min, UPLC-ACQUITY).

Example 74 trans-4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexanol

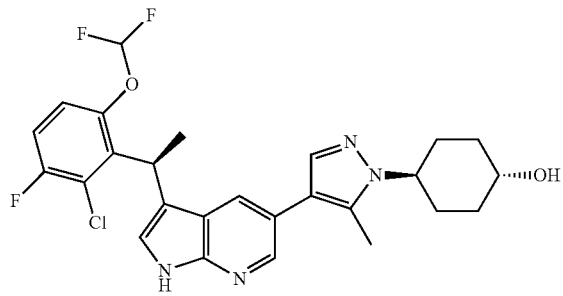 [SMILES: Cc1c(-c2cnc3[nH]cc([C@H](C)c4c(OC(F)F)ccc(F)c4Cl)c3c2)cnn1[C@H]1CC[C@H](O)CC1]

A mixture of tert-butyl 5-bromo-3-{(1S)-1-[2-chloro-6-(difluoromethoxy)-3-fluorophenyl]-ethyl}-1H-pyrrolo[2,3-b]pyridine-1-carboxylate (70.0 mg, 0.135 mmol), trans-4-[5-methyl-4-(4,4,5,5-tetramethyl-1,3,2-dioxaborolan-2-yl)-1H-pyrazol-1-yl]cyclohexanol (53.6 mg, 0.175 mmol), Pd(PPh$_3$)$_4$ (7.78 mg, 0.00673 mmol), K$_2$CO$_3$ (0.0558 g, 0.404 mmol) and 4:1 dioxane:H$_2$O (5 mL, 50 mmol) was heated to 95° C. for 2 h. The solution was cooled to 45° C., and 12 M of HCl in H$_2$O (0.2 mL, 2 mmol) was added, stirring for an additional 2 h. The solution was concentrated in vacuo and transferred to a separation funnel. The material was extracted with DCM and sat. NaHCO$_3$. The organic layer was loaded onto silica gel for column chromatography, eluting with 2-4% (7N NH$_3$ in MeOH)/DCM. The fractions containing the pure product were concentrated in vacuo, redissolved in MeOH, and 2.0 M of HCl in Et$_2$O (1 mL, 2 mmol) was added at rt. The solution was stirred for 1 h, and concentrated in vacuo to afford the title compound as an HCl salt. $^1$H NMR (free base; 400 MHz, CD$_3$OD): δ=1.45-1.57 (m$_c$, 2H), 1.84 (d, J=7.0 Hz, 3H), 1.91-2.12 (m, 6H), 2.22 (s, 3H), 3.67 (tt, J=10.8, 4.4 Hz, 1H), 4.18 (tt, J=11.0, 4.4 Hz, 1H), 5.11 (q, J=7.2 Hz, 1H), 6.44 (brt, J=73.8 Hz, 1H), 7.13 (dd, J=8.8, 4.4 Hz, 1H), 7.19 (dd, J=8.8, 8.4 Hz, 1H), 7.37 (d, J=2.0 Hz, 1H), 7.37 (d, J=2.0 Hz, 1H), 7.39 (d, J=1.2 Hz, 1H), 7.46 (s, 1H), 8.12 (d, J=2.0 Hz, 1H). $^1$H NMR(HCl salt; 400 MHz, CD$_3$OD): δ=1.45-1.57 (m$_c$, 2H), 1.89 (d, J=7.0 Hz, 3H), 1.91-2.12 (m, 6H), 2.23 (s, 3H), 3.67 (tt, J=11.2, 4.2 Hz, 1H), 4.24 (tt, J=11.0, 4.4 Hz, 1H), 5.20 (q, J=7.2 Hz, 1H), 6.71 (brt, J=73.6 Hz, 1H), 7.19 (dd, J=8.8, 4.4 Hz, 1H), 7.26 (dd, J=8.8, 8.0 Hz, 1H), 7.64 (s, 1H), 7.73 (d, J=1.2 Hz, 1H), 7.98 (d, J=1.6 Hz, 1H), 8.38 (d, J=1.6 Hz, 1H). MS (ES+): m/z=519.16/521.18 (100/50) [MH+]. HPLC: $t_R$=1.45 min (polar_3 min, UPLC-ACQUITY).

Alternatively, 1-(trans-4-{[tert-butyl(dimethyl)silyl]oxy}cyclohexyl)-5-methyl-4-(4,4,5,5-tetramethyl-1,3,2-dioxaborolan-2-yl)-1H-pyrazole may be used in place of trans-4-[5-methyl-4-(4,4,5,5-tetramethyl-1,3,2-dioxaborolan-2-yl)-1H-pyrazol-1-yl]cyclohexanol under otherwise similar conditions. The TBDMS group is removed during the treatment with 12 M of HCl in H$_2$O.

1-(trans-4-{[tert-Butyl(dimethyl)silyl]oxy}cyclohexyl)-5-methyl-4-(4,4,5,5-tetramethyl-1,3,2-dioxaborolan-2-yl)-1H-pyrazole To a solution of 1-(trans-4-{[tert-butyl(dimethyl)silyl]oxy}cyclohexyl)-4-iodo-5-methyl-1H-pyrazole (1.15 g, 2.74 mmol) in THF (60 mL, 700 mmol) at rt was added 1.3 M of Isopropylmagnesium Chloride in THF (8.4 mL, 11 mmol), and the mixture was stirred for 1 h. The reaction was quenched with 2-methoxy-4,4,5,5-tetramethyl-1,3,2-dioxaborolane (2.24 mL, 13.7 mmol), and allowed to stir at rt for 1 h. Sat. NH$_4$Cl was added, and the organic solvent was removed in vacuo. The material was extracted with DCM and water. The organic layer was dry-loaded onto silica gel and purified via column chromatography, eluting with 2-7% EtOAc/heptane. The fractions containing the pure product were concentrated in vacuo to afford the title compound as a white solid. $^1$H NMR (400 MHz, methanol-d$_4$): δ=0.12 (s, 6H), 0.93 (s, 9H), 1.32 (s, 12H), 1.47-1.60 (m, 2H), 1.84-2.06 (m, 6H), 2.46 (s, 3H), 3.72-3.82 (m, 1H), 4.10-4.22 (m, 1H), 7.59 (s, 1H).

1-(trans-4-{[tert-Butyl(dimethyl)silyl]oxy}cyclohexyl)-4-iodo-5-methyl-1H-pyrazole A solution of 1-(trans-4-{[tert-Butyl(dimethyl)silyl]oxy}cyclohexyl)-4-iodo-1H-pyrazole (2.00 g, 4.92 mmol) in THF (20 mL, 200 mmol) was cooled to −78° C., and 1.5 M of Lithium Diisopropylamide in Cyclohexane (4.26 mL, 6.40 mmol) was added. After stirring for 5 min, Methyl iodide (2 mL, 20 mmol) was added slowly, and the mixture was stirred at −78° C. for 30 min. Sat. NH$_4$Cl was added to quench, and the organic solvent was removed in vacuo. The material was extracted with DCM and water, and the organic layer was dry-loaded onto silica gel for column chromatography, eluting with 1% EtOAc/heptane. The fractions containing the pure product were concentrated in vacuo to afford the title compound as a clear oil. $^1$H NMR (400 MHz, methanol-d$_4$): δ=0.11 (s, 6H), 0.93 (s, 9H), 1.48-1.60 (m, 2H), 1.85-2.05 (m, 6H), 2.34 (s, 3H), 3.70-3.81 (m, 1H), 4.16-4.26 (m, 1H), 7.43 (s, 1H).

Example 75

(1R,2S,4S)-4-[4-(3-{(1S)-1-[2-Chloro-6-(difluoromethoxy)-3-fluoro-phenyl]ethyl}-1H-pyrrolo[2,3-b]pyridin-5-yl)-5-methyl-1H-pyrazol-1-yl]cyclopentane-1,2-diol

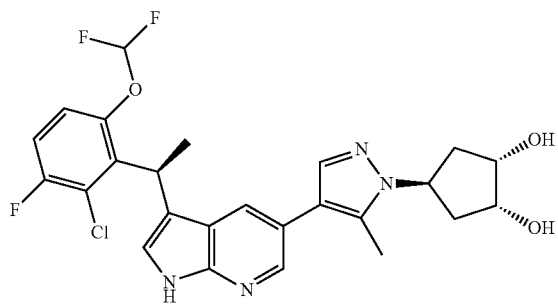 [SMILES: Cc1c(-c2cnc3[nH]cc([C@H](C)c4c(OC(F)F)ccc(F)c4Cl)c3c2)cnn1[C@@H]1C[C@@H](O)[C@@H](O)C1]

Prepared using the procedure described for Example 69. $^1$H NMR (400 MHz, CD$_3$OD): δ=1.84 (d, J=7.1 Hz, 3H), 2.15-2.25 (m, 7H), 4.30-4.40 (m, 2H), 5.01-5.14 (m, 2H), 6.44 (br. s., 1H), 7.08-7.15 (m, 1H), 7.16-7.22 (m, 1H), 7.36 (s, 1H), 7.39 (s, 1H), 7.49 (s, 1H), 8.13 (d, J=2.0 Hz, 1H). MS (ES+): m/z=521.14/523.14 (100/50) [MH$^+$]. HPLC: t$_R$=1.37 min (polar_3 min, UPLC-ACQUITY).

(1R,2S,4S)-4-[5-Methyl-4-(4,4,5,5-tetramethyl-1,3,2-dioxaborolan-2-yl)-1H-pyrazol-1-yl]cyclopentane-1,2-diol To a solution of (1R,2S,4S)-4-(4-iodo-5-methyl-1H-pyrazol-1-yl)cyclopentane-1,2-diol (300.0 mg, 0.9736 mmol) in THF (20 mL, 200 mmol) was added 2 M isopropylmagnesium chloride in THF (2.0 mL, 4.0 mmol) at rt, and the mixture was stirred for 30 min. 2-Methoxy-4,4,5,5-tetramethyl-1,3,2-dioxaborolane (0.64 mL, 3.9 mmol) was added, and the mixture stirred at rt for 2 h. The reaction was quenched with sat. NH$_4$Cl, and the organic solvent was removed in vacuo. The material was extracted with DCM and water, and the organic layer was concentrated in vacuo to afford the title compound as a white solid. The material was used in the next step without further purification.

Example 76 trans-4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexanecarboxamide

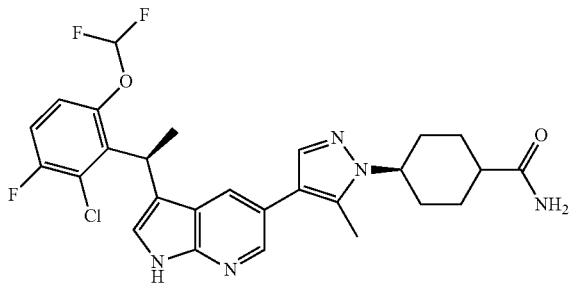

A mixture of tert-butyl 5-bromo-3-{(1S)-1-[2-chloro-6-(difluoromethoxy)-3-fluorophenyl]ethyl}-1H-pyrrolo[2,3-b]pyridine-1-carboxylate (70.0 mg, 0.135 mmol), ethyl trans-4-[5-methyl-4-(4,4,5,5-tetramethyl-1,3,2-dioxaborolan-2-yl)-1H-pyrazol-1-yl]cyclohexane-carboxylate (97.6 mg, 0.269 mmol), Pd(PPh$_3$)$_4$ (7.78 mg, 0.00673 mmol), potassium fluoride (23.5 mg, 0.404 mmol) and 4:1 dioxane:H$_2$O (5 mL, 50 mmol) was heated in a microwave reactor at 95° C. for 30 min. The material was extracted with DCM and water, and the organic layer was dry-loaded onto silica gel for column chromatography, eluting with 1-2% MeOH/DCM. The fractions containing the intermediate were concentrated in vacuo, and redissolved in MeOH. 12 M of HCl in H$_2$O (0.4 mL, 5 mmol) was added, and the solution was heated to 45° C. for 1 h to remove BOC group. Lithium hydroxide monohydrate (56.5 mg, 1.35 mmol) was added to bring to pH=12, and the solution was heated to 40° C. for 2 h to hydrolyze the ester. The material was concentrated in vacuo and transferred to a separatory funnel with DCM and water. The aqueous layer was added 2 M HCl to bring to pH=6, and the material was extracted. The organic layer was concentrated in vacuo, redissolved in DCM (10 mL, 200 mmol), and NH$_4$Cl (72.0 mg, 1.35 mmol), TBTU (64.9 mg, 0.202 mmol) and DIPEA (0.0704 mL, 0.404 mmol) were added at rt. The solution was stirred for 20 min, then extracted with DCM and water. The organic layer was purified via column chromatography, eluting with 2-5% (7N NH$_3$ in MeOH)/DCM. The fractions containing the pure product were concentrated in vacuo to afford the title compound as a white solid. $^1$H NMR (400 MHz, CD$_3$OD): δ=1.65-1.78 (m, 2H), 1.84 (d, J=7.3 Hz, 3H), 1.94-2.08 (m, 6H), 2.22 (s, 3H), 2.35 (tt, J=12.3, 3.3 Hz, 1H), 4.21 (m, J=10.0, 10.0, 5.2, 5.1 Hz, 1H), 5.10 (q, J=7.0 Hz, 1H), 6.44 (br. s., 1H), 7.08-7.16 (m, 1H), 7.16-7.21 (m, 1H), 7.37 (d, J=1.8 Hz, 1H), 7.39 (d, J=1.0 Hz, 1H), 7.48 (s, 1H), 8.13 (d, J=2.0 Hz, 1H). MS (ES+): m/z=546.16/548.16 (100/50) [MH$^+$]. HPLC: t$_R$=1.40 min (polar_3 min, UPLC-ACQUITY).

Example 77 trans-4-[4-(3-{(1S)-1-[2-Chloro-6-(difluoromethoxy)-3-fluorophenyl]ethyl}-1H-pyrrolo[2,3-b]pyridin-5-yl)-3-ethyl-1H-pyrazol-1-yl]cyclohexanol

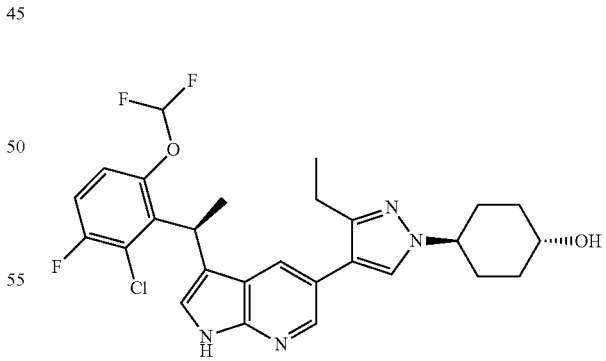

Prepared using the procedure described for Example 69. $^1$H NMR (400 MHz, CD$_3$OD): δ=1.02 (t, J=7.6 Hz, 3H), 1.41-1.54 (m, 2H), 1.83 (d, J=7.3 Hz, 3H), 1.84-1.94 (m, 2H), 2.03-2.17 (m, 4H), 2.44-2.58 (m, 2H), 3.66 (tt, J=11.0, 4.1 Hz, 1H), 4.10 (m, J=11.8, 11.8, 3.9, 3.8 Hz, 1H), 5.09 (q, J=7.1 Hz, 1H), 6.38 (br. s., 1H), 7.12 (dd, J=8.8, 4.3 Hz, 1H), 7.20 (t, J=8.6 Hz, 1H), 7.39 (d, J=1.3 Hz, 1H), 7.40 (d, J=1.8 Hz, 1H), 7.67 (s, 1H), 8.13 (br. s., 1H). MS (ES+):

109 m/z=533.16/535.17 (100/50) [MH+]. HPLC: t_R=1.47 min (polar_3 min, UPLC-ACQUITY).

Example 78 trans-4-[4-(3-{(1S)-1-[2-Chloro-6-(difluoromethoxy)-3-fluorophenyl]ethyl}-1H-pyrrolo[2,3-b]pyridin-5-yl)-5-ethyl-1H-pyrazol-1-yl]cyclohexanol

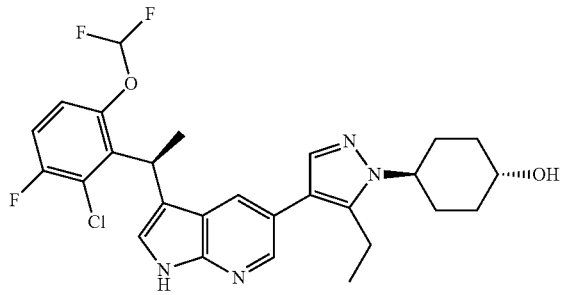 [SMILES: CCc1c(-c2cnc3[nH]cc([C@H](C)c4c(OC(F)F)ccc(F)c4Cl)c3c2)cnn1[C@H]1CC[C@H](O)CC1]

Prepared using the procedure described for Example 69. $^1$H NMR (400 MHz, CD$_3$OD): δ=1.11 (t, J=7.6 Hz, 3H), 1.45-1.59 (m, 2H), 1.83 (d, J=7.3 Hz, 3H), 1.88-1.98 (m, 2H), 2.00-2.15 (m, 4H), 2.52-2.72 (m, 2H), 3.63-3.74 (m, 1H), 4.15 (tt, J=11.5, 4.1 Hz, 1H), 5.11 (q, J=7.3 Hz, 1H), 6.38 (br. s., 1H), 7.13 (dd, J=8.5, 4.2 Hz, 1H), 7.20 (t, J=8.7 Hz, 1H), 7.36 (d, J=1.8 Hz, 1H), 7.41 (d, J=1.0 Hz, 1H), 7.47 (s, 1H), 8.12 (s, 1H). MS (ES+): m/z=533.18/535.19 (100/50) [MH+]. HPLC: t_R=1.45 min (polar_3 min, UPLC-ACQUITY).

Example 79 cis-3-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]-1-methylcyclobutanol

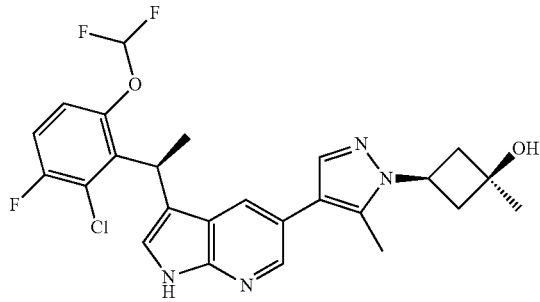 [SMILES: Cc1c(-c2cnc3[nH]cc([C@H](C)c4c(OC(F)F)ccc(F)c4Cl)c3c2)cnn1[C@H]1C[C@@](C)(O)C1]

To a solution of 3-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclobutanone (8.00 mg, 0.0164 mmol) in THF (1.0 mL, 10 mmol) at −78° C. was added 1.4 M of methylmagnesium bromide in THF (0.058 mL, 0.082 mmol), and the mixture was allowed to warm to rt and stir for 2 h. Sat. NH$_4$Cl was added to quench, and the material was extracted with DCM and water. The organic layer was redissolved in MeOH (0.7 mL) and purified via HPLC. The fractions containing the pure product were concentrated in vacuo to afford the title compound as a white solid. $^1$H NMR (400 MHz, CD$_3$OD): δ=1.45 (s, 3H), 1.84 (d, J=7.1 Hz, 3H), 2.18 (s, 3H), 2.55-2.63 (m, 2H), 2.65-2.75 (m, 2H), 4.49 (quin, J=8.1 Hz, 1H), 5.11 (q, J=7.0 Hz, 1H), 6.43 (br. s., 1H), 7.08-7.16 (m, 1H), 7.16-7.21 (m, 1H), 7.36 (d, J=2.0 Hz, 1H), 7.39 (d, J=1.3 Hz, 1H), 7.50 (s, 1H), 8.13 (d, J=2.0 Hz, 1H). MS (ES+): m/z=505.16/507.16 (100/50) [MH+]. HPLC: t_R=1.47 min (polar_3 min, UPLC-ACQUITY).

Example 80

3-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclobutanone

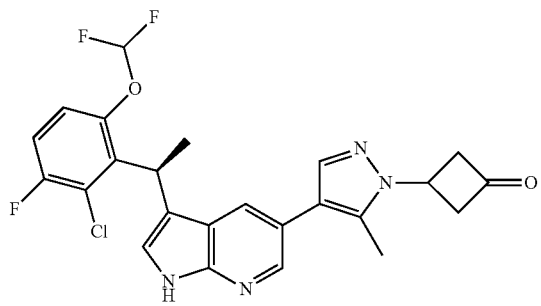 [SMILES: Cc1c(-c2cnc3[nH]cc([C@H](C)c4c(OC(F)F)ccc(F)c4Cl)c3c2)cnn1C1CC(=O)C1]

A mixture of tert-butyl 5-bromo-3-{(1S)-1-[2-chloro-6-(difluoromethoxy)-3-fluorophenyl]ethyl}-1H-pyrrolo[2,3-b]pyridine-1-carboxylate (41.1 mg, 0.0791 mmol), 1-(5,8-dioxaspiro[3.4]oct-2-yl)-5-methyl-4-(4,4,5,5-tetramethyl-1,3,2-dioxaborolan-2-yl)-1H-pyrazole (38.0 mg, 0.119 mmol), Pd(PPh$_3$)$_4$ (4.57 mg, 0.00396 mmol), K$_2$CO$_3$ (32.8 mg, 0.237 mmol) and 4:1 dioxane:H$_2$O (3 mL, 30 mmol) was heated to 95° C. for 1 h. The solution was allowed to cool to rt, and 2 M of HCl in H$_2$O (2 mL, 4 mmol) was added. The mixture was heated at 45° C. overnight. The organic solvent was removed in vacuo, and the material was extracted with DCM and sat. NaHCO$_3$. The organic layer was loaded onto silica gel for column chromatography, eluting with 1-3% MeOH/DCM. The fractions containing the pure product were concentrated in vacuo to afford the title compound as a white solid. MS (ES+): m/z=489.09/491.09 (100/50) [MH+]. HPLC: t_R=4.04 min (polar_5 min, ZQ3).

1-(5,8-Dioxaspiro[3.4]oct-2-yl)-5-methyl-4-(4,4,5,5-tetramethyl-1,3,2-dioxaborolan-2-yl)-1H-pyrazole To a solution of 1-(5,8-dioxaspiro[3.4]oct-2-yl)-4-iodo-5-methyl-1H-pyrazole (50.0 mg, 0.156 mmol) in THF (3 mL, 40 mmol) at was added 2 M isopropylmagnesium chloride in THF (0.23 mL, 0.46 mmol), and the mixture was stirred at rt for 1 h. The reaction was quenched with 2-methoxy-4,4,5,5-tetramethyl-1,3,2-dioxaborolane (0.10 mL, 0.62 mmol) and allowed to stir at rt for 1 h. Sat. NH$_4$Cl was added, and the organic solvent was removed in vacuo. The material was extracted with DCM and water. The organic layer was concentrated in vacuo to afford the title compound as a white solid. The material was used in the next step without further purification.

1-(5,8-Dioxaspiro[3.4]oct-2-yl)-4-iodo-3-methyl-1H-pyrazole and 1-(5,8-Dioxaspiro[3.4]oct-2-yl)-4-iodo-5-methyl-1H-pyrazole

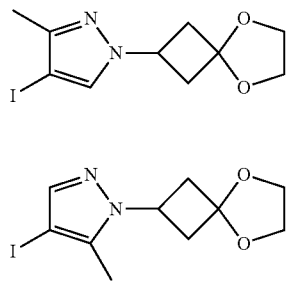

A mixture of 4-iodo-5-methyl-1H-pyrazole (1.401 g, 6.734 mmol), 2-bromo-5,8-dioxaspiro[3.4]octane (1.00 g, 5.18 mmol), sodium hydride (149.2 mg, 6.216 mmol), and DMF (16 mL, 210 mmol) was heated to 90° C. for 2 hours. The material was extracted with EtOAc, and washed with water (3×). The organic layer was purified via column chromatography, eluting with 3-6% EtOAc/hexanes. The fractions containing the separate regioisomers were concentrated in vacuo to afford the title compounds as clear oils. 3-methyl isomer: $^1$H NMR (400 MHz, CD$_3$OD): δ=2.20 (s, 3H), 2.73-2.86 (m, 4H), 3.86-3.97 (m, 4H), 4.61 (quin, J=8.0 Hz, 1H), 7.72 (s, 1H).

2-Bromo-5,8-dioxaspiro[3.4]octane

A mixture of 3-bromocyclobutanone (5.90 g, 39.6 mmol), 1,2-ethanediol (8.6 mL, 158 mmol, 4 eq.) and PPTS (1.90 g, 7.92 mmol) in benzene (40 mL) was heated to reflux using Dean-Stark assembly. After 12 h, the reaction mixture was allowed to cool and washed with water (2×30 mL). The organic phase was dried (Na$_2$SO$_4$) and concentrated. The residue was purified using column chromatography (ethyl acetate/hexanes 1:5) to give the title compound (51% yield starting from 3-oxocyclobutanecarboxylic acid). $^1$H NMR (300 MHz, CDCl$_3$): δ=2.77-2.82 (m, 4H), 2.95-3.00 (m, 4H), 4.19-4.23 (m, 1H).

3-Bromocyclobutanone

A solution of bromine (0.51 mL, 10 mmol) in CCl$_4$ (20 mL) was heated to 70° C. and a mixture of 3-oxocyclobutanecarboxylic acid (1.14 g, 10 mmol) and red mercuric oxide (1.56 g, 7.9 mmol) was added over 30 min. After 1 h, the reaction mixture became colorless. The solids were filtered off and solvent was removed at 30° C. using rotary evaporator (product is volatile, 22° C./0.5 mm). The residue was dissolved in hexanes and filtered through silica and concentrated to give the title compound containing CCl$_4$. It was used directly in the next step. $^1$H NMR (300 MHz, CDCl$_3$): δ=3.44-3.50 (m, 2H), 3.72-3.80 (m, 2H), 4.51-4.55 (m, 1H).

Example 81 cis-3-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclobutanol

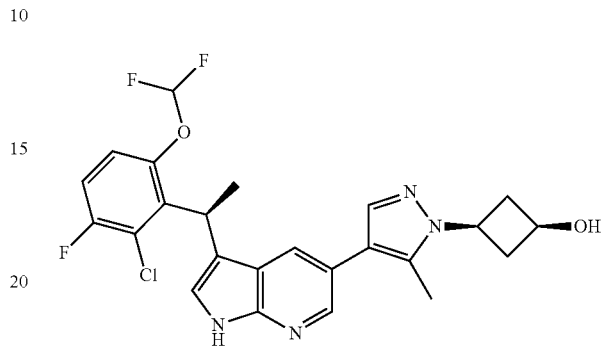

A mixture of 3-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclobutanone (10.0 mg, 0.0204 mmol), sodium borohydride (3.87 mg, 0.102 mmol) and EtOH (1 mL, 20 mmol) was stirred at rt for 30 min. Sat. NH$_4$Cl was added, and the organic solvent was removed in vacuo. The material was extracted with DCM and water. The organic layer was concentrated in vacuo, redissolved in MeOH (0.7 mL) and purified via HPLC. The fractions containing the pure product were concentrated in vacuo to afford the title compound as a white solid. $^1$H NMR (400 MHz, CD$_3$OD): δ=1.84 (d, J=7.1 Hz, 3H), 2.17 (s, 3H), 2.48-2.58 (m, 2H), 2.78-2.87 (m, 2H), 4.07-4.17 (m, 1H), 4.34-4.45 (m, 1H), 5.10 (q, J=7.2 Hz, 1H), 6.42 (br. s., 1H), 7.07-7.15 (m, 1H), 7.15-7.21 (m, 1H), 7.36 (s, 1H), 7.39 (d, J=1.0 Hz, 1H), 7.50 (s, 1H), 8.14 (br. s., 1H). MS (ES+): m/z=491.15/493.15 (100/50) [MH$^+$]. HPLC: t$_R$=1.41 min (polar_3 min, UPLC-ACQUITY).

Example 82 trans-4-[5-Chloro-4-(3-{(1S)-1-[2-chloro-6-(difluoromethoxy)-3-fluorophenyl]ethyl}-1H-pyrrolo[2,3-b]pyridin-5-yl)-1H-pyrazol-1-yl]cyclohexanol

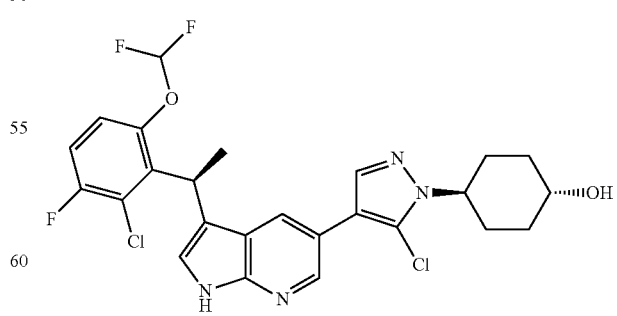

Prepared using the procedure described for Example 69. $^1$H NMR (400 MHz, CD$_3$OD): δ=1.45-1.59 (m, 2H), 1.86 (d, J=7.1 Hz, 3H), 1.95-2.06 (m, 4H), 2.06-2.17 (m, 2H), 3.68 (tt, J=11.0, 4.2 Hz, 1H), 4.34-4.45 (m, 1H), 5.13 (q, J=7.3 Hz, 1H), 6.41 (br. s., 1H), 7.08-7.18 (m, 1H), 7.18-7.24 (m, 1H), 7.42 (d, J=1.3 Hz, 1H), 7.68 (d, J=1.8 Hz, 1H), 7.73 (s, 1H), 8.30 (s, 1H). MS (ES+): m/z=539.13/541.13 (100/50) [MH+]. HPLC: $t_R$=1.48 min (polar_3 min, UPLC-ACQUITY).

Example 83 trans-4-[4-(3-{(1S)-1-[2-Chloro-6-(difluoromethoxy)-3-fluorophenyl]ethyl}-1H-pyrrolo[2,3-b]pyridin-5-yl)-5-(hydroxymethyl)-1H-pyrazol-1-yl]cyclohexanol

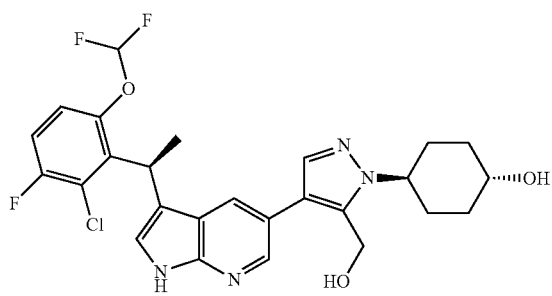 [SMILES: C[C@H](c1c(OC(F)F)ccc(F)c1Cl)c1c[nH]c2ncc(-c3cnn([C@H]4CC[C@H](O)CC4)c3CO)cc12]

Prepared using the procedure described for Example 69. $^1$H NMR (400 MHz, CD$_3$OD): δ=1.45-1.59 (m, 2H), 1.88 (d, J=7.3 Hz, 3H), 1.98-2.14 (m, 6H), 3.70 (tdd, J=11.0, 11.0, 4.3, 4.1 Hz, 1H), 4.36-4.45 (m, 1H), 4.51-4.59 (m, 2H), 5.18 (q, J=1.0 Hz, 1H), 6.61 (t, J=1.0 Hz, 1H), 7.13-7.20 (m, 1H), 7.21-7.27 (m, 1H), 7.56-7.61 (m, 2H), 7.84 (s, 1H), 8.38 (br. s., 1H). MS (ES+): m/z=535.18/537.18 (100/50) [MH+]. HPLC: $t_R$=1.33 min (polar_3 min, UPLC-ACQUITY).

[1-(trans-4-{[tert-Butyl(dimethyl)silyl]oxy}cyclohexyl)-4-(4,4,5,5-tetramethyl-1,3,2-dioxaborolan-2-yl)-1H-pyrazol-5-yl]methanol To a solution of [1-(trans-4-{[tert-butyl(dimethyl)silyl]oxy}cyclohexyl)-4-iodo-1H-pyrazol-5-yl]methanol (40.0 mg, 0.0916 mmol) in THF (2 mL, 20 mmol) at rt was added 1.3 M of isopropylmagnesium chloride in THF (0.28 mL, 0.37 mmol), and the mixture was stirred for 1 h. The reaction was quenched with 2-methoxy-4,4,5,5-tetramethyl-1,3,2-dioxaborolane (0.075 mL, 0.46 mmol), and allowed to stir at rt for 1 h. Sat. NH$_4$Cl was added, and the organic solvent was removed in vacuo. The material was extracted with DCM and water. The organic layer was concentrated in vacuo to afford the title compound as a white solid. The material was used in the next step without further purification. MS (ES+): m/z=437.29 (100) [MH+]. HPLC: $t_R$=1.94 min (polar_3 min, UPLC-ACQUITY).

[1-(Trans-4-{[tert-butyl(dimethyl)silyl]oxy}cyclohexyl)-4-iodo-1H-pyrazol-5-yl]methanol To a solution of 1-(trans-4-{[tert-butyl(dimethyl)silyl]oxy}cyclohexyl)-4-iodo-1H-pyrazole-5-carbaldehyde (50.0 mg, 0.115 mmol) in EtOH (3 mL, 50 mmol) was added sodium borohydride (6.53 mg, 0.173 mmol) at rt, and the mixture was stirred for 10 min. The solution was dry-loaded onto silica gel and purified via column chromatography, eluting with 3-5% EtOH/heptane. The fractions containing the pure product were concentrated in vacuo to afford the title compound as a white solid. MS (ES+): m/z=437.08 (100) [MH+]. HPLC: $t_R$=1.88 min (polar_3 min, UPLC-ACQUITY).

1-(trans-4-{[tert-Butyl(dimethyl)silyl]oxy}cyclohexyl)-4-iodo-1H-pyrazole-5-carbaldehyde A solution of 1-[4-(tert-butyl-dimethylsilanyloxy)-cyclohexyl]-4-iodo-1H-pyrazole (100.0 mg, 0.2461 mmol) in THF (6 mL, 70 mmol) was cooled to -78° C. and added 1.5 M of LDA in cyclohexane (0.213 mL, 0.320 mmol). After stirring for 5 min, DMF (0.1 mL, 1 mmol) was added slowly, and the mixture was stirred at -78° C. for 30 min. Sat. NH$_4$Cl was added to quench, and the organic solvent was removed in vacuo. The material was extracted with DCM and water, and the organic layer was dry-loaded onto silica gel for column chromatography, eluting with 1-3% EtOAc/heptane. The fractions containing the pure product were concentrated in vacuo to afford the title compound as a clear oil. MS (ES+): m/z=435.10 (100) [MH+]. HPLC: $t_R$=2.18 min (polar_3 min, UPLC-ACQUITY).

Example 84 trans-4-[4-(3-{(1S)-1-[2-Chloro-6-(difluoromethoxy)-3-fluorophenyl]ethyl}-1H-pyrrolo[2,3-b]pyridin-5-yl)-5-fluoro-1H-pyrazol-1-yl]cyclohexanol

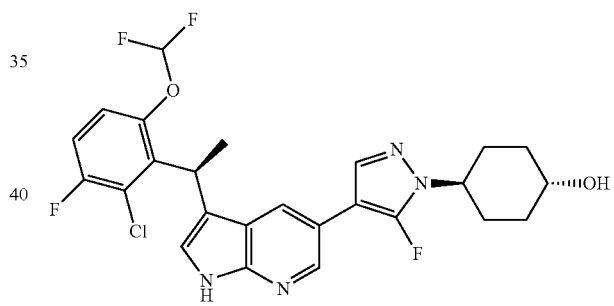

Prepared using the procedure described for Example 69. $^1$H NMR (400 MHz, CD$_3$OD): δ=1.51 (qd, J=11.9, 5.6 Hz, 2H), 1.85 (d, J=7.1 Hz, 3H), 1.93-2.06 (m, 4H), 2.11 (d, J=12.4 Hz, 2H), 3.67 (tt, J=11.0, 4.2 Hz, 1H), 4.24 (tt, J=10.5, 5.4 Hz, 1H), 5.12 (q, J=7.2 Hz, 1H), 6.47 (br. t, J=1.0, 1.0 Hz, 1H), 7.08-7.18 (m, 1H), 7.18-7.25 (m, 1H), 7.40 (d, J=1.0 Hz, 1H), 7.59 (s, 1H), 7.64 (d, J=3.3 Hz, 1H), 8.32 (br. s., 1H). MS (ES+): m/z=523.07/525.06 (100/50) [MH+]. HPLC: $t_R$=3.91 min (polar_5 min, ZQ3).

1-(trans-4-{[tert-Butyl(dimethyl)silyl]oxy}cyclohexyl)-5-fluoro-4-(4,4,5,5-tetramethyl-1,3,2-dioxaborolan-2-yl)-1H-pyrazole To a solution of 1-(trans-4-{[tert-butyl(dimethyl)silyl]oxy}cyclohexyl)-5-fluoro-4-iodo-1H-pyrazole (80.0 mg, 0.188 mmol) in THF (2 mL, 20 mmol) at rt was added 1.3 M of isopropylmagnesium chloride in THF (0.58 mL, 0.75 mmol), and the mixture was stirred for 1 h. The reaction was quenched with 2-methoxy-4,4,5,5-tetramethyl-1,3,2-dioxaborolane (0.15 mL, 0.94 mmol), and allowed to stir at rt for 1 h. Sat. NH$_4$Cl was added, and the organic solvent was removed in vacuo. The material was extracted with DCM and water. The organic layer was dry-loaded onto silica gel and purified via column chromatography, eluting with 2-7% EtOAc/hexanes. The fractions containing the pure product were concentrated in vacuo to afford the title compound as a white solid. MS (ES+): m/z=425.28 (100) [MH$^+$]. HPLC: $t_R$=2.23 min (polar_3 min, UPLC-ACQUITY).

1-(trans-4-{[tert-Butyl(dimethyl)silyl]oxy}cyclohexyl)-5-fluoro-4-iodo-1H-pyrazole A solution of 1-[4-(tert-butyl-dimethylsilanyloxy)-cyclohexyl]-4-iodo-1H-pyrazole (200.0 mg, 0.4922 mmol) in THF (2 mL, 20 mmol) was cooled to −78° C., and 1.5 M of LDA in cyclohexane (0.98 mL, 1.5 mmol) was added. After stirring for 30 min, N-fluoro-N-(phenylsulfonyl)benzenesulfonamide (620.8 mg, 1.969 mmol) was added slowly, and the mixture was stirred at −78° C. for 30 min. Sat. NH$_4$Cl was added to quench, and the organic solvent was removed in vacuo. The material was extracted with DCM and water, and the organic layer was dry-loaded onto silica gel for column chromatography, eluting with 1% EtOAc/heptane. The fractions containing the pure product were concentrated in vacuo to afford the title compound as a clear oil. MS (ES+): m/z=425.10 (100) [MH$^+$]. HPLC: $t_R$=2.22 min (polar_3 min, UPLC-ACQUITY).

Example 85 trans-4-[4-(3-{(1S)-1-[2-Chloro-6-(difluoromethoxy)-3-fluorophenyl]ethyl}-1H-pyrrolo[2,3-b]pyridin-5-yl)-5-($^2$H$_3$)methyl-1H-pyrazol-1-yl]cyclohexanol

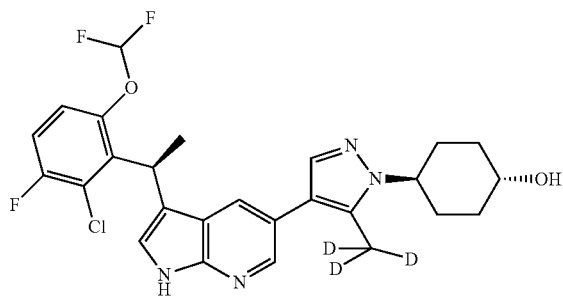 [SMILES: [2H]C([2H])([2H])c1c(-c2cnc3[nH]cc([C@H](C)c4c(OC(F)F)ccc(F)c4Cl)c3c2)cnn1[C@H]1CC[C@H](O)CC1]

Prepared using the procedure described for Example 69. $^1$H NMR (400 MHz, CD$_3$OD): δ=1.44-1.60 (m, 2H), 1.86 (d, J=7.1 Hz, 3H), 1.91-2.15 (m, 6H), 3.65-3.74 (m, 1H), 4.20 (tt, J=11.0, 4.4 Hz, 1H), 5.07-5.18 (m, 1H), 6.46 (br. s., 1H), 7.15 (dd, J=9.0, 4.7 Hz, 1H), 7.21 (t, J=8.7 Hz, 1H), 7.39 (d, J=1.8 Hz, 1H), 7.41 (d, J=1.3 Hz, 1H), 7.48 (s, 1H), 8.14 (d, J=2.0 Hz, 1H). MS (ES+): m/z=522.17/524.18 (100/50) [MH$^+$]. HPLC: $t_R$=1.41 min (polar_3 min, UPLC-ACQUITY).

1-(trans-4-{[tert-Butyl(dimethyl)silyl]oxy}cyclohexyl)-5-($^2$H$_3$)methyl-4-(4,4,5,5-tetramethyl-1,3,2-dioxaborolan-2-yl)-1H-pyrazole To a solution of 1-(trans-4-{[tert-butyl(dimethyl)silyl]oxy}cyclohexyl)-4-iodo-5-($^2$H$_3$)methyl-1H-pyrazole (285.0 mg, 0.6731 mmol) in THF (5 mL, 70 mmol) at rt was added 1.3 M of isopropylmagnesium chloride in THF (2.07 mL, 2.69 mmol), and the mixture was stirred for 2 h. The reaction was quenched with 2-methoxy-4,4,5,5-tetramethyl-1,3,2-dioxaborolane (0.55 mL, 3.4 mmol), and allowed to stir at rt for 3 h. Sat. NH$_4$Cl was added, and the organic solvent was removed in vacuo. The material was extracted with DCM and water. The organic layer was dry-loaded onto silica gel and purified via column chromatography, eluting with 2-7% EtOAc/hexanes. The fractions containing the pure product were concentrated in vacuo to afford the title compound as a white solid. $^1$H NMR (400 MHz, DMSO-d$_6$): δ=0.07 (s, 6H), 0.87 (s, 9H), 1.24 (s, 12H), 1.37-1.52 (m, 2H), 1.73-1.94 (m, 6H), 3.62-3.74 (m, 1H), 4.05-4.15 (m, 1H), 7.45 (s, 1H).

1-(trans-4-{[tert-Butyl(dimethyl)silyl]oxy}cyclohexyl)-4-iodo-5-($^2$H$_3$)methyl-1H-pyrazole A solution of 1-(trans-4-{[tert-Butyl(dimethyl)silyl]oxy}cyclohexyl)-4-iodo-1H-pyrazole (300.0 mg, 0.7382 mmol) in THF (3 mL, 40 mmol) was cooled to −78° C., and 1.5 M of LDA in cyclohexane (2.0 mL, 3.0 mmol) was added. After stirring for 30 min, iodomethane-d$_3$ (0.2 mL, 4 mmol) was added slowly, and the mixture was stirred at −78° C. for 30 min. Sat. NH$_4$Cl was added to quench, and the organic solvent was removed in vacuo. The material was extracted with DCM and water, and the organic layer was dry-loaded onto silica gel for column chromatography, eluting with 1% EtOAc/heptane. The fractions containing the pure product were concentrated in vacuo to afford the title compound as a clear oil. $^1$H NMR (400 MHz, DMSO-d$_6$): δ=0.06 (s, 6H), 0.87 (s, 9H), 1.37-1.52 (m, 2H), 1.74-1.93 (m, 6H), 3.61-3.74 (m, 1H), 4.18 (dt, J=10.3, 5.1 Hz, 1H), 7.42 (s, 1H).

Example 86 cis-4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexanol

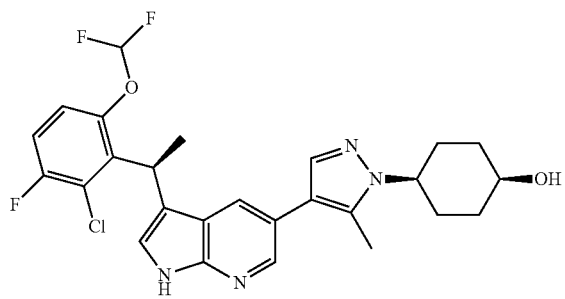 [SMILES: Cc1c(-c2cnc3[nH]cc([C@H](C)c4c(OC(F)F)ccc(F)c4Cl)c3c2)cnn1[C@H]1CC[C@@H](O)CC1]

Prepared using the procedure described for Example 69. $^1$H NMR (400 MHz, CD$_3$OD): δ=1.68-1.81 (m, 4H), 1.86 (d, J=7.3 Hz, 3H), 1.93-2.04 (m, 2H), 2.25 (s, 3H), 2.32-2.46 (m, 2H), 4.00-4.09 (m, 1H), 4.22 (tt, J=11.6, 3.5 Hz, 1H), 5.13 (q, J=7.1 Hz, 1H), 6.45 (br. s., 1H), 7.07-7.18 (m, 1H), 7.18-7.24 (m, 1H), 7.37-7.44 (m, 2H), 7.47 (s, 1H), 8.15 (br. s., 1H). MS (ES+): m/z=519.14/521.14 (100/50) [MH+]. HPLC: $t_R$=1.46 min (polar_3 min, UPLC-ACQUITY).

Example 87

(2R)-3-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]propane-1,2-diol

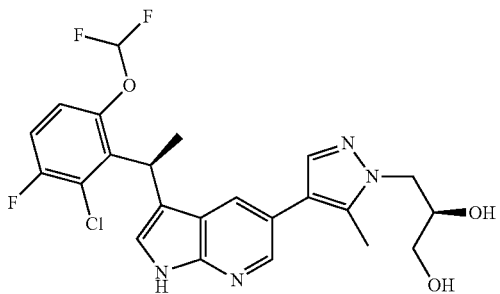 [SMILES: Cc1c(-c2cnc3[nH]cc([C@H](C)c4c(OC(F)F)ccc(F)c4Cl)c3c2)cnn1C[C@@H](O)CO]

A mixture of tert-butyl 5-bromo-3-{(1S)-1-[2-chloro-6-(difluoromethoxy)-3-fluorophenyl]ethyl}-1H-pyrrolo[2,3-b]pyridine-1-carboxylate (50.0 mg, 0.0962 mmol), 1-{[(4R)-2,2-dimethyl-1,3-dioxolan-4-yl]methyl}-5-methyl-4-(4,4,5,5-tetramethyl-1,3,2-dioxaborolan-2-yl)-1H-pyrazole (46.50 mg, 0.1443 mmol), Pd(PPh$_3$)$_4$ (5.558 mg, 0.004810 mmol), K$_2$CO$_3$ (39.89 mg, 0.2886 mmol) and 4:1 dioxane:H$_2$O (2 mL, 20 mmol) was heated to 95° C. for 2 h. The solution was cooled to rt, and 12 M of HCl in H$_2$O (0.08017 mL, 0.9620 mmol) was added. The material was concentrated in vacuo, and extracted with DCM and sat. NaHCO$_3$. The organic layer was dry-loaded onto silica gel and purified via column chromatography, eluting with 3-6% (7N NH$_3$ in MeOH)/DCM. The fractions containing the pure product were concentrated in vacuo, redissolved in MeOH, and 2.0 M of HCl in Et$_2$O (0.4810 mL, 0.9620 mmol) was added at rt. The solution was concentrated in vacuo to afford the title compound as an HCl salt. $^1$H NMR (400 MHz, CD$_3$OD): δ=1.85 (d, J=7.1 Hz, 3H), 2.27 (s, 3H), 3.52-3.63 (m, 2H), 4.00-4.08 (m, 1H), 4.11-4.19 (m, 1H), 4.26 (dd, J=14.1, 4.3 Hz, 1H), 5.12 (q, J=7.2 Hz, 1H), 6.44 (br. s., 1H), 7.14 (dd, J=8.8, 4.5 Hz, 1H), 7.20 (t, J=8.7 Hz, 1H), 7.37-7.43 (m, 2H), 7.52 (s, 1H), 8.16 (d, J=2.0 Hz, 1H). MS (ES+): m/z=495.11/497.11 (100/50) [MH+]. HPLC: $t_R$=1.29 min (polar_3 min, UPLC-ACQUITY).

1-{[(4R)-2,2-Dimethyl-1,3-dioxolan-4-yl]methyl}-5-methyl-4-(4,4,5,5-tetramethyl-1,3,2-dioxaborolan-2-yl)-1H-pyrazole To a solution of 1-{[(4R)-2,2-dimethyl-1,3-dioxolan-4-yl]methyl}-4-iodo-5-methyl-1H-pyrazole (67.0 mg, 0.208 mmol) in THF (2 mL, 20 mmol) at rt was added 1.3 M of isopropylmagnesium chloride in THF (0.64 mL, 0.83 mmol), and the mixture was stirred for 1 h. The reaction was quenched with 2-methoxy-4,4,5,5-tetramethyl-1,3,2-dioxaborolane (0.1704 mL, 1.040 mmol), and allowed to stir at rt for 1 h. Sat. NH$_4$Cl was added, and the organic solvent was removed in vacuo. The material was extracted with DCM and water. The organic layer was concentrated in vacuo to afford the title compound as a clear oil. MS (ES+): m/z=322.21/323.20/324.22 (50/100/50) [MH+]. HPLC: $t_R$=1.49 min (polar_3 min, UPLC-ACQUITY).

1-{[(4R)-2,2-Dimethyl-1,3-dioxolan-4-yl]methyl}-4-iodo-5-methyl-1H-pyrazole

To a solution of 1-{[(4R)-2,2-Dimethyl-1,3-dioxolan-4-yl]methyl}-4-iodo-1H-pyrazole (500 mg, 1.62 mmol) in THF (4 mL, 50 mmol), cooled to −78° C., was added 1.5 M of LDA in cyclohexane (3.25 mL, 4.87 mmol). After stirring for 1 h, methyliodide (1.01 mL, 16.2 mmol) was added slowly, and the mixture was stirred at −78° C. for 1 h. Sat. NH$_4$Cl was added to quench, and the organic solvent was removed in vacuo. The material was extracted with DCM and water, and the organic layer was concentrated in vacuo. The material was purified via column chromatography, eluting with 5-10% EtOAc/hexanes. The fractions containing the pure product were concentrated in vacuo to afford the title compound as a white solid. MS (ES+): m/z=323.06 (100) [MH+]. HPLC: $t_R$=1.20 min (polar_3 min, UPLC-ACQUITY).

1-{[(4R)-2,2-Dimethyl-1,3-dioxolan-4-yl]methyl}-4-iodo-1H-pyrazole

A mixture of 4-iodopyrazole (1.00 g, 5.16 mmol), ((4S)-2,2-dimethyl-1,3-dioxolan-4-yl)methyl 4-methylbenzenesulfonate (1.624 g, 5.671 mmol), Cs$_2$CO$_3$ (2.52 g, 7.73 mmol) and DMF (5 mL, 60 mmol) was heated to 100° C. for 2 h. The solution was extracted with EtOAc, and washed with water (2×). The organic layer was concentrated in vacuo and purified via column chromatography, eluting with 2-10% EtOAc/hexanes. The fractions containing the pure product were concentrated in vacuo to afford the title compound as a white solid. $^1$H NMR (400 MHz, CD$_3$OD): δ=1.34 (d, J=8.8 Hz, 6H), 3.76 (dd, J=8.6, 6.1 Hz, 1H), 4.08 (dd, J=8.6, 6.3 Hz, 1H), 4.23-4.37 (m, 2H), 4.39-4.46 (m, 1H), 7.50-7.55 (m, 1H), 7.77 (s, 1H). MS (ES+): m/z=309.01 (100) [MH+]. HPLC: $t_R$=1.34 min (polar_3 min, UPLC-ACQUITY).

Example 88

4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexanone

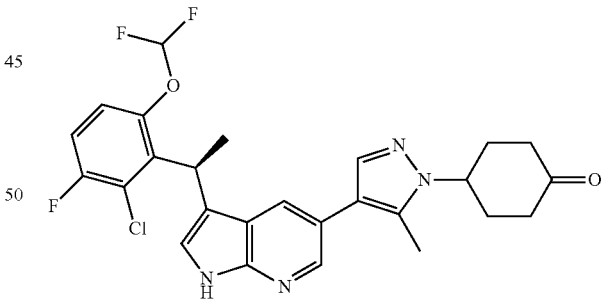

A solution of trans-4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexanol (70.0 mg, 0.135 mmol), Dess-Martin periodinane (85.82 mg, 0.2023 mmol), NaHCO$_3$ (22.66 mg, 0.2698 mmol) and DCM (4 mL, 70 mmol) was stirred at rt for 5 min. The material was extracted with DCM and sat. NaHCO$_3$, and the organic layer was loaded onto silica gel for column chromatography, eluting with 2-4% MeOH/DCM. The fractions containing the pure product were concentrated in vacuo to afford the title compound as a white solid. MS (ES+): m/z=517.11/519.08 (100/50) [MH+]. HPLC: $t_R$=3.99 min (polar_5 min, ZQ3).

Example 89

N-{trans-4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexyl}-N-methylglycine

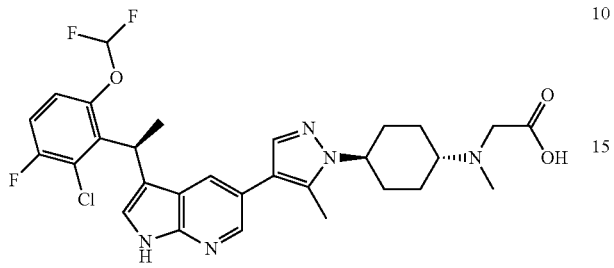

To a mixture of 4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclohexanone (15.0 mg, 0.0290 mmol), sarcosine methyl ester hydrochloride (20.25 mg, 0.1451 mmol), sodium triacetoxyborohydride (12.30 mg, 0.05803 mmol) and 1,2-dichloroethane (4 mL, 50 mmol) was added triethylamine (14.68 mg, 0.1451 mmol), and the reaction was heated to 50° C. overnight. The material was partitioned between DCM and water, and the organic layer was concentrated in vacuo. Lithium hydroxide monohydrate (6.088 mg, 0.1451 mmol) and MeOH (2 mL, 50 mmol) were added, and the mixture was heated to 50° C. for 3 h. The solution was concentrated in vacuo, and the crude product was redissolved in minimal DMF. The solution was purified via HPLC, and the fractions containing the separate cis and trans products were concentrated in vacuo to afford the title compound as white solid. $^1$H NMR (400 MHz, CD$_3$OD): δ=1.75-1.89 (m, 5H), 2.01-2.14 (m, 4H), 2.18-2.23 (m, 2H), 2.23 (s, 3H), 2.90 (s, 3H), 3.40 (tdd, J=12.0, 12.0, 3.1, 2.8 Hz, 1H), 3.65 (br. s., 2H), 4.22-4.34 (m, 1H), 5.06-5.14 (m, 1H), 6.43 (br. s., 1H), 7.12 (dd, J=8.3, 4.3 Hz, 1H), 7.18 (t, J=8.6 Hz, 1H), 7.37 (d, J=1.8 Hz, 1H), 7.40 (d, J=1.3 Hz, 1H), 7.49 (s, 1H), 8.12 (d, J=2.0 Hz, 1H). MS (ES+): m/z=590.14/592.17 (100/50) [MH$^+$]. HPLC: t$_R$=1.01 min (polar_2 min, UPLC-ACQUITY).

Example 90

N-{cis-4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexyl}-N-methylglycine

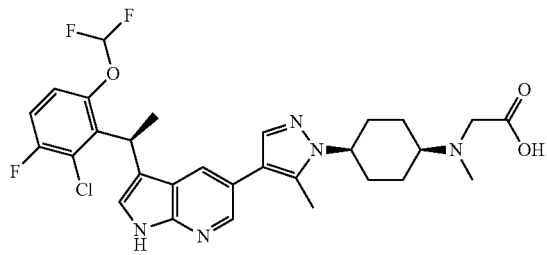 [SMILES: Cc1c(-c2cnc3[nH]cc([C@H](C)c4c(OC(F)F)ccc(F)c4Cl)c3c2)cnn1[C@H]1CC[C@@H](N(C)CC(=O)O)CC1]

Isolated from the reaction described for the previous example. $^1$H NMR (400 MHz, CD$_3$OD): δ=1.83 (d, J=7.3 Hz, 3H), 1.89-2.05 (m, 4H), 2.14-2.24 (m, 5H), 2.35-2.51 (m, 2H), 2.90 (s, 3H), 3.45-3.55 (m, 1H), 3.68 (br. s., 2H), 4.56 (br. s., 1H), 5.10 (q, J=7.0 Hz, 1H), 6.43 (br. s., 1H), 7.12 (dd, J=8.5, 4.7 Hz, 1H), 7.18 (t, J=8.7 Hz, 1H), 7.34-7.38 (m, 1H), 7.38-7.41 (m, 1H), 7.45 (s, 1H), 8.12 (d, J=1.8 Hz, 1H). MS (ES+): m/z=590.16/592.14 (100/50) [MH$^+$]. HPLC: t$_R$=1.06 min (polar_3 min, UPLC-ACQUITY).

Example 91

1-{trans-4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexyl}-L-proline

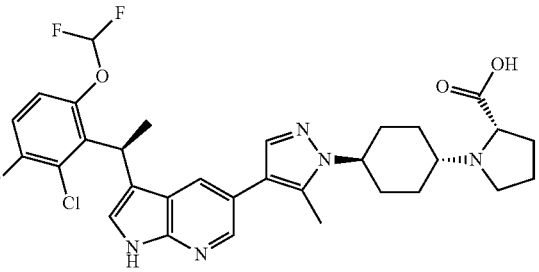

To a mixture of 4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclohexanone (20.0 mg, 0.0387 mmol), H-L-PRO-OME HCl (64.08 mg, 0.3869 mmol), sodium triacetoxyborohydride (32.80 mg, 0.1548 mmol) and 1,2-dichloroethane (5 mL, 70 mmol) was added triethylamine (39.15 mg, 0.3869 mmol), and the reaction was heated to 50° C. overnight. The material was partitioned between DCM and water, and the organic layer was concentrated in vacuo. Lithium hydroxide monohydrate (8.118 mg, 0.1934 mmol) and MeOH (3 mL, 60 mmol) were added, and the mixture was heated to 50° C. for 3 h. The solution was concentrated in vacuo, and the crude product was redissolved in minimal DMF. The solution was purified via HPLC, and the fractions containing the separate cis and trans products were concentrated in vacuo to afford the title compound as white solid. $^1$H NMR (400 MHz, CD$_3$OD): δ=1.74-1.83 (m, 2H), 1.84 (d, J=7.3 Hz, 3H), 1.91 (ddd, J=17.1, 6.6, 3.8 Hz, 1H), 1.97-2.14 (m, 5H), 2.18-2.27 (m, 5H), 2.27-2.45 (m, 2H), 3.21-3.29 (m, 1H), 3.33-3.42 (m, 1H), 3.67-3.79 (m, 1H), 4.08 (dd, J=9.7, 4.2 Hz, 1H), 4.22-4.32 (m, 1H), 5.11 (q, J=7.2 Hz, 1H), 6.44 (br. s., 1H), 7.12 (dd, J=8.5, 4.2 Hz, 1H), 7.19 (t, J=8.6 Hz, 1H), 7.37 (d, J=1.8 Hz, 1H), 7.40 (d, J=1.0 Hz, 1H), 7.49 (s, 1H), 8.13 (br. s., 1H). MS (ES+): m/z=616.22/618.20 (100/50) [MH$^+$]. HPLC: t$_R$=1.06 min (polar_2 min, UPLC-ACQUITY).

Example 92

1-{cis-4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexyl}-L-proline

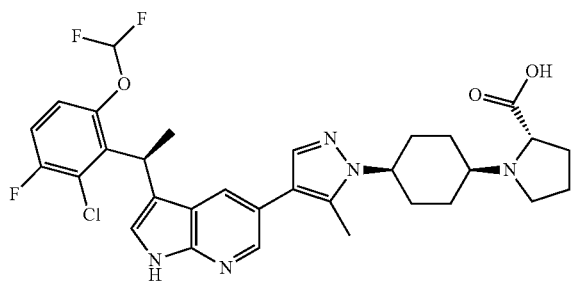 [SMILES: Cc1c(-c2cnc3[nH]cc([C@H](C)c4c(OC(F)F)ccc(F)c4Cl)c3c2)cnn1[C@H]1CC[C@@H](N2CCC[C@H]2C(=O)O)CC1]

Isolated from the reaction described for the previous example. $^1$H NMR (400 MHz, CD$_3$OD): δ=1.84 (d, J=7.3 Hz, 3H), 1.91-1.99 (m, 4H), 2.00-2.14 (m, 2H), 2.21 (s, 3H), 2.22-2.33 (m, 4H), 2.33-2.47 (m, 2H), 3.19-3.28 (m, 1H), 3.47 (dd, J=5.6, 3.5 Hz, 1H), 3.71-3.82 (m, 1H), 4.06 (dd, J=9.9, 4.0 Hz, 1H), 4.44-4.54 (m, 1H), 5.10 (q, J=7.2 Hz, 1H), 6.43 (br. s., 1H), 7.12 (dd, J=8.7, 4.2 Hz, 1H), 7.19 (t, J=8.7 Hz, 1H), 7.37 (d, J=1.8 Hz, 1H), 7.39 (d, J=1.3 Hz, 1H), 7.45 (s, 1H), 8.12 (s, 1H). MS (ES+): m/z=616.22/618.21 (100/50) [MH$^+$]. HPLC: $t_R$=1.11 min (polar_3 min, UPLC-ACQUITY).

Example 93 trans-4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexanamine

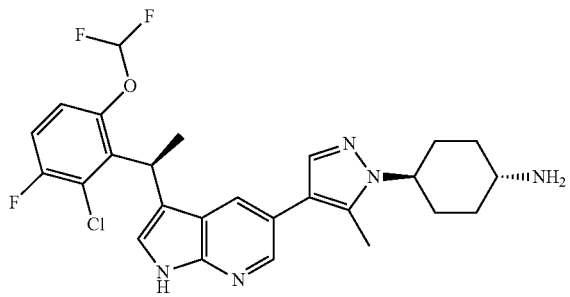 [SMILES: Cc1c(-c2cnc3[nH]cc([C@H](C)c4c(OC(F)F)ccc(F)c4Cl)c3c2)cnn1[C@H]1CC[C@H](N)CC1]

Prepared using the procedure described for Example 69. $^1$H NMR (400 MHz, CD$_3$OD): δ=1.59-1.73 (m, 2H), 1.84 (d, J=7.1 Hz, 3H), 2.03-2.12 (m, 4H), 2.14-2.22 (m, 2H), 2.24 (s, 3H), 3.18-3.26 (m, 1H), 4.19-4.30 (m, 1H), 5.11 (q, J=7.4 Hz, 1H), 6.44 (br. s., 1H), 7.08-7.16 (m, 1H), 7.16-7.21 (m, 1H), 7.38 (d, J=2.0 Hz, 1H), 7.40 (d, J=1.3 Hz, 1H), 7.50 (s, 1H), 8.12 (d, J=2.0 Hz, 1H). MS (ES+): m/z=518.18/520.19 (100/50) [MH$^+$]. HPLC: $t_R$=1.14 min (polar_3 min, UPLC-ACQUITY).

trans-4-[5-Methyl-4-(4,4,5,5-tetramethyl-1,3,2-dioxaborolan-2-yl)-1H-pyrazol-1-yl]cyclohexanamine To a solution of trans-4-(4-iodo-5-methyl-1H-pyrazol-1-yl)cyclohexanamine (170.0 mg, 0.5571 mmol) in THF (4 mL, 60 mmol) at rt was added 1.3 M of isopropylmagnesium chloride in THF (1.7 mL, 2.2 mmol), and the mixture was stirred for 1 h. The reaction was quenched with 2-methoxy-4,4,5,5-tetramethyl-1,3,2-dioxaborolane (0.46 mL, 2.8 mmol), and allowed to stir at rt for 2 h. Sat. NH$_4$Cl was added, and the organic solvent was removed in vacuo. The material was extracted with DCM and water. The organic layer was concentrated in vacuo to afford the title compound, and was used without further purification.

Examples 94 and 95 trans-4-{-4-[3-{(1S)-1-[2-Chloro-6-(difluoromethoxy)-3-fluorophenyl]ethyl}(2-$^2$H)-1H-pyrrolo[2,3-b]pyridin-5-yl]-5-methyl-1H-pyrazol-1-yl}cyclohexanol and trans-4-{-4-[3-{(1R)-1-[2-Chloro-6-(difluoromethoxy)-3-fluorophenyl]-ethyl}(2-$^2$H)-1H-pyrrolo[2,3-b]pyridin-5-yl]-5-methyl-1H-pyrazol-1-yl}cyclohexanol

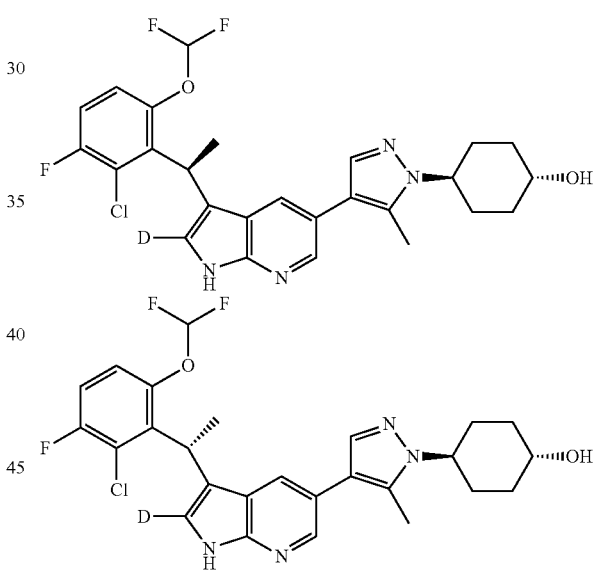

A mixture of 5-bromo-3-{1-[2-chloro-6-(difluoromethoxy)-3-fluorophenyl]ethyl}(2-$^2$H)-1H-pyrrolo[2,3-b]pyridine (150.0 mg, 0.3566 mmol), 1-(trans-4-{[tert-butyl(dimethyl)silyl]-oxy}cyclohexyl)-5-methyl-4-(4,4,5,5-tetramethyl-1,3,2-dioxaborolan-2-yl)-1H-pyrazole (224.9 mg, 0.5349 mmol), Pd(PPh$_3$)$_4$ (20.60 mg, 0.01783 mmol), K$_2$CO$_3$ (148 mg, 1.07 mmol) and 4:1 dioxane:H$_2$O (6 mL, 60 mmol) was heated to 95° C. for 1 h. The solution was cooled to rt, 12 M of HCl in H$_2$O (0.2 mL, 3 mmol) was added, and the solution was heated to 45° C. for 1 h. The solution cooled to rt, basified with sat. K$_2$CO$_3$, and the organic solvent was removed in vacuo. The material was extracted with DCM and sat. NaHCO$_3$, and the organic layer was purified via column chromatography, eluting with 1-3% (7N NH$_3$ in MeOH)/DCM. The fractions containing the products were concentrated in vacuo, redissolved in minimal MeOH, and separated via SFC using a column with chiral stationary phase to afford the title compounds as white solids. The enantiomers were assigned based on comparison of the retention times with those of the undeuterated analogs.

Example 94 (S)

$^1$H NMR (400 MHz, CD$_3$OD): δ=1.43-1.58 (m, 2H), 1.83 (d, J=7.3 Hz, 3H), 1.90-2.11 (m, 6H), 2.22 (s, 3H), 3.67 (tt, J=11.0, 4.2 Hz, 1H), 4.12-4.23 (m, 1H), 5.10 (q, J=7.1 Hz, 1H), 6.43 (br. s., 1H), 7.05-7.16 (m, 1H), 7.16-7.21 (m, 1H), 7.37 (d, J=1.5 Hz, 1H), 7.47 (s, 1H), 8.12 (d, J=2.0 Hz, 1H). MS (ES+): m/z=520.14/522.14 (100/50) [MH$^+$]. HPLC: t$_R$=1.37 min (polar_3 min, UPLC-ACQUITY). Analytical SFC (ChiralPak IA 4.6×100 mm I.D., solvent 90:10 scCO$_2$/methanol (0.2% isopropylamine) isocratic, flow rate 4.0 mL/min, UV detection at 254 nm): t$_R$=14.7 min.

Example 95 (R)

$^1$H NMR (400 MHz, CD$_3$OD): δ=1.42-1.59 (m, 2H), 1.84 (d, J=7.1 Hz, 3H), 1.90-2.14 (m, 6H), 2.22 (s, 3H), 3.67 (tdd, J=10.9, 10.9, 4.3, 4.2 Hz, 1H), 4.12-4.24 (m, 1H), 5.10 (q, J=7.1 Hz, 1H), 6.45 (br. s., 1H), 7.07-7.16 (m, 1H), 7.16-7.22 (m, 1H), 7.37 (s, 1H), 7.46 (s, 1H), 8.12 (d, J=1.8 Hz, 1H). MS (ES+): m/z=520.14/522.14 (100/50) [MH$^+$]. HPLC: t$_R$=1.37 min (polar_3 min, UPLC-ACQUITY). Analytical SFC (ChiralPak IA 4.6×100 mm I.D., solvent 90:10 scCO$_2$/methanol (0.2% isopropylamine) isocratic, flow rate 4.0 mL/min, UV detection at 254 nm): t$_R$=12.0 min.

5-Bromo-3-{1-[2-chloro-6-(difluoromethoxy)-3-fluorophenyl]ethyl}(2-$^2$H)-1H-pyrrolo[2,3-b]pyridine To a solution of the mixture of [5-bromo(2-$^2$H)-1H-pyrrolo[2,3-b]pyridin-3-yl][2-chloro-6-(difluoromethoxy)-3-fluorophenyl]methanol and 5-bromo-3-{[2-chloro-6-(difluoromethoxy)-3-fluorophenyl](methoxy)methyl}(2-$^2$H)-1H-pyrrolo[2,3-b]pyridine (0.740 g, 1.7 mmol) in THF (5 mL) at −78° C. was added BF$_3$·OEt$_2$ (1.7 mL, 13.6 mmol), and the mixture was stirred for 30 min. A 2.0 M solution of dimethyl zinc in toluene (6.8 mL, 13.6 mmol) was added slowly. The reaction mixture was stirred at −78° C. for 1 h, slowly warmed to RT over 2 h, and then heated at 50° C. for 16 h. The mixture was then cooled to −78° C., aqueous saturated ammonium chloride solution (20 mL) was added, and warmed to RT. The aqueous layer was extracted with ethyl acetate (3×30 mL). The combined organic extracts were washed with water (40 mL), dried over sodium sulfate, filtered, and concentrated under reduced pressure. The residue was purified by column chromatography using 5 to 20% ethyl acetate in hexanes to give the title compound (0.410 g, 57%). $^1$H NMR (CDCl$_3$, 300 MHz): □ δ=1.79 (d, J=7.0 Hz, 3H), 5.01 (q, J=7.0 Hz, 1H), 5.94 (t, J=75 Hz, 1H), 7.00-7.10 (m, 2H), 7.61 (d, J=1.8 Hz, 1H), 8.28 (d, J=2.1 Hz, 1H), 9.18 (brs, 1H).

[5-Bromo(2-$^2$H)-1H-pyrrolo[2,3-b]pyridin-3-yl][2-chloro-6-(difluoromethoxy)-3-fluorophenyl]methanol and 5-Bromo-3-{[2-chloro-6-(difluoromethoxy)-3-fluorophenyl]-(methoxy)methyl}(2-$^2$H)-1H-pyrrolo[2,3-b]pyridine A mixture of 5-bromo(2,3-$^2$H$_2$)-1H-pyrrolo[2,3-b]pyridine (0.532 g, 2.67 mmol), 2-chloro-6-(difluoromethoxy)-3-fluorobenzaldehyde (0.622 g, 2.8 mmol) and KOH (0.209 g, 3.7 mmol) in methanol (20 mL) was stirred at 55° C. for 24 h in a sealed tube. The reaction mixture was quenched with water and extracted with ethyl acetate (2×30 mL). The organic layers were dried over sodium sulfate, filtered, and concentrated under reduced pressure to give a ≈1:1 mixture of the title compounds that was used as such in the next reaction. $^1$H NMR (CDCl$_3$, 300 MHz): δ=3.40 (s, 3H), 5.96 (t, J=75 Hz, 2H), 7.00-7.20 (m, 4H), 7.62 (d, J=1.8 Hz, 1H), 7.75 (d, J=1.8 Hz, 1H), 8.24 (d, J=2.1 Hz, 1H), 8.35 (d, J=2.1 Hz, 1H), 8.90 (brs, 1H), 8.98 (brs, 1H).

5-Bromo-1-(phenylsulfonyl)(2,3-$^2$H$_2$)-1H-pyrrolo[2,3-b]pyridine and 5-Bromo(2,3-$^2$H$_2$)-1H-pyrrolo[2,3-b]pyridine To a solution of 5-bromo-1-(phenylsulfonyl)-2-(trimethylsilyl)-1H-pyrrolo[2,3-b]pyridine (2.0 g, 4.89 mmol) in dioxane (20 mL) was added 20% DCl in D$_2$O (20 mL), and the mixture was heated at 85° C. for 72 h. The reaction mixture was diluted with water (20 mL), neutralized with a saturated solution of NaHCO$_3$, and extracted with ethyl acetate (3×40 mL). The combined organic layers were dried over sodium sulfate, filtered, and concentrated under reduced pressure to give a residue that was purified by column chromatography on silica gel eluting with 10% ethyl acetate in hexanes to give 5-bromo(2,3-$^2$H$_2$)-1H-pyrrolo[2,3-b]pyridine (0.090 g, 9%) $^1$H NMR (CDCl$_3$, 300 MHz): δ=8.04 (d, J=1.8 Hz, 1H), 8.18 (d, J=1.8 Hz, 1H), 9.87 (brs, 1H). One also isolated 5-bromo-1-(phenylsulfonyl)(2,3-$^2$H$_2$)-1H-pyrrolo[2,3-b]pyridine (0.25 g, 15%). $^1$H NMR (CDCl$_3$, 300 MHz): δ=7.24-7.60 (m, 3H), 7.94 (d, J=1.8 Hz, 1H), 8.20 (d, J=6.8 Hz, 2H), 8.42 (d, J=1.8 Hz, 1H).

5-Bromo-1-(phenylsulfonyl)-2-(trimethylsilyl)-1H-pyrrolo[2,3-b]pyridine

To a well stirred solution of 5-bromo-1-(phenylsulfonyl)-1H-pyrrolo[2,3-b]pyridine (6.0 g, 17.8 mmol) in dry THF (60 mL) was added LDA (2M in THF; 16.0 mL, 32 mmol) at −78° C. slowly over 15 min. The reaction mixture was stirred at −70° C. for 1 h and then cooled back to −78° C. Chlorotrimethylsilane (4.1 mL, 32 mmol) was added slowly, and the reaction mixture was allowed to warm to ambient temperature over 4 h (TLC monitoring: 20% ethyl acetate in hexanes). Solvent was removed under reduced pressure keeping temperature below 40° C. to give a residue. It was extracted with ethyl acetate (2×50 mL) and washed with water (40 mL), followed by brine (10 mL) and dried over sodium sulfate. The solvent was removed under reduced pressure to yield a brown solid which was purified by column chromatography using 10% ethyl acetate in hexanes to yield the title compound as a white solid (4.8 g, 66%). $^1$H NMR (CDCl$_3$, 300 MHz): δ=0.51 (s, 9H), 6.72 (s, 1H), 7.47-4.59 (m, 3H), 7.91 (d, J=2.1 Hz, 1H), 8.09-8.12 (m, 2H), 8.37 (d, J=2.1 Hz, 1H).

5-Bromo-1-(phenylsulfonyl)-1H-pyrrolo[2,3-b]pyridine

To a well stirred solution of 5-bromo-1H-pyrrolo[2,3-b]pyridine (10.0 g, 50.7 mmol) in dry THF (100 mL) was added NaH (60% oil suspension; 3.0 g, 75 mmol) at 0° C. and stirred for 30 min. Phenylsulfonyl chloride (10.7 g, 60 mmol) was added slowly and the mixture was stirred at ambient temperature for 16 h (TLC monitoring: 60% ethyl acetate in hexanes). Solvent was removed under reduced pressure, water (25 mL) was added to the residue, and the mixture was extracted with dichloromethane (3×100 mL). The combined organic layers were dried over sodium sulfate, filtered, and concentrated in vacuo. The residue thus obtained was crystallized from dichloromethane to yield the title compound (13.0 g, 76%). ¹H NMR (CDCl₃, 300 MHz): δ=6.55 (d, J=4.2 Hz, 1H), 7.46-7.62 (m, 3H), 7.74 (d, J=4.0 Hz, 1H), 7.97 (d, J=2.1 Hz, 1H), 8.15-8.18 (m, 2H), 8.44 (d, J=2.1 Hz, 1H).

Example 96

3-{(1S)-1-[2-Chloro-6-(difluoromethoxy)-3-fluorophenyl]ethyl}-5-[5-methyl-1-(piperidin-4-yl)-1H-pyrazol-4-yl]-1H-pyrrolo[2,3-b]pyridine

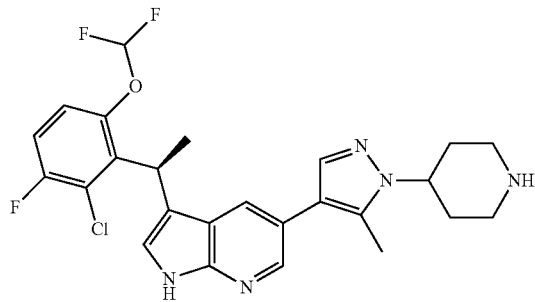 [SMILES: Cc1c(-c2cnc3[nH]cc([C@H](C)c4c(OC(F)F)ccc(F)c4Cl)c3c2)cnn1C1CCNCC1]

A mixture of tert-butyl 5-bromo-3-{(1S)-1-[2-chloro-6-(difluoromethoxy)-3-fluorophenyl]ethyl}-1H-pyrrolo[2,3-b]pyridine-1-carboxylate (60.0 mg, 0.115 mmol), tert-butyl 4-[5-methyl-4-(4,4,5,5-tetramethyl-1,3,2-dioxaborolan-2-yl)-1H-pyrazol-1-yl]piperidine-1-carboxylate (58.73 mg, 0.1501 mmol), Pd(PPh₃)₄ (6.670 mg, 0.005772 mmol), potassium fluoride (20.12 mg, 0.3463 mmol) and 4:1 dioxane:H₂O (3 mL, 30 mmol) was heated in a microwave reactor at 100° C. for 30 min. 12 M of HCl in H₂O (0.19 mL, 2.3 mmol) was added, and the solution was heated to 30° C. overnight. The organic solvent was removed in vacuo, and the material was extracted with DCM and sat. NaHCO₃. The organic layer was concentrated in vacuo and purified via column chromatography, eluting with 3-8% (7N NH₃ in MeOH)/DCM. The fractions containing the pure product were concentrated in vacuo to afford the title compound as white solid. ¹H NMR (400 MHz, CD₃OD): δ=1.84 (d, J=7.3 Hz, 3H), 1.87-1.96 (m, 2H), 2.00-2.12 (m, 2H), 2.23 (s, 3H), 2.72-2.82 (m, 2H), 3.15-3.23 (m, 2H), 4.31 (tt, J=11.6, 3.9 Hz, 1H), 5.11 (q, J=7.3 Hz, 1H), 6.43 (br. s., 1H), 7.12 (dd, J=9.0, 4.7 Hz, 1H), 7.18 (t, J=8.7 Hz, 1H), 7.38 (d, J=1.8 Hz, 1H), 7.39 (d, J=1.3 Hz, 1H), 7.48 (s, 1H), 8.13 (d, J=2.0 Hz, 1H). MS (ES+): m/z=504.15/506.16 (100/50) [MH⁺]. HPLC: t$_R$=1.15 min (polar_3 min, UPLC-ACQUITY).

tert-Butyl 4-[5-methyl-4-(4,4,5,5-tetramethyl-1,3,2-dioxaborolan-2-yl)-1H-pyrazol-1-yl]piperidine-1-carboxylate To a solution of tert-butyl 4-(4-iodo-5-methyl-1H-pyrazol-1-yl)piperidine-1-carboxylate (700.0 mg, 1.789 mmol) in THF (20 mL, 300 mmol) at rt was added 1.3 M of isopropylmagnesium chloride in THF (5.5 mL, 7.2 mmol), and the mixture was stirred for 1 h. The reaction was quenched with 2-methoxy-4,4,5,5-tetramethyl-1,3,2-dioxaborolane (1.5 mL, 8.9 mmol), and allowed to stir at rt for 2 h. Water was added, and the organic solvent was removed in vacuo. The material was extracted with DCM and water. The organic layer was dry-loaded onto silica gel for column chromatography, eluting with 10% EtOAc/heptane. The fractions containing the pure product were concentrated in vacuo to afford the title compound as a white solid. ¹H NMR (400 MHz, CD₃OD): δ=1.30 (s, 12H), 1.48 (s, 9H), 1.84 (d, J=10.4 Hz, 2H), 1.99 (dtd, J=12.6, 12.3, 12.3, 4.5 Hz, 2H), 2.47 (s, 3H), 2.94 (br. s., 2H), 4.21 (d, J=13.6 Hz, 2H), 4.30-4.42 (m, 1H), 7.57 (s, 1H). MS (ES+): m/z=391.26/392.26/393.27 (50/100/50) [MH⁺]. HPLC: t$_R$=1.70 min (polar_3 min, UPLC-ACQUITY).

Example 97

1-{4-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]piperidin-1-yl}ethanone

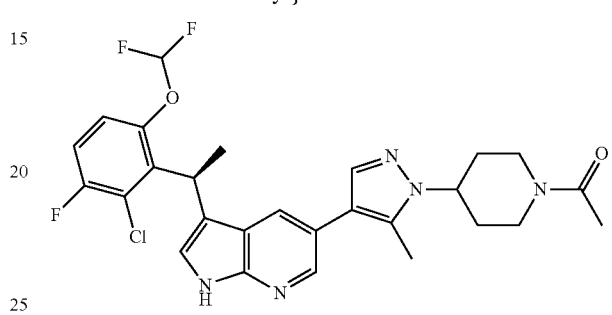

A mixture of 3-{(1S)-1-[2-chloro-6-(difluoromethoxy)-3-fluorophenyl]ethyl}-5-[5-methyl-1-(piperidin-4-yl)-1H-pyrazol-4-yl]-1H-pyrrolo[2,3-b]pyridine (40.0 mg, 0.0794 mmol), acetic acid (23.8 mg, 0.397 mmol), TBTU (51.0 mg, 0.159 mmol), triethylamine (40.2 mg, 0.397 mmol) and DCM (4 mL, 60 mmol) was stirred at rt for 10 min. The solution was extracted with EtOAc, washed with 1 M HCl, and then sat. NaHCO₃. The organic layer was concentrated in vacuo, loaded onto silica gel and purified via column chromatography. The product was eluted with 2-3% (7N NH₃ in MeOH)/DCM, and the fractions containing the pure product were concentrated in vacuo to afford the title compound as a white solid. ¹H NMR (400 MHz, CD₃OD): δ=1.84 (d, J=7.3 Hz, 3H), 1.93-2.04 (m, 3H), 2.12 (dd, J=15.4, 2.5 Hz, 1H), 2.16 (s, 3H), 2.26 (s, 3H), 2.76-2.88 (m, 1H), 3.32-3.35 (m, 1H), 4.08 (dd, J=14.0, 1.9 Hz, 1H), 4.43-4.54 (m, 1H), 4.64-4.73 (m, 1H), 5.11 (q, J=7.0 Hz, 1H), 6.43 (br. s., 1H), 7.12 (dd, J=8.8, 4.5 Hz, 1H), 7.19 (t, J=8.7 Hz, 1H), 7.38 (d, J=1.8 Hz, 1H), 7.39 (d, J=1.3 Hz, 1H), 7.48 (s, 1H), 8.13 (d, J=2.0 Hz, 1H). MS (ES+): m/z=546.17/548.18 (100/50) [MH⁺]. HPLC: t$_R$=1.43 min (polar_3 min, UPLC-ACQUITY).

Example 98 trans-4-[4-(3-{(1R)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclohexanol

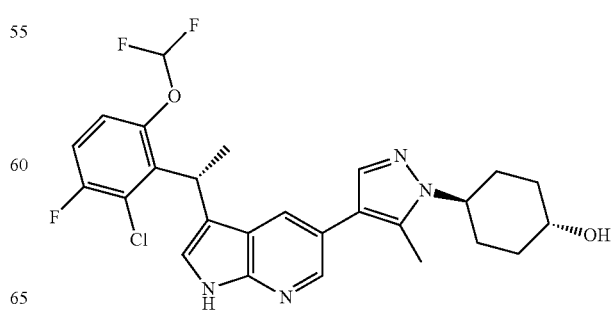

Prepared using the procedure described for Example 69. ¹H NMR (400 MHz, CD₃OD): δ=1.44-1.57 (m, 2H), 1.84 (d, J=7.1 Hz, 3H), 1.91-2.14 (m, 6H), 2.22 (s, 3H), 3.67 (tt, J=11.0, 4.2 Hz, 1H), 4.12-4.24 (m, 1H), 5.11 (q, J=7.5 Hz, 1H), 6.44 (br. s., 1H), 7.12 (dd, J=8.7, 4.7 Hz, 1H), 7.19 (t, J=8.7 Hz, 1H), 7.33-7.41 (m, 2H), 7.46 (s, 1H), 8.12 (d, J=1.8 Hz, 1H). MS (ES+): m/z=519.12/521.13 (100/50) [MH⁺]. HPLC: $t_R$=1.38 min (polar_3 min, UPLC-ACQUITY).

Example 99 trans-4-(4-{3-[(1S)-1-(2-chloro-3-fluoro-6-methoxyphenyl)ethyl]-1H-pyrrolo[2,3-b]pyridin-5-yl}-3-methoxy-1H-pyrazol-1-yl)cyclohexanol

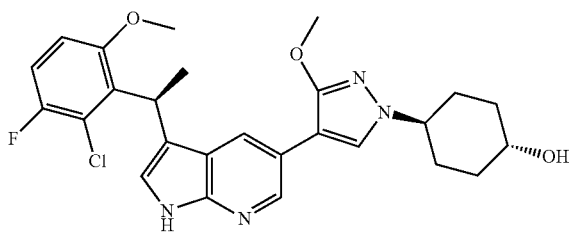 [SMILES: COc1ccc(F)c(Cl)c1[C@@H](C)c1c[nH]c2ncc(-c3cn([C@H]4CC[C@H](O)CC4)nc3OC)cc12]

A solution of 1-(trans-4-{[tert-butyl(dimethyl)silyl]oxy}cyclohexyl)-4-iodo-3-methoxy-1H-pyrazole (0.088 g, 0.20 mmol), 3-[(S)-1-(2-chloro-3-fluoro-6-methoxyphenyl)ethyl]-5-(4,4,5,5-tetramethyl-[1,3,2]dioxaborolan-2-yl)-1H-pyrrolo[2,3-b]pyridine (0.0699 g, 0.162 mmol), potassium carbonate (0.0673 g, 0.487 mmol), potassium fluoride (0.00943 g, 0.162 mmol) in previously degassed dioxane/H₂O (5:1) (4.00 mL) was charged with Pd(PPh₃)₄ (0.00937 g, 0.00811 mmol) and was evacuated and charged with N₂ (3×) and heated under microwave conditions [Biotage, 100° C., 40 min, high absorption]. The reaction mixture was charged with an additional amount of Pd(PPh₃)₄ (0.00938 g, 0.00812 mmol) and 1-(trans-4-{[tert-butyl(dimethyl)silyl]oxy}cyclohexyl)-4-iodo-3-methoxy-1H-pyrazole (0.0354 g, 0.0812 mmol) evacuated and charged with N₂ gas (3×) and heated under microwave conditions [Biotage, 100° C., 30 min, high absorption]. The reaction mixture was charged with 1,1'-bis(diphenylphosphino)ferrocenepalladium (II) dichloride.dichloromethane (0.00663 g, 0.00812 mmol) and evacuated and charged with N₂ and heated under microwave conditions [Biotage, 100° C., 30 min, high absorption]. The reaction was stopped and charged with 4 M of HCl in 1,4-dioxane (0.500 mL) and heated under microwave conditions [Biotage, 60° C., 15 min, high absorption]. The reaction mixture was partitioned between CHCl₃ and sat. NaHCO₃ and separated. The aqueous was re-extracted with CHCl₃ (3×) and the combined organic fractions were washed with brine (1×), dried over Na₂SO₄, filtered and concentrated in vacuo resulting in a crude dark brown oil. This was purified by chromatography on silica gel [ISCO Combiflash, 12 g gold cartridge, eluting with 2% MeOH in DCM→10% MeOH in DCM] resulting in the title compound as a yellow solid. ¹H NMR (400 MHz, CD₃OD): δ=1.42-1.54 (m, 2H), 1.80 (d, J=7.3 Hz, 3H), 1.83-1.94 (m, 1H), 2.05-2.18 (m, 3H), 3.59-3.71 (m, 3H), 3.94 (s, 2H), 3.95-4.04 (m, 1H), 5.09 (q, J=7.0 Hz, 1H), 6.89 (dd, J=4.3, 8.8 Hz, 1H), 7.11 (dd, J=8.8, 8.8 Hz, 1H), 7.28 (d, J=1.3 Hz, 1H), 7.74 (s, 1H), 7.85 (s, 1H), 8.29 (d, J=1.8 Hz, 1H). MS (ES+): m/z 499.18 (75), 501.14 (25) [MH⁺]. HPLC: $t_R$=2.56 min (vvnonpolar_5 min, ZQ3).

Example 100 trans-4-[4-(3-{(1S)-1-[2-chloro-6-(difluoromethoxy)-3-fluorophenyl]ethyl}-1H-pyrrolo[2,3-b]pyridin-5-yl)-3-methoxy-1H-pyrazol-1-yl]cyclohexanol

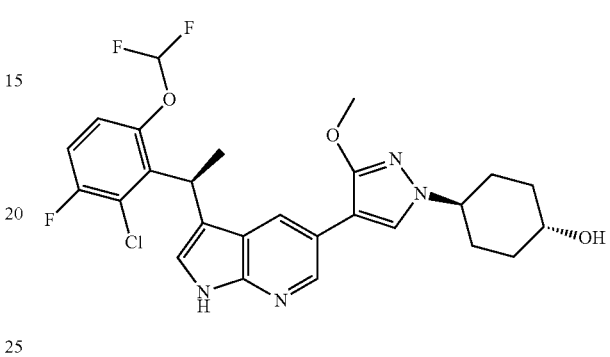

A solution of 1-(trans-4-{[tert-butyl(dimethyl)silyl]oxy}cyclohexyl)-3-methoxy-4-(4,4,5,5-tetramethyl-1,3,2-dioxaborolan-2-yl)-1H-pyrazole (0.0305 g, 0.0698 mmol), tert-butyl 5-bromo-3-{(1S)-1-[2-chloro-6-(difluoromethoxy)-3-fluorophenyl]ethyl}-1H-pyrrolo[2,3-b]pyridine-1-carboxylate (0.0330 g, 0.0635 mmol), potassium carbonate (0.0263 g, 0.190 mmol), and 1,1'-bis(diphenylphosphino)ferrocenepalladium (II) dichloride.dichloromethane (5.18 mg, 0.00635 mmol) in previously degassed dioxane/H₂O (5:1)(2.03 mL) was evacuated and charged with N₂ (3×) and heated to 100° C. for 1 h. The reaction mixture was charged with an additional amount 1-(trans-4-{[tert-butyl(dimethyl)silyl]oxy}cyclohexyl)-3-methoxy-4-(4,4,5,5-tetramethyl-1,3,2-dioxaborolan-2-yl)-1H-pyrazole (0.00800 g, 0.0183 mmol) and 1,1'-bis(diphenylphosphino)ferrocenepalladium (II) dichloride.dichloromethane (5.18 mg, 0.00634 mmol) and evacuated and charged with N₂ gas (3×) and heated 100° C. for an additional 1 h. The reaction was charged with 4 M of HCl in 1,4-dioxane (0.500 mL) and heated to 50° C. for 45 min. The reaction mixture was partitioned between CHCl₃ and sat. NaHCO₃ and separated. The aqueous was re-extracted with CHCl₃/MeOH (4×) and the combined organic fractions were dried over Na₂SO₄, filtered, and concentrated in vacuo resulting in a crude brown oil. The crude material was further purified by chromatography on silica gel [ISCO Combiflash, 4 g gold cartridge, eluting with 100% DCM→8% MeOH in DCM] resulting in the title compound as an orange solid. ¹H NMR (400 MHz, CD₃OD): δ=1.40-1.53 (m, 2H), 1.79-1.92 (m, 5H), 2.02-2.15 (m, 4H), 3.60-3.70 (m, 1H), 3.89-4.01 (m, 4H), 5.09 (q, J=7.2 Hz, 1H), 7.11 (br. s., 1H), 7.17-7.24 (m, 1H), 7.32 (d, J=1.3 Hz, 1H), 7.74 (s, 1H), 7.80 (d, J=1.8 Hz, 1H), 8.30 (d, J=2.0 Hz, 1H). MS (ES+): m/z 535.05 (75), 537.02 (25) [MH⁺], HPLC: $t_R$=2.63 min (vvnonpolar_5 min, ZQ3).

1-(trans-4-{[tert-Butyl(dimethyl)silyl]oxy}cyclohexyl)-3-methoxy-4-(4,4,5,5-tetramethyl-1,3,2-dioxaborolan-2-yl)-1H-pyrazole A solution of 1-(trans-4-{[tert-butyl(dimethyl)silyl]oxy}cyclohexyl)-4-iodo-3-methoxy-1H-pyrazole (0.0500 g, 0.114 mmol) in anhydrous degassed THF (2.0 mL) was cooled to −10° C. and dropwise charged with 1.30 M of isopropylmagnesium chloride in THF (0.352 mL, 0.458 mmol) over a 5 min period under an atmosphere of Argon. The reaction was maintained at −10° C. for 40 min then charged with 2-methoxy-4,4,5,5-tetramethyl-1,3,2-dioxaborolane (0.0939 mL, 0.573 mmol) and stirred for an additional 1 h at 0° C. The reaction mixture was quenched with sat NH$_4$Cl (2.0 mL) and partitioned between EtOAc and H$_2$O. The aqueous was re-extracted with EtOAc (3×) and the combined organic fractions were washed with brine (1×), dried over Na$_2$SO$_4$, filtered and concentrated in vacuo resulting in a crude yellow oil. The crude was purified by chromatography on silica gel [ISCO Combiflash, 4 g gold cartridge, eluting with 100% heptane→30% EtOAc in heptane] resulting in the title compound as a white waxy solid. $^1$H NMR (400 MHz, CD$_3$OD): δ=−0.02-0.02 (m, 6H), 0.79-0.84 (m, 9H), 1.19 (s, 12H), 1.32-1.44 (m, 2H), 1.66-1.78 (m, 2H), 1.85-1.92 (m, 2H), 1.94-2.02 (m, 2H), 3.60-3.69 (m, 1H), 3.76-3.79 (m, 3H), 3.86 (tt, J=3.8, 12 Hz, 1H), 7.50 (s, 1H). MS (ES+): m/z 436.27, 437.26, 438.29 [MH$^+$]. HPLC: t$_R$=4.05 min (vvnonpolar__5 min, ZQ3).

1-(trans-4-{[tert-Butyl(dimethyl)silyl]oxy}cyclohexyl)-4-iodo-3-methoxy-1H-pyrazole A solution of trans-4-(4-iodo-3-methoxy-1H-pyrazol-1-yl)cyclohexanol (0.359 g, 1.11 mmol), 1H-imidazole (0.228 g, 3.34 mmol), and 4-dimethylaminopyridine (0.0272 g, 0.223 mmol) in anhydrous DCM (10.8 mL) was charged with tert-butyldimethylsilyl chloride (0.336 g, 2.23 mmol) and stirred at rt for 20 min. The reaction was partitioned between CHCl$_3$ and 1M NaHCO$_3$ and separated. The aqueous was re-extracted with CHCl$_3$ (3×) and the combined organic fraction were washed with brine (1×), dried over Na$_2$SO$_4$, filtered and concentrated in vacuo resulting in a crude colorless oil. The crude material was purified by chromatography on silica gel [eluting with 5% EtOAc in hexanes] resulting in the title compound as a clear colorless oil. $^1$H NMR (400 MHz, CD$_3$OD): δ=0.09 (d, J=0.51 Hz, 6H), 0.91 (s, 9H), 1.41-1.54 (m, 2H), 1.74-1.87 (m, 2H), 1.93-2.09 (m, 4H), 3.68-3.77 (m, 1H), 3.86 (d, J=0.5 Hz, 3H), 3.96 (tt, J=3.9, 12 Hz, 1H), 7.48 (s, 1H). MS (ES+): m/z 437.17 (100) [MH$^+$]. HPLC: t$_R$=4.98 min (vvnonpolar__5 min, ZQ3).

trans-4-(4-Iodo-3-methoxy-1H-pyrazol-1-yl)cyclohexanol

The mixture of 1-(1,4-dioxaspiro[4.5]dec-8-yl)-4-iodo-3-methoxy-1H-pyrazole (1.00 g, 2.74 mmol), pyridinium p-toluenesulfonate (1.38 g, 5.49 mmol) in acetone (40.3 mL) and H$_2$O (44.5 mL) was heated at 60° C. for 23 h. The reaction mixture was concentrated in vacuo to remove the acetone then partitioned between EtOAc and H$_2$O and separated. The aqueous was re-extracted with EtOAc (3×) and the combined organic fractions were washed with brine (1×), dried over Na$_2$SO$_4$, filtered and concentrated in vacuo resulting in 890 mg of a yellow oil. It was dissolved in anhydrous EtOH (16.0 mL) and charged with sodium borohydride (0.156 g, 4.12 mmol) and stirred at rt for 1 h. The reaction mixture was partitioned between CHCl$_3$ and 1M NaHCO$_3$ and separated. The aqueous was re-extracted with CHCl$_3$ (3×) and the combined organic fractions were washed with brine (1×), dried over Na$_2$SO$_4$, filtered and concentrated in vacuo. The crude material was purified by chromatography on silica gel [ISCO CombiFlash, eluting with 20% EtOAc in heptanes→75% EtOAc in heptanes] resulting in the title compound as clear colorless oil. $^1$H NMR (400 MHz, CD$_3$OD): δ=1.36-1.49 (m, 2H), 1.73-1.86 (m, 2H), 2.00-2.10 (m, 4H), 3.61 (tt, J=4.0, 11 Hz, 1H), 3.86 (s, 3H), 3.96 (tt, J=3.8, 12 Hz, 1H), 7.48 (s, 1H). MS (ES+): m/z 323.08 [MH$^+$]. HPLC: t$_R$=3.40 min (nonpolar__5 min, ZQ3).

1-(1,4-Dioxaspiro[4.5]dec-8-yl)-4-iodo-3-methoxy-1H-pyrazole

A solution of 4-iodo-3-methoxy-1H-pyrazole (0.783 g, 3.50 mmol), 1,4-dioxaspiro[4.5]dec-8-yl 4-methylbenzenesulfonate (1.20 g, 3.84 mmol), and Cs$_2$CO$_3$ (1.71 g, 5.24 mmol) in anhydrous degassed DMF (26.1 mL) was heated to 100° C. for 3 h. From LCMS, there was still starting material (pyrazole) therefore the reaction mixture was charged with an additional 1,4-dioxaspiro[4.5]dec-8-yl 4-methylbenzenesulfonate (0.437 g, 1.40 mmol) and Cs$_2$CO$_3$ (0.683 g, 2.10 mmol) and heated to 100° C. for an additional 16 h. The reaction mixture was partitioned between EtOAc (100 mL) and H$_2$O (25 mL) and separated. The aqueous was re-extracted with EtOAc (3×) and the combined organic fractions were washed with H$_2$O (3×25 mL), brine (1×), dried over Na$_2$SO$_4$, filtered and concentrated in vacuo resulting in 1.29 g of a crude orange oil/solid mixture. The crude was crystallized from MeOH and the white crystals were filtered through a fritted funnel resulting in the title compound as white crystals. $^1$H NMR (400 MHz, CD$_3$OD): δ=1.63-1.74 (m, 2H), 1.81-1.89 (m, 2H), 1.98-2.07 (m, 4H), 3.87 (s, 3H), 3.91-3.99 (m, 4H), 4.00-4.09 (m, 1H), 7.48 (s, 1H). MS (ES+): m/z 365.05 [MH$^+$]. HPLC: t$_R$=3.98 min (polar__5 min, ZQ3).

4-Iodo-3-methoxy-1H-pyrazole

A solution of 3-methoxy-1H-pyrazole (0.500 g, 5.10 mmol) in anhydrous DMF (8.00 mL) was cooled to −30° C. and charged with NIS (1.15 g, 5.10 mmol). The reaction mixture was stirred at −30° C. for 1.5 h. The reaction mixture was charged with H$_2$O at −30° C. then the reaction was charged with EtOAc and separated. The aqueous was re-extracted with EtOAc (3×) and the combined organic fractions were washed with H$_2$O (2×), 1M Na$_2$S$_2$O$_3$ (1×), brine (1×), dried over Na$_2$SO$_4$, filtered and concentrated in vacuo resulting in the title compound as a light yellow solid. This material was taken on to the next step without further purification. $^1$H NMR (400 MHz, CD$_3$OD): δ=3.88 (s, 3H), 7.50 (s, 1H). MS (ES+): m/z 225.04 [MH$^+$]. HPLC: t$_R$=2.97 min (polar__5 min, ZQ3).

3-Methoxy-1H-pyrazole

A solution of 1-acetyl-1,2-dihydro-3H-pyrazol-3-one (1.50 g, 11.9 mmol), potassium carbonate (1.64 g, 11.9 mmol) in 2-butanone (36.0 mL) was charged with dimethyl sulfate (1.24 mL, 13.1 mmol) and heated to reflux for 90 min. An additional amount of dimethyl sulfate (0.225 mL, 2.38 mmol) was added and the reaction was heated for an additional 1 h. The reaction mixture was allowed to cool to rt and filtered through a fritted funnel and the filtrate was concentrated in vacuo resulting in a dark yellow oil. The crude oil was charged with a 10 M NaOH (0.595 mL) dissolved in a 1:1 mixture of THF/MeOH (40 mL) and stirred at rt for 30 min. The reaction mixture was concentrated in vacuo and partitioned between EtOAc and brine and separated. The organic was dried over Na$_2$SO$_4$, filtered and concentrated in vacuo resulting in the title compound as an orange oil. $^1$H NMR (400 MHz, CDCl$_3$): δ=3.92 (s, 3H), 5.75 (d, J=2.5 Hz, 1H), 7.37 (d, J=2.5 Hz, 1H). MS (ES+): m/z 99.13 (100) [MH+]. HPLC: $t_R$=1.56 min (polar_5 min, ZQ3).

1-Acetyl-1,2-dihydro-3H-pyrazol-3-one

A mixture of 1,2-dihydro-3H-pyrazol-3-one (4.50 g, 26.8 mmol), in pyridine (20.4 mL, 252 mmol) was heated to 95° C. then charged with a solution of acetic anhydride (5.10 mL, 54.0 mmol) in pyridine (9.64 mL, 119 mmol) over a 15 min period. The reaction was heated for an additional 1 h at 95° C. The reaction mixture was concentrated in vacuo resulting in a dark red oil which was triturated with MeOH and filtered resulting in the title compound as a light yellow solid. A 2nd crop of product was isolated from the mother liquors. $^1$H NMR (400 MHz, DMSO-$d_6$): δ=2.48 (s, 3H) 6.00 (d, J=3.0 Hz, 1H), 8.12 (d, J=3.0 Hz, 1H), 10.95 (br. s., 1H). MS (ES+): m/z 127.23 (100) [MH+]. HPLC: $t_R$=0.82 min (polar_5 min, ZQ3).

Example 101

(2R)-3-(4-{3-[(1S)-1-(2-Chloro-6-ethoxy-3-fluorophenyl)ethyl]-1H-pyrrolo[2,3-b]pyridin-5-yl}-3,5-dimethyl-1H-pyrazol-1-yl)propane-1,2-diol

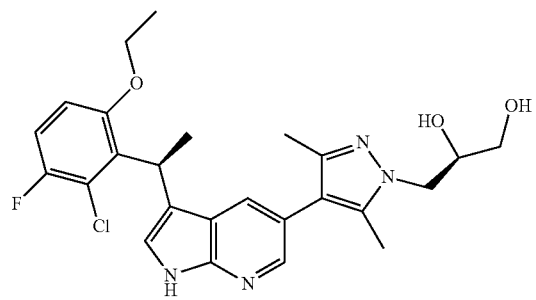 [SMILES: CCOc1ccc(F)c(Cl)c1[C@@H](C)c1c[nH]c2ncc(-c3c(C)nn(C[C@@H](O)CO)c3C)cc12]

Prepared using the procedure described for Example 69. $^1$H NMR (400 MHz, CD$_3$OD): δ=1.15 (t, J=5.9 Hz, 3H), 1.81 (d, J=7.1 Hz, 3H), 2.03 (s, 3H), 2.16 (s, 3H), 3.47-3.69 (m, 3H), 3.89-4.09 (m, 3H), 4.11-4.20 (m, 1H), 5.08 (q, J=6.6 Hz, 1H), 6.83 (dd, J=8.8, 4.3 Hz, 1H), 7.00-7.08 (m, 1H), 7.26 (s, 1H), 7.35 (s, 1H), 7.97 (s, 1H). MS (ES+): m/z=487.18/489.19 (100/50) [MH+]. HPLC: $t_R$=1.36 min (polar_3 min, UPLC-ACQUITY).

Example 102

3-Chloro-4-fluoro-2-[(1S)-1-{5-[1-(trans-4-hydroxycyclohexyl)-5-methyl-1H-pyrazol-4-yl]-1H-pyrrolo[2,3-b]pyridin-3-yl}ethyl]phenol

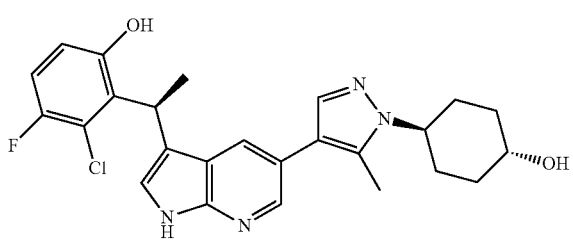 [SMILES: Cc1c(-c2cnc3[nH]cc([C@H](C)c4c(O)ccc(F)c4Cl)c3c2)cnn1[C@H]1CC[C@H](O)CC1]

Prepared using the procedure described for Example 69. $^1$H NMR (400 MHz, CD$_3$OD): δ=1.44-1.57 (m, 2H), 1.82 (d, J=7.1 Hz, 3H), 1.89-2.01 (m, 4H), 2.05-2.11 (m, 2H), 2.22 (s, 3H), 3.67 (m, J=10.9, 10.9, 4.3, 4.2 Hz, 1H), 4.15-4.23 (m, 1H), 5.04-5.14 (m, 1H), 6.68 (dd, J=8.8, 4.5 Hz, 1H), 6.92 (t, J=8.8 Hz, 1H), 7.35 (d, J=1.3 Hz, 1H), 7.47 (s, 1H), 7.50 (d, J=1.5 Hz, 1H), 8.09 (br. s., 1H). MS (ES+): m/z=469.15/471.16 (100/50) [MH+]. HPLC: $t_R$=1.30 min (polar_3 min, UPLC-ACQUITY).

Example 103 trans-4-(4-{3-[(1S)-1-(2-Chloro-6-ethoxy-3-fluorophenyl)ethyl]-1H-pyrrolo[2,3-b]pyridin-5-yl}-5-methyl-1H-pyrazol-1-yl)cyclohexanol

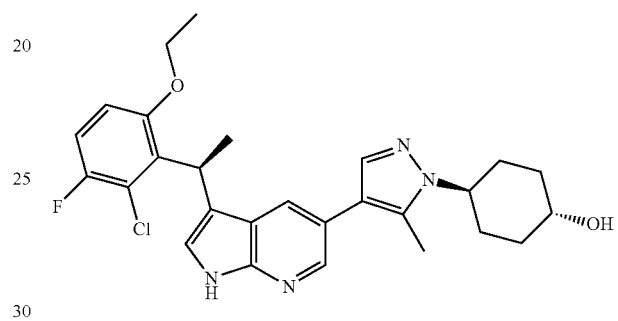

Prepared using the procedure described for Example 69. $^1$H NMR (400 MHz, CD$_3$OD): δ=1.16 (t, J=5.7 Hz, 3H), 1.44-1.59 (m, 2H), 1.81 (d, J=7.3 Hz, 3H), 1.89-2.14 (m, 6H), 2.21 (s, 3H), 3.56-3.73 (m, 2H), 3.95 (qd, J=7.1, 6.8 Hz, 1H), 4.13-4.24 (m, 1H), 5.03-5.13 (m, 1H), 6.84 (dd, J=9.1, 4.3 Hz, 1H), 7.06 (t, J=9.0 Hz, 1H), 7.34 (d, J=1.3 Hz, 1H), 7.36 (d, J=2.0 Hz, 1H), 7.45 (s, 1H), 8.09 (d, J=2.0 Hz, 1H). MS (ES+): m/z=497.31/499.33 (100/50) [MH+]. HPLC: $t_R$=1.28 min (polar_2 min, UPLC-ACQUITY).

Example 104 trans-4-[4-(3-{(1S)-1-[2-Chloro-3-fluoro-6-(propan-2-yloxy)phenyl]ethyl}-1H-pyrrolo[2,3-b]pyridin-5-yl)-5-methyl-1H-pyrazol-1-yl]cyclohexanol

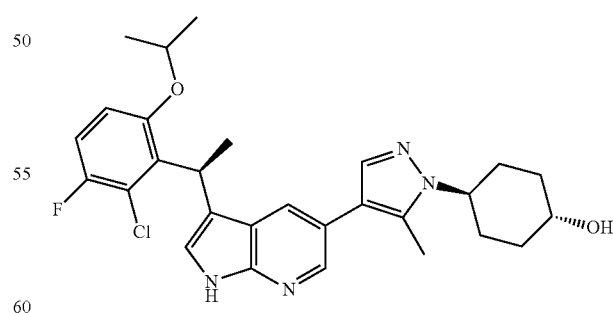

To a solution of tert-butyl 5-bromo-3-[(1S)-1-(2-chloro-3-fluoro-6-hydroxyphenyl)ethyl]-1H-pyrrolo[2,3-b]pyridine-1-carboxylate (13.0 mg, 0.0277 mmol) and K$_2$CO$_3$ (12.7 mg, 0.0919 mmol) in DMF (0.8 mL, 10 mmol) was added isopropyl iodide (16.06 mg, 0.09451 mmol), and the mixture was heated to 40° C. for 2 h. The reaction mixture was diluted with EtOAc and washed with water (3×). The organic layer was concentrated in vacuo, and trans-4-[5-methyl-4-(4,4,5,5-tetramethyl-1,3,2-dioxaborolan-2-yl)-1H-pyrazol-1-yl]cyclohexanol (12.71 mg, 0.04151 mmol), Pd(PPh$_3$)$_4$ (1.599 mg, 0.001384 mmol), K$_2$CO$_3$ (3 eq) and 4:1 dioxane:H$_2$O (1 mL, 10 mmol) were added. The mixture was heated in a microwave reactor at 95° C. for 20 min. 12 M of HCl in H$_2$O (0.069 mL, 0.83 mmol) was added, and the solution was heated to 45° C. for 1 h. The solution was used directly for HPLC purification, and the fractions containing the pure product were concentrated in vacuo to afford the title compound as a white solid. $^1$H NMR (400 MHz, CD$_3$OD): δ=0.68 (br. s., 3H), 1.24 (d, J=5.8 Hz, 3H), 1.45-1.57 (m, 2H), 1.80 (d, J=7.1 Hz, 3H), 1.94-2.11 (m, 6H), 2.19 (s, 3H), 3.68 (tt, J=11.0, 4.2 Hz, 1H), 4.12-4.24 (m, 1H), 4.35-4.51 (m, 1H), 5.01-5.12 (m, 1H), 6.83 (dd, J=8.3, 3.8 Hz, 1H), 7.05 (t, J=8.8 Hz, 1H), 7.33 (dd, J=2.9, 1.6 Hz, 2H), 7.45 (s, 1H), 8.09 (d, J=2.0 Hz, 1H). MS (ES+): m/z=511.34/513.33 (100/50) [MH$^+$]. HPLC: t$_R$=1.33 min (polar_2 min, UPLC-ACQUITY).

Example 105 trans-4-[4-(3-{(1S)-1-[2-Chloro-3-fluoro-6-(2,2,2-trifluoroethoxy)-phenyl]ethyl}-1H-pyrrolo[2,3-b]pyridin-5-yl)-5-methyl-1H-pyrazol-1-yl]cyclohexanol

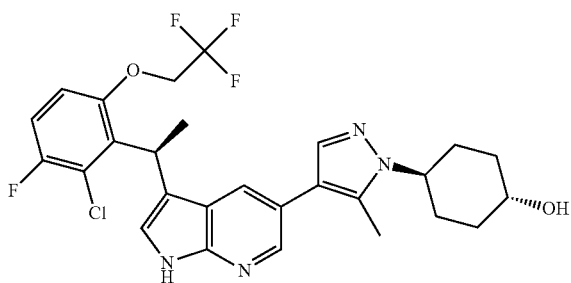 [SMILES: Cc1c(-c2cnc3[nH]cc([C@H](C)c4c(OCC(F)(F)F)ccc(F)c4Cl)c3c2)cnn1[C@H]1CC[C@H](O)CC1]

To a solution of tert-butyl 5-bromo-3-[(1S)-1-(2-chloro-3-fluoro-6-hydroxyphenyl)ethyl]-1H-pyrrolo[2,3-b]pyridine-1-carboxylate (13.0 mg, 0.0277 mmol) and K$_2$CO$_3$ (12.7 mg, 0.0919 mmol) in DMF (0.8 mL, 10 mmol) was added 2,2,2-trifluoromethyl triflate (21.94 mg, 0.09451 mmol), and the mixture was stirred at rt for 1 h. The reaction mixture was diluted with EtOAc and washed with water (3×). The organic layer was concentrated in vacuo, and trans-4-[5-methyl-4-(4,4,5,5-tetramethyl-1,3,2-dioxaborolan-2-yl)-1H-pyrazol-1-yl]cyclohexanol (12.71 mg, 0.04151 mmol), Pd(PPh$_3$)$_4$ (1.599 mg, 0.001384 mmol), K$_2$CO$_3$ (3 eq) and 4:1 dioxane:H$_2$O (1 mL, 10 mmol) were added. The mixture was heated in a microwave reactor at 95° C. for 20 min. 12 M of HCl in H$_2$O (0.069 mL, 0.83 mmol) was added, and the solution was heated to 45° C. for 1 h. The solution was used directly for HPLC purification, and the fractions containing the pure product were concentrated in vacuo to afford the title compound as a white solid. $^1$H NMR (400 MHz, CD$_3$OD): δ=1.43-1.59 (m, 2H), 1.82 (d, J=7.1 Hz, 3H), 1.89-2.14 (m, 6H), 2.22 (s, 3H), 3.61-3.73 (m, 1H), 4.07-4.26 (m, 2H), 4.42 (dd, J=14.4, 5.3 Hz, 1H), 5.11 (q, J=7.5 Hz, 1H), 6.91 (dd, J=8.7, 3.7 Hz, 1H), 7.10-7.16 (m, 1H), 7.35 (d, J=1.3 Hz, 1H), 7.37 (d, J=1.8 Hz, 1H), 7.45 (s, 1H), 8.10 (s, 1H). MS (ES+): m/z=551.32/553.33 (100/50) [MH$^+$]. HPLC: t$_R$=1.28 min (polar_2 min, UPLC-ACQUITY).

Example 106 trans-4-(4-{3-[(1S)-1-(2,6-Dichloro-3,5-dimethoxyphenyl)ethyl]-1H-pyrrolo[2,3-b]pyridin-5-yl}-5-methyl-1H-pyrazol-1-yl)cyclohexanol

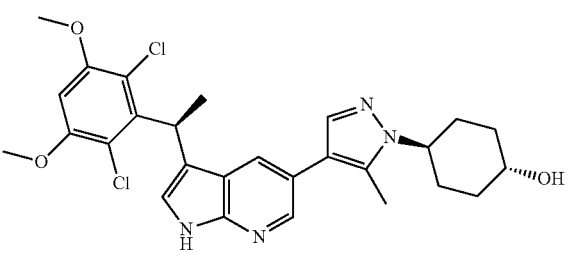 [SMILES: COc1cc(OC)c(Cl)c([C@@H](C)c2c[nH]c3ncc(-c4cnn([C@H]5CC[C@H](O)CC5)c4C)cc23)c1Cl]

Prepared using the procedure described for Example 69. $^1$H NMR (400 MHz, CD$_3$OD): δ=1.45-1.58 (m, 2H), 1.85 (d, J=7.3 Hz, 3H), 1.93-2.04 (m, 4H), 2.06-2.13 (m, 2H), 2.18 (s, 3H), 3.69 (tt, J=10.9, 4.2 Hz, 1H), 3.83 (br. s., 3H), 3.95 (br. s., 3H), 4.18 (tt, J=11.1, 4.3 Hz, 1H), 5.35 (q, J=7.2 Hz, 1H), 6.75 (s, 1H), 7.23 (d, J=2.0 Hz, 1H), 7.35 (d, J=1.5 Hz, 1H), 7.46 (s, 1H), 8.12 (d, J=1.8 Hz, 1H). MS (ES+): m/z=529.17/531.17 (100/50) [MH$^+$]. HPLC: t$_R$=1.40 min (polar_3 min, UPLC-ACQUITY).

5-Bromo-3-[(1S)-1-(2,6-dichloro-3,5-dimethoxyphenyl)ethyl]-1H-pyrrolo[2,3-b]pyridine The title compound was prepared from the known 2,6-dichloro-3,5-dimethoxybenzaldehyde [Synth. Commun. 2000, 30 (12), 2133-2141] following the procedures for the synthesis of 5-bromo-3-[(1S)-(2-chloro-3-fluoro-6-methoxyphenyl)ethyl]-1H-pyrrolo[2,3-b]pyridine from 2-chloro-3-fluoro-6-methoxybenzaldehyde, vide supra. $^1$H NMR (300 MHz, DMSO-d$_6$): δ=1.74 (d, J=7.2 Hz, 3H), 3.90 (brs, 6H), 5.14 (q, J=7.0 Hz, 1H), 6.84 (s, 1H), 7.27 (d, J=2.4 Hz, 1H), 7.46 (s, 1H), 8.16 (d, J=2.4 Hz, 1H), 11.75 (brs, 1H).

Example 107 trans-4-(4-{3-[(1S)-1-{2-Chloro-3-fluoro-6-[($^2$H$_3$)methyloxy]phenyl}ethyl]-1H-pyrrolo[2,3-b]pyridin-5-yl}-5-methyl-1H-pyrazol-1-yl)cyclohexanol

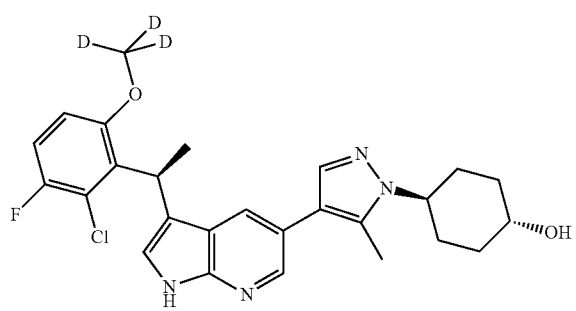 [SMILES: [2H]C([2H])([2H])Oc1ccc(F)c(Cl)c1[C@@H](C)c1c[nH]c2ncc(-c3cnn([C@H]4CC[C@H](O)CC4)c3C)cc12]

To a solution of tert-butyl 5-bromo-3-[(1S)-1-(2-chloro-3-fluoro-6-hydroxyphenyl)ethyl]-1H-pyrrolo[2,3-b]pyridine-1-carboxylate (40.0 mg, 0.0852 mmol) and K$_2$CO$_3$ (35.31 mg, 0.2555 mmol) in DMF (2 mL, 30 mmol) was added iodomethane-d$_3$ (0.026 mL, 0.43 mmol), and the mixture was stirred at rt for 30 min. The reaction mixture was diluted with EtOAc and washed with water (3×). The organic layer was concentrated in vacuo, and 1-(trans-4-{[tert-butyl(dimethyl)silyl]oxy}cyclohexyl)-5-methyl-4-(4,4,5,5-tetramethyl-1,3,2-dioxaborolan-2-yl)-1H-pyrazole (53.71 mg, 0.1277 mmol), Pd(PPh$_3$)$_4$ (4.920 mg, 0.004258 mmol), K$_2$CO$_3$ (3 eq) and 4:1 dioxane:H$_2$O (3 mL, 30 mmol) were added. The mixture was heated in a microwave reactor at 95° C. for 20 min. 12 M of HCl in H$_2$O (0.21 mL, 2.6 mmol) was added, and the solution was heated to 45° C. for 1 h. The material was concentrated in vacuo, extracted with DCM and sat. NaHCO$_3$, and loaded onto silica gel for column chromatography. The product was eluted with 1-3% (7N NH$_3$ in MeOH)/DCM, and the fractions containing the product were concentrated in vacuo, redissolved in MeOH, and added 2.0 M of HCl in Et$_2$O (0.43 mL, 0.86 mmol). The solution was stirred at rt for 30 min, and concentrated in vacuo to afford the title compound as an HCl salt. $^1$H NMR (400 MHz, CD$_3$OD): δ=1.44-1.59 (m, 2H), 1.81 (d, J=7.1 Hz, 3H), 1.93-2.14 (m, 6H), 2.24 (s, 3H), 3.69 (tt, J=11.0, 4.2 Hz, 1H), 4.20 (tdd, J=11.1, 11.1, 4.5, 4.2 Hz, 1H), 5.11 (q, J=7.0 Hz, 1H), 6.89 (dd, J=9.1, 4.3 Hz, 1H), 7.09 (t, J=8.8 Hz, 1H), 7.36 (d, J=1.3 Hz, 1H), 7.42 (s, 1H), 7.48 (s, 1H), 8.11 (d, J=2.0 Hz, 1H). MS (ES+): m/z=486.21/488.21 (100/50) [MH$^+$]. HPLC: t$_R$=1.39 min (polar_3 min, UPLC-ACQUITY).

Example 108

(2,6-Dichloro-3-fluorophenyl){5-[1-(trans-4-hydroxycyclohexyl)-5-methyl-1H-pyrazol-4-yl]-1H-pyrrolo[2,3-b]pyridin-3-yl}acetonitrile

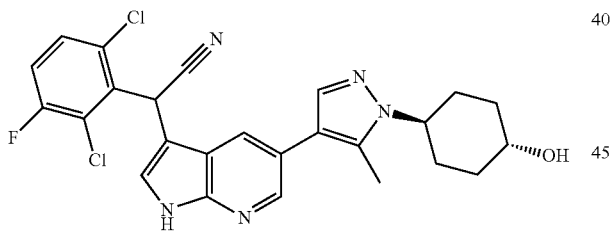

Prepared using the procedure described for Example 69. $^1$H NMR (400 MHz, CD$_3$OD): δ=1.46-1.61 (m, 2H), 1.93-2.17 (m, 6H), 2.34 (s, 3H), 3.70 (tt, J=11.0, 4.2 Hz, 1H), 4.17-4.30 (m, 1H), 6.52-6.60 (m, 1H), 7.37-7.48 (m, 2H), 7.56 (s, 1H), 7.61 (dd, J=9.0, 4.9 Hz, 1H), 7.75 (d, J=2.0 Hz, 1H), 8.27 (d, J=1.5 Hz, 1H). MS (ES+): m/z=498.12/500.12 (100/50) [MH$^+$]. HPLC: t$_R$=1.30 min (polar_3 min, UPLC-ACQUITY).

(5-Bromo-1H-pyrrolo[2,3-b]pyridin-3-yl)(2,6-dichloro-3-fluorophenyl)acetonitrile To a stirred mixture of trimethylsilyl cyanide (0.51 mL, 3.8 mmol) and indium(III) bromide (34.1 mg, 0.0961 mmol) in DCM (5.00 mL, 78.0 mmol) was added (5-bromo-1H-pyrrolo[2,3-b]pyridin-3-yl)-(2,6-dichloro-3-fluorophenyl)methanol (150.0 mg, 0.3846 mmol). The resulting mixture was stirred at rt overnight. The solvent was removed under reduced pressure and the residue was purified by silica gel chromatography (DCM/Hexane 1:1 as eluent). $^1$H NMR (400 MHz, CD$_3$OD): δ=6.52 (s, 1H), 7.39 (d, J=1.0 Hz, 1H), 7.45 (t, J=8.7 Hz, 1H), 7.63 (dd, J=9.1, 4.8 Hz, 1H), 8.02 (d, J=2.0 Hz, 1H), 8.31 (d, J=2.3 Hz, 1H). MS (ES+): m/z 397.85, 399.88, 401.85 [MH+]. HPLC: t$_R$=4.19 min (OpenLynx, polar_5 min).

Example 109

Dichloro-3-fluoro-phenyl)-{5-[5-fluoro-1-(4-hydroxy-cyclohexyl)-1H-pyrazol-4-yl]-1H-pyrrolo[2,3-b]pyridin-3-yl}-acetonitrile

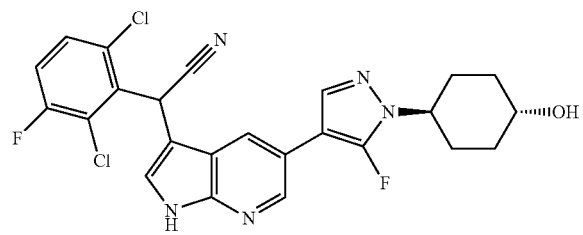 [SMILES: N#CC(c1c(Cl)ccc(F)c1Cl)c1c[nH]c2ncc(-c3cnn([C@H]4CC[C@H](O)CC4)c3F)cc12]

Prepared using the procedure described for Example 69. Purification by Teledyne/ISCO eluting with 0→10% MeOH in DCM afforded the title compound as a white solid. $^1$H NMR (400 MHz, CD$_3$OD): δ=1.37-1.60 (m, 2H), 1.88-2.20 (m, 6H), 3.57-3.76 (m, 1H), 4.15-4.35 (m, 1H), 6.56 (s, 1H), 7.38-7.50 (m, 2H), 7.63 (dd, J=9.1, 4.8 Hz, 1H), 7.75 (d, J=3.5 Hz, 1H), 7.95 (d, J=1.8 Hz, 1H), 8.45 (d, J=2.0 Hz, 1H).

Example 110 trans-4-(4-{3-[(1S)-1-(2-Chloro-3-fluoro-6-methoxyphenyl)(1-$^2$H)ethyl]-1H-pyrrolo[2,3-b]pyridin-5-yl}-5-methyl-1H-pyrazol-1-yl)cyclohexanol

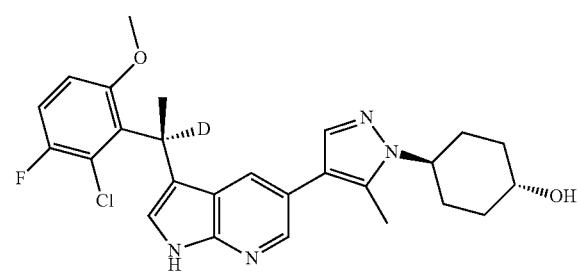 [SMILES: [2H][C@@](C)(c1c(OC)ccc(F)c1Cl)c1c[nH]c2ncc(-c3cnn([C@H]4CC[C@H](O)CC4)c3C)cc12]

Prepared using the procedure described for Example 69. $^1$H NMR (400 MHz, CD$_3$OD): δ=1.45-1.58 (m, 2H), 1.79 (s, 3H), 1.91-2.05 (m, 4H), 2.08 (d, J=12.6 Hz, 2H), 2.22 (s, 3H), 3.56-3.79 (m, 4H), 4.15-4.23 (m, 1H), 6.89 (dd, J=8.5, 3.8 Hz, 1H), 7.09 (t, J=8.9 Hz, 1H), 7.35 (s, 1H), 7.40 (br. s., 1H), 7.47

(s, 1H), 8.11 (br. s., 1H). MS (ES+): m/z=484.18/486.19 (100/50) [MH+]. HPLC: $t_R$=1.39 min (polar_3 min, UPLC-ACQUITY).

Example 111 trans-4-(4-{3-[(1S)-1-(2-Chloro-3-fluoro-6-methoxyphenyl)(2,2,2-$^2$H$_3$)ethyl]-1H-pyrrolo[2,3-b]pyridin-5-yl}-5-methyl-1H-pyrazol-1-yl)cyclohexanol

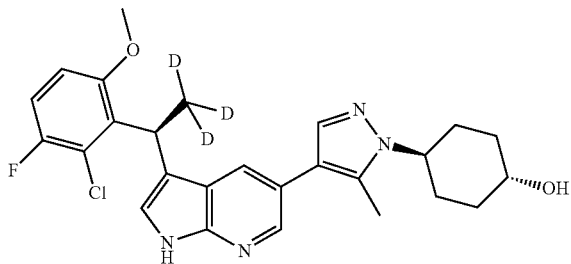 [SMILES: [2H]C([2H])([2H])[C@H](c1c(OC)ccc(F)c1Cl)c1c[nH]c2ncc(-c3cnn([C@H]4CC[C@H](O)CC4)c3C)cc12]

A mixture of 5-bromo-3-[(1S)-1-(2-chloro-3-fluoro-6-methoxyphenyl)(2,2,2-$^2$H$_3$)ethyl]-1H-pyrrolo[2,3-b]pyridine (50.0 mg, 0.129 mmol), 1-(trans-4-{[tert-butyl(dimethyl)silyl]oxy}-cyclohexyl)-5-methyl-4-(4,4,5,5-tetramethyl-1,3,2-dioxaborolan-2-yl)-1H-pyrazole (81.56 mg, 0.1940 mmol), Pd(PPh$_3$)$_4$ (7.471 mg, 0.006466 mmol), K$_2$CO$_3$ (53.62 mg, 0.3879 mmol) and 4:1 dioxane:H$_2$O (3 mL, 30 mmol) was heated to 95° C. for 2 h. The solution was cooled to rt, and 12 M of HCl in H$_2$O (0.108 mL, 1.29 mmol) was added. The material was concentrated in vacuo, and extracted with DCM and sat. NaHCO$_3$. The organic layer was dry-loaded onto silica gel and purified via column chromatography, eluting with 2-4% (7N NH$_3$ in MeOH)/DCM. The fractions containing the pure product were concentrated in vacuo, redissolved in MeOH, and 2.0 M of HCl in Et$_2$O (0.65 mL, 1.3 mmol) was added at rt. The solution was concentrated in vacuo to afford the title compound as an HCl salt. $^1$H NMR (400 MHz, CD$_3$OD): δ=1.45-1.60 (m, 2H), 1.94-2.05 (m, 4H), 2.07-2.15 (m, 2H), 2.24 (s, 3H), 3.58-3.76 (m, 4H), 4.15-4.25 (m, 1H), 5.09 (s, 1H), 6.89 (dd, J=9.1, 4.0 Hz, 1H), 7.09 (t, J=8.8 Hz, 1H), 7.35 (d, J=1.3 Hz, 1H), 7.42 (s, 1H), 7.48 (s, 1H), 8.11 (d, J=2.0 Hz, 1H). MS (ES+): m/z=486.17/488.17 (100/50) [MH+]. HPLC: $t_R$=1.39 min (polar_3 min, UPLC-ACQUITY).

5-Bromo-3-[(1S)-1-(2-chloro-3-fluoro-6-methoxyphenyl)(2,2,2-$^2$H$_3$)ethyl]-1H-pyrrolo[2,3-b]pyridine Racemic 5-bromo-3-[1-(2-chloro-3-fluoro-6-methoxyphenyl)(2,2,2-$^2$H$_3$)ethyl]-1H-pyrrolo[2,3-b]pyridine was prepared from 5-bromo-3-[(2-chloro-6-methoxy-3-fluorophenyl)-hydroxymethyl]-1H-pyrrolo[2,3-b]pyridine as described for the non-deuterated compound, except that a solution of Zn(CD$_3$)$_2$ in Et$_2$O prepared from commercially available CD$_3$MgI was used. The racemic mixture was separated into the enantiomers by SFC on a chiral stationary phase. Analytical SFC for the (1S)enantiomer (ChiralPak IA 4.6×100 mm I.D., solvent 90:10 scCO$_2$/methanol isocratic, flow rate 4.0 mL/min, UV detection at 254 nm): $t_R$=3.8 min.

Example 112 trans-4-(4-{3-[1-(6-Chloro-3-fluoro-2-methoxyphenyl)ethyl]-1H-pyrrolo[2,3-b]pyridin-5-yl}-5-methyl-1H-pyrazol-1-yl)cyclohexanol

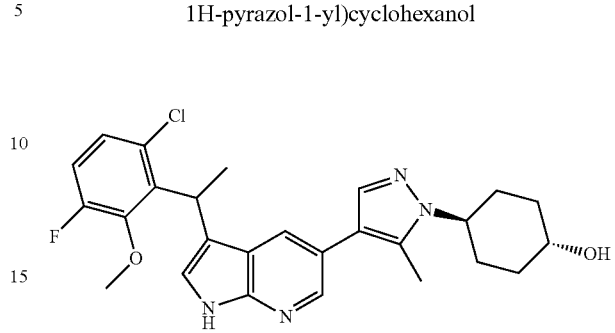

Prepared using the procedure described for Example 69. $^1$H NMR (400 MHz, CD$_3$OD): δ=1.45-1.59 (m, 2H), 1.83 (d, J=7.1 Hz, 3H), 1.93-2.16 (m, 6H), 2.24 (s, 3H), 3.37 (br. s., 3H), 3.69 (tt, J=11.0, 4.3 Hz, 1H), 4.20 (tt, J=11.1, 4.4 Hz, 1H), 5.02 (q, J=7.0 Hz, 1H), 7.05 (dd, J=11.0, 9.0 Hz, 1H), 7.19 (dd, J=9.0, 4.7 Hz, 1H), 7.40 (d, J=1.3 Hz, 1H), 7.44 (d, J=1.8 Hz, 1H), 7.49 (s, 1H), 8.15 (br. s., 1H). MS (ES+): m/z=483.19/485.19 (100/50) [MH+]. HPLC: $t_R$=1.41 min (polar_3min, UPLC-ACQUITY).

5-Bromo-3-[1-(6-chloro-3-fluoro-2-methoxyphenyl) ethyl]-1H-pyrrolo[2,3-b]pyridine The title compound was prepared from 6-chloro-3-fluoro-2-methoxybenzaldehyde following the procedures for the synthesis of 5-bromo-3-[1-(2-chloro-3-fluoro-6-methoxyphenyl)ethyl]-1H-pyrrolo[2,3-b]pyridine from 2-chloro-3-fluoro-6-methoxybenzaldehyde, vide supra. 6-Chloro-3-fluoro-2-methoxybenzaldehyde was prepared from the known 6-chloro-2,3-difluorobenzaldehyde by reaction with sodium methoxide in methanol. $^1$H NMR (300 MHz, CDCl$_3$): δ=1.78 (d, J=7.2 Hz, 3H), 3.44 (brs, 3H), 4.94 (q, J=7.2 Hz, 1H), 6.93 (dd, J=9.0, 9.0 Hz, 1H), 7.09 (dd, J=8.7, 4.5 Hz, 1H), 7.30 (s, 1H), 7.71 (d, J=1.5 Hz, 1H), 8.28 (d, J=1.5 Hz, 1H), 9.68 (brs, 1H).

Example 113 trans-4-(4-{3-[(1S)-1-[2-Chloro-6-(difluoromethoxy)-3-fluorophenyl](2,2,2-$^2$H$_3$)ethyl]-1H-pyrrolo[2,3-b]pyridin-5-yl}-5-methyl-1H-pyrazol-1-yl)cyclohexanol

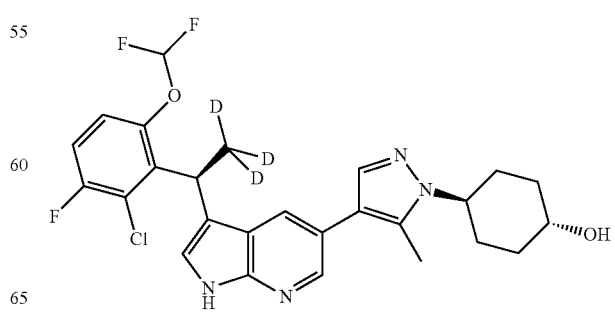

A mixture of tert-butyl 5-bromo-3-[(1S)-1-[2-chloro-6-(difluoromethoxy)-3-fluorophenyl](2,2,2-$^2$H$_3$)ethyl]-1H-pyrrolo[2,3-b]pyridine-1-carboxylate (50.0 mg, 0.0956 mmol), 1-(trans-4-{[tert-butyl(dimethyl)silyl]oxy}cyclohexyl)-5-methyl-4-(4,4,5,5-tetramethyl-1,3,2-dioxaborolan-2-yl)-1H-pyrazole (60.32 mg, 0.1435 mmol), Pd(PPh$_3$)$_4$ (5.526 mg, 0.004782 mmol), K$_2$CO$_3$ (39.66 mg, 0.2869 mmol) and 4:1 dioxane:H$_2$O (2 mL, 20 mmol) was heated to 95° C. for 2 h. The solution was cooled to rt, and 12 M of HCl in H$_2$O (0.079 mL, 0.96 mmol) was added. The reaction mixture was concentrated in vacuo, and partitioned between DCM and sat. NaHCO$_3$. The organic layer was dry-loaded onto silica gel and purified via column chromatography, eluting with 2-4% (7N NH$_3$ in MeOH)/DCM. The fractions containing the pure product were concentrated in vacuo, redissolved in MeOH, and 2.0 M of HCl in Et$_2$O (0.48 mL, 0.96 mmol) was added at rt. The solution was concentrated in vacuo to afford the title compound as an HCl salt. $^1$H NMR (400 MHz, CD$_3$OD): δ=1.45-1.59 (m, 2H), 1.92-2.15 (m, 6H), 2.24 (s, 3H), 3.69 (tt, J=11.0, 4.2 Hz, 1H), 4.20 (tt, J=11.1, 4.5 Hz, 1H), 5.10 (s, 1H), 6.45 (br. s., 1H), 7.09-7.17 (m, 1H), 7.17-7.22 (m, 1H), 7.40 (dd, J=5.2, 1.6 Hz, 2H), 7.48 (s, 1H), 8.14 (d, J=2.0 Hz, 1H). MS (ES+): m/z=522.18/524.19 (100/50) [MH$^+$]. HPLC: t$_R$=1.41 min (polar_3 min, UPLC-ACQUITY).

tert-Butyl 5-bromo-3-[(1S)-1-[2-chloro-6-(difluoromethoxy)-3-fluorophenyl](2,2,2-$^2$H$_3$)ethyl]-1H-pyrrolo[2,3-b]pyridine-1-carboxylate To a solution of tert-butyl 5-bromo-3-[(1S)-1-(2-chloro-3-fluoro-6-hydroxyphenyl)(2,2,2-$^2$H$_3$)ethyl]-1H-pyrrolo[2,3-b]pyridine-1-carboxylate (240.0 mg, 0.5077 mmol), K$_2$CO$_3$ (140.3 mg, 1.015 mmol) and DMF (5 mL, 60 mmol) was added chlorodifluoroacetic acid ethyl ester (0.64 mL, 5.1 mmol), and the reaction was heated to 70° C. for 4 h. The solution was cooled to rt, and extracted with EtOAc. The organic layer was washed with sat. NaHCO$_3$ (2×) and concentrated in vacuo. The material was purified via column chromatography, eluting with 5-10% EtOAc/hexanes. The fractions containing the pure product were concentrated in vacuo to afford the title compound as a white solid. MS (ES+): m/z=522.04/524.04/526.04 (85/100/30) [MH$^+$]. HPLC: t$_R$=1.99 min (polar_3 min, UPLC-ACQUITY).

tert-Butyl 5-bromo-3-[(1S)-1-(2-chloro-3-fluoro-6-hydroxyphenyl)(2,2,2-$^2$H$_3$)ethyl]-1H-pyrrolo[2,3-b]pyridine-1-carboxylate To a solution of 2-[(1S)-1-(5-bromo-1H-pyrrolo[2,3-b]pyridin-3-yl)(2,2,2-$^2$H$_3$)ethyl]-3-chloro-4-fluorophenol (250.0 mg, 0.6709 mmol) in THF at 0° C., sodium hydride (48.30 mg, 2.013 mmol) was added via suspension in THF. A solution of di-tert-butyldicarbonate (585.7 mg, 2.684 mmol) in THF (10 mL, 100 mmol) was added and the reaction was warmed to rt overnight. Sat. NH$_4$Cl was added, and the organic solvent was removed in vacuo. The material was extracted with DCM and sat. NaHCO$_3$. The organic layer was concentrated in vacuo, redissolved in DCM (50 mL, 800 mmol), and piperidine (5 mL, 50 mmol) was added. The reaction was heated to 32° C. overnight to remove the O—BOC group. The solution was extracted with DCM and water, which was titrated using 2M HCl to pH=5. The organic layer was concentrated in vacuo and purified via column chromatography, eluting with 10-20% EtOAc/hexanes. The fractions containing the pure product were concentrated in vacuo to afford the title compound as a white solid. MS (ES+): m/z=472.05/474.06/476.05 (85/100/30) [MH$^+$]. HPLC: t$_R$=1.86 min (polar_3 min, UPLC-ACQUITY).

2-[(1S)-1-(5-Bromo-1H-pyrrolo[2,3-b]pyridin-3-yl)(2,2,2-$^2$H$_3$)ethyl]-3-chloro-4-fluorophenol To a −78° C. solution of 5-bromo-3-[(1S)-1-(2-chloro-3-fluoro-6-methoxyphenyl)(2,2,2-$^2$H$_3$)ethyl]-1H-pyrrolo[2,3-b]pyridine (235.0 mg, 0.6078 mmol) in DCM (5.7 mL, 90 mmol) was added 1.0 M of BBr$_3$ in DCM (3.04 mL, 3.04 mmol) slowly. The solution was allowed to warm to rt overnight. The flask was cooled to 0° C., and the reaction was quenched with MeOH (5 mL) followed by 7N NH$_3$ in MeOH (5 mL). The solvent was removed in vacuo, and the material was extracted with DCM and sat. NaHCO$_3$. The organic layer was concentrated in vacuo to afford the title compound as a white solid. The material was used without further purification. MS (ES+): m/z=413.02/415.02/417.02 (80/100/30) [MH$^+$]. HPLC: t$_R$=1.56 min (polar_3 min, UPLC-ACQUITY).

Example 114 trans-4-(4-{3-[(1S)-1-[2-Chloro-6-(difluoromethoxy)-3-fluorophenyl](1-$^2$H)ethyl]-1H-pyrrolo[2,3-b]pyridin-5-yl}-5-methyl-1H-pyrazol-1-yl)cyclohexanol

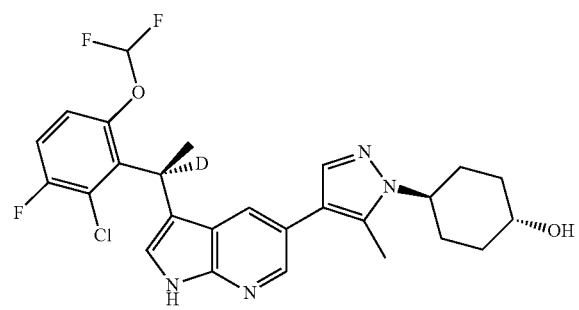 [SMILES: [2H][C@@](C)(c1c(OC(F)F)ccc(F)c1Cl)c1c[nH]c2ncc(-c3cnn([C@H]4CC[C@H](O)CC4)c3C)cc12]

A mixture of tert-butyl 5-bromo-3-[(1S)-1-[2-chloro-6-(difluoromethoxy)-3-fluorophenyl](1-$^2$H)ethyl]-1H-pyrrolo[2,3-b]pyridine-1-carboxylate (50.0 mg, 0.0960 mmol), 1-(trans-4-{[tert-butyl(dimethyl)silyl]oxy}cyclohexyl)-5-methyl-4-(4,4,5,5-tetramethyl-1,3,2-dioxaborolan-2-yl)-1H-pyrazole (60.56 mg, 0.1440 mmol), Pd(PPh$_3$)$_4$ (5.548 mg, 0.004801 mmol), K$_2$CO$_3$ (39.81 mg, 0.2880 mmol) and 4:1 dioxane:H$_2$O (2 mL, 20 mmol) was heated to 95° C. for 2 h. The solution was cooled to rt, and 12 M of HCl in H$_2$O (0.08001 mL, 0.9602 mmol) was added. The reaction mixture was concentrated in vacuo, and the residue was partitioned between DCM and sat. NaHCO$_3$. The organic layer was dry-loaded onto silica gel and purified via column chromatography, eluting with 2-4% (7N NH$_3$ in MeOH)/DCM. The fractions containing the pure product were concentrated in vacuo, redissolved in MeOH, and 2.0 M of HCl in Et$_2$O (0.48 mL, 0.96 mmol) was added at rt. The solution was concentrated in vacuo to afford the title compound as an HCl salt. $^1$H NMR (400 MHz, CD$_3$OD): δ=1.45-1.59 (m, 2H), 1.84 (s, 3H), 1.90-2.15 (m, 6H), 2.23 (s, 3H), 3.69 (tt, J=11.0, 4.1 Hz, 1H), 4.19 (tdd, J=11.1, 11.1, 4.5, 4.3 Hz, 1H), 6.45 (br. s., 1H), 7.08-7.16 (m, 1H), 7.16-7.22 (m, 1H), 7.36-7.44 (m, 2H), 7.48 (s, 1H), 8.14 (d, J=2.0 Hz, 1H). MS (ES+): m/z=520.16/522.17 (100/50) [MH$^+$]. HPLC: t$_R$=1.41 min (polar_3 min, UPLC-ACQUITY).

tert-Butyl 5-bromo-3-[(1S)-1-[2-chloro-6-(difluoromethoxy)-3-fluorophenyl](1-²H)ethyl]-1H-pyrrolo[2,3-b]pyridine-1-carboxylate To a mixture of tert-butyl 5-bromo-3-[(1S)-1-(2-chloro-3-fluoro-6-hydroxyphenyl)(1-²H)ethyl]-1H-pyrrolo[2,3-b]pyridine-1-carboxylate (258.0 mg, 0.5481 mmol), K₂CO₃ (151.5 mg, 1.096 mmol) and DMF (5 mL, 70 mmol) was added chlorodifluoroacetic acid ethyl ester (0.70 mL, 5.5 mmol), and the reaction was heated to 70° C. for 4 h. The solution was cooled to rt, and extracted with EtOAc. The organic layer was washed with sat. NaHCO₃ (2×) and concentrated in vacuo. The material was purified via column chromatography, eluting with 5-10% EtOAc/hexanes. The fractions containing the pure product were concentrated in vacuo to afford the title compound as a white solid. MS (ES+): m/z=520.97/522.97/524.98 (85/100/30) [MH⁺]. HPLC: $t_R$=1.99 min (polar_3 min, UPLC-ACQUITY).

tert-Butyl 5-bromo-3-[(1S)-1-(2-chloro-3-fluoro-6-hydroxyphenyl)(1-²H)ethyl]-1H-pyrrolo[2,3-b]pyridine-1-carboxylate To a solution of 2-[(1S)-1-(5-bromo-1H-pyrrolo[2,3-b]pyridin-3-yl)(1-²H)ethyl]-3-chloro-4-fluorophenol (248.6 mg, 0.6709 mmol) in THF (10 mL, 100 mmol) at 0° C. was added a suspension of sodium hydride (48.30 mg, 2.013 mmol) in THF. A solution of di-tert-butyldicarbonate (585.7 mg, 2.684 mmol) in THF was added and the reaction was warmed to rt overnight. Sat. NH₄Cl was added, and the organic solvent was removed in vacuo. The material was extracted with DCM and sat. NaHCO₃. The organic layer was concentrated in vacuo, redissolved in DCM (50 mL, 800 mmol), and piperidine (4 mL, 40 mmol) was added. The reaction was heated to 32° C. overnight to remove the O—BOC group. The solution was extracted with DCM and water, which was titrated using 2M HCl to pH=5. The organic layer was concentrated in vacuo and purified via column chromatography, eluting with 10-20% EtOAc/hexanes. The fractions containing the pure product were concentrated in vacuo to afford the title compound as a white solid. MS (ES+): m/z=470.03/472.04/474.04 (85/100/30) [MH⁺]. HPLC: $t_R$=1.86 min (polar_3 min, UPLC-ACQUITY).

2-[(1S)-1-(5-Bromo-1H-pyrrolo[2,3-b]pyridin-3-yl)(1-²H)ethyl]-3-chloro-4-fluorophenol To a −78° C. solution of 5-bromo-3-[(1S)-1-(2-chloro-3-fluoro-6-methoxyphenyl)(1-²H)ethyl]-1H-pyrrolo[2,3-b]pyridine (255.0 mg, 0.6629 mmol) in DCM (15 mL, 230 mmol) was added 1.0 M of BBr₃ in DCM (3.3 mL, 3.3 mmol) slowly. The solution was allowed to warm to rt overnight. The flask was cooled to 0° C., and the reaction was quenched with MeOH (5 mL) followed by 7N NH₃ in MeOH (5 mL). The solvent was removed in vacuo, and the material was extracted with DCM and sat. NaHCO₃. The organic layer was concentrated in vacuo to afford the title compound as a white solid. The material was used without further purification. MS (ES+): m/z=369.98/371.98/373.98 (85/100/30) [MH⁺]. HPLC: $t_R$=1.56 min (polar_3 min, UPLC-ACQUITY).

5-Bromo-3-[(1S)-1-(2-chloro-3-fluoro-6-methoxyphenyl)(1-²H)ethyl]-1H-pyrrolo[2,3-b]pyridine Racemic 5-bromo-3-[1-(2-chloro-3-fluoro-6-methoxyphenyl)(1-²H)ethyl]-1H-pyrrolo[2,3-b]pyridine was prepared as described for the non-deuterated compound, except that in the first step of the sequence the lithiated 3-chloro-4-fluoroanisole was reacted with DMF-d, instead of methyl formate. The racemic mixture was separated into the enantiomers by SFC on a chiral stationary phase. Analytical SFC for the (1S)enantiomer (ChiralPak IA 4.6×100 mm I.D., solvent 90:10 scCO₂/methanol isocratic, flow rate 4.0 mL/min, UV detection at 254 nm): $t_R$=3.8 min.

Example 115

3-Chloro-6-fluoro-2-(1-{5-[1-(trans-4-hydroxycyclohexyl)-5-methyl-1H-pyrazol-4-yl]-1H-pyrrolo[2,3-b]pyridin-3-yl}ethyl)-phenol

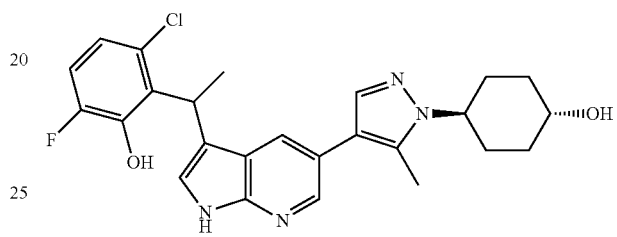

A mixture of 5-Bromo-3-[1-(6-chloro-3-fluoro-2-hydroxyphenyl)ethyl]pyrrolo[2,3-b]pyridine-1-carboxylic acid tert-butyl ester (100.00 mg, 0.21289 mmol), 1-(trans-4-{[tert-butyl(dimethyl)silyl]oxy}cyclohexyl)-5-methyl-4-(4,4,5,5-tetramethyl-1,3,2-dioxaborolan-2-yl)-1H-pyrazole (134 mg, 0.319 mmol), Pd(PPh₃)₄ (12.3 mg, 0.0106 mmol), potassium carbonate (147.1 mg, 1.064 mmol) and 4:1 Dioxane:water (4:1,1,4-Dioxane:H₂O, 8 mL, 80 mmol) was heated in a microwave reactor at 100° C. for 30 min. Reaction mixture was cooled to rt, 12 M HCl in H₂O (0.8 mL, 10 mmol) was added, and the solution was heated at 40° C. for 2 h. Purification by Teledyne/ISCO eluting with 0-15% MeOH in DCM afforded the title compound as a white solid. ¹H NMR (400 MHz, CD₃OD): δ=1.37-1.59 (m, 2H), 1.84 (d, J=7.3 Hz, 3H), 1.89-2.14 (m, 6H), 2.16-2.27 (m, 3H), 3.68 (ddd, J=10.9, 6.8, 4.3 Hz, 1H), 4.08-4.26 (m, 1H), 5.09 (br. s., 1H), 6.76-6.88 (m, 1H), 6.90-7.00 (m, 1H), 7.37 (d, J=1.3 Hz, 1H), 7.44-7.56 (m, 2H), 8.09 (d, J=2.0 Hz, 1H).

5-Bromo-3-[1-(6-chloro-3-fluoro-2-hydroxyphenyl)ethyl]pyrrolo[2,3-b]pyridine-1-carboxylic acid tert-butyl ester The title compound was prepared from 5-bromo-3-[1-(6-chloro-3-fluoro-2-methoxyphenyl)ethyl]-1H-pyrrolo[2,3-b]pyridine following the procedures described for the preparation of 5-Bromo-3-[1-(2-chloro-3-fluoro-6-hydroxyphenyl)ethyl]pyrrolo[2,3-b]pyridine-1-carboxylic acid tert-butyl ester from 5-bromo-3-[1-(2-chloro-3-fluoro-6-methoxyphenyl)ethyl]-1H-pyrrolo[2,3-b]pyridine. ¹H NMR (CDCl₃, 300 MHz): δ=8.42 (d, J=2.1 Hz, 1H), 7.62-7.59 (m, 2H), 6.97-6.93 (m, 2H), 5.37 (d, J=5.1 Hz, 1H), 4.87 (q, J=7.2 Hz, 1H), 1.79 (d, J=7.2 Hz, 3H), 1.68 (s, 9H).

Example 116 trans-4-(4-{3-[1-(2,6-Dichloro-3-fluorophenyl)-2-fluoroethyl]-1H-pyrrolo[2,3-b]pyridin-5-yl}-5-methyl-1H-pyrazol-1-yl)cyclohexanol

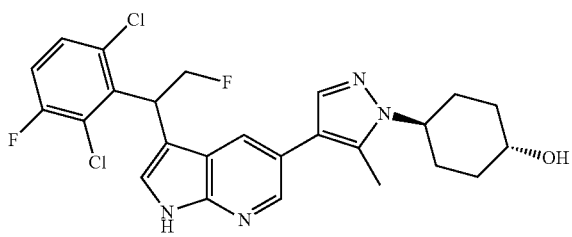 [SMILES: Cc1c(-c2cnc3[nH]cc(C(CF)c4c(Cl)ccc(F)c4Cl)c3c2)cnn1[C@H]1CC[C@H](O)CC1]

To a mixture of 5-[1-(trans-4-{[tert-butyl(dimethyl)silyl]oxy}cyclohexyl)-5-methyl-1H-pyrazol-4-yl]-3-[1-(2,6-dichloro-3-fluorophenyl)-2-fluoro-2,2-bis(phenylsulfonyl)ethyl]-1H-pyrrolo[2,3-b]pyridine (30.00 mg, 0.03333 mmol) and Disodium hydrogen phosphate (94.64 mg, 0.6667 mmol) in methanol (5.00 mL, 123 mmol) and THF (0.300 mL, 3.70 mmol) at −20° C. was added Sodium Mercury Amalgam (5% sodium; 0.28 g, 0.67 mmol). The resulting mixture was stirred between −15° C. and −5° C. for 1.5 h. The mixture was transferred into another flask by filtration to remove the inorganic insolubles. Sat. aq. solution of NH$_4$Cl (2 ml) was added to the MeOH mixture, then the solvent was removed under reduced pressure to give a residue, which was diluted by DCM and extracted by DCM (20 mL×3). The organic phase were combined, dried and concentrated to give a desulfonylated intermediate [MS (ES+): m/z 619.23, 621.23 [MH$^+$]. HPLC: t$_R$=2.02 min (polar_3 min, TOF)]. This intermediate was dissolved in THF (0.3 mL) at 0° C., 2.0 M aq. HCl (0.50 mL, 1.0 mmol) was added, and the resulting mixture was stirred at rt for 30 min. NaHCO$_3$ (112.0 mg, 1.333 mmol) was added to the mixture slowly to adjust pH=≈9. Then the solvent was removed under reduced pressure to give a residue, which was diluted by DCM and extracted by DCM (20 mL×3). The organic phase were combined, dried and concentrated to give a crude residue which was purified by silica gel chromatography (eluent: 5% MeOH in DCM) to give the title compound. $^1$H NMR (400 MHz, CD$_3$OD): δ=1.48-1.60 (m, 2H), 1.94-2.16 (m, 6H), 2.26 (s, 3H), 3.63-3.77 (m, 1H), 4.15-4.28 (m, 1H), 5.20-5.54 (m, 2H), 5.62-5.75 (m, 1H), 7.28 (t, J=8.6 Hz, 1H), 7.35-7.64 (m, 4H), 8.20 (d, J=2.0 Hz, 1H). MS (ES+): m/z 505.06, 507.07 [MH$^+$]. HPLC: t$_R$=1.33 min (polar_3 min, TOF).

5-[1-(trans-4-{[tert-Butyl(dimethyl)silyl]oxy}cyclohexyl)-5-methyl-1H-pyrazol-4-yl]-3-[1-(2,6-dichloro-3-fluorophenyl)-2-fluoro-2,2-bis(phenylsulfonyl)ethyl]-1H-pyrrolo[2,3-b]pyridine To a mixture of 1-(trans-4-{[tert-butyl(dimethyl)silyl]oxy}cyclohexyl)-5-methyl-4-(4,4,5,5-tetramethyl-1,3,2-dioxaborolan-2-yl)-1H-pyrazole (202.16 mg, 0.48079 mmol), Potassium fluoride (76.18 mg, 1.311 mmol) and 3-[2,2-Bis-benzenesulfonyl-1-(2,6-dichloro-3-fluoro-phenyl)-2-fluoroethyl]-5-bromo-1H-pyrrolo[2,3-b]pyridine (300.00 mg, 0.43708 mmol) in 1,4-Dioxane (10.00 mL, 128.1 mmol) and H$_2$O (2.500 mL, 138.8 mmol) was added (1,1'-bis-(diphenylphosphino)-ferrocene) palladium dichloride (15.99 mg, 0.02185 mmol) under Nitrogen atmosphere, the resulting mixture was then stirred at 90° C. for 90 min. Then the solvent was removed under reduced pressure to give a residue, which was purified by silica gel chromatography (eluent: 20-30% AcOEt in DCM) to give the title compound. MS (ES+): m/z 899.20, 901.21 [MH$^+$]. HPLC: t$_R$=1.98 min (polar_3 min, TOF).

3-[2,2-Bis-benzenesulfonyl-1-(2,6-dichloro-3-fluorophenyl)-2-fluoroethyl]-5-bromo-1H-pyrrolo[2,3-b]pyridine To a stirred solution of 1-(fluoro(phenylsulfonyl)methylsulfonyl)benzene (836 mg, 2.66 mmol) in THF (8.0 mL) was added 2.5 M of n-BuLi in Hexane (1.18 mL, 2.95 mmol) at −78° C.; the resulting mixture was stirred for 30 min at −78° C. before use. To a stirred solution of (5-bromo-1H-pyrrolo[2,3-b]pyridin-3-yl)-(2,6-dichloro-3-fluorophenyl)methanol (250.0 mg, 0.6410 mmol) in THF (5.0 mL, 62 mmol) was added thionyl chloride (0.12 mL, 1.6 mmol) at 0° C. The resulting mixture was stirred for 30 min at rt, then the solvent was removed and the residue was dried under high vacuum. To this residue was added THF (10.0 mL) followed by adding the previously prepared solution (lithiated 1-(fluoro(phenylsulfonyl)methylsulfonyl)benzene) by canula at −78° C. The resulting mixture was allowed to warm up to rt in about 1 hr. Then the solvent was removed under reduced pressure to give a residue, which was diluted by DCM and extracted by DCM (20 mL×3). The organic phase were combined, dried (Na$_2$SO$_4$) and concentrated to give a crude residue, which was purified by silica gel chromatography (eluent: 20% AcOEt in DCM) to give the title compound. MS (ES+): m/z 684.92, 686.92, 688.92 [MH$^+$]. HPLC: t$_R$=1.65 min (polar_3 min, TOF)

Examples 117 & 118 trans-4-(4-{3-[(1R)-1-(2,6-dichloro-3-fluorophenyl)-2-fluoroethyl]-1H-pyrrolo[2,3-b]pyridin-5-yl}-5-methyl-1H-pyrazol-1-yl)cyclohexanol and trans-4-(4-{3-[(1S)-1-(2,6-Dichloro-3-fluorophenyl)-2-fluoroethyl]-1H-pyrrolo[2,3-b]pyridin-5-yl}-5-methyl-1H-pyrazol-1-yl)cyclohexanol

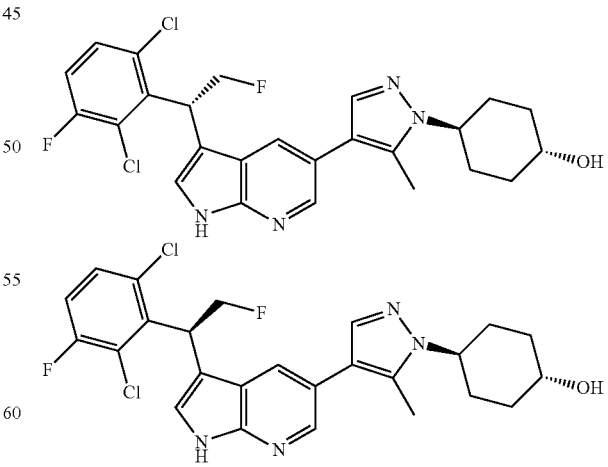

The racemic compound of Example 116 was subjected to chiral SFC separation to give two enantiomers. Preparative SFC (ChiralPak IA 21×250 mm I.D., solvent 50:50 scCO$_2$/methanol (0.1% isopropylamine) isocratic, flow rate 30 mL/min, UV detection at 254 nm): $t_R$=13.1 min [(1R) enantiomer=Example 117]; $t_R$=18.5 min [(1S) enantiomer=Example 118]. ¹HNMR and LC-MS data for both enantiomers are identical to the data obtained from the racemic mixture. Analytical SFC (ChiralPak IA 4.6×100 mm I.D., solvent 70:30 scCO$_2$/methanol (0.2% isopropylamine) isocratic, flow rate 4.0 mL/min, UV detection at 254 nm): $t_R$=1.8 min [(1R)enantiomer=Example 117]; $t_R$=3.2 min [(1S)enantiomer=Example 118].

Example 119 trans-4-(4-{3-[1-(2-Chloro-3-fluoro-6-methoxyphenyl)-2-fluoroethyl]-1H-pyrrolo[2,3-b]pyridin-5-yl}-5-methyl-1H-pyrazol-1-yl)cyclohexanol

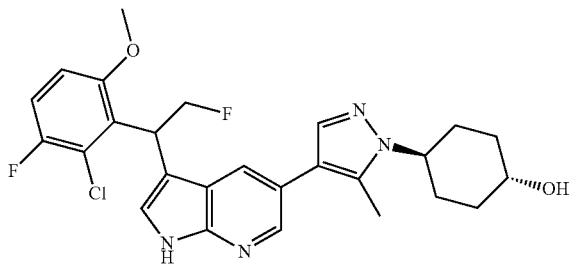

The title compound was prepared following the procedures for Example 116, starting from (5-bromo-1H-pyrrolo[2,3-b]pyridin-3-yl)-(2-chloro-3-fluoro-6-methoxyphenyl)methanol. ¹H NMR (400 MHz, CD$_3$OD): δ=1.46-1.60 (m, 2H), 1.94-2.17 (m, 6H), 2.31 (s, 3H), 3.65-3.71 (m, 1H), 3.74 (s, 3H), 4.15-4.27 (m, 1H), 5.02-5.35 (m, 2H), 5.35-5.45 (m, 1H), 6.94 (dd, J=9.1, 4.3 Hz, 1H), 7.14 (t, J=8.8 Hz, 1H), 7.34 (s, 1H), 7.53 (s, 1H), 7.70 (s, 1H), 8.17 (s, 1H). MS (ES+): m/z 501.11, 503.13 [MH⁺]. HPLC: $t_R$=1.30 min (polar_3 min, TOF).

Examples 120 & 121 trans-4-(4-{3-[(1R)-1-(2-Chloro-3-fluoro-6-methoxyphenyl)-2-fluoroethyl]-1H-pyrrolo[2,3-b]pyridin-5-yl}-5-methyl-1H-pyrazol-1-yl)cyclohexanol and trans-4-(4-{3-[(1S)-1-(2-Chloro-3-fluoro-6-methoxyphenyl)-2-fluoroethyl]-1H-pyrrolo[2,3-b]pyridin-5-yl}-5-methyl-1H-pyrazol-1-yl)cyclohexanol

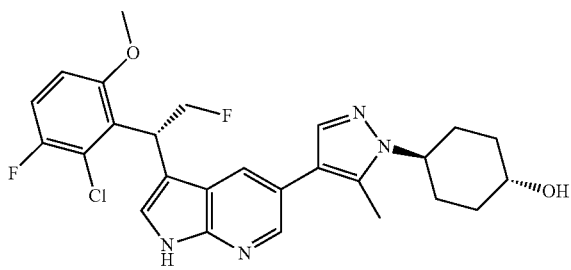 [SMILES: COc1ccc(F)c(Cl)c1C(CF)c1c[nH]c2ncc(-c3cnn([C@H]4CC[C@H](O)CC4)c3C)cc12]

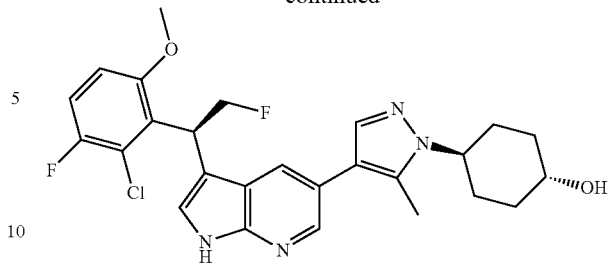

The racemic compound of Example 119 was subjected to chiral SFC separation to give two enantiomers. Preparative SFC (ChiralPak IA 21×250 mm I.D., solvent 45:55 scCO$_2$/methanol (0.2% isopropylamine) isocratic, flow rate 30 mL/min, UV detection at 254 nm): $t_R$=9.4 min [(1R) enantiomer=Example 120]; $t_R$=11.4 min [(1S) enantiomer=Example 121]. ¹HNMR and LC-MS data for both enantiomers are identical to the data obtained from the racemic mixture. Analytical SFC (ChiralPak IA 4.6×100 mm I.D., solvent 70:30 scCO$_2$/methanol (0.2% isopropylamine) isocratic, flow rate 4.0 mL/min, UV detection at 254 nm): $t_R$=1.5 min [(1R)enantiomer=Example 120]; $t_R$=2.1 min [(1S)enantiomer=Example 121].

Example 122 trans-4-[4-(3-{1-[2-Chloro-6-(difluoromethoxy)-3-fluorophenyl]-2-fluoroethyl}-1H-pyrrolo[2,3-b]pyridin-5-yl)-5-methyl-1H-pyrazol-1-yl]cyclohexanol

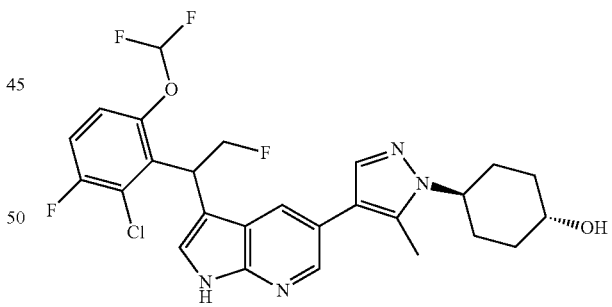

The title compound was prepared following the procedures for Example 116, starting from (5-bromo-1H-pyrrolo[2,3-b]pyridin-3-yl)-(2-chloro-6-difluoromethoxy-3-fluorophenyl)-methanol. ¹H NMR (400 MHz, CD$_3$OD): δ=1.46-1.62 (m, 2H), 1.92-2.16 (m, 6H), 2.31 (s, 3H), 3.63-3.77 (m, 1H), 4.16-4.30 (m, 1H), 5.09-5.40 (m, 2H), 5.48 (dt, J=14.7, 7.1 Hz, 1H), 6.65 (t, J=73.5 Hz, 1H), 7.18-7.24 (m, 1H), 7.25-7.33 (m, 1H), 7.39 (s, 1H), 7.53 (s, 1H), 7.63 (d, J=1.8 Hz, 1H), 8.19 (d, J=2.0 Hz, 1H). MS (ES+): m/z 537.15, 539.16 [MH⁺]. HPLC: $t_R$=1.36 min (polar_3 min, TOF).

Examples 123 & 124 trans-4-[4-(3-{(1R)-1-[2-chloro-6-(difluoromethoxy)-3-fluorophenyl]-2-fluoroethyl}-1H-pyrrolo[2,3-b]pyridin-5-yl)-5-methyl-1H-pyrazol-1-yl]cyclohexanol and trans-4-[4-(3-{(1S)-1-[2-chloro-6-(difluoromethoxy)-3-fluorophenyl]-2-fluoroethyl}-1H-pyrrolo[2,3-b]pyridin-5-yl)-5-methyl-1H-pyrazol-1-yl]cyclohexanol

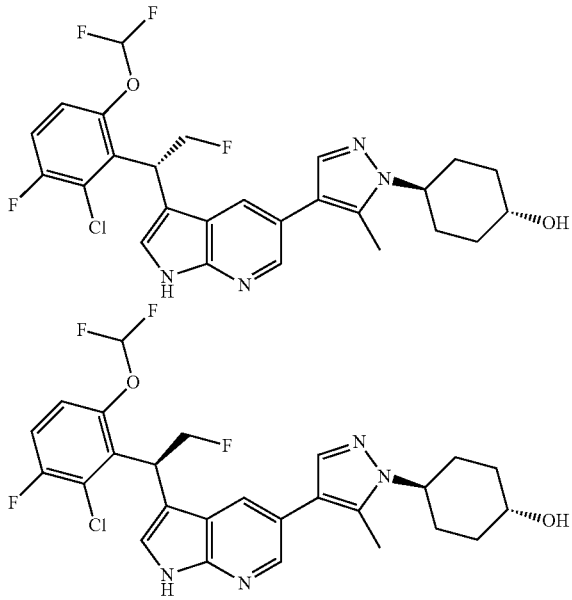

The racemic compound of Example 122 was subjected to chiral SFC separation to give two enantiomers. Preparative SFC (ChiralPak IA 21×250 mm I.D., solvent 60:40 scCO$_2$/isopropanol (0.2% isopropylamine) isocratic, flow rate 30 mL/min, UV detection at 254 nm): $t_R$=21.6 min [(1R) enantiomer=Example 123]; $t_R$=29.8 min [(1S) enantiomer=Example 124]. $^1$HNMR and LC-MS data for both enantiomers are identical to the data obtained from the racemic mixture. Analytical SFC (ChiralPak IA 4.6×100 mm I.D., solvent 80:20 scCO$_2$/isopropanol (0.2% isopropylamine) isocratic, flow rate 4.0 mL/min, UV detection at 254 nm): $t_R$=4.9 min [(1R)enantiomer=Example 123]; $t_R$=7.1 min [(1S)enantiomer=Example 124].

Example 125

1-[5-(3-{(1S)-1-[2-Chloro-6-(difluoromethoxy)-3-fluorophenyl]ethyl}-1H-pyrrolo[2,3-b]pyridin-5-yl)-1-methyl-1H-imidazol-2-yl]piperidin-4-ol

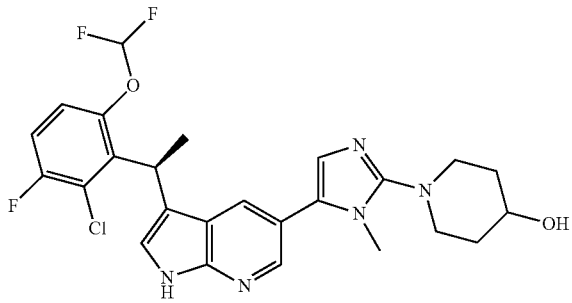 [SMILES: C[C@H](c1c(OC(F)F)ccc(F)c1Cl)c1c[nH]c2ncc(-c3cnc(N4CCC(O)CC4)n3C)cc12]

Prepared using the procedure described for Example 69, except that the heptane solution from the preparation of the boronate was used instead of the isolated boronate. The title compound was obtained as a light beige solid. MS (ES+): m/z=520.19/522.15 (100/53) [MH$^+$]. HPLC: $t_R$=2.13 min (nonpolar_5 min, ZQ3).

4-{[tert-Butyl(dimethyl)silyl]oxy}-1-[1-methyl-5-(4,4,5,5-tetramethyl-1,3,2-dioxaborolan-2-yl)-1H-imidazol-2-yl]piperidine A mixture of 4-{[tert-Butyl(dimethyl)silyl]oxy}-1-(1-methyl-1H-imidazol-2-yl)piperidine (0.100 g, 0.340 mmol), [Ir(OMe)(COD)]$_2$ (8.2 mg, 0.012 mmol), 4,4'-Di-tert-butyl-[2,2']bipyridinyl (4.9 mg, 0.018 mmol), and bis(pinacolato)diboron (88.0 mg, 0.346 mmol) in a microwave vial was taken up in Heptane (1.0 mL, 6.8 mmol). The mixture was flushed with nitrogen, sealed and heated in a microwave reactor to 100° C. for 30 min. LC/MS of the reaction mixture indicated clean and complete conversion of the imidazole starting material to the boronate. The title compound was not isolated; instead, the heptane solution was directly used in the next step. MS (ES+): m/z=339.34/340.26/341.31 (48/100/50) [MH$^+$]. HPLC: $t_R$=2.44 min (nonpolar_5 min, ZQ3). UV: $\lambda_{max}$≈240 nm.

4-{[tert-Butyl(dimethyl)silyl]oxy}-1-(1-methyl-1H-imidazol-2-yl)piperidine

A mixture of 1-(1-Methyl-1H-imidazol-2-yl)piperidin-4-ol (0.200 g, 1.10 mmol), tert-Butyldimethylsilyl chloride (0.333 g, 2.21 mmol), 4-Dimethylaminopyridine (30 mg, 0.2 mmol), 1H-Imidazole (225 mg, 3.31 mmol) and DCM (6.0 mL, 94 mmol) was stirred at ambient temperature for 1 h. The reaction mixture was diluted with DCM to ≈60 mL, washed with sat. NaHCO$_3$ solution, water, and brine, dried over Na$_2$SO$_4$, filtered, and concentrated in vacuo. The residue was chromatographed on silica gel [Isco Combiflash, 2.5 g loading column/12 g column, eluting with DCM→5% MeOH in DCM]. Fractions containing the title compound were combined and dried in vacuo overnight, giving the title compound as yellow oil. $^1$H NMR (400 MHz, CDCl$_3$): δ=6.77 (d, J=1.2 Hz, 1H), 6.65 (d, J=1.4 Hz, 1H), 3.85 (tt, J=8.0, 3.8 Hz, 1H), 3.47 (s, 3H), 3.28-3.21 (m, 2H), 2.91 (br ddd, J=12.0, 9.0, 3.0 Hz, 2H), 1.92-1.84 (m, 2H), 1.73-1.64 (m, 2H), 0.90 (s, 9H), 0.07 (s, 6H). MS (ES+): m/z=296.29 (100) [MH$^+$]. HPLC: $t_R$=3.22 min (verypolar_5 min, ZQ3). UV: $\lambda_{max}$≈240 nm.

1-(1-Methyl-1H-imidazol-2-yl)piperidin-4-ol

A mixture of N-methyl-2-bromoimidazole (7.3 g, 45.3 mmol) and 4-hydroxypiperidine (11.4 g, 113 mmol, 2.5 eq) was stirred at 140° C. for 16 h. After cooling to room temperature, the reaction mixture was diluted with 10% aq. NaOH solution to pH 12. The organic layer was separated and the aqueous layer was extracted with ethyl acetate (2×25 mL). The combined organic layers were washed with water (20 mL) followed by brine (20 mL), dried over sodium sulfate, filtered, and evaporated under vacuum. The solid residue was purified by column chromatography by eluting with 5% to 20% methanol in dichloromethane to yield the title compound as yellow solid. $^1$H NMR (CDCl$_3$, 300 MHz): δ=6.64 (d, J=0.9 Hz, 1H), 6.75 (d, J=0.9 Hz, 1H), 3.85-3.84 (m, 1H), 3.47 (s, 3H), 3.24-3.22 (m, 2H), 2.94-2.92 (m, 2H), 2.01-1.98

(m, 2H), 1.71-1.69 (m, 2H). MS (ES+): m/z=182.28 (100) [MH+]. HPLC: $t_R$=0.74 & 1.13 min (verypolar__5 min, ZQ3).

Example 126 trans-4-[5-(3-{(1S)-1-[2-Chloro-6-(difluoromethoxy)-3-fluorophenyl]ethyl}-1H-pyrrolo[2,3-b]pyridin-5-yl)-1-methyl-1H-imidazol-2-yl]cyclohexanol

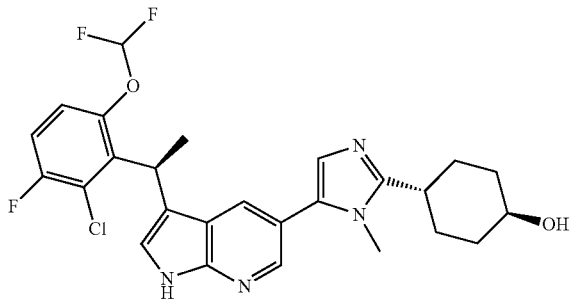 [SMILES: C[C@H](c1c(OC(F)F)ccc(F)c1Cl)c1c[nH]c2ncc(-c3cnc([C@H]4CC[C@H](O)CC4)n3C)cc12]

Prepared using the procedure described for Example 69, except that the heptane solution from the preparation of the boronate was used instead of the isolated boronate. The title compound was obtained as a light beige solid. MS (ES+): m/z=519.14/521.12 (100/51) [MH+]. HPLC: $t_R$=2.10 min (nonpolar__5 min, ZQ3).

2-(trans-4-{[tert-Butyl(dimethyl)silyl]oxy}cyclohexyl)-1-methyl-5-(4,4,5,5-tetramethyl-1,3,2-dioxaborolan-2-yl)-1H-imidazole A mixture of 2-(trans-4-{[tert-Butyl(dimethyl)silyl]oxy}cyclohexyl)-1-methyl-1H-imidazole (0.157 g, 0.533 mmol), [Ir(OMe)(COD)]$_2$ (13 mg, 0.019 mmol), 4,4'-Di-tert-butyl-[2,2']bipyridinyl (7.7 mg, 0.029 mmol), and bis(pinacolato)diboron (138 mg, 0.544 mmol) in a microwave vial was taken up in Heptane (1.5 mL, 10 mmol). The mixture was flushed with nitrogen, sealed and heated in a microwave reactor to 100° C. for 30 min. LC/MS of the reaction mixture indicated clean and complete conversion of the imidazole starting material to the boronate. The title compound was not isolated; instead, the heptane solution was directly used in the next step. MS (ES+): m/z=338.30/339.24/340.31 (48/100/51) [MH+]. HPLC: $t_R$=2.40 min (nonpolar__5 min, ZQ3). UV: $\lambda_{max}$≈220 nm.

2-(trans-4-{[tert-Butyl(dimethyl)silyl]oxy}cyclohexyl)-1-methyl-1H-imidazole

A mixture of trans-4-(1-Methyl-1H-imidazol-2-yl)cyclohexanol (0.106 g, 0.588 mmol), tert-Butyldimethylsilyl chloride (0.177 g, 1.18 mmol), 4-Dimethylaminopyridine (10 mg, 0.1 mmol), 1H-Imidazole (120 mg, 1.76 mmol) and DCM (3.0 mL, 47 mmol) was stirred at ambient temperature for 1.5 h. The reaction mixture was diluted with DCM to ≈60 mL, washed with sat. NaHCO$_3$ solution, water, and brine, dried over Na$_2$SO$_4$, filtered, and concentrated in vacuo. The residue was chromatographed on silica gel [Isco Combiflash, 2.5 g loading column/12 g column, eluting with DCM→4.9% MeOH in DCM]. Fractions containing the title compound were combined and dried in vacuo overnight, giving the title compound as yellow oil. $^1$H NMR (CDCl$_3$, 400 MHz): δ=6.97 (brs, 1H), 6.78 (s, 1H), 3.69 (tt, J=10.6, 4.0 Hz, 1H), 3.61 (s, 3H), 2.60 (tt, J=11.8, 3.2 Hz, 1H), 2.04-1.96 (m, 2H), 1.95-1.87 (m, 2H), 1.87-1.72 (brm, 2H), 1.47-1.36 (m, 2H), 0.89 (s, 9H), 0.07 (s, 6H). MS (ES+): m/z=295.24 (100) [MH+]. HPLC: $t_R$=3.20 min (verypolar__5 min, ZQ3). UV: $\lambda_{max}$=216 nm.

trans-4-(1-Methyl-1H-imidazol-2-yl)cyclohexanol

A mixture of trans-N-(2,2-Dimethoxyethyl)-4-hydroxy-N-methylcyclohexanecarboxamide (265 mg, 1.08 mmol) and Ammonium acetate (2.2 g, 29 mmol) in AcOH (3.0 mL, 53 mmol) was heated to reflux (oil bath temperature 125° C.) for 16.5 h. To the cooled solution were added 10 N NaOH (≈10 mL) and water (≈10 mL), and the mixture was extracted with DCM (3×20 mL). The combined DCM extracts were washed with brine, dried over MgSO$_4$, filtered, and concentrated to give the title compound as light orange solid. Additional material was obtained by saturating the aqueous layer from the previous extractions with NaCl and extracting with more DCM (4×25 mL). The light orange solid was chromatographed on silica gel [Isco Combiflash, 2.5 g loading column/4 g Gold column, eluting with DCM→10% 7N NH$_3$ in MeOH] to give the title compound as yellow solid. $^1$H NMR (400 MHz, CDCl$_3$): δ=6.92 (d, J=1.4 Hz, 1H), 6.77 (d, J=1.4 Hz, 1H), 3.73 (tt, J=10.8, 4.2 Hz, 1H), 3.60 (s, 3H), 2.60 (tt, J=12.0, 3.6 Hz, 1H), 2.18-2.08 (m, 2H), 1.99-1.91 (m, 2H), 1.88 (brs, 1H), 1.83-1.71 (m, 2H), 1.46-1.35 (m, 2H). MS (ES+): m/z=181.13 (100) [MH+]. HPLC: $t_R$=0.69 min (very polar__5 min, ZQ3). UV: $\lambda_{max}$=216 nm.

trans-N-(2,2-Dimethoxyethyl)-4-hydroxy-N-methylcyclohexanecarboxamide

To a solution of trans-4-hydroxycyclohexanecarboxylic acid (1.00 g, 6.94 mmol), 2,2-dimethoxy-N-methylethanamine (0.909 g, 7.63 mmol), and 1-Hydroxybenzotriazole hydrate (1.17 g, 7.63 mmol) in DMF (25 mL, 320 mmol) was added N-(3-Dimethylaminopropyl)-W-ethylcarbodiimide hydrochloride (1.46 g, 7.63 mmol) at ambient temperature, and the solution was stirred at ambient temperature overnight. Most of the DMF was evaporated in vacuo, and the residue was partitioned between water and EtOAc. The layers were separated, and the aqueous layer was extracted with EtOAc (4×25 mL), saturated with NaCl, and extracted again with EtOAc (5×25 mL). The combined EtOAc extracts were washed with brine, dried over MgSO$_4$, filtered, and concentrated in vacuo to give the title compound as yellow oil that was used without further purification in the next step. $^1$H NMR (400 MHz, CDCl$_3$): δ=4.48 (t, J=5.4 Hz, 1H, major rotamer), 4.39 (t, J=5.4 Hz, 1H, minor rotamer), 3.70-3.61 (m, 1H), 3.45-3.42 (m, 2H), 3.43 (s, 6H, minor rotamer), 3.40 (s, 6H, major rotamer), 3.11 (s, 3H, major rotamer), 2.97 (s, 3H, minor rotamer), 2.56 (tt, J=11.6, 3.8 Hz, 1H, minor rotamer), 2.46 (tt, J=11.8, 3.4 Hz, 1H, major rotamer), 2.11-2.00 (m, 2H), 1.86-1.74 (m, 2H), 1.71-1.55 (m, 3H), 1.36-1.23 (m, 2H). MS (ES+): m/z=268.11 (87) [MNa+], 246.15 (42) [MH+], 214.13 (100) [MH+−MeOH]. HPLC: $t_R$=2.36 min (polar__5 min, ZQ3).

Example 127

(2R)-3-(3-Chloro-2-{(1S)-1-[5-(1,5-dimethyl-1H-pyrazol-4-yl)-1H-pyrrolo[2,3-b]pyridin-3-yl]ethyl}-4-fluorophenoxy)propane-1,2-diol

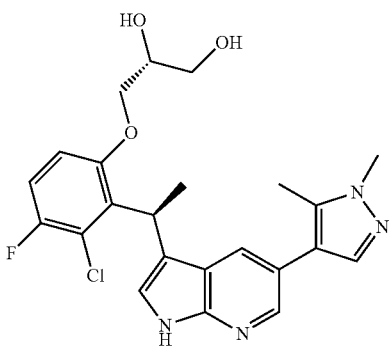 [SMILES: Cc1c(-c2cnc3[nH]cc([C@H](C)c4c(OC[C@H](O)CO)ccc(F)c4Cl)c3c2)cnn1C]

Prepared using the procedure described for Example 69. $^1$H NMR (400 MHz, CD$_3$OD): δ=1.82 (d, J=7.1 Hz, 3H), 2.18 (s, 3H), 3.46-3.57 (m, 2H), 3.58-3.77 (m, 2H), 3.81 (s, 3H), 3.95 (br. s., 1H), 5.13 (q, J=6.7 Hz, 1H), 6.85-6.95 (m, 1H), 7.08 (t, J=8.8 Hz, 1H), 7.33 (s, 1H), 7.38 (s, 1H), 7.43 (s, 1H), 8.11 (br. s., 1H). MS (ES+): m/z=459.16/461.15 (100/50) [MH$^+$]. HPLC: t$_R$=1.23 min (polar__3 min, UPLC-ACQUITY).

tert-Butyl-5-bromo-3-[(1S)-1-(2-chloro-6-{[(4S)-2,2-dimethyl-1,3-dioxolan-4-yl]methoxy}-3-fluorophenyl)ethyl]-1H-pyrrolo[2,3-b]pyridine-1-carboxylate A suspension of tert-butyl 5-bromo-3-[(1S)-1-(2-chloro-3-fluoro-6-hydroxyphenyl)ethyl]-1H-pyrrolo[2,3-b]pyridine-1-carboxylate (82.9 mg, 0.176 mmol), (R)-(−)-(2,2-dimethyl-1,3-dioxolan-4-yl)methyl p-toluenesulfonate (77.8 mg, 0.272 mmol), and potassium carbonate (102.5 mg, 0.7416 mmol) in DMF (3 mL) was subjected to microwave heating [Biotage, 110° C.] for 90 min. EtOAc was added to dilute the reaction mixture and a standard aqueous workup was performed. The combined organic layers were washed with brine, dried over anhydrous Na$_2$SO$_4$, filtered, and concentrated in vacuo. The crude was adsorbed onto a pre-filled silica gel loading cartridge [RediSepRf 5 g] and purified using the Teledyne/ISCO system [RediSepRf silica 12 gram GOLD column], eluting with a solvent system of 5-20% EtOAc:heptane. Fractions containing product were combined and concentrated in vacuo. The recovered material was dissolved in minimal MeOH, passed through a syringe filter, and purified a second time by MDP, under acidic conditions (formic acid). Fractions were combined and concentrated in vacuo, giving the title material as an off-white solid. $^1$H NMR (400 MHz, CDCl$_3$): δ=8.42 (d, J=2.3 Hz, 1H), 7.50 (d, J=1.5 Hz, 1H), 7.47 (d, J=2.3 Hz, 1H), 7.01 (dd, J=9.1, 8.3 Hz, 1H), 6.70 (dd, J=9.1, 4.0 Hz, 1H), 4.91 (q, J=6.8 Hz, 1H), 4.01-4.18 (m, 2H), 3.81-3.89 (m, 1H), 3.78 (dd, J=7.7, 4.9 Hz, 1H), 3.73 (br s, 1H), 1.73 (d, J=7.1 Hz, 3H), 1.68 (s, 9H), 1.34 (d, J=14.9 Hz, 6H). MS (ES$^+$): m/z 604.96/606.80/608.57 (21/100/24) [MH$^+$+Na]. HPLC: t$_R$=4.13 min (ZQ3, nonpolar__5 min).

BIOLOGICAL DATA

The cellular activity of the compounds of the present invention against c-MET may be determined by the following procedure. MKN45 cells were plated in Falcon 3072 96-well plates in growth media (RPMI, 10% FBS, 1% L-glutamine) at a density of 5000 cells/well and incubated at 37° C., 5% CO$_2$ overnight. The following day, one-tenth volume of a 10× concentration of compounds was added to the wells in a 6-point dilution series. The dilutions series was composed of an initial 1:5 dilution in DMSO, followed by a 1:10 dilution in growth media, for a final DMSO concentration on cells of 0.5%. Control wells were treated with 0.5% DMSO. The typical range of dilution was 10 μM to 3 nM. Once compound was added to the cells, plates were incubated for 4 hours at 37° C., 5% CO$_2$. Plates were then washed in PBS, and lysed in triton-based lysis buffer. Lysates were transferred to a pre-coated capture plate made by Biosource (Cat # KHO0281). The phosphorylated MET levels were measured by incubating with a rabbit polyclonal antibody against phosphorylated MET ([pYpYpY1230/1234/1235]) followed by an anti-rabbit antibody conjugated to HRP. Signal was measured on a Wallac Victor plate reader at 450 nm. The DMSO signal of the control wells was defined as 100% and the percent of inhibition of phosphorylated MET was expressed as percent of control. IC$_{50}$ values were determined from the percent of control data using a standard four-parameter model.

The IC$_{50}$ values of exemplary compounds of the present invention determined in a MET cell mechanistic assay using the MKN45 cell line according to the procedures described herein in at least duplicate experiments are abbreviated as follows and are shown in Table 1: A, IC$_{50}$≦0.05 μM; B, 0.05 μM<IC$_{50}$≦0.2 μM; C, 0.2 μM<IC$_{50}$≦1 μM; D, IC$_{50}$>1 μM; ND, not determined. The Example # of Table 1 corresponds to the compound example number as illustrated in the Examples section.

TABLE 1

| IC$_{50}$ values of examples in MET cell mechanistic assay (MKN45) | | | | | | | | | |
|---|---|---|---|---|---|---|---|---|---|
| Example | 1 | 2 | 3 | 4 | 5 | 6 | 7 | 8 | 9 | 10 |
| MET mech IC$_{50}$ | ND | ND | ND | ND | ND | ND | ND | ND | ND | ND |
| Example | 11 | 12 | 13 | 14 | 15 | 16 | 17 | 18 | 19 | 20 |
| MET mech IC$_{50}$ | ND | ND | ND | ND | ND | ND | ND | ND | ND | ND |
| Example | 21 | 22 | 23 | 24 | 25 | 26 | 27 | 28 | 29 | 30 |
| MET mech IC$_{50}$ | ND | ND | ND | ND | ND | ND | A | ND | ND | ND |
| Example | 31 | 32 | 33 | 34 | 35 | 36 | 37 | 38 | 39 | 40 |
| MET mech IC$_{50}$ | ND | ND | ND | ND | ND | ND | ND | ND | ND | ND |
| Example | 41 | 42 | 43 | 44 | 45 | 46 | 47 | 48 | 49 | 50 |
| MET mech IC$_{50}$ | ND | ND | ND | ND | ND | ND | ND | ND | ND | ND |

TABLE 1-continued

IC$_{50}$ values of examples in MET cell mechanistic assay (MKN45)

| Example | | | | | | | | | | |
|---|---|---|---|---|---|---|---|---|---|---|
| Example | 51 | 52 | 53 | 54 | 55 | 56 | 57 | 58 | 59 | 60 |
| MET mech IC$_{50}$ | ND | ND | ND | ND | ND | ND | ND | ND | ND | ND |
| Example | 61 | 62 | 63 | 64 | 65 | 66 | 67 | 68 | 69 | 70 |
| MET mech IC$_{50}$ | ND | ND | ND | ND | ND | ND | ND | ND | ND | ND |
| Example | 71 | 72 | 73 | 74 | 75 | 76 | 77 | 78 | 79 | 80 |
| MET mech IC$_{50}$ | ND | ND | ND | A | ND | ND | ND | ND | ND | ND |
| Example | 81 | 82 | 83 | 84 | 85 | 86 | 87 | 88 | 89 | 90 |
| MET mech IC$_{50}$ | ND | ND | ND | ND | ND | ND | ND | ND | ND | ND |
| Example | 91 | 92 | 93 | 94 | 95 | 96 | 97 | 98 | 99 | 100 |
| MET mech IC$_{50}$ | ND | ND | ND | ND | ND | A | A | ND | A | A |
| Example | 101 | 102 | 103 | 104 | 105 | 106 | 107 | 108 | 109 | 110 |
| MET mech IC$_{50}$ | ND | ND | A | ND | ND | ND | ND | ND | ND | ND |
| Example | 111 | 112 | 113 | 114 | 115 | 116 | 117 | 118 | 119 | 120 |
| MET mech IC$_{50}$ | ND | ND | ND | ND | ND | ND | ND | ND | ND | ND |
| Example | 121 | 122 | 123 | 124 | 125 | 126 | 127 | | | |
| MET mech IC$_{50}$ | A | ND | C | A | A | A | ND | | | |

The effect of inhibitors on the proliferation of MKN45 cells was determined using the following protocol. MKN45 cells were plated in Corning 3917 96-well white tissue culture treated plates in growth medium (RPMI, 10% FCS) at a density of 5000 cells/well in a total volume of 135 µL and incubated at 37° C., 5% CO$_2$, 95% humidity overnight. The following day, one-tenth volume of a 10× concentration of compounds was added to the wells in an 8-point dilution series. The dilution series was composed of an initial 1:5 dilution of a 10 mM stock of compound in DMSO, followed by serial 1:4 dilutions in DMSO, then a 1:20 dilution in growth medium prior to the 1:10 dilution into the cell plate. Final DMSO concentration on the cells was 0.1%, there were control wells treated with both 0.1% DMSO and no DMSO. The typical dilution range is 10 µM to 0.6 nM. Once the compound was added to the cells, plates were incubated for 3 days at 37° C., 5% CO$_2$ at 95% humidity. On the third day, after allowing all cells and reagents to come to room temperature, 25 µL of CellTiter-Glo reagent (Promega #G7573) was added to the wells. Plates were shaken on a platform for 10 minutes prior to reading luminescence for 0.1 seconds. The signal of the control wells was taken as 100% growth and growth inhibition was expressed as percent of control. IC$_{50}$ values were determined from the percent of control data using a standard four-parameter model.

The IC$_{50}$ values of exemplary compounds of the present invention determined in a cell proliferation assay using the MKN45 cell line according to the procedures described herein in at least duplicate experiments are abbreviated as follows and are shown in Table 2: A, IC$_{50}$≦0.05 µM; B, 0.05 µM<IC$_{50}$≦0.2 µM; C, 0.2 µM<IC$_{50}$≦1 µM; D, IC$_{50}$>1 µM; ND, not determined. The Example # of Table 2 corresponds to the compound example number as illustrated in the Examples section.

MKN45 is a human gastric carcinoma cell line that shows a high level of amplification of c-MET and constitutive activation of c-MET. Treatment of this cell line with a selective c-MET inhibitor led to induction of apoptosis and inhibition of proliferation, whereas non-MET-amplified cell lines were not affected [Smolen et al., Proc. Natl. Acad. Sci. USA, 103 (7):2316-2321 (2006)]. This cell line is thus "driven" by c-MET, and antiproliferative effects correlate very well with the inhibition of c-MET phosphorylation so that the cell proliferation IC$_{50}$ values can be used as surrogate for the c-MET cell mechanistic IC$_{50}$ values. Under the assay conditions described herein, the IC$_{50}$ values correlate nearly 1:1.

TABLE 2

IC$_{50}$ values of examples in MKN45 cell proliferation assay

| Example | | | | | | | | | | |
|---|---|---|---|---|---|---|---|---|---|---|
| Example | 1 | 2 | 3 | 4 | 5 | 6 | 7 | 8 | 9 | 10 |
| Prolif. IC$_{50}$ | A | B | A | C | B | A | A | A | A | A |
| Example | 11 | 12 | 13 | 14 | 15 | 16 | 17 | 18 | 19 | 20 |
| Prolif. IC$_{50}$ | B | B | A | A | ND | ND | A | A | A | ND |
| Example | 21 | 22 | 23 | 24 | 25 | 26 | 27 | 28 | 29 | 30 |
| Prolif. IC$_{50}$ | ND | A | A | A | ND | ND | A | A | D | C |
| Example | 31 | 32 | 33 | 34 | 35 | 36 | 37 | 38 | 39 | 40 |
| Prolif. IC$_{50}$ | A | A | A | B | B | B | C | A | B | B |
| Example | 41 | 42 | 43 | 44 | 45 | 46 | 47 | 48 | 49 | 50 |
| Prolif. IC$_{50}$ | D | B | C | B | C | B | A | A | A | B |
| Example | 51 | 52 | 53 | 54 | 55 | 56 | 57 | 58 | 59 | 60 |
| Prolif. IC$_{50}$ | B | A | A | A | ND | B | A | A | | B |
| Example | 61 | 62 | 63 | 64 | 65 | 66 | 67 | 68 | 69 | 70 |
| Prolif. IC$_{50}$ | A | B | C | B | B | A | A | D | A | A |
| Example | 71 | 72 | 73 | 74 | 75 | 76 | 77 | 78 | 79 | 80 |
| Prolif. IC$_{50}$ | A | B | A | A | A | A | A | A | A | ND |

TABLE 2-continued

IC$_{50}$ values of examples in MKN45 cell proliferation assay

| Example | 81 | 82 | 83 | 84 | 85 | 86 | 87 | 88 | 89 | 90 |
|---|---|---|---|---|---|---|---|---|---|---|
| Prolif. IC$_{50}$ | A | A | A | A | A | A | A | A | A | B |
| Example | 91 | 92 | 93 | 94 | 95 | 96 | 97 | 98 | 99 | 100 |
| Prolif. IC$_{50}$ | B | C | A | A | C | A | A | D | A | A |
| Example | 101 | 102 | 103 | 104 | 105 | 106 | 107 | 108 | 109 | 110 |
| Prolif. IC$_{50}$ | A | A | A | A | A | A | A | B | B | A |
| Example | 111 | 112 | 113 | 114 | 115 | 116 | 117 | 118 | 119 | 120 |
| Prolif. IC$_{50}$ | A | D | A | A | B | ND | D | B | ND | C |
| Example | 121 | 122 | 123 | 124 | 125 | 126 | 127 | | | |
| Prolif. IC$_{50}$ | A | ND | C | A | A | A | D | | | |

The cellular activity of the compounds of the present invention against RON may be determined by the following procedure. HeLa cells were plated in Falcon 3072 96-well plates in growth media (DMEM, 10% FBS, 1% L-glutamine) at a density of 10000 cells/well and incubated at 37° C., 5% CO$_2$ overnight. The following day, cells were transfected with 0.2 µg sfRON-pcDNA plasmid DNA with 0.5 µL Lipofectamine-2000 per well in the presence of 50 µL OPTI-MEM, incubated at 37° C., 5% CO$_2$ overnight. Costar 3915 96-well assay plates were coated with rabbit Anti-RON antibody at 2.0 µg/mL, sealed, and incubated overnight at 4° C. On the third day, coated plates were washed with PBS and blocked with 3% BSA. For the sfRON transfected cells, one-tenth volume of a 10× concentration of compounds was added to the wells in a 6-point dilution series. The dilution series was composed of an initial 1:5 dilution of a 10 mM DMSO stock solution of compound in DMSO, followed by a 1:10 dilution in growth media, for a final DMSO concentration on cells of 0.5%. Control wells were treated with 0.5% DMSO. The typical range of dilution was 10 µM to 3 nM. Once compound was added to the cells, plates were incubated for four hours at 37° C., 5% CO$_2$. Plates were then washed in PBS, and lysed in triton-based lysis buffer. Lysates were transferred to the blocked capture plates. The phosphorylated RON levels were measured by incubating with a Goat polyclonal antibody against phosphorylated RON ([pYpY1238/1239]) followed by an anti-Goat antibody conjugated to HRP. Signal was measured on a Wallac Victor plate reader with luminance. The DMSO signal of the control wells was defined as 100% and the percent of inhibition of phosphorylated RON was expressed as percent of control. IC$_{50}$ values were determined from the percent of control data using a standard four-parameter model.

The IC$_{50}$ values of exemplary compounds of the present invention determined in a sfRON cell mechanistic assay using the HeLa cell line according to the procedures described herein in at least duplicate experiments are abbreviated as follows and are shown in Table 3: A, IC$_{50}$≦0.2 µM; B, 0.2 µM<IC$_{50}$≦1.0 µM; C, IC$_{50}$>1 µM; ND, not determined. The Example # of Table 3 corresponds to the compound example number as illustrated in the Examples section.

TABLE 3

IC$_{50}$ values of examples in sfRON cell mechanistic assay (HeLa)

| Example | 1 | 2 | 3 | 4 | 5 | 6 | 7 | 8 | 9 | 10 |
|---|---|---|---|---|---|---|---|---|---|---|
| sfRON mech IC$_{50}$ | B | B | B | C | C | B | B | B | ND | A |
| Example | 11 | 12 | 13 | 14 | 15 | 16 | 17 | 18 | 19 | 20 |
| sfRON mech IC$_{50}$ | B | B | B | B | ND | ND | A | B | A | ND |
| Example | 21 | 22 | 23 | 24 | 25 | 26 | 27 | 28 | 29 | 30 |
| sfRON mech IC$_{50}$ | ND | A | A | B | ND | ND | B | A | ND | ND |
| Example | 31 | 32 | 33 | 34 | 35 | 36 | 37 | 38 | 39 | 40 |
| sfRON mech IC$_{50}$ | B | A | B | C | C | ND | ND | B | C | C |
| Example | 41 | 42 | 43 | 44 | 45 | 46 | 47 | 48 | 49 | 50 |
| sfRON mech IC$_{50}$ | C | C | C | C | C | C | B | C | C | C |
| Example | 51 | 52 | 53 | 54 | 55 | 56 | 57 | 58 | 59 | 60 |
| sfRON mech IC$_{50}$ | C | B | B | B | ND | C | C | B | C | C |
| Example | 61 | 62 | 63 | 64 | 65 | 66 | 67 | 68 | 69 | 70 |
| sfRON mech IC$_{50}$ | B | C | C | C | C | B | B | ND | A | A |
| Example | 71 | 72 | 73 | 74 | 75 | 76 | 77 | 78 | 79 | 80 |
| sfRON mech IC$_{50}$ | A | B | B | A | A | A | A | B | B | ND |
| Example | 81 | 82 | 83 | 84 | 85 | 86 | 87 | 88 | 89 | 90 |
| sfRON mech IC$_{50}$ | B | B | B | B | B | B | A | B | C | C |
| Example | 91 | 92 | 93 | 94 | 95 | 96 | 97 | 98 | 99 | 100 |
| sfRON mech IC$_{50}$ | C | C | A | ND | ND | A | A | ND | A | A |
| Example | 101 | 102 | 103 | 104 | 105 | 106 | 107 | 108 | 109 | 110 |
| sfRON mech IC$_{50}$ | ND | B | A | B | A | B | B | C | B | B |

TABLE 3-continued

| IC$_{50}$ values of examples in sfRON cell mechanistic assay (HeLa) | | | | | | | | | | |
|---|---|---|---|---|---|---|---|---|---|---|
| Example | 111 | 112 | 113 | 114 | 115 | 116 | 117 | 118 | 119 | 120 |
| sfRON mech IC$_{50}$ | B | C | A | A | C | ND | ND | B | ND | C |
| Example | 121 | 122 | 123 | 124 | 125 | 126 | 127 | | | |
| sfRON mech IC$_{50}$ | B | ND | B | A | A | A | ND | | | |

The cellular activity of the compounds of the present invention against Aurora B may be determined by the following procedure. HT-29 cells grown in complete growth media (McCoy's 5A, 10% FCS, 1% L-glutamine) were plated into wells of a 96 well tissue culture plate (Falcon 3072) at a cell density of $4 \times 10^4$ cells/0.09 ml media/well. Cells were subsequently incubated overnight in a 5% $CO_2$ humidified 37° C. incubator. The following day 10 μl of a 10× stock of test compound serially diluted in media was added to the cells and incubated for 1 h at 37° C. at which time Calyculin A (Cell Signaling #9902) was added at a concentration of 100 nM and cells incubated for an additional 30 minutes in a 5% $CO_2$ humidified 37° C. incubator. Media was then aspirated and cells lysed using a Triton based lysis buffer. Lysates were transferred to a pre-coated anti-Histone H3 antibody coated plate supplied by Cell Signaling in their PathScan phospho-Histone H3 (Ser10) ELISA kit (#7155). After an overnight incubation with lysate the ELISA was continued following the manufacturer's instructions. Signal was measured on a Wallac Victor plate reader at 450 nm. DMSO control treated cells served as 100% signal and an Aurora B kinase inhibitor served as 100% inhibition. The percent inhibition of phospho-Histone H3 (Ser10) was expressed as % control. IC$_{50}$ values were calculated from the percent control data using a standard four-parameter model.

The IC$_{50}$ values of exemplary compounds of the present invention determined in a Aurora B cell mechanistic assay using the HT-29 cell line according to the procedures described herein in at least duplicate experiments are abbreviated as follows and are shown in Table 4: A, IC$_{50}$≦0.05 μM; B, 0.05 μM<IC$_{50}$≦0.2 μM; C, 0.2 μM<IC$_{50}$≦1 μM; D, IC$_{50}$>1 μM; ND, not determined. If only data from single experiments are available, the abbreviations are italicized. The Example # of Table 4 corresponds to the compound example number as illustrated in the Examples section.

TABLE 4

| IC$_{50}$ values of examples in Aurora B cell mechanistic assay (HT-29) | | | | | | | | | | |
|---|---|---|---|---|---|---|---|---|---|---|
| Example | 1 | 2 | 3 | 4 | 5 | 6 | 7 | 8 | 9 | 10 |
| Aurora B mech IC$_{50}$ | C | B | D | D | D | D | C | C | C | C |
| Example | 11 | 12 | 13 | 14 | 15 | 16 | 17 | 18 | 19 | 20 |
| Aurora B mech IC$_{50}$ | D | D | D | D | ND | ND | C | C | B | ND |
| Example | 21 | 22 | 23 | 24 | 25 | 26 | 27 | 28 | 29 | 30 |
| Aurora B mech IC$_{50}$ | ND | B | B | D | ND | ND | D | B | D | D |
| Example | 31 | 32 | 33 | 34 | 35 | 36 | 37 | 38 | 39 | 40 |
| Aurora B mech IC$_{50}$ | D | B | D | D | D | ND | ND | C | D | ND |
| Example | 41 | 42 | 43 | 44 | 45 | 46 | 47 | 48 | 49 | 50 |
| Aurora B mech IC$_{50}$ | D | C | D | D | D | D | D | D | D | C |
| Example | 51 | 52 | 53 | 54 | 55 | 56 | 57 | 58 | 59 | 60 |
| Aurora B mech IC$_{50}$ | D | D | B | C | ND | ND | ND | ND | D | C |
| Example | 61 | 62 | 63 | 64 | 65 | 66 | 67 | 68 | 69 | 70 |
| Aurora B mech IC$_{50}$ | D | D | D | D | D | D | D | D | D | C |
| Example | 71 | 72 | 73 | 74 | 75 | 76 | 77 | 78 | 79 | 80 |
| Aurora B mech IC$_{50}$ | B | C | D | C | C | C | C | D | D | ND |
| Example | 81 | 82 | 83 | 84 | 85 | 86 | 87 | 88 | 89 | 90 |
| Aurora B mech IC$_{50}$ | D | D | D | C | C | ND | ND | ND | ND | ND |
| Example | 91 | 92 | 93 | 94 | 95 | 96 | 97 | 98 | 99 | 100 |
| Aurora B mech IC$_{50}$ | ND | ND | ND | ND | ND | ND | ND | ND | ND | ND |
| Example | 101 | 102 | 103 | 104 | 105 | 106 | 107 | 108 | 109 | 110 |
| Aurora B mech IC$_{50}$ | D | D | D | C | B | D | D | D | ND | D |
| Example | 111 | 112 | 113 | 114 | 115 | 116 | 117 | 118 | 119 | 120 |
| Aurora B mech IC$_{50}$ | D | ND | ND | ND | ND | ND | ND | ND | ND | ND |
| Example | 121 | 122 | 123 | 124 | 125 | 126 | 127 | | | |
| Aurora B mech IC$_{50}$ | ND | ND | ND | ND | ND | D | | | | |

The effect of inhibitors on the proliferation of Karpas-299 cells (DSMZ no. ACC 31) was determined using the following protocol. Karpas-299 cells were plated in 96-well white tissue culture treated plates (Corning 3917) in growth medium (RPMI, 10% FCS) at a density of 5000 cells/well in a total volume of 135 µL and incubated at 37° C., 5% $CO_2$, 95% humidity overnight. The following day, one-tenth volume of a 10× concentration of compounds was added to the wells in an 8-point dilution series. Compounds were serially diluted (1:4) in DMSO from a 10 mM stock solution prior to dilution in growth media to the 10× working concentrations (5% DMSO). Final concentration of DMSO in compound-treated wells was 0.5%. Control wells containing growth media or growth media/0.5% DMSO were included in all test plates. The typical dilution range is 10 µM to 0.1 nM. Once the compounds were added to the cells, plates were incubated for 3 days at 37° C., 5% $CO_2$ at 95% humidity. After 72 hours, all cells and reagents were equilibrated to room temperature and 15 µL of CellTiter-Glo reagent (Promega # G7573) was added to each well. Plates were shaken on a platform for 10 minutes at room temperature prior to reading luminescence. The value of the signal of the control wells was set as 100% growth and growth inhibition was expressed as percent of control. $IC_{50}$ values were determined from the percent of control data using a standard four-parameter curve fit equation.

The $IC_{50}$ values of exemplary compounds of the present invention determined in a cell proliferation assay using the Karpas-299 cell line according to the procedures described herein in at least duplicate experiments are abbreviated as follows and are shown in Table 5: A, $IC_{50} \leq 0.05$ µM; B, 0.05 µM<$IC_{50} \leq 0.2$ µM; C, 0.2 µM<$IC_{50} \leq 1$ µM; D, $IC_{50}$>1 µM; ND, not determined. The Example # of Table 5 corresponds to the compound example number as illustrated in the Examples section.

The Karpas-299 cell line has a t(2; 5) chromosomal translocation and expresses the NPM-ALK fusion protein, resulting in constitutively active ALK. A small-molecule ALK inhibitor inhibited growth of Karpas-299 cells at concentrations that showed a strong correlation to the inhibition of NPM-ALK total tyrosine phosphorylation [Christensen at al., Mol. Cancer. Ther. 6(12):3314-22 (2007)]. With this "ALK-driven" cell line, the cell proliferation $IC_{50}$ values can thus be used as surrogate for the p-ALK cell mechanistic $IC_{50}$ values.

TABLE 5

$IC_{50}$ values of examples in Karpas-299 cell proliferation assay

| Example | 1 | 2 | 3 | 4 | 5 | 6 | 7 | 8 | 9 | 10 |
|---|---|---|---|---|---|---|---|---|---|---|
| Prolif. $IC_{50}$ | B | B | B | B | A | A | B | B | A | A |
| Example | 11 | 12 | 13 | 14 | 15 | 16 | 17 | 18 | 19 | 20 |
| Prolif. $IC_{50}$ | C | B | A | A | ND | ND | A | A | A | ND |
| Example | 21 | 22 | 23 | 24 | 25 | 26 | 27 | 28 | 29 | 30 |
| Prolif. $IC_{50}$ | ND | A | A | A | A | A | A | A | D | C |
| Example | 31 | 32 | 33 | 34 | 35 | 36 | 37 | 38 | 39 | 40 |
| Prolif. $IC_{50}$ | A | A | A | C | C | C | C | B | C | D |
| Example | 41 | 42 | 43 | 44 | 45 | 46 | 47 | 48 | 49 | 50 |
| Prolif. $IC_{50}$ | D | B | D | B | B | C | B | B | B | C |
| Example | 51 | 52 | 53 | 54 | 55 | 56 | 57 | 58 | 59 | 60 |
| Prolif. $IC_{50}$ | B | B | A | A | ND | B | B | A | C | B |
| Example | 61 | 62 | 63 | 64 | 65 | 66 | 67 | 68 | 69 | 70 |
| Prolif. $IC_{50}$ | C | C | C | C | C | A | B | C | A | A |
| Example | 71 | 72 | 73 | 74 | 75 | 76 | 77 | 78 | 79 | 80 |
| Prolif. $IC_{50}$ | A | B | B | A | A | A | B | A | B | ND |
| Example | 81 | 82 | 83 | 84 | 85 | 86 | 87 | 88 | 89 | 90 |
| Prolif. $IC_{50}$ | A | B | B | B | A | A | A | A | B | B |
| Example | 91 | 92 | 93 | 94 | 95 | 96 | 97 | 98 | 99 | 100 |
| Prolif. $IC_{50}$ | B | C | A | A | C | A | A | ND | B | B |
| Example | 101 | 102 | 103 | 104 | 105 | 106 | 107 | 108 | 109 | 110 |
| Prolif. $IC_{50}$ | A | B | A | A | A | C | B | C | C | A |
| Example | 111 | 112 | 113 | 114 | 115 | 116 | 117 | 118 | 119 | 120 |
| Prolif. $IC_{50}$ | A | C | A | A | A | ND | D | B | ND | C |
| Example | 121 | 122 | 123 | 124 | 125 | 126 | 127 | | | |
| Prolif. $IC_{50}$ | A | ND | B | A | A | A | C | | | |

COMPOSITIONS

The invention includes pharmaceutical compositions comprising a compound or pharmaceutically acceptable salt thereof of the invention, which is formulated for a desired mode of administration with or without one or more pharmaceutically acceptable and useful carriers. The compounds can also be included in pharmaceutical compositions in combination with one or more other therapeutically active compounds.

The pharmaceutical compositions of the present invention comprise a compound of the invention (or a pharmaceutically acceptable salt thereof) as an active ingredient, optional pharmaceutically acceptable carrier(s) and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

A formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Compounds of the invention can be provided for formulation at high purity, for example at least about 90%, 95%, or 98% pure by weight.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

USES

Compounds of the invention inhibit the activity of tyrosine kinase enzymes in animals, including humans, and are useful in the treatment and/or prevention of various diseases and conditions such as hyperproliferative disorders such as cancer. In particular, compounds disclosed herein are inhibitors of at least one of MET, RON, and ALK kinases.

In some aspects, compounds of the invention are useful as inhibitors of kinases, including one or more of AXL, Tie-2, Flt3, FGFR3, Abl, Jak2, c-Src, IGF-1R, IR, TRK, PAK1, PAK2, and TAK1 kinases. In some aspects, compounds of the invention are inhibitors of kinases, including one or more of Blk, c-Raf, PRK2, Lck, Mek1, PDK-1, GSK313, EGFR, p70S6K, BMX, SGK, CaMKII, and Tie-2 kinases.

In some aspects, compounds of the invention are useful as selective inhibitors of one or more of MET and/or RON and/or ALK. In some embodiments, the compound is useful as a selective inhibitor of MET and/or RON and/or ALK over other kinase targets, such as KDR and/or Aurora kinase B (AKB). In some aspects, compounds of the invention are useful as selective inhibitors of one or more of MET, RON, and ALK with selectivity over Aurora kinase B (AKB). In some aspects, compounds of the invention are useful as selective inhibitors of one or more of MET, RON, and ALK with selectivity over AKB of at least about 2, 4, 8, 10, 16, 20, 32, 40-fold, or greater.

In some aspects, the invention includes a method of treating cancer, tumors, and tumor metastases, comprising administering to a mammal in need thereof a therapeutically effective amount of a compound or salt of the invention.

In some aspects, compounds of the invention are in particular useful in treating proliferative disease, particularly cancers, including cancers mediated by MET and/or RON and/or ALK, alone or in combination with other agents.

In some aspects, the invention includes a method of treating a cancer mediated at least in part by RON and/or MET comprising administering to a mammal in need thereof a therapeutically effective amount of a compound or salt of Formula I.

In some aspects, the invention includes a method of treating a cancer selected from bladder, colorectal, non-small cell lung, breast, or pancreatic, ovarian, gastric, head and neck, prostate, hepatocellular, renal, glioma, or sarcoma cancer comprising administering to a mammal in need thereof a therapeutically effective amount of a compound or salt of Formula I.

In some aspects thereof, at least one additional anti-cancer agent is administered in a therapeutically effective combination regimen. In some aspects thereof, the additional agent comprises an agent that acts on a biological target involved in compensatory signaling or cross-talk with at least one of RON, MET, or ALK. In some aspects thereof, the agents in the combination regimen behave synergistically. In some aspects thereof, the at least one additional anti-cancer agent comprises a VEGF, IGF-1R, or EGFR inhibitor.

The compounds of Formula I of the present invention are useful in the treatment of a variety of cancers, including, but not limited to, solid tumor, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

In some aspects, the above methods are used to treat one or more of bladder, colorectal, nonsmall cell lung, breast, or pancreatic cancer. In some aspects, the above methods are used to treat one or more of ovarian, gastric, head and neck, prostate, hepatocellular, renal, glioma, glioma, or sarcoma cancer.

In some aspects, the invention includes a method, including the above methods, wherein the compound is used to inhibit EMT.

In some aspects, the invention includes a method of treating cancer comprising administering to a mammal in need thereof a therapeutically effective amount of a compound or salt of the invention, wherein at least one additional active anti-cancer agent is used as part of the method. In some aspects, the additional agent(s) is an EGFR inhibitor and/or an IGF-1R inhibitor.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In some aspects, the invention includes a method of treating cancer comprising administering to a mammal in need thereof a therapeutically effective amount of a compound or salt of the invention, wherein at least one additional active anti-cancer agent is used as part of the method.

GENERAL DEFINITIONS AND ABBREVIATIONS

Except where otherwise indicated, the following general conventions and definitions apply. Unless otherwise indicated herein, language and terms are to be given their broadest reasonable interpretation as understood by the skilled artisan. Any examples given are nonlimiting.

Any section headings or subheadings herein are for the reader's convenience and/or formal compliance and are non-limiting.

A recitation of a compound herein is open to and embraces any material or composition containing the recited compound (e.g., a composition containing a racemic mixture, tautomers, epimers, stereoisomers, impure mixtures, etc.). In that a salt, solvate, or hydrate, polymorph, or other complex of a compound includes the compound itself, a recitation of a compound embraces materials containing such forms. Isotopically labeled compounds are also encompassed except where specifically excluded. For example, hydrogen is not limited to hydrogen containing zero neutrons.

The term "active agent" of the invention means a compound of the invention in any salt, polymorph, crystal, solvate, or hydrated form.

The term "pharmaceutically acceptable salt(s)" is known in the art and includes salts of acidic or basic groups which can be present in the compounds and prepared or resulting from pharmaceutically acceptable bases or acids.

The term "substituted" and substitutions contained in formulas herein refer to the replacement of one or more hydrogen radicals in a given structure with a specified radical, or, if not specified, to the replacement with any chemically feasible radical. When more than one position in a given structure can be substituted with more than one substituent selected from specified groups, the substituents can be either the same or different at every position (independently selected) unless otherwise indicated. In some cases, two positions in a given structure can be substituted with one shared substituent. It is understood that chemically impossible or highly unstable configurations are not desired or intended, as the skilled artisan would appreciate.

In descriptions and claims where subject matter (e.g., substitution at a given molecular position) is recited as being selected from a group of possibilities, the recitation is specifically intended to include any subset of the recited group. In the case of multiple variable positions or substituents, any combination of group or variable subsets is also contemplated. Unless indicated otherwise, a substituent, diradical or other group referred to herein can be bonded through any suitable position to a referenced subject molecule. For example, the term "indolyl" includes 1-indolyl, 2-indolyl, 3-indolyl, etc.

The convention for describing the carbon content of certain moieties is "($C_{a-b}$)" or "$C_a$-$C_b$" meaning that the moiety can contain any number of from "a" to "b" carbon atoms. $C_0$alkyl means a single covalent chemical bond when it is a connecting moiety, and a hydrogen when it is a terminal moiety. Similarly, "x-y" can indicate a moiety containing from x to y atoms, e.g., $_{5-6}$heterocycloalkyl means a heterocycloalkyl having either five or six ring members. "$C_{x-y}$" may be used to define number of carbons in a group. For example, "$C_{0-}$ $_{12}$alkyl" means alkyl having 0-12 carbons, wherein C$_0$alkyl means a single covalent chemical bond when a linking group and means hydrogen when a terminal group.

The term "absent," as used herein to describe a structural variable (e.g., "—R— is absent") means that diradical R has no atoms, and merely represents a bond between other adjoining atoms, unless otherwise indicated.

Unless otherwise indicated (such as by a connecting "—"), the connections of compound name moieties are at the rightmost recited moiety. That is, the substituent name starts with a terminal moiety, continues with any bridging moieties, and ends with the connecting moiety. For example, "heteroarylthioC$_{1-4}$alkyl is a heteroaryl group connected through a thio sulfur to a C$_{1-4}$ alkyl, which alkyl connects to the chemical species bearing the substituent.

The term "aliphatic" means any hydrocarbon moiety, and can contain linear, branched, and cyclic parts, and can be saturated or unsaturated. The term includes, e.g., alkyl, alkenyl, alkynyl, cycloalkyl, carbocyclic, and others.

The term "alkyl" means any saturated hydrocarbon group that is straight-chain or branched. Examples of alkyl groups include methyl, ethyl, propyl, 2-propyl, n-butyl, iso-butyl, tert-butyl, pentyl, and the like.

The term "alkenyl" means any ethylenically unsaturated straight-chain or branched hydrocarbon group. Representative examples include, but are not limited to, ethenyl, 1-propenyl, 2-propenyl, 1-, 2-, or 3-butenyl, and the like.

The term "alkynyl" means any acetylenically unsaturated straight-chain or branched hydrocarbon group. Representative examples include, but are not limited to, ethynyl, 1-propynyl, 2-propynyl, 1-, 2-, or 3-butynyl, and the like.

The term "alkoxy" means —O-alkyl, —O-alkenyl, or —O-alkynyl. "Haloalkoxy" means an —O-(haloalkyl) group. Representative examples include, but are not limited to, trifluoromethoxy, tribromomethoxy, and the like.

"Haloalkyl" means an alkyl, preferably lower alkyl, that is substituted with one or more same or different halo atoms.

"Hydroxyalkyl" means an alkyl, preferably lower alkyl, that is substituted with one, two, or three hydroxy groups; e.g., hydroxymethyl, 1 or 2-hydroxyethyl, 1,2-, 1,3-, or 2,3-dihydroxypropyl, and the like.

The term "alkanoyl" means —C(O)-alkyl, —C(O)-alkenyl, or —C(O)-alkynyl.

"Alkylthio" means an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

The term "cyclic" means any ring system with or without heteroatoms (N, O, or S(O)$_{0-2}$), and which can be saturated or unsaturated. Ring systems can be bridged and can include fused rings. The size of ring systems may be described using terminology such as "$_{x-y}$cyclic," which means a cyclic ring system that can have from x to y ring atoms. For example, the term "$_{9-10}$carbocyclic" means a 5, 6 or 6,6 fused bicyclic carbocyclic ring system which can be satd., unsatd. or aromatic. It also means a phenyl fused to one 5 or 6 membered satd. or unsatd. carbocyclic group. Nonlimiting examples of such groups include naphthyl, 1,2,3,4 tetrahydronaphthyl, indenyl, indanyl, and the like.

The term "carbocyclic" means a cyclic ring moiety containing only carbon atoms in the ring(s) without regard to aromaticity. A 3-10 membered carbocyclic means chemically feasible monocyclic and fused bicyclic carbocyclics having from 3 to 10 ring atoms. Similarly, a 4-6 membered carbocyclic means monocyclic carbocyclic ring moieties having 4 to 6 ring carbons, and a 9-10 membered carbocyclic means fused bicyclic carbocyclic ring moieties having 9 to 10 ring carbons.

The term "cycloalkyl" means a non-aromatic 3-12 carbon mono-cyclic, bicyclic, or polycyclic aliphatic ring moiety. Cycloalkyl can be bicycloalkyl, polycycloalkyl, bridged, or spiroalkyl. One or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like.

The term "unsaturated carbocyclic" means any cycloalkyl containing at least one double or triple bond. The term "cycloalkenyl" means a cycloalkyl having at least one double bond in the ring moiety.

The terms "bicycloalkyl" and "polycycloalkyl" mean a structure consisting of two or more cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" means a structure consisting of two cycloalkyl moieties that have exactly one atom in common. Examples include, but are not limited to, spiro[4.5]decyl, spiro[2.3]hexyl, and the like.

The term "aromatic" means a planar ring moieties containing 4n+2 pi electrons, wherein n is an integer.

The term "aryl" means an aromatic moieties containing only carbon atoms in its ring system. Non-limiting examples include phenyl, naphthyl, and anthracenyl. The terms "arylalkyl" or "arylalkyl" or "aralkyl" refer to any alkyl that forms a bridging portion with a terminal aryl.

"Aralkyl" means alkyl, preferably lower alkyl, that is substituted with an aryl group as defined above; e.g., —CH$_2$phenyl, —(CH$_2$)$_2$-phenyl, —(CH$_2$)$_3$ phenyl, CH$_3$CH(CH$_3$)CH$_2$-phenyl, and the like and derivatives thereof.

The term "heterocyclic" means a cyclic ring moiety containing at least one heteroatom (N, O, or S(O)$_{0-2}$), including heteroaryl, heterocycloalkyl, including unsaturated heterocyclic rings.

The term "heterocycloalkyl" means a non-aromatic monocyclic, bicyclic, or polycyclic heterocyclic ring moiety of 3 to 12 ring atoms containing at least one ring having one or more heteroatoms. The rings may also have one or more double bonds. However, the rings do not have a completely conjugated pi-electron system. Examples of heterocycloalkyl rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocycloalkyl rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocycloalkyl rings. The term "heterocycloalkyl" also includes fused ring systems and can include a carbocyclic ring that is partially or fully unsaturated, such as a benzene ring, to form benzofused heterocycloalkyl rings. For example, 3,4-dihydro-1,4-benzodioxine, tetrahydroquinoline, tetrahydroisoquinoline and the like. The term "heterocycloalkyl" also includes heterobicycloalkyl, heteropolycycloalkyl, or heterospiroalkyl, which are bicycloalkyl, polycycloalkyl, or spiroalkyl, in which one or more carbon atom(s) are replaced by one or more heteroatoms selected from O, N, and S. For example, 2-oxa-spiro[3.3]heptane, 2,7-diaza-spiro[4.5]decane, 6-oxa-2-thia-spiro[3.4]octane, octahydropyrrolo[1,2-a]pyrazine, 7-aza-bicyclo[2.2.1]heptane, 2-oxa-bicyclo[2.2.2]octane, and the like, are such heterocycloalkyls.

Examples of saturated heterocyclic groups include, but are not limited to oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl Non-aryl heterocyclic groups include satd. and unsatd. systems and can include groups having only 4 atoms in their ring system. The heterocyclic groups include benzo-fused ring systems and ring systems substituted with one or more oxo moieties. Recitation of ring sulfur is understood to include the sulfide, sulfoxide or sulfone where feasible. The heterocyclic groups also include partially unsatd. or fully satd. 4-10 membered ring systems, e.g., single rings of 4 to 8 atoms in size and bicyclic ring systems, including aromatic 6-membered aryl or heteroaryl rings fused to a non-aromatic ring. Also included are 4-6 membered ring systems ("4-6 membered heterocyclic"), which include 5-6 membered heteroaryls, and include groups such as azetidinyl and piperidinyl. Heterocyclics can be heteroatom-attached where such is possible. For instance, a group derived from pyrrole can be pyrrol-1-yl (N-attached) or pyrrol-3-yl (C-attached). Other heterocyclics include imidazo[4,5-b]pyridin-3-yl and benzoimidazol-1-yl.

Examples of heterocyclic groups include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, and the like.

The term "unsaturated heterocyclic" means a heterocycloalkyl containing at least one unsaturated bond. The term "heterobicycloalkyl" means a bicycloalkyl structure in which at least one carbon atom is replaced with a heteroatom. The term "heterospiroalkyl" means a spiroalkyl structure in which at least one carbon atom is replaced with a heteroatom.

Examples of partially unsaturated heteroalicyclic groups include, but are not limited to 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

The terms "heteroaryl" or "hetaryl" mean a monocyclic, bicyclic, or polycyclic aromatic heterocyclic ring moiety containing 5-12 atoms. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

Heteroaryls include, e.g., 5 and 6 membered monocyclics such as pyrazinyl and pyridinyl, and 9 and 10 membered fused bicyclic ring moieties, such as quinolinyl. Other examples of heteroaryl include quinolin-4-yl, 7-methoxyquinolin-4-yl, pyridin-4-yl, pyridin-3-yl, and pyridin-2-yl. Other examples of heteroaryl include pyridinyl, imidazolyl, pyrimidinyl, pyrazolyl, triazolyl, pyrazinyl, tetrazolyl, furanyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. Examples of 5-6 membered heteroaryls include, thiophenyl, isoxazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazolyl, 1,2,5-triazinyl, 1,3,5-triazinyl, and the like.

"Heteroaralkyl" group means alkyl, preferably lower alkyl, that is substituted with a heteroaryl group; e.g., —CH$_2$ pyridinyl, —(CH$_2$)$_2$pyrimidinyl, —(CH$_2$)$_3$imidazolyl, and the like, and derivatives thereof.

A pharmaceutically acceptable heteroaryl is one that is sufficiently stable to be attached to a compound of the invention, formulated into a pharmaceutical composition and subsequently administered to a patient in need thereof.

Examples of monocyclic heteroaryl groups include, but are not limited to: pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl.

Examples of fused ring heteroaryl groups include, but are not limited to: benzoduranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, azaquinazoline, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]

pyrazinyl, pyrido[3,4-b]pyrazinyl, pyrimido[5,4-d]pyrimidinyl, pyrimido[2,3-b]pyrazinyl, pyrimido[4,5-d]pyrimidinyl.

"Arylthio" means an —S-aryl or an —S-heteroaryl group, as defined herein. Representative examples include, but are not limited to, phenylthio, pyridinylthio, furanylthio, thienylthio, pyrimidinylthio, and the like and derivatives thereof.

The term "9-10 membered heterocyclic" means a fused 5, 6 or 6,6 bicyclic heterocyclic ring moiety, which can be satd., unsatd. or aromatic. The term "9-10 membered fused bicyclic heterocyclic" also means a phenyl fused to one 5 or 6 membered heterocyclic group. Examples include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3 benzo[1,3]dioxolyl, 2H-chromanyl, isochromanyl, 5-oxo-2,3 dihydro-5H-[1,3]thiazolo[3,2-a]pyrimidyl, 1,3-benzothiazolyl, 1,4,5,6 tetrahydropyridazyl, 1,2,3,4,7,8 hexahydropteridinyl, 2-thioxo-2,3,6,9-tetrahydro-1H-purin-8-yl, 3,7-dihydro-1H-purin-8-yl, 3,4-dihydropyrimidin-1-yl, 2,3-dihydro-1,4-benzodioxinyl, benzo[1,3]dioxolyl, 2H-chromenyl, chromanyl, 3,4-dihydrophthalazinyl, 2,3-dihydro-1H-indolyl, 1,3-dihydro-2H-isoindol-2-yl, 2,4,7-trioxo-1,2,3,4,7,8-hexahydropteridin-yl, thieno[3,2-d]pyrimidinyl, 4-oxo-4,7-dihydro-3H-pyrrolo[2,3-d]pyrimidin-yl, 1,3-dimethyl-6-oxo-2-thioxo-2,3,6,9-tetrahydro-1H-purinyl, 1,2-dihydroisoquinolinyl, 2-oxo-1,3-benzoxazolyl, 2,3-dihydro-5H-1,3-thiazolo-[3,2-a]pyrimidinyl, 5,6,7,8-tetrahydro-quinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4-dihydropyrimidin-1-yl imidazolylpyridyl, quinoliyl, isoquinolinyl, quinazolinyl, quinoxalinyl, naphthyridinyl, pyrazolyl[3,4]pyridine, 1,2-dihydroisoquinolinyl, cinnolinyl, 2,3-dihydro-benzo[1,4]dioxin-4-yl, 4,5,6,7-tetrahydrobenzo[b]-thiophenyl-2-yl, 1,8-naphthyridinyl, 1,5-napthyridinyl, 1,6-naphthyridinyl, 1,7-napthyridinyl, 3,4-dihydro-2H-1,4-benzothiazine, 4,8-dihydroxy-quinolinyl, 1-oxo-1,2-dihydro-isoquinolinyl, 4-phenyl-[1,2,3]thiadiazolyl, and the like.

"Aryloxy" means an —O-aryl or an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

One in the art understands that an "oxo" requires a second bond from the atom to which the oxo is attached. Accordingly, it is understood that oxo cannot be substituted onto an aryl or heteroaryl ring.

The term "halo" means fluoro, chloro, bromo, or iodo.

"Acyl" means a —C(O)R group, where R can be selected from the nonlimiting group of hydrogen or optionally substituted lower alkyl, trihalomethyl, unsubstituted cycloalkyl, aryl. "Thioacyl" or "thiocarbonyl" means a —C(S)R" group, with R as defined above.

The term "protecting group" means a suitable chemical group that can be attached to a functional group and removed at a later stage to reveal the intact functional group. Examples of suitable protecting groups for various functional groups are described in T. W. Greene and P. G. M. Wuts, Protective Groups in Organic Synthesis, 2d Ed., John Wiley and Sons (1991 and later editions); L. Fieser and M. Fieser, Fieser and Fieser's Reagents for Organic Synthesis, John Wiley and Sons (1994); and L. Paquette, ed. Encyclopedia of Reagents for Organic Synthesis, John Wiley and Sons (1995). The term "hydroxy protecting group", as used herein, unless otherwise indicated, includes Ac, CBZ, and various hydroxy protecting groups familiar to those skilled in the art including the groups referred to in Greene.

As used herein, the term "pharmaceutically acceptable salt" means those salts which retain the biological effectiveness and properties of the parent compound and do not present insurmountable safety or toxicity issues.

The term "pharmaceutical composition" means an active compound in any form suitable for effective administration to a subject, e.g., a mixture of the compound and at least one pharmaceutically acceptable carrier.

As used herein, a "physiologically/pharmaceutically acceptable carrier" means a carrier or diluent that does not cause significant irritation to an organism and does not abrogate the biological activity and properties of the administered compound.

A "pharmaceutically acceptable excipient" means an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "treat," "treatment," and "treating" means reversing, alleviating, inhibiting the progress of, or partially or completely preventing the disorder or condition to which such term applies, or one or more symptoms of such disorder or condition. "Preventing" means treating before an infection occurs.

"Therapeutically effective amount" means that amount of the compound being administered which will relieve to some extent one or more of the symptoms of the disorder being treated, or result in inhibition of the progress or at least partial reversal of the condition.

The following abbreviations may be used:

| | |
|---|---|
| min. | minute(s) |
| h | hour(s) |
| d | day(s) |
| RT or rt | room temperature |
| $t_R$ | retention time |
| L | liter |
| mL | milliliter |
| mmol | millimole |
| μmol | micromole |
| equiv. or eq. | equivalents |
| NMR | nuclear magnetic resonance |
| MDP(S) | mass-directed HPLC purification (system) |
| LC/MS | liquid chromatography mass spectrometry |
| HPLC | high performance liquid chromatography |
| TLC | thin layer chromatography |
| $CDCl_3$ | deuterated chloroform |
| $CD_3OD$ or MeOD | deuterated methanol |
| DMSO-$d_6$ | deuterated dimethylsulfoxide |
| LDA | lithium diisopropylamide |
| DCM | dichloromethane |
| THF | tetrahydrofuran |
| EtOAc | ethyl acetate |
| MeCN | acetonitrile |
| DMSO | dimethylsulfoxide |
| Boc | tert-butyloxycarbonyl |
| DME | 1,2-dimethoxyethane |
| DMF | N,N-dimethylformamide |
| DIPEA | diisopropylethylamine |
| PS-DIEA | polymer-supported diisopropylethylamine |
| PS-PPh$_3$-Pd | polymer-supported Pd(PPh$_3$)$_4$ |
| EDC | 1-(3-dimethylaminopropyl)-3-ethylcarbodiimide |
| HOBt | 1-hydroxybenzotriazole |
| DMAP | 4-dimethylaminopyridine |
| TBTU | O-(benzotriazol-1-yl)-N,N,N',N'-tetramethyluronium tetrafluoroborate |
| TEMPO | 2,2,6,6-tetramethylpiperidine-1-oxyl |
| TFA | trifluoroacetic acid |

The invention claimed is:

1. A compound, or pharmaceutically acceptable salt thereof, having the formula:

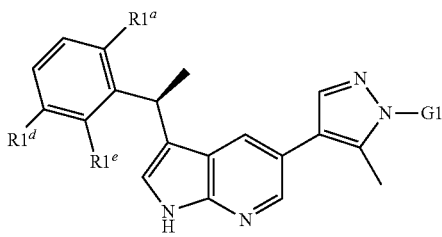

wherein:
G1 is $_{3-7}$cyclic optionally substituted by one or more independent halo, —OH, —OC$_{1-3}$aliphatic, or —C$_{1-3}$aliphatic;
R$^{1a}$ is halo, or is methoxy optionally substituted by 1-3 halo;
R$^{1d}$ and R$^{1e}$ are independently halo.

2. The compound or salt of claim 1, wherein:
G1 is $_{4-7}$cycloalkyl optionally substituted with one or more independent halo, —OH, —OCH$_3$, or —C$_{1-3}$aliphatic;
R$^{1a}$ is halo, or is methoxy optionally substituted by 1-3 fluorine atoms;
R$^{1d}$ and R$^{1e}$ are independently halo.

3. The compound or salt of claim 2, which is present as a material that is substantially free of its (R)-1-(phenyl)ethyl enantiomer.

4. The compound or salt of claim 3, which is present as a substantially pure material.

5. The compound or salt of claim 4, which exhibits inhibition of MET in a cellular mechanistic assay with an IC$_{50}$ of 50 nM or less.

6. The compound or salt of claim 5, which exhibits inhibition of RON and/or ALK in a cellular mechanistic assay with an IC$_{50}$ of 200 nM or less.

7. The compound or salt of claim 6, which is 40-fold or more selective for MET over KDR in a cellular assay.

8. The compound or salt of claim 6, which is 40-fold or more selective for MET over Aurora kinase B (AKB) in a cellular assay.

9. The compound of claim 1, which is (1R,2S,4S)-4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclopentane-1,2-diol, or a pharmaceutically acceptable salt thereof.

10. The compound of claim 1, which is trans-4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclohexanol, or a pharmaceutically acceptable salt thereof.

11. The compound of claim 1, which is cis-3-[4-(3-{(1S)-1-[2-Chloro-6-(difluoromethoxy)-3-fluorophenyl]ethyl}-1H-pyrrolo[2,3-b]pyridin-5-yl)-5-methyl-1H-pyrazol-1-yl]cyclobutanol, or a pharmaceutically acceptable salt thereof.

12. The compound of claim 1, which is cis-4-[4-(3-{(1S)-1-[2-chloro-6-(difluoromethoxy)-3-fluorophenyl]ethyl}-1H-pyrrolo[2,3-b]pyridin-5-yl)-5-methyl-1H-pyrazol-1-yl]cyclohexanol, or a pharmaceutically acceptable salt thereof.

13. The compound of claim 1, which is 3-{(1S)-1-[2-chloro-6-(difluoromethoxy)-3-fluorophenyl]ethyl}-5-[5-methyl-1-(piperidin-4-yl)-1H-pyrazol-4-yl]-1H-pyrrolo[2,3-b]pyridine, or a pharmaceutically acceptable salt thereof.

14. A pharmaceutical composition comprising the compound or salt of claim 1, formulated with or without one or more pharmaceutical carriers.

15. A method of treating human cancer for which inhibition of at least one of RON, MET, or ALK is effective, in a human patient in need thereof, wherein the patient has cancer selected from bladder, colorectal, non-small cell lung, breast, or pancreatic, ovarian, gastric, head and neck, prostate, hepatocellular, renal, glioma, or sarcoma, the method comprising administering an effective amount of the compound or salt of claim 1.

* * * * *